United States Patent
Chu et al.

(10) Patent No.: US 12,421,235 B2
(45) Date of Patent: Sep. 23, 2025

(54) BRIDGED TRICYCLIC CARBAMOYLPYRIDONE COMPOUNDS AND USES THEREOF

(71) Applicant: Gilead Sciences, Inc., Foster City, CA (US)

(72) Inventors: Hang Chu, San Mateo, CA (US); Hongyan Guo, San Mateo, CA (US); Lan Jiang, Foster City, CA (US); Jiayao Li, Foster City, CA (US); David W. Lin, Berkeley, CA (US); Hyung-Jung Pyun, Fremont, CA (US); Qiaoyin Wu, Foster City, CA (US); Hong Yang, Fremont, CA (US); Adam D. Zajdlik, San Francisco, CA (US); Jennifer R. Zhang, Union City, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 17/489,406

(22) Filed: Sep. 29, 2021

(65) Prior Publication Data

US 2022/0135565 A1 May 5, 2022

Related U.S. Application Data

(60) Provisional application No. 63/085,704, filed on Sep. 30, 2020.

(51) Int. Cl.
C07D 471/18 (2006.01)
A61P 31/18 (2006.01)
C07D 491/22 (2006.01)

(52) U.S. Cl.
CPC ............ C07D 471/18 (2013.01); A61P 31/18 (2018.01); C07D 491/22 (2013.01)

(58) Field of Classification Search
None
See application file for complete search history.

(56) References Cited

U.S. PATENT DOCUMENTS

| | | |
|---|---|---|
| 9,522,912 B2 | 12/2016 | Bacon et al. |
| 10,087,178 B2 | 10/2018 | Miyazaki et al. |
| 11,084,832 B2 | 8/2021 | Chu et al. |
| 11,492,352 B2 | 11/2022 | Ishii et al. |
| 11,548,902 B1 | 1/2023 | Chu et al. |
| 11,613,546 B2 | 3/2023 | Chu et al. |
| 11,697,652 B2 | 7/2023 | Jiang et al. |
| 11,897,892 B2 | 2/2024 | Chu et al. |
| 12,024,528 B2 | 7/2024 | Chu et al. |
| 12,187,734 B2 | 1/2025 | Chu et al. |
| 2009/0253681 A1 | 10/2009 | Summa et al. |
| 2009/0270412 A1 | 10/2009 | Hung et al. |
| 2013/0171214 A1 | 7/2013 | Mundhra et al. |
| 2018/0155365 A1 | 6/2018 | Graham et al. |
| 2019/0284208 A1 | 9/2019 | Johns et al. |
| 2019/0315769 A1 | 10/2019 | Graham et al. |
| 2019/0322666 A1 | 10/2019 | Yu et al. |
| 2020/0317689 A1 | 10/2020 | Chu et al. |
| 2021/0284642 A1 | 9/2021 | Jiang et al. |
| 2022/0135565 A1 | 5/2022 | Chu et al. |
| 2022/0267343 A1 | 8/2022 | Chu et al. |
| 2023/0058677 A1 | 2/2023 | Tomida et al. |
| 2023/0203061 A1 | 6/2023 | Chu et al. |
| 2023/0257389 A1 | 8/2023 | Chu et al. |
| 2024/0010650 A1 | 1/2024 | Jiang et al. |

FOREIGN PATENT DOCUMENTS

| | | |
|---|---|---|
| CN | 104995198 | 10/2015 |
| CN | 116390924 | 7/2023 |
| EP | 3938047 A1 | 1/2022 |
| JP | 2006342115 A | 12/2006 |
| JP | 2011515412 A | 5/2011 |
| JP | 2012516333 A | 7/2012 |
| JP | 2016508134 A | 3/2016 |
| JP | 2018510168 A | 4/2018 |

(Continued)

OTHER PUBLICATIONS

Williams etal (Foye's Principles of Medicinal Chemistry, 5th Edition, pp. 59-63, 2002) (Year: 2002).*

(Continued)

*Primary Examiner* — Craig D Ricci
(74) *Attorney, Agent, or Firm* — Fish & Richardson P.C.

(57) ABSTRACT

Compounds for use in treating or preventing human immunodeficiency virus (HIV) infection are disclosed. The compounds have the following Formula (I):

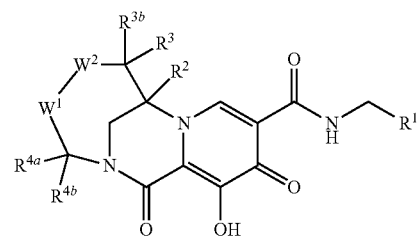

including stereoisomers and pharmaceutically acceptable salts thereof. Methods associated with the preparation and use of the disclosed compounds, as well as pharmaceutical compositions comprising such compounds are also disclosed.

22 Claims, No Drawings

(56) References Cited

FOREIGN PATENT DOCUMENTS

| | | |
|---|---|---|
| TW | 200716635 A | 5/2007 |
| TW | 202106689 A | 2/2021 |
| TW | 202120510 A | 6/2021 |
| WO | WO-2006088173 A1 | 8/2006 |
| WO | WO-2006116764 A1 | 11/2006 |
| WO | WO-2007/019098 A2 | 2/2007 |
| WO | WO-2007049675 A1 | 5/2007 |
| WO | WO-2007050510 A2 | 5/2007 |
| WO | WO-2007148780 A1 | 12/2007 |
| WO | WO-2008010964 A1 | 1/2008 |
| WO | WO-2008048538 A1 | 4/2008 |
| WO | WO-2009088729 A1 | 7/2009 |
| WO | WO-2009154870 A1 | 12/2009 |
| WO | WO-2010000030 A1 | 1/2010 |
| WO | WO-2010011812 A1 | 1/2010 |
| WO | WO-2010011814 A1 | 1/2010 |
| WO | WO-2010011815 A1 | 1/2010 |
| WO | WO-2010011816 A1 | 1/2010 |
| WO | WO-2010011818 A1 | 1/2010 |
| WO | WO-2010011819 A1 | 1/2010 |
| WO | WO-2010042391 A3 | 4/2010 |
| WO | WO-2010068253 A1 | 6/2010 |
| WO | WO-2010088167 A1 | 8/2010 |
| WO | WO-2010147068 A1 | 12/2010 |
| WO | WO-2011011483 A1 | 1/2011 |
| WO | WO-2011025683 A1 | 3/2011 |
| WO | WO-2011045330 A1 | 4/2011 |
| WO | WO-2011094150 A1 | 8/2011 |
| WO | WO-2011105590 A1 | 9/2011 |
| WO | WO-2011121105 A1 | 10/2011 |
| WO | WO-2011129095 A1 | 10/2011 |
| WO | WO-2012018065 A1 | 2/2012 |
| WO | WO-2012058173 A1 | 5/2012 |
| WO | WO-2012078834 A1 | 6/2012 |
| WO | WO-2013054862 A1 | 4/2013 |
| WO | WO-2014004279 A1 | 1/2014 |
| WO | WO-2014008636 A1 | 1/2014 |
| WO | WO-2014014933 A1 | 1/2014 |
| WO | WO-2014028384 A1 | 2/2014 |
| WO | WO-2014072188 A1 | 5/2014 |
| WO | WO-2014/100323 A1 | 6/2014 |
| WO | WO-2014099586 A1 | 6/2014 |
| WO | WO-2014/172188 A2 | 10/2014 |
| WO | WO-2014183532 A1 | 11/2014 |
| WO | WO-2014200880 A1 | 12/2014 |
| WO | WO-2015006731 A1 | 1/2015 |
| WO | WO-2015006733 A1 | 1/2015 |
| WO | WO-2015039348 A1 | 3/2015 |
| WO | WO-2015048363 A1 | 4/2015 |
| WO | WO-2015/095258 A1 | 6/2015 |
| WO | WO-2015089847 A1 | 6/2015 |
| WO | WO-2015/196116 A1 | 12/2015 |
| WO | WO-2016027879 A1 | 2/2016 |
| WO | WO-2016033009 A1 | 3/2016 |
| WO | WO-2016/094197 A1 | 6/2016 |
| WO | WO-2016090545 A1 | 6/2016 |
| WO | WO-2016094198 A1 | 6/2016 |
| WO | WO-2016106237 A1 | 6/2016 |
| WO | WO-2016154527 A1 | 9/2016 |
| WO | WO-2016161382 A1 | 10/2016 |
| WO | WO-2016187788 A1 | 12/2016 |
| WO | WO-2017087256 A1 | 5/2017 |
| WO | WO-2017087257 A1 | 5/2017 |
| WO | WO-2017106071 A1 | 6/2017 |
| WO | WO-2017/116928 A1 | 7/2017 |
| WO | WO-2017113288 A1 | 7/2017 |
| WO | WO-2017223280 A2 | 12/2017 |
| WO | WO-2018102485 A1 | 6/2018 |
| WO | WO-2018102634 A1 | 6/2018 |
| WO | WO-2018109786 A1 | 6/2018 |
| WO | WO-2018140368 A1 | 8/2018 |
| WO | WO-2019/058393 A1 | 3/2019 |
| WO | WO-2019160783 A1 | 8/2019 |
| WO | WO-2019209667 A1 | 10/2019 |
| WO | WO-2019223408 A1 | 11/2019 |
| WO | WO-2019/232216 A1 | 12/2019 |
| WO | WO-2019230857 A1 | 12/2019 |
| WO | WO-2019230858 A1 | 12/2019 |
| WO | WO-2019236396 A1 | 12/2019 |
| WO | WO-2019244066 A2 | 12/2019 |
| WO | WO-2020/003093 A1 | 1/2020 |
| WO | WO 2020075080 | 4/2020 |
| WO | WO-2020086555 A1 | 4/2020 |
| WO | WO-2020112931 A1 | 6/2020 |
| WO | WO-2020197991 A1 | 10/2020 |
| WO | WO 2020/221294 * 11/2020 ........... C07D 471/00 |
| WO | WO-2020221294 A1 | 11/2020 |
| WO | WO-2020246910 A1 | 12/2020 |
| WO | WO 2021007506 | 1/2021 |
| WO | WO-2021093846 A1 | 5/2021 |
| WO | WO-21107066 A1 | 6/2021 |
| WO | WO 2022089562 | 5/2022 |
| WO | WO-2022/177840 A1 | 8/2022 |

OTHER PUBLICATIONS (2020) "Product Monograph Including Patient Medication Information" ViiV Healthcare ULC, 51 pages.

Benn, P. et al. (2021) "Long-Acting Cabotegravir + Rilpivirine in Older Adults: Pooled Phase 3 Week 48 Results" CROI 2021, Science Spotlight, 1-11.

Bowers, G. et al. (2016) "Disposition and metabolism of cabotegravir: a comparison of biotransformation and excretion between different species and routes of administration in humans" Xenobiotica, 46(2):147-162.

Brooks, K. et al. (2019) "Integrase Inhibitors: After 10 Years of Experience, Is the Best Yet to Come?" Pharmacotherapy, 1-23.

Burns, J. et al. (2020) "No overall change in the rate of weight gain after switching to an integrase-inhibitor in virologically suppressed adults with HIV" AIDS, 34:109-114.

Castellino, S et al. (2013) "Metabolism, Excretion, and Mass Balance of the HIV-1 Integrase Inhibitor Dolutegravir in Humans" 57(8):3536-3546.

Cook, N. et al. (2019) "Structural basis of second-generation HIV Integrase inhibitor action and viral resistance" Science, 1-9.

Cottura, N. (2021) "In-Silico Prediction of Long-Acting Cabotegravir PK in Liver Impaired Patients" CROI 2021, Science Spotlight, 6 pages.

Flexner, C. (2020) "Novel Approaches to HIV Treatment and Prevention using Long Acting Drug Delivery" Johns Hopkins University, Division of Clinical Pharmacology, 45 pages.

Friedman, E. et al. (2016) "A Single Monotherapy Dose of MK-8591, a Novel NRTI, Suppresses HIV for 10 Days" CROI 2016, Poster, Abstract #437LB.

Gallant, J. et al. (2017) "Antiviral Activity, Safety, and Pharmacokinetics of Bictegravir as 10-Day Monotherapy in HIV-1-Infected Adults" J Acquir Immune Defic Syndr, 75(1):61-66.

Grobler, J. et al. (2019) "MK-8591 Potency and PK Provide High Inhibitory Quotients at Low Doses QD and QW" CROI 2019, Poster, Abstract #481.

Groseclose, M. et al. (2019) "Intramuscular and subcutaneous drug depot characterization of a long-acting abotegravir nanoformulation by MALDI IMS" International Journal of Mass Spectometry, 437:92-98.

Han, K. et al. (2021) "Cabotegravir Population Pharmacokinetic (PPK) Simulation to Inform Q2M Strategies Following Dosing Interruptions" CROI 2021, Science Spotlight, 9 pages.

Hill, L. et al. (2018) "Profile of bictegravir/emtricitabine/tenofovir alafenamide fixed dose combination and its potential in the treatment of HIV-1 infection: evidence to date" HIV/AIDS—Research and Palliative Care, 10:203-213.

Hughes, D. (2019) "Review of Synthetic Routes and Final Forms of Integrase Inhibitors Dolutegravir, Cabotegravir, and Bictegravir" Organic Process Research & Development, 23:716-729.

Jaeger, H. et al. (2021) "Week 96 Efficacy and Safety of Long-Acting Cabotegravir + Rilpivirine Every 2 Months: ATLAS-2M" CROI 2021, Science Spotlight, 1-9.

(56) References Cited

OTHER PUBLICATIONS

Jiskoot, W. (2020) "Long-actinginjectables& implantables: immunogenicityconcerns" Third Long-Acting Injectables & Implantables Conference, 32 pages.

Jogiraju, V. (2021) "Pharmacokinetics of Lenacapavir, an HIV-1 CAPSID Inhibitor, in Hepatic Impairment" CROI 2021, Science Spotlight, 6 pages.

Johns, B. et al. (2013) "Carbamoyl Pyridone HIV?1 Integrase Inhibitors 3. A Diastereomeric Approach to Chiral Nonracemic Tricyclic Ring Systems and the Discovery of Dolutegravir (S/GSK1349572) and (S/GSK1265744)" J. Med. Chem., 56:5901-5916.

Jucker, B. et al. (2021) "Multiparametric magnetic resonance imaging to characterize cabotegravir long-acting formulation depot kinetics in healthy adult volunteers" Br J Clin Pharmacol., 1-12.

Kandala, B. et al. (2021) "Model-informed dose selection for Islatravir/MK-8507 oral once-weekly phase 2B study" CROI 2021, Science Spotlight, 6 pages.

Kandel, C. et al. (2015) "Dolutegravir—a review of the pharmacology, efficacy, and safety in the treatment of HIV" Drug Design, Development and Therapy, 9:3547-3555.

Kinvig, H. (2021) "In-Silico Prediction of Monthly Bictegravir Microneedle Array Patches" CROI 2021, Science Spotlight, 6 pages.

Lalezari, J. et al. (2009) "Potent Antiviral Activity of S/GSK1349572, A Next Generation Integrase Inhibitor (INI), in INI-Naïve HIV-1-Infected Patients: ING111521 Protocol" IAS 2009, 5th Conference on HIV Pathogenesis, Abstract TUAB105, 15 pages.

Landovitz, R. et al. (2018) "Safety, tolerability, and pharmacokinetics of long-acting injectable cabotegravir in low-risk HIV-uninfected individuals: HPTN 077, a phase 2a randomized controlled trial" PLoS Med, 15(11):1-22.

Le Hingrat, Q. et al. (2018) "A New Mechanism of Resistance of Human Immunodeficiency Virus Type 2 to Integrase Inhibitors: A 5-Amino-Acid Insertion in the Integrase C-Terminal Domain" Clinical Infectious Diseases, 1-11.

Liu, S. et al. (2019) "Mechanistic Assessment of Extrahepatic Contributions to Glucuronidation of Integrase Strand Transfer Inhibitors" Drug Metabolism and Disposition, 47(5) 535-544.

Martin, C. et al. (2021) "Bictegravir and Cabotegravir: In Vitro Phenotypic Susceptibility of HIV-1 Nongroup M" CROI 2021, Science Spotlight, 1-6.

McMillan, J. et al. (2019) "Pharmacokinetic testing of a first generation cabotegravir prodrug in rhesus macaques" AIDS, 33(3):585-588.

Muller, R. et al. (2011) "State of the art of nanocrystals—Special features, production, nanotoxicology aspects and intracellular delivery" European Journal of Pharmaceuticals and Biopharmaceutics, 78:1-9.

Neary, M. (2021) "In Vitro / In Vivo Development of Long Acting Biodegradable Emtricitabine Implants" CROI 2021, Science Spotlight, 6 pages.

Orkin, C. et al. (2020) "Long-Acting Cabotegravir + Rilpivirine for HIV Treatment: Flair Week 96 Results" Conference on Retroviruses and Opportunistic Infections, Poster 0482, 1 page.

Passos, D. et al. (2020) "Structural basis for strand transfer inhibitor binding to HIV intasomes" Science, 1-9.

Passos, D. et al. (2020) Supplementary Materials for "Structural basis for strand transfer inhibitor binding to HIV intasomes" Science, Supplementary Text, 38 pages.

Provisional Application as filed on Apr. 6, 2022 for U.S. Appl. No. 63/328,061.

Raheem, I. et al. (2015) "Discovery of 2?Pyridinone Aminals: A Prodrug Strategy to Advance a Second Generation of HIV?1 Integrase Strand Transfer Inhibitors" J. Med. Chem., 58:8154-8165.

Rossenu, S. et al. (2021) "Population PK Modeling of Every 2 Months IM RPV LA for Managing Dosing Interruptions in HIV-1 Patients" CROI 2021, Science Spotlight, 1-7.

Rudd, D. et al. (2020) "Modeling-Supported Islatravir Dose Selection for Phase 3" CROI 2020, Poster, Abstract #462.

Scarsi, K. et al. (2020) "HIV-1 Integrase Inhibitors: A Comparative Review of Efficacy and Safety" Drugs, 80(16):1649-1676.

Shaik, J. et al. (2019) "A Phase 1 Study to Evaluate the Pharmacokinetics and Safety of Cabotegravir in Patients With Hepatic Impairment and Healthy Matched Controls" Clinical Pharmacology in Drug Development, 00(0):1-10.

Spreen, W. et al. (2013) "Pharmacokinetics, Safety, and Monotherapy Antiviral Activity of GSK1265744, an HIV Integrase Strand Transfer Inhibitor" HIV Clinical Trials, 14(5):192-203.

Spreen, W. et al. (2014) "GSK1265744 Pharmacokinetics in Plasma and Tissue After Single-Dose Long-Acting Injectable Administration in Healthy Subjects" J Acquir Immune Defic Syndr, 67(5):481-486.

Trezza, C. et al. (2015) "Formulation and pharmacology of long-acting cabotegravir" Current Opinion—HIV and AIDS, 10(4):239-245.

Walji, A. et al. (2015) "Discovery of MK-8970: An Acetal Carbonate Prodrug of Raltegravir with Enhanced Colonic Absorption" ChemMedChem, 10:245-252.

Weller, S. et al. (2014) "Pharmacokinetics of dolutegravir in HIV-seronegative subjects with severe renal impairment" Eur J Clin Pharmacol 70:29-35.

Yoshinaga, T. et al. (2015) "Antiviral Characteristics of GSK1265744, an HIV Integrase Inhibitor Dosed Orally or by Long-Acting Injection" 59(1):397-406.

Yoshinaga, T. et al. (2018) "Novel secondary mutations C56S and G149A confer resistance to HIV-1 integrase strand transfer inhibitors" Antiviral Research, 152:1-9.

Zhang, W. et al. (2018) "Accumulation of Multiple Mutations In Vivo Confers Cross-Resistance to New and Existing Integrase Inhibitors" The Journal of Infectious Diseases, 218:1773-1776.

Office Action dated Jun. 23, 2022 for ROC (Taiwan) Application No. 110136191.

Intl. Search Report and Written Opinion dated Dec. 14, 2021 for Intl. Appl. No. PCT/US2021/052683.

Rahnfeld, L. et al. (2020) "Injectable Lipid-Based Depot Formulations: Where Do We Stand?" Pharmaceutics 12(0567):1-28.

Kalicharan, R. et al. (2017) "New Insights Into Drug Absorption From Oil Depots" University Medical Center Utrecht, Utrecht, the Netherlands, Thesis, 152 pages.

Shi, Y. et al. (2021) "A review of existing strategies for designing longacting parenteral formulations: Focus on underlying mechanisms, and future perspectives" Acta Pharmaceutica Sinica B, 11(8): 2396-2415.

Correll, C. et al. (2021) "Pharmacokinetic Characteristics of Long-Acting Injectable Antipsychotics for Schizophrenia: An Overview" CNS Drugs, 35: 39-59.

Klooster, G. et al. (2010) "Pharmacokinetics and Disposition of Rilpivirine (TMC278) Nanosuspension as a Long-Acting Injectable Antiretroviral Formulation" Antimicrobial Agents and Chemotherapy, 54(5): 2042-2050.

Wilkinson, J. et al. (2022) "Lipid based intramuscular long-acting injectables: Current state of the art" European Journal of Pharmaceutical Sciences, 178(106253): 1-20.

Kalicharan, R. et al. (2016) "Fundamental understanding of drug absorption from a parenteral oil depot" European Journal of Pharmaceutical Sciences, 83: 19-27.

Intl. Preliminary Report on Patentability dated Apr. 13, 2023 for Intl. Appl. No. PCT/US2021/052683.

Office Action dated Apr. 25, 2023 for ROC (Taiwan) Application No. 110136191.

Akiyama, T. et al. (2013) "Discovery of Novel HIV Integrase Inhibitors Part 2. Selection and Evaluation of an Azabicyclic Carbamoyl Pyridone as a Pre-clinical Candidate", 245th ACS National Meeting and Exposition, Poster MEDI 403.

Andersson, V. et al. (2016) "Macrocyclic Prodrugs of a Selective Nonpeptidic Direct Thrombin Inhibitor Display High Permeability, Efficient Bioconversion but Low Bioavailability", J Med Chem, 59(14):6658-6670.

Anonymous (2013) "Thomson Reuters Drug News: Results from phase III trials of dolutegravir presented", Thomson Reuters. Retrieved from the Internet Jul. 5, 2013<URL: http://drugnews.thomsonpharma.com/ddn/article.do?printerFriendlyFormat=true>.

(56) References Cited

OTHER PUBLICATIONS

Bari, H. (2010) "A Prolonged Release Parenteral Drug Delivery System—An Overview", Int J Pharm Sci Rev Res, 3(1):1-11.
Bocedi, A. et al. (2004) "Binding of Anti-HIV Drugs to Human Serum Albumin", IUBMB Life, 56(10):609-614.
Brinson, C. et al. (2013) "Dolutegravir Treatment Response and Safety by Key Subgroups in Treatment Naive HIV Infected Individuals", 20th CROI, Poster 554.
Cottrell, M. et al. (2013) "Clinical Pharmacokinetic, Pharmacodynamic and Drug-Interaction Profile of the Integrase Inhibitor Dolutegravir", Clin Pharmacokinet, 52(11): 981-994.
Curley, P. et al. (2019) "Long-Acting Emtricitabine Prodrugs Provide Protection From HIV Infection In Vivo", 2019 CROI, Poster 2262.
Del Mar Gutierrez, M. et al. (2014) "Drug safety profile of integrase strand transfer inhibitors", Expert Opin Drug Saf, 13(4):431-445.
Dicker, I. et al. (2011) "Simple and Accurate In Vitro Method for Predicting Serum Protein Binding of HIV Integrase Strand Transfer Inhibitors", HIV-1 Integrase: Mechanism and Inhibitor Design, First Edition.
EFSA (European Food Safety Authority), (2005) "Opinion of the Scientific Panel on Dietetic Products, Nutrition and Allergies on a request from the Commission related to the Tolerable Upper Intake Level of Potassium", EFSA Journal 2005, 3(3):193, 19 pp.
Gelé, T. et al. (2020) "Characteristics of Dolutegravir and Bictegravir Plasma Protein Binding: a First Approach for the Study of Pharmacologic Sanctuaries", Antimicrob Agents Chemother, 64(11):e00895-20.
Grobler, J. et al. (2016) "Efficacy of once-weekly MK-8591 in SIV infected rhesus macaques", Merck & Co., Inc., 7th International Workshop on Clinical Pharmacology of HIV & Hepatitis Therapy.
Günthard, H. et al. (2016) "Antiretroviral Drugs for Treatment and Prevention of HIV Infection in Adults: 2016 Recommendations of the International Antiviral Society-USA Panel", JAMA, 316(2):191-210.
Gurevich, K. (2013) "Effect of blood protein concentrations on drug-dosing regimes: practical guidance", Theor Biol Med Model, 10:20.
Hare, S. et al. (2011) "Structural and Functional Analyses of the Second-Generation Integrase Strand Transfer Inhibitor Dolutegravir (S/GSK1349572)", Mol Pharmacol, 80(4):565-572.
Hurt, C. et al. (2013) "Characterization of Resistance to Integrase Strand Transfer Inhibitors among Clinical Specimens in the United States, 2009-2012", 20th CROI, Poster 591.
Johns, B. et al. (2010) "The Discovery of S/GSK1349572: A Once Daily Next Generation Integrase Inhibitor with a Superior Resistance Profile", 17th CROI.
Kochansky, C. et al. (2008) "Impact of pH on Plasma Protein Binding in Equilibrium Dialysis", Mol Pharm, 5(3): 438-448.
Kulkarni, T. et al. (2019) "Prodrugs extend the half life and potency of Cabotegravir", CROI, Poster 489.
Kulkarni, T. et al. (2020) "A Year-Long Extended Release Nanoformulated Cabotegravir Prodrug", Nat Mater, 19(8):910-920.
Landovitz, R. et al. (2020) "Cabotegravir Is Not Associated With Weight Gain in Human Immunodeficiency Virus-uninfected Individuals in HPTN 077", Clin Infect Dis, 70(2):319-322.
Letendre, S. et al. (2013) "Distribution and Antiviral Activity in Cerebrospinal Fluid (CSF) of the Integrase Inhibitor, Dolutegravir (DTG): ING116070 Week 16 Results", 20th CROI, Poster 178LB.
Nair, V. et al. (2014) "Pharmacokinetics and Dose-range Finding Toxicity of a Novel anti-HIV Active Integrase Inhibitor", Antiviral Res, 108:25-29.
Nair, V. et al. (2014) "Pharmacokinetics and Dose-range Finding Toxicity of a Novel anti-HIV Active Integrase Inhibitor" Supplementary Materials.
Markowitz, M. (2017) "Weekly Oral MK-8591 Protects Male Rhesus Macaques against Repeated Low Dose Intrarectal Challenge with SHIV109CP3", 9th IAS Conference on HIV Science (IAS 2017), PowerPoint Presentation.
Matthews, R. et al. (2017) "Single doses as low as 0.5 mg of the novel NRTTI MK-8591 suppress HIV for at least seven days", IAS 2017: Conference on HIV Pathogenesis, Poster.
McElnay, J. & D'arcy, P. (1983) "Protein Binding Displacement Interactions and their Clinical Importance", Drugs, 25(5):495-513.
Menéndez-Arias, L. & Alvarez, M. (2014) "Antiretroviral therapy and drug resistance in human immunodeficiency virus type 2 infection", Antiviral Res, 102:70-86.
Métifiot, M. et al. (2013) "HIV Integrase Inhibitors: 20-Year Landmark and Challenges", Adv Pharmacol, 67:75-105.
Min, S. et al. (2011) "Antiviral activity, safety, and pharmacokinetics/pharmacodynamics of dolutegravir as 10-day monotherapy in HIV-1-infected adults" AIDS 25(14):1737-1745.
Mullokandov, E. et al. (2014) "Protein Binding Drug-Drug Interaction between Warfarin and Tizoxanide in Human Plasma", Austin J Pharmacol Ther, 2(7):id1038.
Orkin, C. et al. (2019) "Long-Acting Cabotegravir + Rilpivirine for HIV Maintenance: Flair Week 48 Results", CROI 2019, PowerPoint Presentation.
Park, B. et al. (2001) "Metabolism of Fluorine-Containing Drugs" Annu. Rev. Pharmacol. Toxicol. 41:443-470.
Podany, A. et al. (2017) "Comparative Clinical Pharmacokinetics and Pharmacodynamics of HIV-1 Integrase Strand Transfer Inhibitors", Clin Pharmacokinet, 56(1):25-40.
Pozniak, A. et al. (2013) "Dolutegravir (DTG) Versus Raltegravir (RAL) in ART-Experienced, Integrase-Naive Subjects: 24-Week Interim Results From Sailing (ING111762)", 20th CROI.
Quashie, P. et al. (2013) "Evolution of HIV integrase resistance mutations", Curr Opin Infect Dis, 26(1):43-49.
Raffi, F. et al. (2013) "Once-daily dolutegravir versus raltegravir in antiretroviral-naive adults with HIV-1 infection: 48 week results from the randomised, double-blind, non-inferiority SPRING-2 study", Lancet, 381(9868):735-743.
Rajoli, R. et al. (2019) "In Silico Simulation Of Long-Acting Tenofovir Alafenamide Subcutaneous Implant", CROI 2019, Poster 487.
Rautio, J. et al. (2018), "The expanding role of prodrugs in contemporary drug design and development", Nat Rev Drug Discov, 17(8):559-587.
Reese, M. et al. (2013) "In Vitro Investigations into the Roles of Drug Transporters and Metabolizing Enzymes in the Disposition and Drug Interactions of Dolutegravir, a HIV Integrase Inhibitor" Drug Metab Dispos 41:353-361.
Rhodes, M. et al. (2012) "Assessing a Theoretical Risk of Dolutegravir-Induced Developmental Immunotoxicity in Juvenile Rats", Toxicol Sci, 130(1): 70-81.
Roberts, J. et al. (2013) "The Clinical Relevance of Plasma Protein Binding Changes", Clin Pharmacokinet, 52(1): 1-8.
Song, I. et al. (2013) "Dolutegravir Has No Effect on the Pharmacokinetics of Methadone or Oral Contraceptives With Norgestimate and Ethinyl Estradiol", 20th CROI.
Taoada, Y. et al. (2013) "Discovery of Novel HIV Integrase Inhibitors Part 1. Molecular Design and SAR of Azabicyclic Carbamoyl Pyridone Inhibitors", 245th ACS National Meeting and Exposition, Poster MEDI 402.
Tian, H. et al. (2018) "Effects of Plasma Albumin on the Pharmacokinetics of Esomeprazole in ICU Patients", Biomed Res Int, 2018:6374374.
Van Der Galiën, R. et al. (2019) "Pharmacokinetics of HIV-Integrase Inhibitors During Pregnancy: Mechanisms, Clinical Implications and Knowledge Gaps", Clin Pharmacokinet, 58(3):309-323.
Wang, Y. C. et al. (2002) "Switch in asymmetric induction sense in cycloadditions using camphor-based nitroso dienophiles", Tetrahedron: Asymmetry, 13(7):691-695.
Weaving, G. et al. (2016) "Age and sex variation in serum albumin concentration: an observational study", Ann Clin Biochem, 53(1):106-111.
Wolkowicz, U. et al. (2014) "Structural Basis of Mos1 Transposase Inhibition by the Anti-retroviral Drug Raltegravir", ACS Chem Biol, 9(3):743-751.
Wu, J. et al. (2012) "Implications of Plasma Protein Binding for Pharmacokinetics and Pharmacodynamics of the γ-Secretase Inhibitor RO4929097", Clin Cancer Res, 18(7):2066-2079.

(56) References Cited

OTHER PUBLICATIONS

Zhao, X. et al. (2014) "4-Amino-1-hydroxy-2-oxo-1,8-naphthyridine-Containing Compounds Having High Potency against Raltegravir-Resistant Integrase Mutants of HIV-1", J Med Chem, 57(12):5190-5202.
Office Action in Australian Appln. No. 2021351491, mailed Sep. 19, 2023, 4 pages.
Fulmali et al., "Phosphate moiety in FDA-approved pharmaceutical salts and prodrugs," Drug Dev. Res., Jun. 2, 2022, 83(5):1059-1074.
Ivashchenko et al., "Synthesis, biological evaluation and in silico modeling of novel integrase strand transfer inhibitors (INSTIs)," European Journal of Medicinal Chemistry, Mar. 1, 2020, 189:112064.
Levine et al., "Trimethyl lock: A trigger for molecular release in chemistry, biology, and pharmacology," Chem. Sci., Jan. 2012, 3(8):2412-2420.
Patani et al., "Bioisoterism: A Rational Approach in Drug Design," Chem Rev., Dec. 1996, 8:3147-3176.
Randolph et al., "Prodrug Strategies to Improve the Solubility of the HCV NS5A Inhibitor Pibrentasvir (ABT-530)," J. Med. Chem., Sep. 3, 2020, 63:11034-11044.
Tantra et al., "Phosphate Prodrugs: An Approach to Improve the Bioavailability of Clinically Approved Drugs," Curr. Med. Chem., Mar. 21, 2023, 31(3):336-357.
Thenin-Houssier et al. Antimicrobial Agents and Chemotherapy 2016, 60, 2195-2208 (Year: 2016).
Thierry et al., "Different Pathways Leading to Integrase Inhibitors Resistance," Front. Microbiol., Jan. 11, 2017, 7:2165, 13 pages.
Voight et al., "Desymmetrization of pibrentasvir for efficient prodrug synthesis," Chem. Sci., Jun. 29, 2021, 12(29):10076-10082.
Office Action in Australian Appln. No. 2021351491, dated Apr. 30, 2024, 3 pages.
Office Action in European Appln. No. 21801304.3, dated May 27, 2024, 3 pages.
Office Action in Japanese Appln. No. 2023-519489, dated Mar. 29, 2024, 12 pages (with English translation).
Office Action in Chinese Appln. No. 202180067050.X, dated Sep. 28, 2024, 15 pages (with English translation).
Office Action in Japanese Appln. No. 2023-519489, mailed on Nov. 20, 2024, 5 pages (with English translation).
Office Action in Korean Appln. No. 10-2023-7014237, mailed on Mar. 26, 2025, 10 pages (with English translation).
Office Action in Taiwanese Appln. No. 110136191, mailed on Mar. 6, 2025, 17 pages (with English translation).
Office Action in Chinese Appln. No. 202180067050.X, dated Apr. 24, 2025, 8 pages (with English translation).

\* cited by examiner

BRIDGED TRICYCLIC CARBAMOYLPYRIDONE COMPOUNDS AND USES THEREOF

CROSS REFERENCE

This application claims priority to U.S. Provisional Application No. 63/085,704, filed Sep. 30, 2020, which is incorporated herein in its entirety for all purposes.

FIELD

This disclosure relates generally to certain bridged tricyclic compounds, pharmaceutical compositions comprising said compounds, and methods of making and using said compounds and pharmaceutical compositions.

BACKGROUND

Human immunodeficiency virus infection and related diseases are a major public health problem worldwide. Human immunodeficiency virus encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains may limit their usefulness (Palella, et al. *N. Engl. J Med.* (1998) 338:853-860; Richman, D. D. *Nature* (2001) 410:995-1001). Accordingly, there is a need for new agents that inhibit the replication of HIV.

A goal of antiretroviral therapy is to achieve viral suppression in the HIV infected patient. Current treatment guidelines published by the United States Department of Health and Human Services provide that achievement of viral suppression requires the use of combination therapies, i.e., several drugs from at least two or more drug classes (Panel on Antiretroviral Guidelines for Adults and Adolescents. Guidelines for the Use of Antiretroviral Agents in Adults and Adolescents Living with HIV. Department of Health and Human Services. Available at https://files.aidsinfo.nih.gov/contentfiles/lvguidelines/AdultandAdolescentGL.pdf. Accessed Feb. 20, 2020). In addition, decisions regarding the treatment of HIV infected patients are complicated when the patient requires treatment for other medical conditions. Because the standard of care requires the use of multiple different drugs to suppress HIV, as well as to treat other conditions the patient may be experiencing, the potential for drug interaction is a criterion for selection of a drug regimen. As such, there is a need for antiretroviral therapies having a decreased potential for drug interactions.

In addition, the HIV virus is known to mutate in infected subjects (Tang, et al. *Drugs* (2012) 72 (9) e1-e25). Because of the proclivity of the HIV virus to mutate, there is a need for anti-HIV drugs to be effective against a range of known HIV variants (Hurt, et al. *HIV/AIDS CID* (2014) 58, 423-431).

For certain patients, for example, those with difficult or limited access to health care, adherence to daily oral treatment or prophylactic regimens can be challenging. Drugs that offer favorable pharmaceutical properties (for example, improved potency, long-acting pharmacokinetics, low solubility, low clearance, and/or other properties) are amenable to less frequent administration and provide for better patient compliance. Such improvements can, in turn, optimize drug exposure and limit the emergence of drug resistance.

SUMMARY

In some embodiments, the disclosure provides a compound of Formula I:

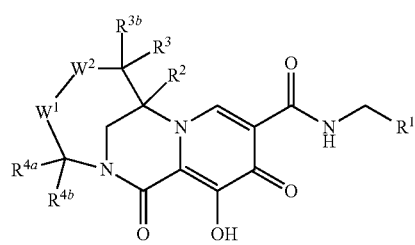

Formula I or a pharmaceutically acceptable salt thereof, wherein
$R^1$ is $C_{6-10}$aryl or 5 to 10 membered heteroaryl, wherein the $C_{6-10}$aryl or 5 to 10 membered heteroaryl is optionally substituted with one to four $R^{41}$, wherein each $R^{41}$ is independently halo, $C_{1-6}$alkyl, $C_{1-4}$haloalkyl, cyano, —O—$C_{1-4}$alkyl, or $C_{1-4}$alkyl-O—$C_{1-4}$alkyl;
$R^2$ is H, $C_{1-6}$alkyl, or $C_{1-4}$haloalkyl;
$R^3$ is halo or —$OR^{3a}$, wherein $R^{3a}$ is H, —$C_{1-6}$alkyl, —$C_{1-4}$haloalkyl, or —$C_{3-6}$cycloalkyl; or
$R^{3a}$ and any one of $R^2$, $R^{5a}$, and $R^{6a}$ together with the carbons to which they are attached from a 4 to 6 membered heterocyclic ring containing one or two heteroatoms independently selected from N, O, and S;
$R^{3b}$ is H, —$C_{1-6}$alkyl, —$C_{1-4}$haloalkyl, or —$C_{1-4}$alkylene-O—$C_{1-4}$alkyl;
$R^{4a}$ is —$C_{1-6}$alkyl or —$C_{1-4}$haloalkyl;
$R^{4b}$ is H, halo, —$C_{1-6}$alkyl, or —$C_{1-4}$haloalkyl;
$W^1$ is a bond or —$CR^{5a}R^{5b}$—;
  $R^{5a}$ and $R^{5b}$ are independently H, $C_{1-6}$alkyl, $C_{1-4}$haloalkyl, or halo; or
  $R^{5a}$ and $R^{3a}$ together with the carbons to which they are attached from a 4 to 6 membered heterocyclic ring containing one or two heteroatoms independently selected from N, O, and S; and $R^{5b}$ is H, $C_{1-6}$alkyl, $C_{1-4}$haloalkyl, or halo;
$W^2$ is —$CR^{6a}R^{6b}$— or —$CR^{7a}$=$CR^{7b}$—;
  $R^{6a}$ and $R^{6b}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl; or
  $R^6$ and $R^{3a}$ together with the carbons to which they are attached from a 4 to 6 membered heterocyclic ring containing one or two heteroatoms independently selected from N, O, and S; and $R^{6b}$ is H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl;
  $R^{7a}$ and $R^{7b}$ are independently H, halo, $C_{1-4}$haloalkyl, or $C_{1-6}$alkyl; or
  $R^{7a}$ and $R^{7b}$ together with the carbons to which they are attached form a $C_{5-10}$aryl optionally substituted with one to four $R^{42}$, wherein each $R^{42}$ is independently halo, cyano, or $C_{1-4}$alkyl.

In some embodiments, the disclosure provides a pharmaceutical composition comprising a therapeutically effective amount of a compound of Formula I, or pharmaceutically acceptable salt thereof, and a pharmaceutically acceptable excipient.

In some embodiments, the disclosure provides a kit comprising a compound of Formal I, or a pharmaceutically acceptable salt thereof, and instructions for use.

In some embodiments, the disclosure provides a method of treating an HIV infection in a human having or at risk of having the infection, comprising administering to the human a therapeutically effective amount of a compound of Formula I, or pharmaceutically acceptable salt thereof, or a pharmaceutical composition thereof.

In some embodiments, the disclosure provides use of a compound of Formula I, or pharmaceutically acceptable salt thereof, or a pharmaceutical composition thereof, for treating an HIV infection in a human having or at risk of having the infection.

In some embodiments, the disclosure provides a compound of Formula I, or pharmaceutically acceptable salt thereof, or a pharmaceutical composition thereof, for use in medical therapy.

In some embodiments, the disclosure provides a compound of Formula I, or pharmaceutically acceptable salt thereof, or a pharmaceutical composition thereof, for use in treating an HIV infection.

In some embodiments, the disclosure provides use of a compound of Formula I, or pharmaceutically acceptable salt thereof, or a pharmaceutical composition thereof, in the manufacture of a medicament for treating an HIV infection in a human having or at risk of having the infection.

DETAILED DESCRIPTION

In the following description, certain specific details are set forth in order to provide a thorough understanding of various embodiments disclosed herein. However, one skilled in the art will understand that the embodiments disclosed herein may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

I. DEFINITIONS

Unless the context requires otherwise, throughout the present disclosure and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment disclosed herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.

"Hydroxy" or "hydroxyl" refers to the —OH radical.

"Oxo" refers to the =O substituent.

A prefix such as "$C_{u-v}$" or ($C_u$-$C_v$) indicates that the following group has from u to v carbon atoms. For example, "$C_{1-6}$alkyl" indicates that the alkyl group has from 1 to 6 carbon atoms.

"Alkyl" refers to a straight or branched chain hydrocarbon radical consisting of carbon and hydrogen atoms, which is saturated, having from one to twelve carbon atoms ($C_{1-12}$alkyl), in certain embodiments one to eight carbon atoms ($C_{1-8}$alkyl), one to six carbon atoms ($C_{1-6}$alkyl), one to four carbon atoms ($C_{1-4}$alkyl), or one to three carbon atoms ($C_{1-3}$alkyl), and which is attached to the rest of the molecule by a single bond, e.g., methyl, ethyl, n-propyl, 1-methylethyl (iso-propyl), n-butyl, 1-methylpropyl (sec-butyl), 2-methylpropyl (iso-butyl), 1,1-dimethylethyl (t-butyl), n-pentyl, hexyl, 3-methylhexyl, 2-methylhexyl, and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1 ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, but are not limited to, phenyl, naphthyl, fluorenyl, and anthryl. Aryl, however, does not encompass or overlap in any way with heteroaryl defined below.

"Cyano" refers to the carbonitrile group (—CN).

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Halo" or "halogen" refers to bromo, chloro, fluoro or iodo.

"Haloalkyl" refers to an alkyl group, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heteroaryl" refers to an aromatic group having a single ring, multiple rings, or multiple fused rings, with one or more ring heteroatoms independently selected from nitrogen, oxygen, and sulfur. As used herein, heteroaryl includes 5 to 20 ring atoms (5 to 20 membered heteroaromatic ring), 5 to 12 ring atoms (5 to 12 membered heteroaromatic ring), 5 to 10 ring atoms (5 to 10 membered heteroaromatic ring) or 5 to 6 ring atoms (5 to 6 membered heteroaromatic ring); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclic ring" refers to a non-aromatic radical or ring having from three to fifteen atoms wherein from one to six atoms are heteroatoms selected from the group consisting of nitrogen, oxygen and sulfur and attached to the rest of the molecule by a single bond. In certain embodiments, "heterocyclyl" has from three to ten atoms, wherein from one to four atoms are heteroatoms selected from the group consisting of nitrogen, oxygen and sulfur, or from three to seven atoms, wherein from one to two atoms are heteroatoms selected from the group consisting of nitrogen, oxygen and sulfur. The nitrogen, carbon or sulfur atoms in the heterocyclyl may be optionally oxidized; the nitrogen atom may be optionally quaternized. As used herein, heterocyclic ring refers to rings that are saturated or partially saturated. Examples of such heterocyclic ring include, but are not limited to, dioxolanyl, imidazolidinyl, isothiazolidinyl, isoxazolidinyl, morpholinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuranyl, trithianyl, tetrahydropyranyl, thiomorpholinyl, thiamorpholinyl, 1-oxo-thiomorpholinyl, and 1,1-dioxo-thiomorpholinyl. The term includes groups having a single ring or multiple rings including fused, bridged, and spiro ring systems.

The embodiments disclosed herein are also meant to encompass all pharmaceutically acceptable compounds of Formula I being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. In certain embodiments, these radiolabeled compounds are useful to help determine or measure the effectiveness of the compounds, by characterizing, for example, the site or mode of action, or binding affinity to pharmacologically important site of action. Certain isotopically-labeled compounds of Formula I, Ia, Ib, Ic, Id, or II, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

In certain embodiments, substitution with heavier isotopes such as deuterium, i.e., $^2$H, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}$C, $^{18}$F, $^{15}$O, and $^{13}$N, can be useful in Positron Emission Topography (PET) studies for examining substrate receptor occupancy. Isotopically-labeled compounds of Formula I, Ia, Ib, Ic, Id or II can be prepared by techniques known to those skilled in the art or by processes analogous to those described in the Examples as set out below using an appropriate isotopically-labeled reagent in place of the non-labeled reagent previously employed.

The methods, compositions, kits and articles of manufacture provided herein use or include compounds (e.g., a compound of Formula I, Ia, Ib, Ic, Id, or II) or pharmaceutically acceptable salts thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds increase resistance to metabolism, and thus are useful for increasing the half-life of compounds or pharmaceutically acceptable salts thereof, when administered to a mammal. See, e.g., Foster, "Deuterium Isotope Effects in Studies of Drug Metabolism", *Trends Pharmacol. Sci.*, 5(12):524-527 (1984). Such compounds can be synthesized by means known in the art, for example by employing starting materials in which one or more hydrogen atoms have been replaced by deuterium.

The embodiments disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments disclosed herein include compounds produced by a process comprising administering a compound according to the embodiments disclosed herein to a mammal for a period of time sufficient to yield a metabolic product thereof. Such products are typically identified by administering a radiolabeled compound according to the embodiments disclosed herein in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event or circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or other pharmacologically inactive substance that is formulated in combination with a pharmacologically active ingredient of a pharmaceutical composition and is compatible with the other ingredients of the formulation and suitable for use in humans or domestic animals without undue toxicity, irritation, allergic response, and the like.

Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_{1-4}$alkyl). Pharmaceutically acceptable salts of a nitrogen atom or an amino group include, for example, salts of organic carboxylic acids such as acetic, trifluoroacetic, adipic, ascorbic, aspartic, butyric, camphoric, cinnamic, citric, digluconic, glutamic, glycolic, glycerophosphoric, formic, hexanoic, benzoic, lactic, fumaric, tartaric, maleic, hydroxymaleic, malonic, malic, mandelic, isethionic, lactobionic, nicotinic, oxalic, pamoic, pectinic, phenylacetic, 3-phenylpropionic, pivalic, propionic, pyruvic, salicylic, stearic, sulfanilic, tartaric, undecanoic, and succinic acids; organic sulfonic acids, such as methanesulfonic, ethanesulfonic, camphorsulfonic, mesitylenesulfonic, benzenesulfonic, p-toluenesulfonic acids, naphthalenesulfonic, and 2-naphthalenesulfonic; and inorganic acids, such as hydrochloric, hydrobromic, sulfuric, phosphoric, nitric, and sulfamic acids. Pharmaceutically acceptable salts of a compound of a hydroxy group include the anion of said compound in combination with a suitable cation such as $Na^+$ and $NX_4^+$ (wherein X is independently selected from H or a $C_{1-4}$alkyl group).

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of Formula I or another compound of the embodiments disclosed herein. All salts, whether or not derived from a physiologically acceptable acid or base, are within the scope of the embodiments disclosed herein.

Metal salts typically are prepared by reacting the metal hydroxide with a compound according to the embodiments disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds disclosed herein in their un-ionized, as well as zwitterionic form.

A "pharmaceutical composition" refers to a formulation of a compound of the embodiments disclosed herein and a medium generally accepted in the art for the delivery of the biologically active compound to mammals, e.g., humans. Such a medium includes all pharmaceutically acceptable excipients.

"Effective amount" or "therapeutically effective amount" refers to an amount of a compound according to the embodiments disclosed herein, which when administered to a patient in need thereof, is sufficient to effect treatment of disease-states, conditions, or disorders disclosed herein. Such an amount would be sufficient to elicit the biological or medical response of a tissue system, or patient that is sought by a researcher or clinician. The amount of a compound according to the embodiments disclosed herein which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination, or coincidentally, with the compounds of the embodiments disclosed herein, and the age, body weight, general health, sex and diet of the patient. Such a therapeutically effective amount can be determined by one of ordinary skill in the art having regard to their own knowledge, the state of the art, and this disclosure.

The terms "treating" and "treatment" as used herein are intended to mean the administration of a compound or composition according to the present embodiments disclosed herein to alleviate or eliminate one or more symptoms of HIV infection and/or to reduce viral load in a patient. In certain embodiments, the terms "treating" and "treatment" also encompass the administration of a compound or composition according to the present embodiments disclosed herein post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present embodiments disclosed herein to prevent perinatal transmission of HIV from mother to baby, by administration to the mother before giving birth and to the child within the first days of life. The terms "treating" and "treatment" also encompass the administration of a compound or composition according to the present embodiments disclosed herein before the exposure of the individual to the virus (also called pre-exposure prophylaxis or PrEP), to prevent HIV infection from taking hold if the individual is exposed to the virus and/or to keep the virus from establishing a permanent infection and/or to prevent the appearance of symptoms of the disease and/or to prevent the virus from reaching detectable levels in the blood. The terms "treating" and "treatment" also encompass the administration of a compound or composition according to the present embodiments disclosed herein both before and after the exposure of the individual to the virus.

As used herein, the terms "preventing" and "prevention" refer to the administration of a compound, composition, or pharmaceutically salt according to the present disclosure pre- or post-exposure of the human to the virus but before the appearance of symptoms of the disease, and/or prior to the detection of the virus in the blood. The terms also refer to prevention of the appearance of symptoms of the disease and/or to prevent the virus from reaching detectible levels in the blood. The terms include both pre-exposure prophylaxis (PrEP), as well as post-exposure prophylaxis (PEP) and event driven or "on demand" prophylaxis. The terms also refer to prevention of perinatal transmission of HIV from mother to baby, by administration to the mother before giving birth and to the child within the first days of life. The terms also refer to prevention of transmission of HIV through blood transfusion.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic, scalemic, and optically pure forms. Optically active (+) and (−), (R)- and (S)-, or (D)- and (L)-isomers may be prepared using chiral synthons or chiral reagents, or resolved using methods such as chromatography and fractional crystallization. Techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another. In any of the embodiments disclosed herein, compounds disclosed herein may be in the form of a stereoisomer thereof.

"Partially saturated" refers to a cyclic group which contains at least one double bond but is not aromatic.

II. COMPOUNDS

In some embodiments, the present disclosure provides a compound of Formula I.

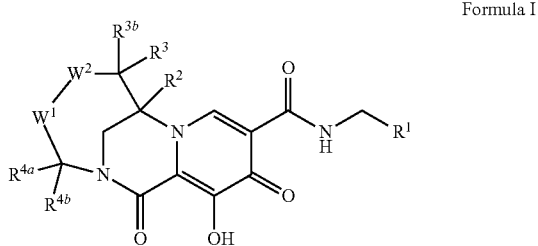

Formula I or a pharmaceutically acceptable salt thereof, wherein
$R^1$ is $C_{6-10}$aryl or 5 to 10 membered heteroaryl, wherein the $C_{6-10}$aryl or 5 to 10 membered heteroaryl is optionally substituted with one to four $R^{41}$, wherein each $R^{41}$ is independently halo, $C_{1-6}$alkyl, $C_{1-4}$haloalkyl, cyano, —O—$C_{1-4}$alkyl, or $C_{1-4}$alkyl-O—$C_{1-4}$alkyl;
$R^2$ is H, $C_{1-6}$alkyl, or $C_{1-4}$haloalkyl;
$R^3$ is halo or —$OR^{3a}$, wherein $R^{3a}$ is H, —$C_{1-6}$alkyl, —$C_{1-4}$haloalkyl, or —$C_{3-6}$cycloalkyl; or
$R^{3a}$ and any one of $R^2$, $R^{5a}$, and $R^{6a}$ together with the carbons to which they are attached from a 4 to 6 membered heterocyclic ring containing one or two heteroatoms independently selected from N, O, and S;
$R^{3b}$ is H, —$C_{1-6}$alkyl, —$C_{1-4}$haloalkyl, or —$C_{1-4}$alkylene-O—$C_{1-4}$alkyl;
$R^{4a}$ is —$C_{1-6}$alkyl or —$C_{1-4}$haloalkyl;
$R^{4b}$ is H, halo, —$C_{1-6}$alkyl, or —$C_{1-4}$haloalkyl;
$W^1$ is a bond or —$CR^{5a}R^{5b}$—;
$R^{5a}$ and $R^{5b}$ are independently H, $C_{1-6}$alkyl, $C_{1-4}$haloalkyl, or halo; or
$R^{5a}$ and $R^{3a}$ together with the carbons to which they are attached from a 4 to 6 membered heterocyclic ring containing one or two heteroatoms independently selected from N, O, and S; and $R^{5b}$ is H, $C_{1-6}$alkyl, $C_{1-4}$haloalkyl, or halo; $W^2$ is —$CR^{6a}R^{6b}$— or —$CR^{7a}$=$CR^{7b}$—;
$R^{6a}$ and $R^{6b}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl; or
$R^{6a}$ and $R^{3a}$ together with the carbons to which they are attached from a 4 to 6 membered heterocyclic ring containing one or two heteroatoms independently selected from N, O, and S; and $R^{6b}$ is H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl; and
$R^{7a}$ and $R^{7b}$ are independently H, halo, $C_{1-4}$haloalkyl, or $C_{1-6}$alkyl; or
$R^{7a}$ and $R^{7b}$ together with the carbons to which they are attached form a $C_{5-10}$aryl optionally substituted with one to four $R^{A2}$, wherein each $R^{A2}$ is independently halo, cyano, or $C_{1-4}$alkyl.

It is a desirable to discover compounds, or pharmaceutically acceptable salts thereof, that have good stability, i.e. physical, chemical stability, and/or metabolic stability. An increase in overall stability of a compound can provide an increase in circulation time in the body. With less degradation, a stable compound can be administered in lower doses and still maintain efficacy. Also, with less degradation there are less concerns about by-products from degradation of the compound. Higher stability of the drug means that more drug is available for target cells without being metabolized.

It is further desirable to discover compounds, or pharmaceutically acceptable salts thereof, that have improved pharmacokinetic and/or pharmacodynamic profiles and long half-life. It is advantageous for a drug to have a moderate or low clearance and a long half-life, as this can lead to a good bioavailability and high systemic exposure. Reducing the clearance and/or increasing half-life time of a compound could reduce the daily dose required for efficacy and therefore give a better efficacy and safety profile. Thus, improved pharmacokinetic and/or pharmacodynamic profiles and long half-life can provide for better patient compliance.

As shown below, the compounds of Formula I provided herein are characterized by (i) at least one oxygen linked or halogen substitution at the "a" position ($R^3$ is halo or —$OR^{3a}$) and (ii) at least one alkyl or haloalkyl substituent the "b" position ($R^{4a}$ is —$C_{1-6}$alkyl or —$C_{1-4}$haloalkyl):

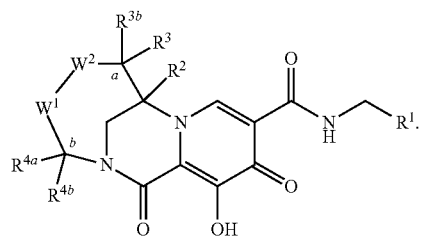

Advantageously, certain compounds of Formula I provided herein exhibit improved properties, for example improved stability as compared to structurally related compounds lacking (i) the at least one oxygen linked or halogen substitution at the "a" position and (ii) the at least one alkyl or haloalkyl substituent the "b" position. In some embodiments, the compounds of Formula I provided herein exhibit improved metabolic stability as compared to structurally related compounds lacking (i) the at least one oxygen linked or halogen substitution at the "a" position and (ii) the at least one alkyl or haloalkyl substituent the "b" position. In some embodiments, the improved metabolic stability of the compounds of Formula I provided herein results in their reduced intrinsic clearance, for example from their reduced intrinsic clearance in human liver microsomal assay (HLM).

In some embodiments, the compound of Formula I provided herein is a compound of Formula Ia:

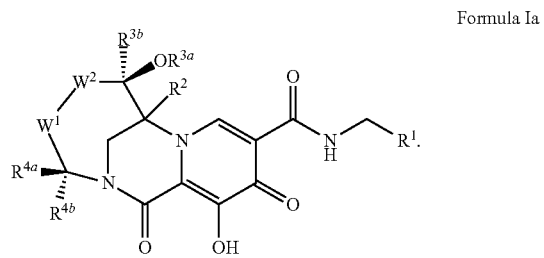

Formula Ia

In some embodiments, the compound of Formula I provided herein is a compound of Formula Ib:

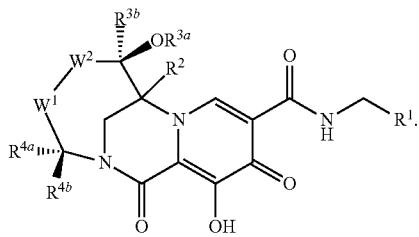

Formula Ib

In some embodiments, the compound of Formula I provided herein is a compound of Formula Ic:

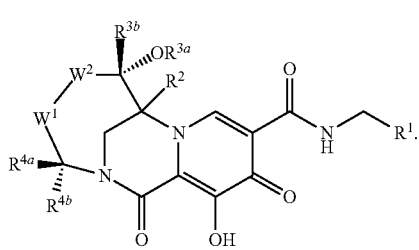

Formula Ic

In some embodiments, the compound of Formula I provided herein is a compound of Formula Id:

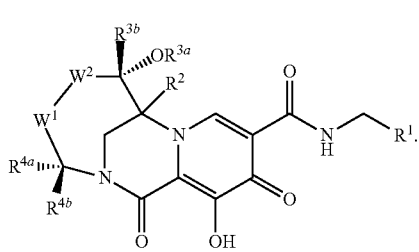

Formula Id

In some embodiments of the compounds of Formula I, Ia, Ib, Ic, or Id, or the pharmaceutically acceptable salt thereof, $R^1$ is $C_{6-10}$aryl or 5 to 10 membered heteroaryl, wherein the $C_{6-10}$aryl or 5 to 10 membered heteroaryl is optionally substituted with one to four $R^{41}$, wherein each $R^{41}$ is independently halo, $C_{1-6}$alkyl, $C_{1-4}$haloalkyl, cyano, —O—$C_{1-4}$alkyl, or $C_{1-4}$ alkyl-O—$C_{1-4}$alkyl. In some embodiments, $R^1$ is phenyl, pyridyl, pyridazine, pyrazine, or pyrimidine, wherein the phenyl, pyridyl, pyridazine, pyrazine, or pyrimidine is optionally substituted with one, two, three, or four $R^{41}$, wherein each $R^{41}$ is independently halo, $C_{1-6}$alkyl, $C_{1-4}$haloalkyl, cyano, —O—$C_{1-4}$alkyl, or $C_{1-4}$alkyl-O—$C_{1-4}$alkyl. In some embodiments, $R^1$ is phenyl, pyridyl, pyridazine, pyrazine, or pyrimidine, optionally substituted with one, two, three, or four $R^{41}$, wherein each $R^{41}$ is independently halo, $C_{1-4}$alkyl, $C_{1-4}$haloalkyl, or —O—$C_{1-4}$ alkyl. In some embodiments, $R^1$ is phenyl, pyridyl, pyridazine, pyrazine, or pyrimidine, optionally substituted with one, two, three, or four $R^{41}$, wherein each $R^{41}$ is independently halo, $C_{1-4}$alkyl, or —O—$C_{1-4}$alkyl. In some embodiments, $R^1$ is phenyl, pyridyl, pyridazine, pyrazine, or pyrimidine, optionally substituted with one, two, three, or four $R^{41}$, wherein each $R^{41}$ is independently halo or $C_{1-4}$alkyl. In some embodiments, $R^1$ is phenyl, pyridyl, pyridazine, pyrazine, or pyrimidine, optionally substituted with one, two, three, or four $R^{41}$, wherein each $R^{41}$ is independently halo or —O—$C_{1-4}$alkyl. In some embodiments, $R^1$ is phenyl, pyridyl, pyridazine, pyrazine, or pyrimidine substituted with one, two, three, or four $R^{41}$, wherein each $R^{41}$ is independently a halogen. In some embodiments, $R^1$ is phenyl, pyridyl, pyridazine, pyrazine, or pyrimidine substituted with two or three $R^{41}$, wherein each $R^{41}$ is independently a halogen. In some embodiments, $R^1$ is phenyl, pyridyl, pyridazine, pyrazine, or pyrimidine substituted with two or three $R^{41}$, wherein each $R^{41}$ is independently selected from chloro and fluoro.

In some embodiments of the compounds of Formula I, Ia, Ib, Ic, or Id, or the pharmaceutically acceptable salt thereof, $R^1$ is phenyl or pyridyl, wherein the phenyl or pyridyl is optionally substituted with one, two, three, or four $R^{41}$, wherein each $R^{41}$ is independently halo, $C_{1-6}$alkyl, $C_{1-4}$haloalkyl, cyano, —O—$C_{1-4}$alkyl, or —$C_{1-4}$alkyl-O—$C_{1-4}$alkyl. In some embodiments, $R^1$ is phenyl or pyridyl, wherein the phenyl or pyridyl is optionally substituted with one, two, three, or four $R^{41}$, wherein each $R^{41}$ is independently halo, $C_{1-4}$alkyl, $C_{1-4}$ haloalkyl, or —O—$C_{1-4}$alkyl. In some embodiments, $R^1$ is phenyl or pyridyl, wherein the phenyl or pyridyl is optionally substituted with one, two, three, or four $R^{41}$, wherein each $R^{41}$ is independently halo, $C_{1-4}$alkyl, or —O—$C_{1-4}$alkyl. In some embodiments, $R^1$ is phenyl or pyridyl, wherein the phenyl or pyridyl is optionally substituted with one, two, three, or four $R^{41}$, wherein each $R^{41}$ is independently halo or $C_{1-4}$alkyl. In some embodiments, $R^1$ is phenyl or pyridyl, wherein the phenyl or pyridyl is optionally substituted with one, two, three, or four $R^{41}$, wherein each $R^{41}$ is independently halo or —O—$C_{1-4}$alkyl. In some embodiments, $R^1$ is phenyl or pyridyl, wherein the phenyl or pyridyl is substituted with one, two, three, or four $R^{41}$, wherein each $R^{41}$ is independently a halogen. In some embodiments, $R^1$ is phenyl or pyridyl, wherein the phenyl or pyridyl is substituted with two or three $R^{41}$, wherein each $R^{41}$ is independently a halogen. In some embodiments, $R^1$ is phenyl or pyridyl, wherein the phenyl of pyridyl is substituted with two or three $R^{41}$, wherein each $R^{41}$ is independently selected from chloro and fluoro.

In some embodiments of the compounds of Formula I, Ia, Ib, Ic, or Id, or the pharmaceutically acceptable salt thereof, $R^1$ is pyridyl, wherein the pyridyl is optionally substituted with one, two, three, or four $R^{41}$, wherein each $R^{41}$ is independently halo, $C_{1-6}$alkyl, $C_{1-4}$haloalkyl, cyano, —O—$C_{1-4}$alkyl, or —$C_{1-4}$alkyl-O—$C_{1-4}$alkyl. In some embodiments, $R^1$ is pyridyl, wherein the pyridyl is optionally substituted with one, two, three, or four $R^{41}$, wherein each $R^{41}$ is independently halo, $C_{1-4}$alkyl, $C_{1-4}$haloalkyl, or —O—$C_{1-4}$alkyl. In some embodiments, $R^1$ is pyridyl, wherein the pyridyl is optionally substituted with one, two, three, or four $R^{41}$ wherein each $R^{41}$ is independently halo, $C_{1-4}$alkyl, or —O—$C_{1-4}$alkyl. In some embodiments, $R^1$ is pyridyl, wherein the pyridyl is optionally substituted with one, two, three, or four $R^{41}$, wherein each $R^{41}$ is independently halo or $C_{1-4}$alkyl. In some embodiments, $R^1$ is pyridyl, wherein the pyridyl is optionally substituted with one, two, three, or four $R^{41}$, wherein each $R^{41}$ is independently halo or —O—$C_{1-4}$alkyl. In some embodiments, $R^1$ is pyridyl, wherein the pyridyl is substituted with one, two, three, or four $R^{41}$, wherein each $R^{41}$ is independently a halogen. In some embodiments, $R^1$ is pyridyl, wherein the pyridyl is substituted with two or three $R^{41}$ wherein each $R^{41}$ is independently a halogen. In some embodiments, $R^1$ is pyridyl, wherein the pyridyl is substituted with two or three $R^{A1}$, wherein each $R^{A1}$ is independently selected from chloro and fluoro.

In some embodiments of the compounds of Formula I, Ia, Ib, Ic, or Id, or the pharmaceutically acceptable salt thereof, $R^1$ is phenyl, wherein the phenyl is optionally substituted with one, two, three, or four $R^{A1}$, wherein each $R^{A1}$ is independently halo, $C_{1-6}$alkyl, $C_{1-4}$haloalkyl, cyano, —O—$C_{1-4}$alkyl, or —$C_{1-4}$alkyl-O—$C_{1-4}$alkyl. In some embodiments, $R^1$ is phenyl, wherein the phenyl is optionally substituted with one, two, three, or four $R^{A1}$, wherein each $R^{A1}$ is independently halo, $C_{1-4}$alkyl, $C_{1-4}$haloalkyl, or —O—$C_{1-4}$alkyl. In some embodiments, $R^1$ is phenyl, wherein the phenyl is optionally substituted with one, two, three, or four $R^{A1}$ wherein each $R^{A1}$ is independently halo, $C_{1-4}$alkyl, or —O—$C_{1-4}$alkyl. In some embodiments, $R^1$ is phenyl, wherein the phenyl is optionally substituted with one, two, three, or four $R^{A1}$, wherein each $R^{A1}$ is independently halo or $C_{1-4}$alkyl. In some embodiments, $R^1$ is phenyl, wherein the phenyl is optionally substituted with one, two, three, or four $R^{A1}$, wherein each $R^{A1}$ is independently halo or —O—$C_{1-4}$alkyl. In some embodiments, $R^1$ is phenyl, wherein the phenyl is substituted with one, two, three, or four $R^{A1}$, wherein each $R^{A1}$ is independently a halogen. In some embodiments, $R^1$ is phenyl, wherein the phenyl is substituted with two or three $R^{A1}$ wherein each $R^{A1}$ is independently a halogen. In some embodiments, $R^1$ is phenyl, wherein the phenyl is substituted with two or three $R^{A1}$, wherein each $R^{A1}$ is independently selected from chloro and fluoro.

In some embodiments of the compounds of Formula I, Ia, Ib, Ic, or Id, or the pharmaceutically acceptable salt thereof, $R^1$ is selected from the group consisting of:

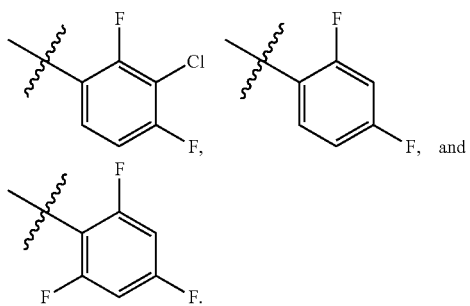

In some embodiments, the compound of Formula I, Ia, Ib, Ic, or Id is a compound of Formula II:

Formula II

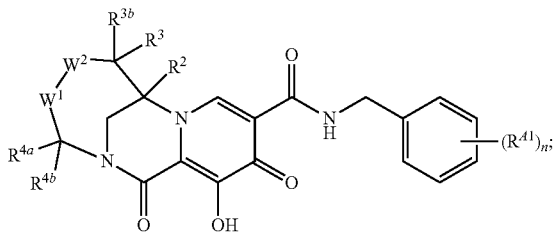

wherein n is 0, 1, 2, 3, or 4; and each $R^{A1}$ is independently halo, $C_{1-6}$alkyl, $C_{1-4}$haloalkyl, cyano, —O—$C_{1-4}$alkyl, or $C_{1-4}$alkyl-O—$C_{1-4}$alkyl.

In some embodiments of the compound of Formula II, n is 2, 3, or 4 and each $R^{A1}$ is independently halo, $C_{1-4}$alkyl, $C_{1-4}$haloalkyl, cyano, or —O—$C_{1-4}$alkyl. In some embodiments, n is 2, 3, or 4 and each $R^{A1}$ is independently halo, $C_{1-4}$alkyl, $C_{1-4}$haloalkyl, or —O—$C_{1-4}$alkyl. In some embodiments, n is 2, 3, or 4, and each $R^{A1}$ is independently halo, $C_{1-4}$alkyl, or —O—$C_{1-4}$alkyl. In some embodiments, n is 2, 3, or 4, and each $R^{A1}$ is independently halo or $C_{1-4}$alkyl. In some embodiments, n is 2, 3, or 4, and each $R^{A1}$ is independently halo or —O—$C_{1-4}$alkyl. In some embodiments, n is 2, 3, or 4, and each $R^{A1}$ is independently a halogen. In some embodiments, n is 2, 3, or 4, and each $R^{A1}$ is independently selected from chloro and fluoro.

In some embodiments of the compound of Formula II, n is 2 or 3 and each $R^{A1}$ is independently halo, $C_{1-4}$alkyl, $C_{1-4}$haloalkyl, cyano, or —O—$C_{1-4}$alkyl. In some embodiments, n is 2 or 3 and each $R^{A1}$ is independently halo, $C_{1-4}$alkyl, $C_{1-4}$haloalkyl, or —O—$C_{1-4}$alkyl. In some embodiments, n is 2 or 3, and each $R^{A1}$ is independently halo, $C_{1-4}$alkyl, or —O—$C_{1-4}$alkyl. In some embodiments, n is 2 or 3, and each $R^{A1}$ is independently halo or $C_{1-4}$alkyl. In some embodiments, n is 2 or 3, and each $R^{A1}$ is independently halo or —O—$C_{1-4}$alkyl. In some embodiments, n is 2 or 3, and each $R^{A1}$ is independently a halogen. In some embodiments, n is 2 or 3, and each $R^{A1}$ is independently selected from chloro and fluoro.

In some embodiments of the compounds of Formula I, Ia, Ib, Ic, Id, or II, or the pharmaceutically acceptable salt thereof, $R^2$ is H, $C_{1-6}$ alkyl, or $C_{1-4}$haloalkyl. In some embodiments, $R^2$ is H or $C_{1-6}$alkyl. In some embodiments, $R^2$ is H or $C_{1-4}$haloalkyl. In some embodiments, $R^2$ is $C_{1-6}$alkyl or $C_{1-4}$haloalkyl. In some embodiments, $R^2$ is a $C_{1-3}$alkyl. In some embodiments, $R^2$ is methyl. In some embodiments $R^2$ is H.

In some embodiments of the compounds of Formula I, Ia, Ib, Ic, Id, or II, or the pharmaceutically acceptable salt thereof, $R^3$ is halo. In some embodiments, $R^3$ is chloro.

In some embodiments of the compounds of Formula I, Ia, Ib, Ic, Id, or II, or the pharmaceutically acceptable salt thereof, $R^3$ is $OR^{3a}$, wherein $R^{3a}$ is H, —$C_{1-6}$alkyl, —$C_{1-4}$haloalkyl, or —$C_{3-6}$cycloalkyl and $R^{3b}$ is H, —$C_{1-6}$alkyl, —$C_{1-4}$haloalkyl, or —$C_{1-4}$alkylene-O—$C_{1-4}$ alkyl. In some embodiments, $R^{3a}$ is —$C_{1-6}$alkyl, —$C_{1-4}$haloalkyl, or —$C_{3-6}$ cycloalkyl; and $R^{3b}$ is H, —$C_{1-6}$alkyl, —$C_{1-4}$haloalkyl, or —$C_{1-4}$alkylene-O—$C_{1-4}$alkyl. In some embodiments, $R^{3a}$ is —$C_{1-6}$ alkyl or —$C_{1-4}$haloalkyl; and $R^{3b}$ is H, —$C_{1-6}$alkyl, —$C_{1-4}$haloalkyl, or —$C_{1-4}$alkylene-O—$C_{1-4}$alkyl. In some embodiments, $R^{3a}$ is —$C_{1-6}$alkyl; and $R^{3b}$ is H, —$C_{1-6}$alkyl, —$C_{1-4}$haloalkyl, or —$C_{1-4}$ alkylene-O—$C_{1-4}$ alkyl. In some embodiments, $R^{3a}$ is methyl or ethyl; and $R^{3b}$ is H, —$C_{1-6}$alkyl, —$C_{1-4}$haloalkyl, or —$C_{1-4}$alkylene-O—$C_{1-4}$alkyl. In some embodiments, $R^{3a}$ is methyl; and $R^{3b}$ is H, —$C_{1-6}$alkyl, —$C_{1-4}$haloalkyl, or —$C_{1-4}$alkylene-O—$C_{1-4}$ alkyl.

In some embodiments of the compounds of Formula I, Ia, Ib, Ic, Id, or II, or the pharmaceutically acceptable salt thereof, $R^3$ is $OR^{3a}$, wherein $R^{3a}$ is H, —$C_{1-6}$alkyl, —$C_{1-4}$haloalkyl, or —$C_{3-6}$cycloalkyl and $R^{3b}$ is H, —$C_{1-6}$alkyl, or —$C_{1-4}$haloalkyl. In some embodiments, $R^{3a}$ is —$C_{1-6}$alkyl, —$C_{1-4}$haloalkyl, or —$C_{3-6}$cycloalkyl and $R^{3b}$ is H, —$C_{1-6}$ alkyl, or —$C_{1-4}$haloalkyl. In some embodiments, $R^{3a}$ is —$C_{1-6}$alkyl or —$C_{1-4}$haloalkyl and $R^{3b}$ is H, —$C_{1-6}$alkyl, or —$C_{1-4}$ haloalkyl. In some embodiments, $R^{3a}$ is —$C_{1-6}$alkyl and $R^{3b}$ is H, —$C_{1-6}$alkyl, or —$C_{1-4}$haloalkyl. In some embodiments, $R^{3a}$ is methyl or ethyl and $R^{3b}$ is H, —$C_{1-6}$ alkyl, or —$C_{1-4}$haloalkyl. In some embodiments, $R^{3a}$ is methyl and $R^{3b}$ is H, —$C_{1-6}$alkyl, or —$C_{1-4}$haloalkyl.

In some embodiments of the compounds of Formula I, Ia, Ib, Ic, Id, or II, or the pharmaceutically acceptable salt thereof, $R^3$ is $OR^{3a}$, wherein $R^{3a}$ is H, —$C_{1-6}$alkyl, —$C_{1-4}$haloalkyl, or —$C_{3-6}$cycloalkyl and $R^{3b}$ is H or —$C_{1-6}$alkyl. In some embodiments, $R^{3a}$ is —$C_{1-6}$alkyl, —$C_{1-4}$haloalkyl, or —$C_{3-6}$cycloalkyl and $R^{3b}$ is H or —$C_{1-6}$alkyl. In some embodiments, $R^{3a}$ is —$C_{1-6}$alkyl or —$C_{1-4}$haloalkyl and $R^{3b}$ is H or —$C_{1-6}$alkyl. In some embodiments, $R^{3a}$ is —$C_{1-6}$alkyl; and $R^{3b}$ is H or —$C_{1-6}$alkyl. In some embodiments, $R^{3a}$ is methyl or ethyl and $R^{3b}$ is H or —$C_{1-6}$alkyl. In some embodiments, $R^{3a}$ is methyl and $R^{3b}$ is H or —$C_{1-6}$alkyl.

In some embodiments of the compounds of Formula I, Ia, Ib, Ic, Id, or II, or the pharmaceutically acceptable salt thereof, $R^3$ is $OR^{3a}$, wherein $R^{3a}$ is H, —$C_{1-6}$alkyl, —$C_{1-4}$haloalkyl, or —$C_{3-6}$cycloalkyl and $R^{3b}$ is H or —$C_{1-3}$alkyl. In some embodiments, $R^{3a}$ is —$C_{1-6}$alkyl, —$C_{1-4}$haloalkyl, or —$C_{3-6}$cycloalkyl and $R^{3b}$ is H or —$C_{1-3}$alkyl. In some embodiments, $R^{3a}$ is —$C_{1-6}$alkyl or —$C_{1-4}$haloalkyl and $R^{3b}$ is H or —$C_{1-3}$alkyl. In some embodiments, $R^{3a}$ is —$C_{1-6}$alkyl and $R^{3b}$ is H or —$C_{1-3}$alkyl. In some embodiments, $R^{3a}$ is methyl or ethyl and $R^{3b}$ is H or —$C_{1-6}$alkyl. In some embodiments, $R^{3a}$ is methyl and $R^{3b}$ is H or —$C_{1-3}$alkyl.

In some embodiments of the compounds of Formula I, Ia, Ib, Ic, Id, or II, or the pharmaceutically acceptable salt thereof, $R^3$ is $OR^{3a}$, wherein $R^{3a}$ is H, —$C_{1-6}$alkyl, —$C_{1-4}$haloalkyl, or —$C_{3-6}$cycloalkyl and $R^{3b}$ is H or methyl. In some embodiments, $R^{3a}$ is —$C_{1-6}$alkyl, —$C_{1-4}$haloalkyl, or —$C_{3-6}$cycloalkyl and $R^{3b}$ is H or methyl. In some embodiments, $R^{3a}$ is —$C_{1-6}$alkyl or —$C_{1-4}$haloalkyl and $R^{3b}$ is H or methyl. In some embodiments, $R^{3a}$ is —$C_{1-6}$alkyl and $R^{3b}$ is H or methyl. In some embodiments, $R^{3a}$ is methyl or ethyl and $R^{3b}$ is H or methyl. In some embodiments, $R^{3a}$ is methyl and $R^{3b}$ is H or methyl.

In some embodiments of the compounds of Formula I, Ia, Ib, Ic, Id, or II, or the pharmaceutically acceptable salt thereof, $R^3$ is $OR^{3a}$, wherein $R^{3a}$ is H, —$C_{1-6}$alkyl, —$C_{1-4}$haloalkyl, or —$C_{3-6}$cycloalkyl and $R^{3b}$ is H. In some embodiments, $R^{3a}$ is —$C_{1-6}$alkyl, —$C_{1-4}$haloalkyl, or —$C_{3-6}$cycloalkyl and $R^{3b}$ is H. In some embodiments, $R^{3a}$ is —$C_{1-6}$alkyl or —$C_{1-4}$haloalkyl and $R^{3b}$ is H. In some embodiments, $R^{3a}$ is —$C_{1-6}$alkyl and $R^{3b}$ is H. In some embodiments, $R^{3a}$ is methyl or ethyl and $R^{3b}$ is H. In some embodiments, $R^{3a}$ is methyl and $R^{3b}$ is H.

In some embodiments of the compounds of Formula I, Ia, Ib, Ic, Id, or II, or the pharmaceutically acceptable salt thereof, $R^{3a}$ and any one of $R^2$, $R^{5a}$ and $R^{6a}$ together with the carbons to which they are attached from a 4 to 6 membered heterocyclic ring containing one or two heteroatoms independently selected from N, O, and S; and $R^{3b}$ is H, —$C_{1-6}$alkyl, —$C_{1-4}$haloalkyl, or —$C_{1-4}$alkylene-O—$C_{1-4}$alkyl. In some embodiments, $R^{3a}$ and any one of $R^2$, $R^{5a}$ and $R^{6a}$ together with the carbons to which they are attached from a 4 to 6 membered heterocyclic ring containing one or two heteroatoms independently selected from N, O, and S; and $R^{3b}$ is H, —$C_{1-6}$alkyl, or —$C_{1-4}$haloalkyl. In some embodiments, $R^{3a}$ and any one of $R^2$, $R^{5a}$ and $R^{6a}$ together with the carbons to which they are attached from a 4 to 6 membered heterocyclic ring containing one or two heteroatoms independently selected from N, O, and S; and $R^{3b}$ is H or —$C_{1-6}$alkyl. In some embodiments, $R^{3a}$ and any one of $R^2$, $R^{5a}$ and $R^{6a}$ together with the carbons to which they are attached from a 4 to 6 membered heterocyclic ring containing one or two heteroatoms independently selected from N, O, and S; and $R^{3b}$ is H or —$C_{1-3}$alkyl. In some embodiments, $R^{3a}$ and any one of $R^2$, $R^{5a}$ and $R^{6a}$ together with the carbons to which they are attached from a 4 to 6 membered heterocyclic ring containing one or two heteroatoms independently selected from N, O, and S; and $R^{3b}$ is H or methyl. In some embodiments, $R^{3a}$ and any one of $R^2$, $R^{5a}$ and $R^{6a}$ together with the carbons to which they are attached from a 4 to 6 membered heterocyclic ring containing one or two heteroatoms independently selected from N, O, and S; and $R^{3b}$ is H.

In some embodiments of the compounds of Formula I, Ia, Ib, Ic, Id, or II, or the pharmaceutically acceptable salt thereof, $R^{3a}$ and any one of $R^2$, $R^{5a}$ and $R^{6a}$ together with the carbons to which they are attached from a 4 to 6 membered heterocyclic ring containing one oxygen atom; and $R^{3b}$ is H, —$C_{1-6}$alkyl, —$C_{1-4}$haloalkyl, or —$C_{1-4}$alkylene-O—$C_{1-4}$alkyl. In some embodiments, $R^{3a}$ and any one of $R^2$, $R^{5a}$ and $R^{6a}$ together with the carbons to which they are attached from a 4 to 6 membered heterocyclic ring containing one oxygen atom; and $R^{3b}$ is H, —$C_{1-6}$alkyl, or —$C_{1-4}$haloalkyl. In some embodiments, $R^{3a}$ and any one of $R^2$, $R^{5a}$ and $R^{6a}$ together with the carbons to which they are attached from a 4 to 6 membered heterocyclic ring containing one oxygen atom; and $R^{3b}$ is H or —$C_{1-6}$alkyl. In some embodiments, $R^{3a}$ and any one of $R^2$, $R^{5a}$ and $R^{6a}$ together with the carbons to which they are attached from a 4 to 6 membered heterocyclic ring containing one oxygen atom; and $R^{3b}$ is H or —$C_{1-3}$alkyl. In some embodiments, $R^{3a}$ and any one of $R^2$, $R^{5a}$ and $R^{6a}$ together with the carbons to which they are attached from a 4 to 6 membered heterocyclic ring containing one oxygen atom; and $R^{3b}$ is H or methyl. In some embodiments, $R^{3a}$ and any one of $R^2$, $R^{5a}$ and $R^{6a}$ together with the carbons to which they are attached from a 4 to 6 membered heterocyclic ring containing one oxygen atom; and $R^{3b}$ is H.

In some embodiments of the compounds of Formula I, Ia, Ib, Ic, Id, or II, or the pharmaceutically acceptable salt thereof, $R^{3a}$ and $R^2$ together with the carbons to which they are attached from a 4 to 6 membered heterocyclic ring containing one or two heteroatoms independently selected from N, O, and S; and $R^{3b}$ is H, —$C_{1-6}$alkyl, —$C_{1-4}$haloalkyl, or —$C_{1-4}$alkylene-O—$C_{1-4}$alkyl. In some embodiments, $R^{3a}$ and $R^2$ together with the carbons to which they are attached from a 4 to 6 membered heterocyclic ring containing one or two heteroatoms independently selected from N, O, and S; and $R^{3b}$ is H, —$C_{1-6}$alkyl, or —$C_{1-4}$haloalkyl. In some embodiments, $R^{3a}$ and $R^2$ together with the carbons to which they are attached from a 4 to 6 membered heterocyclic ring containing one or two heteroatoms independently selected from N, O, and S; and $R^{3b}$ is H or —$C_{1-6}$alkyl. In some embodiments, $R^{3a}$ and $R^2$ together with the carbons to which they are attached from a 4 to 6 membered heterocyclic ring containing one or two heteroatoms independently selected from N, O, and S; and $R^{3b}$ is H or —$C_{1-3}$alkyl. In some embodiments, $R^{3a}$ and $R^2$ together with the carbons to which they are attached from a 4 to 6 membered heterocyclic ring containing one or two heteroatoms independently selected from N, O, and S; and $R^{3b}$ is H or methyl. In some embodiments, $R^{3a}$ and $R^2$ together with the carbons to which they are attached from a 4 to 6 membered heterocyclic ring containing one or two heteroatoms independently selected from N, O, and S; and $R^{3b}$ is H.

In some embodiments of the compounds of Formula I, Ia, Ib, Ic, Id, or II, or the pharmaceutically acceptable salt thereof, $R^{3a}$ and $R^2$ together with the carbons to which they are attached from a 4 to 6 membered heterocyclic ring containing one oxygen atom; and $R^{3b}$ is H, —$C_{1-6}$alkyl, —$C_{1-4}$haloalkyl, or —$C_{1-4}$alkylene-O—$C_{1-4}$alkyl. In some embodiments, $R^{3a}$ and $R^2$ together with the carbons to which they are attached from a 4 to 6 membered heterocyclic ring containing one oxygen atom; and $R^{3b}$ is H, —$C_{1-6}$alkyl, or —$C_{1-4}$haloalkyl. In some embodiments, $R^{3a}$ and $R^2$ together with the carbons to which they are attached from a 4 to 6 membered heterocyclic ring containing one oxygen atom; and $R^{3b}$ is H or —$C_{1-6}$alkyl. In some embodiments, $R^{3a}$ and $R^2$ together with the carbons to which they are attached from a 4 to 6 membered heterocyclic ring containing one oxygen atom; and $R^{3b}$ is H or —$C_{1-3}$alkyl. In some embodiments, $R^{3a}$ and $R^2$ together with the carbons to which they are attached from a 4 to 6 membered heterocyclic ring containing one oxygen atom; and $R^{3b}$ is H or methyl. In some embodiments, $R^{3a}$ and $R^2$ together with the carbons to which they are attached from a 4 to 6 membered heterocyclic ring containing one oxygen atom; and $R^{3b}$ is H.

In some embodiments of the compounds of Formula I, Ia, Ib, Ic, Id, or II, $R^{3a}$ and $R^{5a}$ together with the carbons to which they are attached from a 4 to 6 membered heterocyclic ring containing one or two heteroatoms independently selected from N, O, and S; and $R^{3b}$ is H, —$C_{1-6}$alkyl, —$C_{1-4}$haloalkyl, or —$C_{1-4}$alkylene-O—$C_{1-4}$alkyl. In some embodiments, $R^{3a}$ and $R^{5a}$ together with the carbons to which they are attached from a 4 to 6 membered heterocyclic ring containing one or two heteroatoms independently selected from N, O, and S; and $R^{3b}$ is H, —$C_{1-6}$alkyl, or —$C_{1-4}$haloalkyl. In some embodiments, $R^{3a}$ and $R^{5a}$ together with the carbons to which they are attached from a 4 to 6 membered heterocyclic ring containing one or two heteroatoms independently selected from N, O, and S; and $R^{3b}$ is H or —$C_{1-6}$alkyl. In some embodiments, $R^{3a}$ and $R^{5a}$ together with the carbons to which they are attached from a 4 to 6 membered heterocyclic ring containing one or two heteroatoms independently selected from N, O, and S; and $R^{3b}$ is H or —$C_{1-3}$alkyl. In some embodiments, $R^{3a}$ and $R^{5a}$ together with the carbons to which they are attached from a 4 to 6 membered heterocyclic ring containing one or two heteroatoms independently selected from N, O, and S; and $R^{3b}$ is H methyl. In some embodiments, $R^{3a}$ and $R^{5a}$ together with the carbons to which they are attached from a 4 to 6 membered heterocyclic ring containing one or two heteroatoms independently selected from N, O, and S; and $R^{3b}$ is H.

In some embodiments of the compounds of Formula I, Ia, Ib, Ic, Id, or II, or the pharmaceutically acceptable salt thereof, $R^{3a}$ and $R^{5a}$ together with the carbons to which they are attached from a 4 to 6 membered heterocyclic ring containing one oxygen atom; and $R^{3b}$ is H, —$C_{1-6}$alkyl, —$C_{1-4}$haloalkyl, or —$C_{1-4}$alkylene-O—$C_{1-4}$alkyl. In some embodiments, $R^{3a}$ and $R^{5a}$ together with the carbons to which they are attached from a 4 to 6 membered heterocyclic ring containing one oxygen atom; and $R^{3b}$ is H, —$C_{1-6}$alkyl, or —$C_{1-4}$haloalkyl. In some embodiments, $R^{3a}$ and $R^{5a}$ together with the carbons to which they are attached from a 4 to 6 membered heterocyclic ring containing one oxygen atom; and $R^{3b}$ is H or —$C_{1-6}$alkyl. In some embodiments, $R^{3a}$ and $R^{5a}$ together with the carbons to which they are attached from a 4 to 6 membered heterocyclic ring containing one oxygen atom; and $R^{3b}$ is H or —$C_{1-3}$alkyl. In some embodiments, $R^{3a}$ and $R^{5a}$ together with the carbons to which they are attached from a 4 to 6 membered heterocyclic ring containing one oxygen atom; and $R^{3b}$ is H or methyl. In some embodiments, $R^{3a}$ and $R^{5a}$ together with the carbons to which they are attached from a 4 to 6 membered heterocyclic ring containing one oxygen atom; and $R^{3b}$ is H.

In some embodiments of the compounds of Formula I, Ia, Ib, Ic, Id, or II, or the pharmaceutically acceptable salt thereof, $R^{3a}$ and $R^{6a}$ together with the carbons to which they are attached from a 4 to 6 membered heterocyclic ring containing one or two heteroatoms independently selected from N, O, and S; and $R^{3b}$ is H, —$C_{1-6}$haloalkyl, or —$C_{1-4}$ alkylene-O—$C_{1-4}$alkyl. In some embodiments, $R^{3a}$ and $R^{6a}$ together with the carbons to which they are attached from a 4 to 6 membered heterocyclic ring containing one or two heteroatoms independently selected from N, O, and S; and $R^{3b}$ is H, —$C_{1-6}$alkyl, or —$C_{1-4}$haloalkyl. In some embodiments, $R^{3a}$ and $R^{6a}$ together with the carbons to which they are attached from a 4 to 6 membered heterocyclic ring containing one or two heteroatoms independently selected from N, O, and S; and $R^{3b}$ is H or —$C_{1-6}$alkyl. In some embodiments, $R^{3a}$ and $R^{6a}$ together with the carbons to which they are attached from a 4 to 6 membered heterocyclic ring containing one or two heteroatoms independently selected from N, O, and S; and $R^{3b}$ is H or —$C_{1-3}$alkyl. In some embodiments, $R^{3a}$ and $R^{6a}$ together with the carbons to which they are attached from a 4 to 6 membered heterocyclic ring containing one or two heteroatoms independently selected from N, O, and S; and $R^{3b}$ is H or methyl. In some embodiments, $R^{3a}$ and $R^{6a}$ together with the carbons to which they are attached from a 4 to 6 membered heterocyclic ring containing one or two heteroatoms independently selected from N, O, and S; and $R^{3b}$ is H.

In some embodiments of the compound of Formula I, Ia, Ib, Ic, Id, or II, or the pharmaceutically acceptable salt thereof, $R^{3a}$ and $R^{6a}$ together with the carbons to which they are attached from a 4 to 6 membered heterocyclic ring containing one oxygen atom; and $R^{3b}$ is H, —$C_{1-6}$alkyl, —$C_{1-4}$haloalkyl, or —$C_{1-4}$alkylene-O—$C_{1-4}$alkyl. In some embodiments, $R^{3a}$ and $R^{6a}$ together with the carbons to which they are attached from a 4 to 6 membered heterocyclic ring containing one oxygen atom; and $R^{3b}$ is H, —$C_{1-6}$alkyl, or —$C_{1-4}$haloalkyl. In some embodiments, $R^{3a}$ and $R^{6a}$ together with the carbons to which they are attached from a 4 to 6 membered heterocyclic ring containing one oxygen atom; and $R^{3b}$ is H or —$C_{1-6}$alkyl. In some embodiments, $R^{3a}$ and $R^{6a}$ together with the carbons to which they are attached from a 4 to 6 membered heterocyclic ring containing one oxygen atom; and $R^{3b}$ is H or —$C_{1-3}$alkyl. In some embodiments, $R^{3a}$ and $R^{6a}$ together with the carbons to which they are attached from a 4 to 6 membered heterocyclic ring containing one oxygen atom; and $R^{3b}$ is H or methyl. In some embodiments, $R^{3a}$ and $R^{6a}$ together with the carbons to which they are attached from a 4 to 6 membered heterocyclic ring containing one oxygen atom; and $R^{3b}$ is H.

In some embodiments of the compounds of Formula I, Ia, Ib, Ic, Id, or II, or the pharmaceutically acceptable salt thereof, $R^{4a}$ is —$C_{1-6}$alkyl or —$C_{1-4}$haloalkyl. In some embodiments, $R^{4a}$ is —$C_{1-3}$alkyl. In some embodiments, $R^{4a}$ is methyl. In some embodiments, $R^{4a}$ is —$C_{1-4}$haloalkyl.

In some embodiments of the compounds of Formula I, Ia, Ib, Ic, Id, or II, or the pharmaceutically acceptable salt thereof, $R^{4b}$ is H, halo, —$C_{1-6}$alkyl, or —$C_{1-4}$haloalkyl. In some embodiments, $R^{4b}$ is H, —$C_{1-3}$alkyl, or —$C_{1-4}$haloalkyl. In some embodiments, $R^{4b}$ is H or $C_{1-3}$ alkyl. In some embodiments, $R^{4b}$ is —$C_{1-3}$alkyl or —$C_{1-4}$haloalkyl. In some embodiments, $R^{4b}$ is —$C_{1-3}$alkyl. In some embodiments, $R^{4b}$ is —$C_{1-4}$haloalkyl. In some embodiments, $R^{4b}$ is H.

In some embodiments of the compounds of Formula I, Ia, Ib, Ic, Id, or II, or the pharmaceutically acceptable salt thereof, $R^{4a}$ is —$C_{1-6}$alkyl or —$C_{1-4}$haloalkyl and $R^{4b}$ is H, halo, —$C_{1-6}$alkyl, or —$C_{1-4}$haloalkyl. In some embodiments, $R^{4a}$ is —$C_{1-6}$alkyl or —$C_{1-4}$haloalkyl and $R^{4b}$ is H or $C_{1-3}$alkyl. In some embodiments, $R^{4a}$ is —$C_{1-6}$alkyl or —$C_{1-4}$haloalkyl and $R^{4b}$ is —$C_{1-3}$alkyl or —$C_{1-4}$haloalkyl. In some embodiments, $R^{4a}$ is —$C_{1-6}$alkyl or —$C_{1-4}$haloalkyl and $R^{4b}$ is —$C_{1-3}$alkyl. In some embodiments, $R^{4a}$ is —$C_{1-6}$alkyl or —$C_{1-4}$haloalkyl and $R^{4b}$ is —$C_{1-4}$haloalkyl. In some embodiments, $R^{4a}$ is —$C_{1-6}$alkyl or —$C_{1-4}$haloalkyl and $R^{4b}$ is H.

In some embodiments of the compounds of Formula I, Ia, Ib, Ic, Id, or II, or the pharmaceutically acceptable salt thereof, $R^{4a}$ is —$C_{1-3}$alkyl and $R^{4b}$ is H, halo, —$C_{1-6}$alkyl, or —$C_{1-4}$ haloalkyl. In some embodiments, $R^{4a}$ is —$C_{1-3}$alkyl and $R^{4b}$ is H, —$C_{1-3}$alkyl, or —$C_{1-4}$haloalkyl. In some embodiments, $R^{4a}$ is —$C_{1-3}$alkyl and $R^{4b}$ is H or $C_{1-3}$alkyl. In some embodiments, $R^{4a}$ is —$C_{1-3}$ alkyl and $R^{4b}$ is —$C_{1-3}$alkyl or —$C_{1-4}$haloalkyl. In some embodiments, $R^{4a}$ is —$C_{1-3}$alkyl and $R^{4b}$ is —$C_{1-3}$alkyl. In some embodiments, $R^{4a}$ is —$C_{1-3}$alkyl and $R^{4b}$ is —$C_{1-4}$haloalkyl. In some embodiments, $R^{4a}$ is —$C_{1-3}$alkyl and $R^{4b}$ is H.

In some embodiments of the compounds of Formula I, Ia, Ib, Ic, Id, or II, or the pharmaceutically acceptable salt thereof, $R^{4a}$ is methyl and $R^{4b}$ is H, halo, —$C_{1-6}$alkyl, or —$C_{1-4}$ haloalkyl. In some embodiments, $R^{4a}$ is methyl and $R^{4b}$ is H, —$C_{1-3}$alkyl, or —$C_{1-4}$haloalkyl. In some embodiments, $R^{4a}$ is methyl and $R^{4b}$ is H or $C_{1-3}$alkyl. In some embodiments, $R^{4a}$ is methyl and $R^{4b}$ is —$C_{1-3}$alkyl or —$C_{1-4}$haloalkyl. In some embodiments, $R^{4a}$ is methyl and $R^{4b}$ is —$C_{1-3}$ alkyl. In some embodiments, $R^{4a}$ is methyl and $R^{4b}$ is —$C_{1-4}$haloalkyl. In some embodiments, $R^{4a}$ is methyl and $R^{4b}$ is H.

In some embodiments of the compounds of Formula I, Ia, Ib, Ic, Id, or II, or the pharmaceutically acceptable salt thereof, $R^{4a}$ is —$C_{1-4}$haloalkyl and $R^{4b}$ is H, halo, —$C_{1-6}$alkyl, or —$C_{1-4}$haloalkyl. In some embodiments, $R^{4a}$ is —$C_{1-4}$haloalkyl and $R^{4b}$ is H, —$C_{1-3}$alkyl, or —$C_{1-4}$haloalkyl. In some embodiments, $R^{4a}$ is —$C_{1-4}$haloalkyl and $R^{4b}$ is H or $C_{1-3}$alkyl. In some embodiments, $R^{4a}$ is —$C_{1-4}$ haloalkyl and $R^{4b}$ is —$C_{1-3}$alkyl or —$C_{1-4}$haloalkyl. In some embodiments, $R^{4a}$ is —$C_{1-4}$haloalkyl and $R^{4b}$ is —$C_{1-3}$alkyl. In some embodiments, $R^{4a}$ is —$C_{1-4}$ haloalkyl and $R^{4b}$ is —$C_{1-4}$haloalkyl. In some embodiments, $R^{4a}$ is —$C_{1-4}$haloalkyl and $R^{4b}$ is H.

In some embodiments of the compounds of Formula I, Ia, Ib, Ic, Id, or II, or the pharmaceutically acceptable salt thereof, $W^1$ is a bond.

In some embodiments of the compounds of Formula I, Ia, Ib, Ic, Id, or II, or the pharmaceutically acceptable salt thereof, $W^1$ is —$CR^{5a}R^{5b}$—, wherein $R^{5a}$ and $R^{5b}$ are independently H, $C_{1-6}$alkyl, $C_{1-4}$haloalkyl, or halo. In some embodiments, $R^{5a}$ is H, $C_{1-6}$alkyl, $C_{1-4}$ haloalkyl, or halo and $R^{5b}$ is H, $C_{1-6}$alkyl, or halo. In some embodiments, $R^{5a}$ is H, $C_{1-6}$alkyl, $C_{1-4}$ haloalkyl, or halo and $R^{5b}$ is H or $C_{1-6}$alkyl. In some embodiments, $R^{5a}$ is H, $C_{1-6}$alkyl, $C_{1-4}$ haloalkyl, or halo and $R^{5b}$ is $C_{1-6}$alkyl. In some embodiments, $R^{5a}$ is H, $C_{1-6}$alkyl, $C_{1-4}$haloalkyl, or halo and $R^{5b}$ is H.

In some embodiments of the compounds of Formula I, Ia, Ib, Ic, Id, or II, or the pharmaceutically acceptable salt thereof, $W^1$ is —$CR^{5a}R^{5b}$—, wherein $R^{5a}$ is H, $C_{1-6}$alkyl, or $C_{1-4}$ haloalkyl and $R^{5b}$ is H, $C_{1-6}$alkyl, $C_{1-4}$haloalkyl, or halo. In some embodiments, $R^{5a}$ is H, $C_{1-6}$ alkyl, or $C_{1-4}$haloalkyl and $R^{5b}$ is H, $C_{1-6}$alkyl, or halo. In some embodiments, $R^{5a}$ is H, $C_{1-6}$ alkyl, or $C_{1-4}$haloalkyl and $R^{5b}$ is H or $C_{1-6}$alkyl. In some embodiments, $R^{5a}$ is H, $C_{1-6}$alkyl, or $C_{1-4}$haloalkyl and $R^{5b}$ is $C_{1-6}$alkyl. In some embodiments, $R^{5a}$ is H, $C_{1-6}$alkyl, or $C_{1-4}$haloalkyl and $R^{5b}$ is H.

In some embodiments of the compounds of Formula I, Ia, Ib, Ic, Id, or II, or the pharmaceutically acceptable salt thereof, $W^1$ is —$CR^{5a}R^{5b}$—, wherein $R^{5a}$ is H or $C_{1-6}$alkyl and $R^{5b}$ is H, $C_{1-6}$alkyl, $C_{1-4}$haloalkyl, or halo. In some embodiments, $R^{5a}$ is H or $C_{1-6}$alkyl and $R^{5b}$ is H, $C_{1-6}$alkyl, or halo. In some embodiments, $R^{5a}$ is H or $C_{1-6}$alkyl and $R^{5b}$ is H or $C_{1-6}$alkyl. In some embodiments, $R^{5a}$ is H or $C_{1-6}$alkyl and $R^{5b}$ is $C_{1-6}$alkyl. In some embodiments, $R^{5a}$ is H or $C_{1-6}$alkyl and $R^{5b}$ is H.

In some embodiments of the compounds of Formula I, Ia, Ib, Ic, Id, or II, or the pharmaceutically acceptable salt thereof, $W^1$ is —$CR^{5a}R^{5b}$—, wherein $R^{5a}$ is $C_{1-6}$alkyl and $R^{5b}$ is H, $C_{1-6}$alkyl, $C_{1-4}$haloalkyl, or halo. In some embodiments, $R^{5a}$ is $C_{1-6}$alkyl and $R^{5b}$ is H, $C_{1-6}$alkyl, or halo. In some embodiments, $R^{5a}$ is $C_{1-6}$alkyl and $R^{5b}$ is H or $C_{1-6}$alkyl. In some embodiments, $R^{5a}$ is $C_{1-6}$alkyl and $R^{5b}$ is $C_{1-6}$alkyl. In some embodiments, $R^{5a}$ is $C_{1-6}$alkyl and $R^{5b}$ is H.

In some embodiments of the compounds of Formula I, Ia, Ib, Ic, Id, or II, or the pharmaceutically acceptable salt thereof, $W^1$ is —$CR^{5a}R^{5b}$—, wherein $R^{5a}$ is H and $R^{5b}$ is H, $C_{1-6}$ alkyl, $C_{1-4}$haloalkyl, or halo. In some embodiments, $R^{5a}$ is H and $R^{5b}$ is H, $C_{1-6}$alkyl, or halo. In some embodiments, $R^{5a}$ is H and $R^{5b}$ is H or $C_{1-6}$alkyl. In some embodiments, $R^{5a}$ is H and $R^{5b}$ is $C_{1-6}$alkyl. In some embodiments, $R^{5a}$ is H and $R^{5b}$ is H.

In some embodiments of the compounds of Formula I, Ia, Ib, Ic, Id, or II, or the pharmaceutically acceptable salt thereof, $W^2$ is —$CR^{6a}R^{6b}$—, wherein $R^{6a}$ and $R^{6b}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl. In some embodiments, $R^{6a}$ and $R^{6b}$ are independently H, $C_{1-6}$alkyl, $C_{1-4}$haloalkyl, halo, hydroxyl, cyano, or —O—$C_{1-4}$alkyl. In some embodiments, $R^{6a}$ and $R^{6b}$ are independently H, $C_{1-6}$alkyl, $C_{1-4}$haloalkyl, halo, hydroxyl or cyano. In some embodiments, $R^{6a}$ and $R^{6b}$ are independently H, $C_{1-6}$alkyl, $C_{1-4}$haloalkyl, halo, or hydroxyl. In some embodiments, $R^{6a}$ and $R^{6b}$ are independently H, $C_{1-6}$alkyl, $C_{1-4}$haloalkyl, or halo. In some embodiments, $R^{6a}$ and $R^{6b}$ are independently H, $C_{1-6}$alkyl, or $C_{1-4}$haloalkyl. In some embodiments, $R^{6a}$ and $R^{6b}$ are independently H or $C_{1-6}$alkyl. In some embodiments, $R^{6a}$ and $R^{6b}$ are both H.

In some embodiments of the compound of Formula I, Ia, Ib, Ic, Id, or II, or the pharmaceutically acceptable salt thereof, $W^2$ is —$CR^{6a}R^{6b}$—, wherein $R^{6a}$ is H and $R^{6b}$ is H, $C_{1-6}$ alkyl, $C_{1-4}$haloalkyl, halo, hydroxyl, cyano, —O—$C_{1-4}$alkyl, or $C_{1-4}$alkylene-O—$C_{1-4}$alkyl. In some embodiments, $R^{6a}$ is H and $R^{6b}$ is H, $C_{1-6}$alkyl, $C_{1-4}$haloalkyl, halo, hydroxyl, cyano, or —O—$C_{1-4}$ alkyl. In some embodiments, $R^{6a}$ is H and $R^{6b}$ is H, $C_{1-6}$alkyl, $C_{1-4}$haloalkyl, halo, hydroxyl or cyano. In some embodiments, $R^{6a}$ is H and $R^{6b}$ is H, $C_{1-6}$alkyl, $C_{1-4}$haloalkyl, halo, or hydroxyl. In some embodiments, $R^{6a}$ is H and $R^{6b}$ is H, $C_{1-6}$alkyl, $C_{1-4}$haloalkyl, or halo. In some embodiments, $R^{6a}$ is H and $R^{6b}$ is H, $C_{1-6}$alkyl, or $C_{1-4}$haloalkyl. In some embodiments, $R^{6a}$ is H and $R^{6b}$ is H or $C_{1-6}$alkyl. In some embodiments, $R^{6a}$ is H and $R^{6b}$ is H.

In some embodiments of the compounds of Formula I, Ia, Ib, Ic, Id, or II, or the pharmaceutically acceptable salt thereof $W^2$ is —$CR^{6a}R^{6b}$—, $R^{6a}$ and $R^{3a}$ together with the carbons to which they are attached from a 4 to 6 membered heterocyclic ring containing one or two heteroatoms independently selected from N, O, and S; and $R^{6b}$ is H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl. In some embodiments, $R^{6a}$ and $R^{3a}$ together with the carbons to which they are attached from a 4 to 6 membered heterocyclic ring containing one or two heteroatoms independently selected from N, O, and S; and $R^{6b}$ is H, $C_{1-6}$alkyl, $C_{1-4}$haloalkyl, halo. In some embodiments, $R^{6a}$ and $R^{3a}$ together with the carbons to which they are attached from a 4 to 6 membered heterocyclic ring containing one or two heteroatoms independently selected from N, O, and S; and $R^{6b}$ is H.

In some embodiments of the compounds of Formula I, Ia, Ib, Ic, Id, or II, or the pharmaceutically acceptable salt thereof $W^2$ is —$CR^{6a}R^{6b}$—, $R^{6a}$ and $R^{3a}$ together with the carbons to which they are attached from a 4 to 6 membered heterocyclic ring containing one heteroatom selected from N, O, and S; and $R^{6b}$ is H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl. In some embodiments, $R^{6a}$ and $R^{3a}$ together with the carbons to which they are attached from a 4 to 6 membered heterocyclic ring containing one heteroatom selected from N, O, and S; and $R^{6b}$ is H, $C_{1-6}$alkyl, $C_{1-4}$haloalkyl, halo. In some embodiments, $R^{6a}$ and $R^{3a}$ together with the carbons to which they are attached from a 4 to 6 membered heterocyclic ring containing one heteroatom selected from N, O, and S; and $R^{6b}$ is H.

In some embodiments of the compound of Formula I, Ia, Ib, Ic, Id, or II, or the pharmaceutically acceptable salt thereof, $W^2$ is —$CR^{7a}$=$CR^{7b}$—, wherein $R^{7a}$ and $R^{7b}$ are independently H, halo, $C_{1-4}$haloalkyl, or $C_{1-6}$alkyl or $R^{7a}$ and $R^{7b}$ together with the carbons to which they are attached form a $C_{5-10}$aryl optionally substituted with one to four $R^A$, wherein each $R^{A2}$ is independently halo, cyano, or $C_{1-4}$alkyl. In some embodiments, $W^2$ is —$CR^{7a}$=$CR^{7b}$—, wherein $R^{7a}$ and $R^{7b}$ are independently H, halo, $C_{1-4}$haloalkyl, or $C_{1-6}$alkyl. In some embodiments, $W^2$ is —$CR^{7a}$=$CR^{7b}$—, wherein $R^{7a}$ and $R^{7b}$ are independently H, halo, or $C_{1-6}$alkyl. In some embodiments, $W^2$ is —$CR^{7a}$=$CR^{7b}$—, wherein $R^{7a}$ and $R^{7b}$ are independently H or $C_{1-6}$ alkyl. In some embodiments, $W^2$ is —$CR^{7a}$=$CR^{7b}$—, wherein $R^{7a}$ and $R^{7b}$ are both H.

In some embodiments of the compound of Formula I, Ia, Ib, Ic, Id, or II, or the pharmaceutically acceptable salt thereof, $W^2$ is —$CR^{7a}$=$CR^{7b}$—, wherein $R^{7a}$ and $R^{7b}$ together with the carbon atoms to which they are attached form a $C_{5-10}$aryl optionally substituted with one to four $R^{A2}$, wherein each $R^{A2}$ is independently halo, cyano, or $C_{1-4}$alkyl. In some embodiments, $R^{7a}$ and $R^{7b}$ together with the carbon atoms to which they are attached form a fused phenyl optionally substituted with one to four $R^{A2}$, wherein each $R^{A4}$ is independently halo, cyano, or $C_{1-4}$alkyl. In some embodiments, $R^{7a}$ and $R^{7b}$ together with the carbon atoms to which they are attached form an unsubstituted fused phenyl.

In some embodiments, the compound of Formula I, Ia, Ib, Ic, or Id, or the pharmaceutically acceptable salt thereof,
$R^1$ is $C_{6-10}$aryl, wherein the $C_{6-10}$aryl is optionally substituted with one to four $R^{41}$ wherein each $R^{41}$ is independently halo, $C_{1-6}$alkyl, $C_{1-4}$haloalkyl, cyano, —O—$C_{1-4}$alkyl, or $C_{1-4}$alkyl-O—$C_{1-4}$alkyl;
$R^2$ is H, $C_{1-6}$alkyl, or $C_{1-4}$haloalkyl;
$R^3$ is halo or —$OR^{3a}$, wherein $R^{3a}$ is H, —$C_{1-6}$alkyl, —$C_{1-4}$haloalkyl, or —$C_{3-6}$cycloalkyl;
$R^{3b}$ is H, —$C_{1-6}$alkyl, —$C_{1-4}$haloalkyl, or —$C_{1-4}$alkylene-O—$C_{1-4}$alkyl;
$R^{4a}$ is —$C_{1-6}$alkyl or —$C_{1-4}$haloalkyl;
$R^{4b}$ is H, halo, —$C_{1-6}$alkyl, or —$C_{1-4}$haloalkyl;
$W^1$ is a bond or —$CR^{5a}R^{5b}$—;
$R^{5a}$ and $R^{5b}$ are independently H, $C_{1-6}$alkyl, $C_{1-4}$haloalkyl, or halo; $W^2$ is —$CR^{6a}R^{6b}$— or —$CR^{7a}$=$CR^{7b}$—;
$R^{6a}$ and $R^{6b}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl; and
$R^{7a}$ and $R^{7b}$ are independently H, halo, $C_{1-4}$haloalkyl, or $C_{1-6}$alkyl.

In some embodiments, the compound of Formula I, Ia, Ib, Ic, Id, or II, or the pharmaceutically acceptable salt thereof,
$R^1$ is $C_{6-10}$aryl, wherein the $C_{6-10}$aryl is optionally substituted with one to four $R^{41}$ wherein each $R^{41}$ is independently halo, $C_{1-6}$alkyl, $C_{1-4}$haloalkyl, cyano, —O—$C_{1-4}$alkyl, or $C_{1-4}$alkyl-O—$C_{1-4}$alkyl;
$R^2$ is H, $C_{1-6}$alkyl, or $C_{1-4}$haloalkyl;
$R^3$ is —$OR^{3a}$, wherein $R^{3a}$ is H, —$C_{1-6}$alkyl, —$C_{1-4}$haloalkyl, or —$C_{3-6}$cycloalkyl;
$R^{3b}$ is H, —$C_{1-6}$alkyl, —$C_{1-4}$haloalkyl, or —$C_{1-4}$alkylene-O—$C_{1-4}$alkyl;
$R^{4a}$ is —$C_{1-6}$alkyl or —$C_{1-4}$haloalkyl;
$R^{4b}$ is H, halo, —$C_{1-6}$alkyl, or —$C_{1-4}$haloalkyl;
$W^1$ is a bond or —$CR^{5a}R^{5b}$—;
$R^{5a}$ and $R^{5b}$ are independently H, $C_{1-6}$alkyl, $C_{1-4}$haloalkyl, or halo; $W^2$ is —$CR^{6a}R^{6b}$— or —$CR^{7a}$=$CR^{7b}$—;
$R^{6a}$ and $R^{6b}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl; and
$R^{7a}$ and $R^{7b}$ are independently H, halo, $C_{1-4}$haloalkyl, or $C_{1-6}$alkyl.

In some embodiments, the compound of Formula I, Ia, Ib, Ic, Id, or II, or the pharmaceutically acceptable salt thereof,
$R^1$ is phenyl substituted with two, three, or four $R^{41}$, wherein each $R^{41}$ is independently halo, $C_{1-6}$alkyl, $C_{1-4}$haloalkyl, cyano, —O—$C_{1-4}$alkyl, or $C_{1-4}$alkyl-O—$C_{1-4}$alkyl;
$R^2$ is H, $C_{1-6}$alkyl, or $C_{1-4}$haloalkyl;
$R^3$ is —$OR^{3a}$, wherein $R^{3a}$ is H, —$C_{1-6}$alkyl, —$C_{1-4}$haloalkyl, or —$C_{3-6}$cycloalkyl;
$R^{3b}$ is H, —$C_{1-6}$alkyl, —$C_{1-4}$haloalkyl, or —$C_{1-4}$alkylene-O—$C_{1-4}$alkyl;
$R^{4a}$ is —$C_{1-6}$alkyl or —$C_{1-4}$haloalkyl;
$R^{4b}$ is H, halo, —$C_{1-6}$alkyl, or —$C_{1-4}$haloalkyl;
$W^1$ is a bond or —$CR^{5a}R^{5b}$—;
$R^{5a}$ and $R^{5b}$ are independently H, $C_{1-6}$alkyl, $C_{1-4}$haloalkyl, or halo;
$W^2$ is —$CR^{6a}R^{6b}$— or —$CR^{7a}$=$CR^{7b}$—;
$R^{6a}$ and $R^{6b}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl; and
$R^{7a}$ and $R^{7b}$ are independently H, halo, $C_{1-4}$haloalkyl, or $C_{1-6}$alkyl.

In some embodiments, the compound of Formula I, Ia, Ib, Ic, Id or II, is selected form the group consisting of:

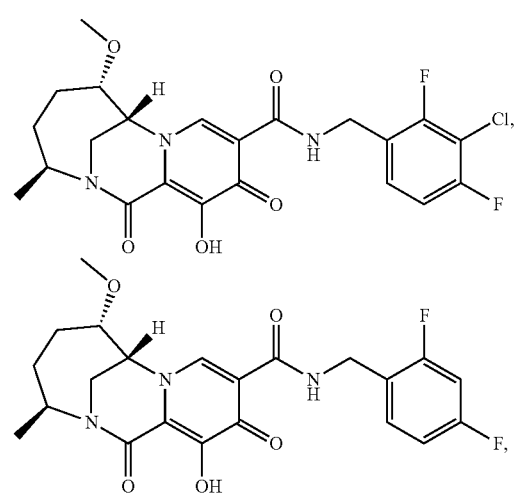

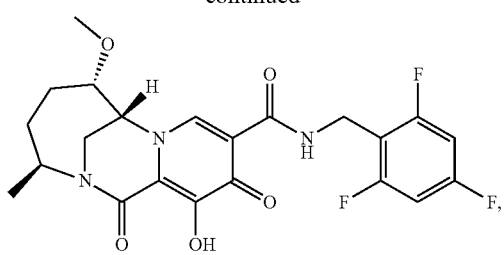
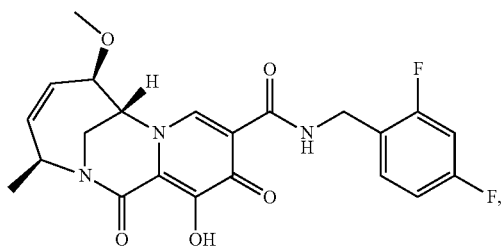
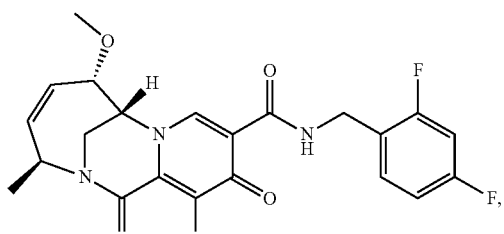
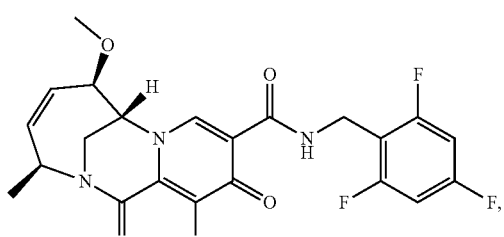
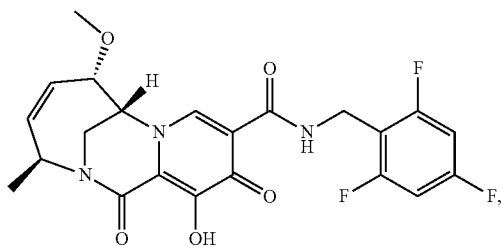
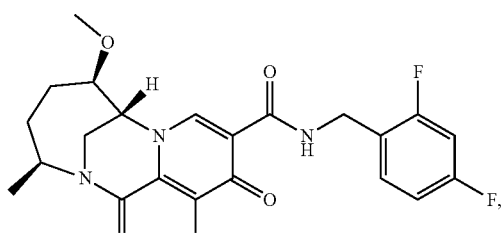
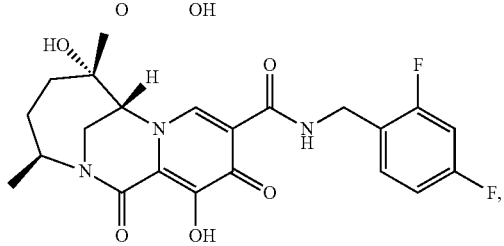
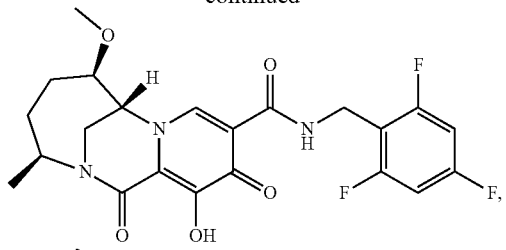
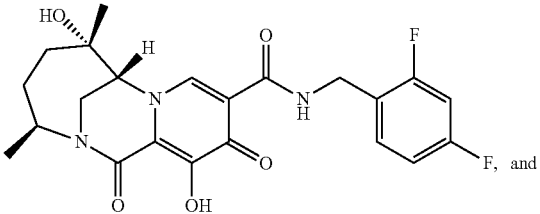
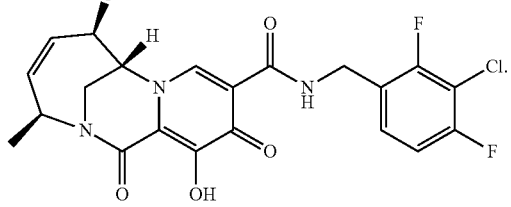
In some embodiments, the compound of Formula I, Ia, Ib, Ic, Id or II, is selected form the group consisting of:
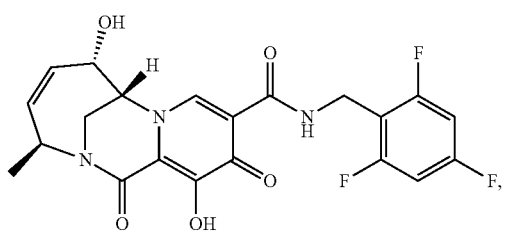
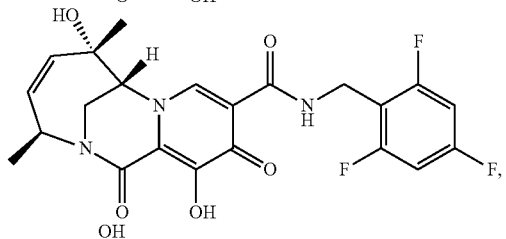
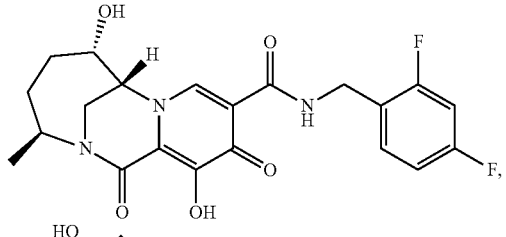
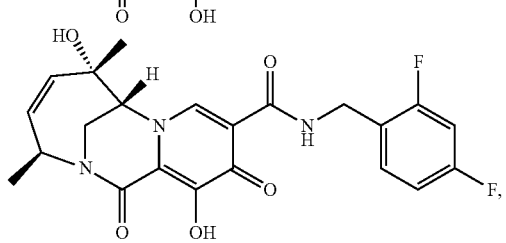

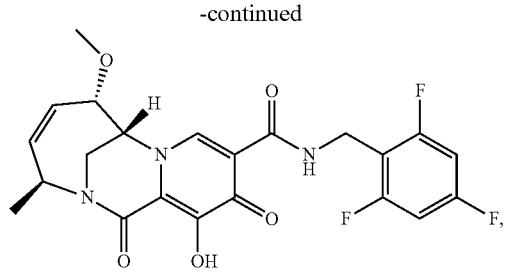
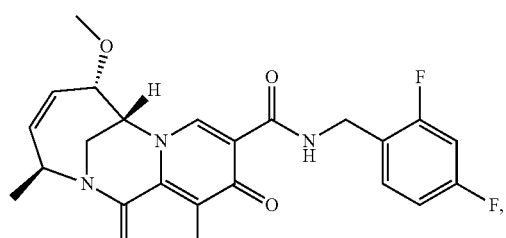
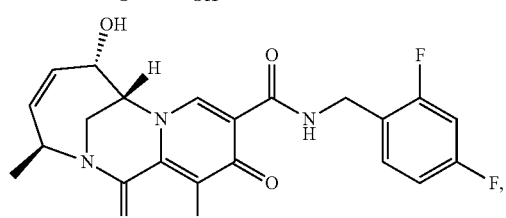
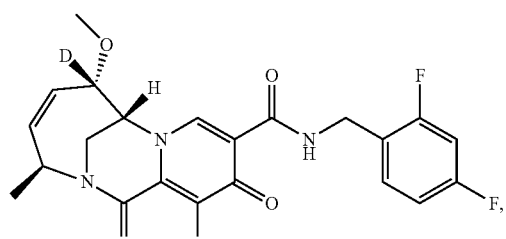
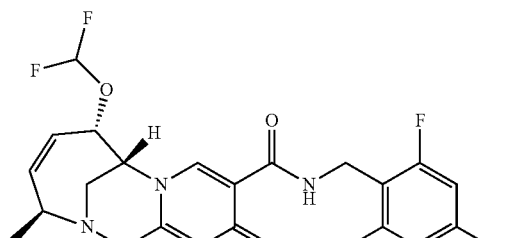
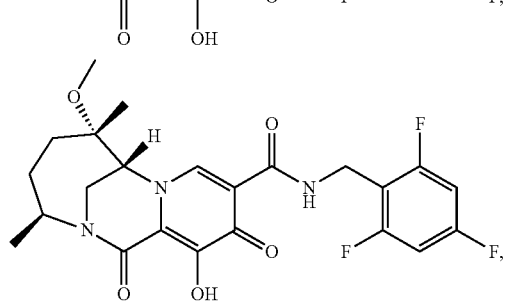
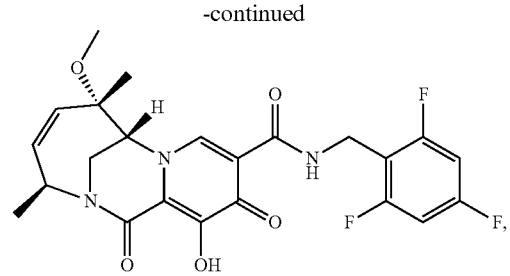
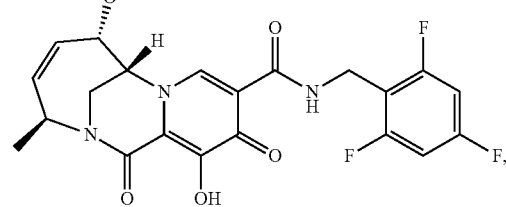
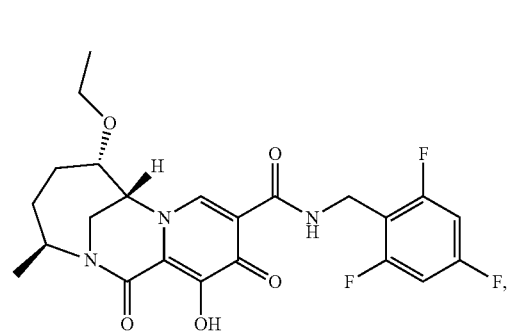
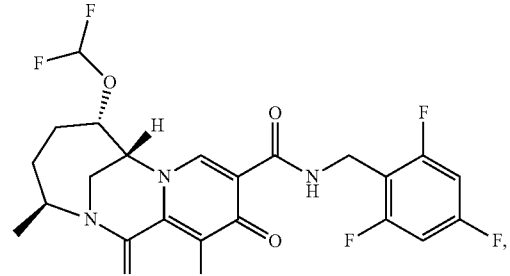
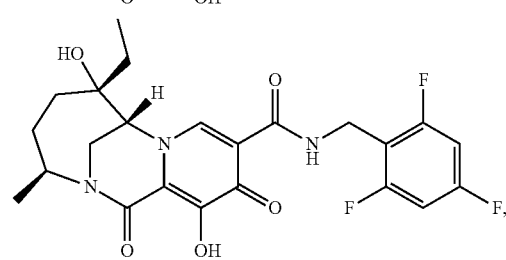
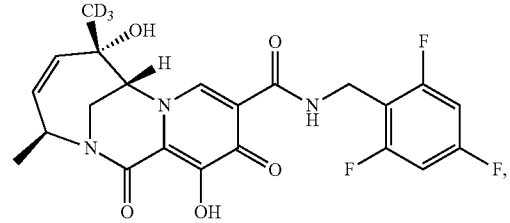

27
-continued
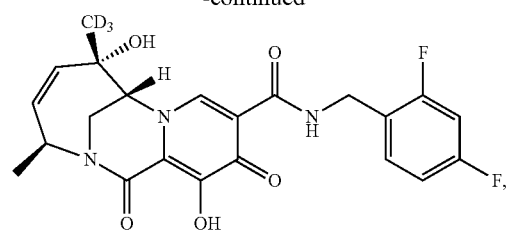
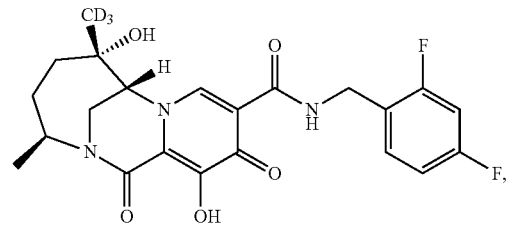
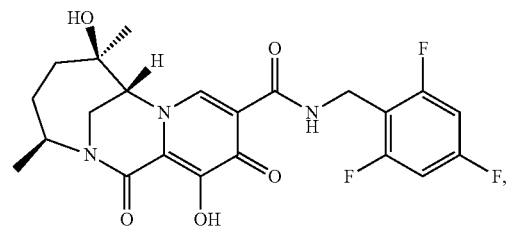
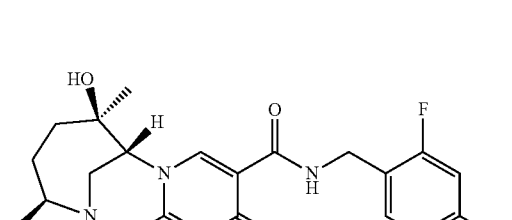
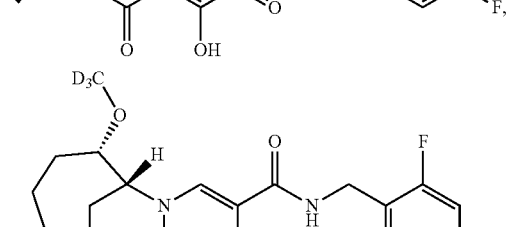
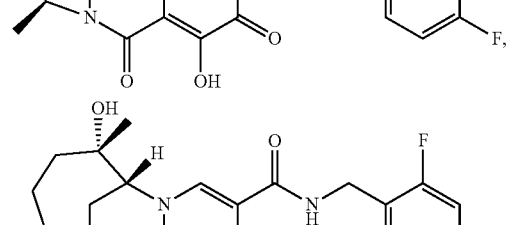
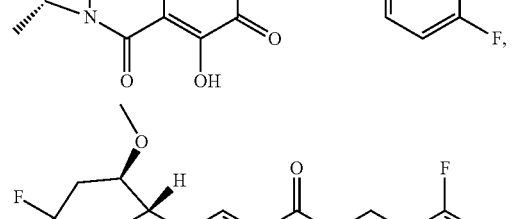
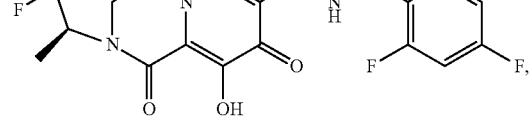
28
-continued
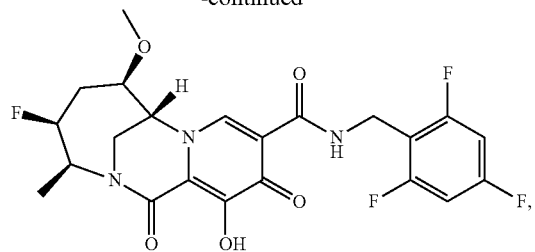
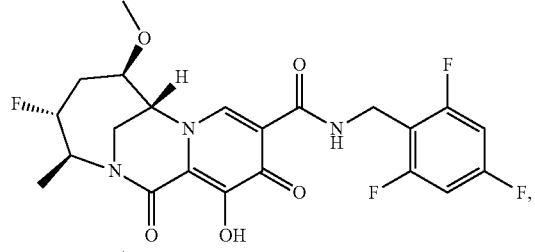
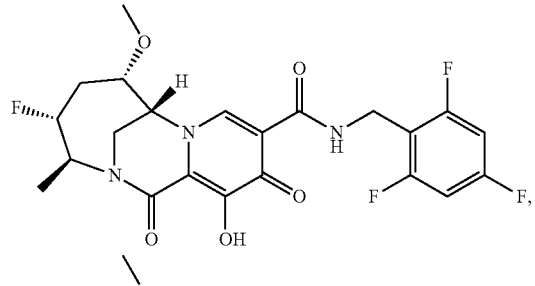
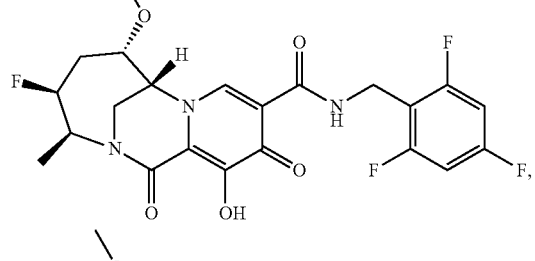
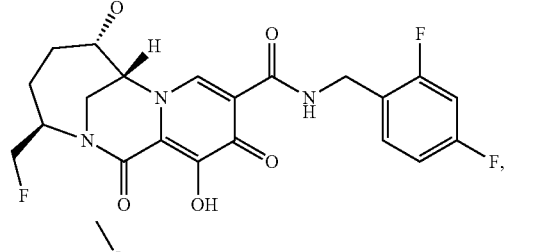
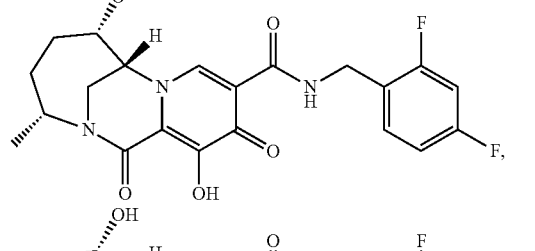
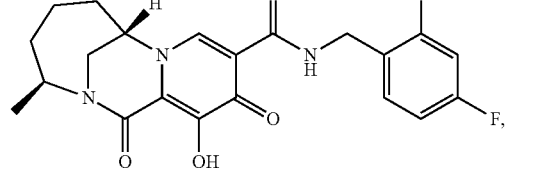

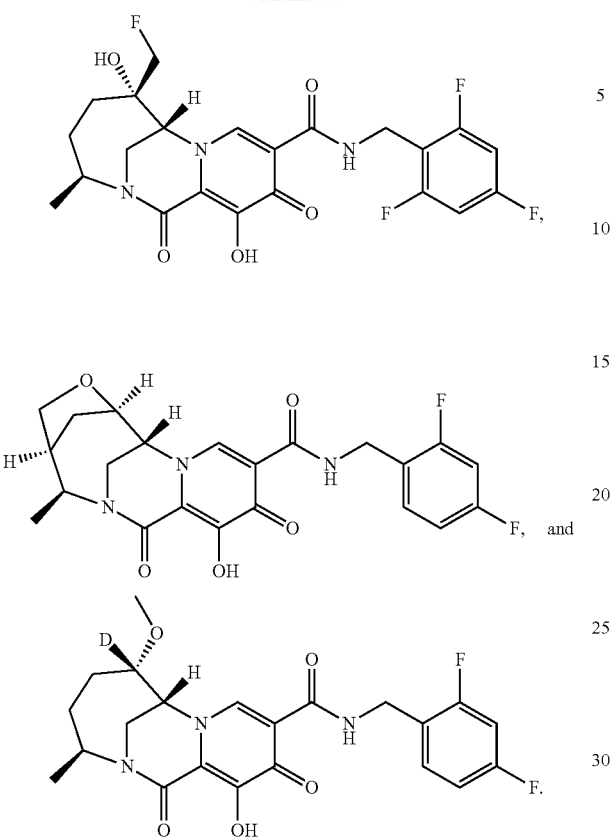
In some embodiments, the compound of Formula I, Ia, or II is selected from the group consisting of:
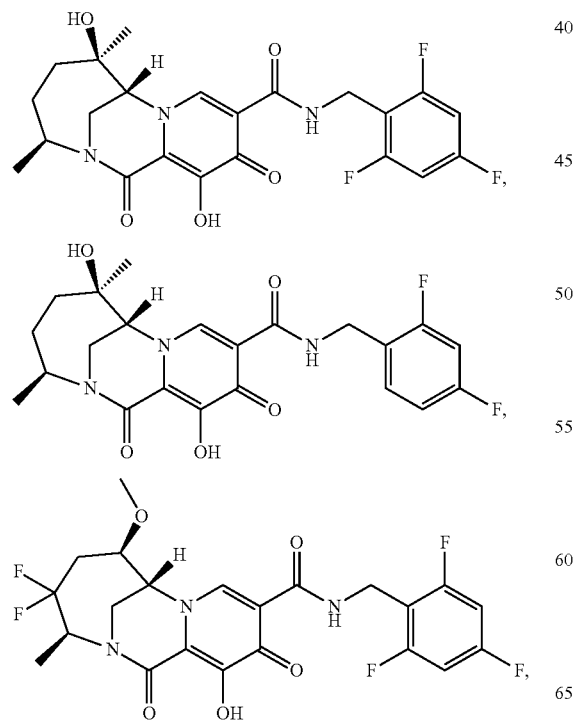
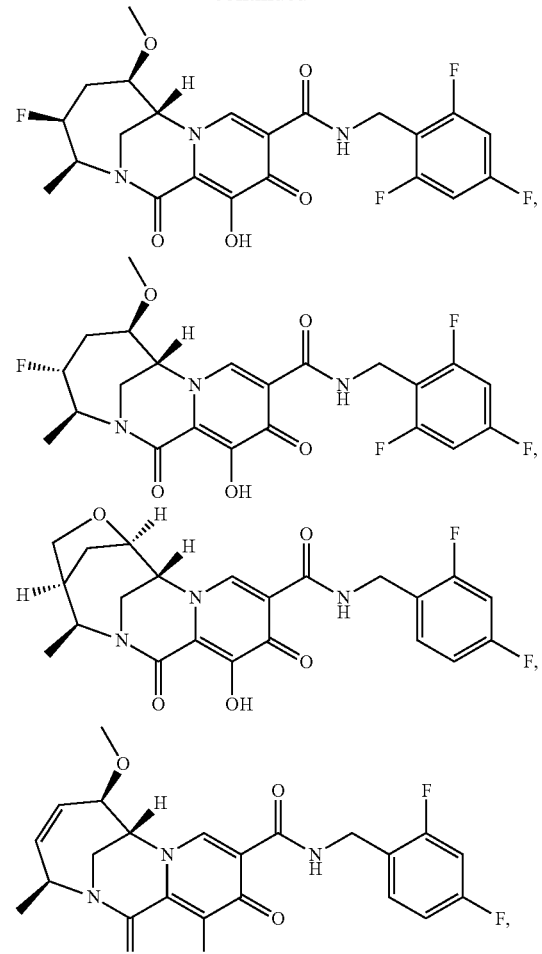

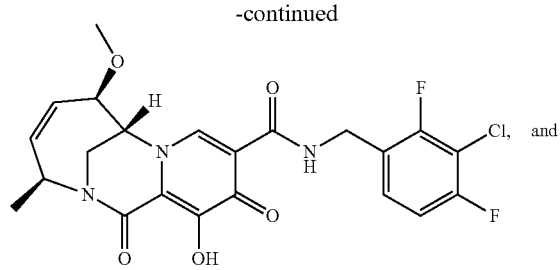
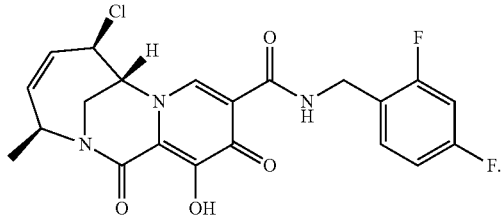
In some embodiments, the compound of Formula I, Ic, or II is selected from the group consisting of:
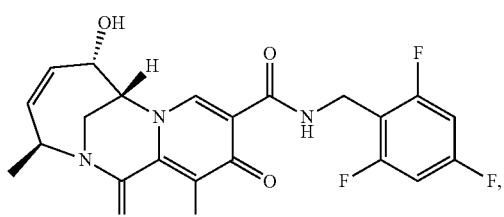
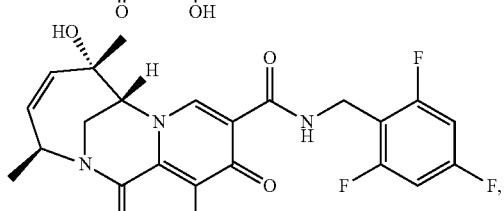
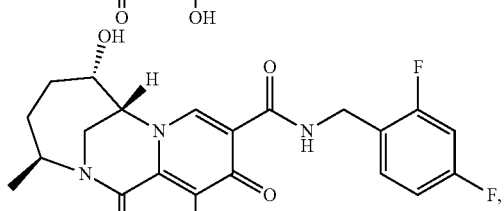
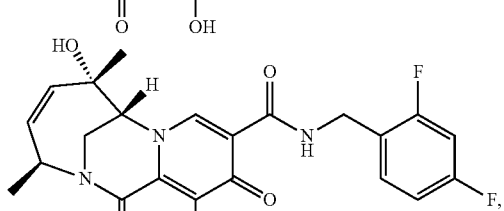
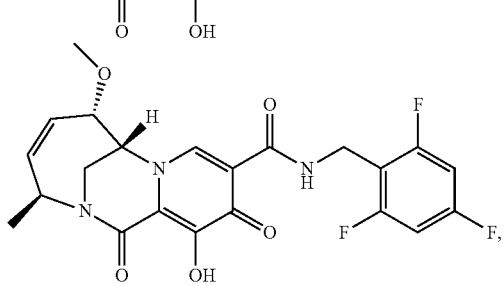
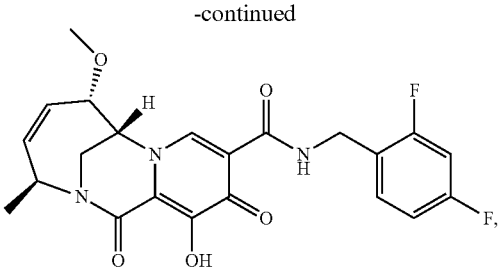
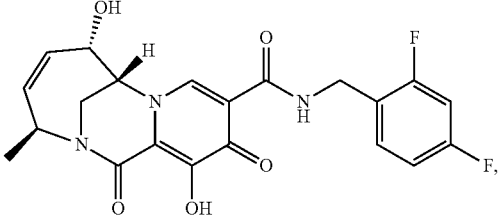
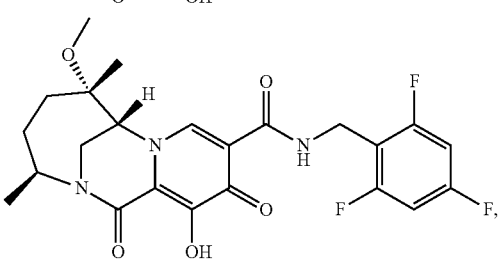
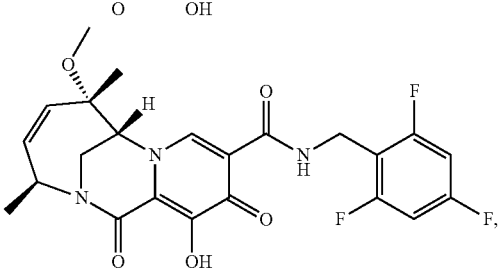

33
-continued
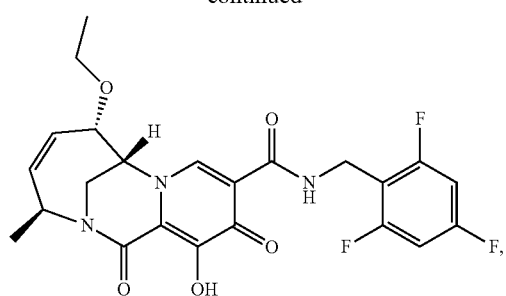
34
-continued
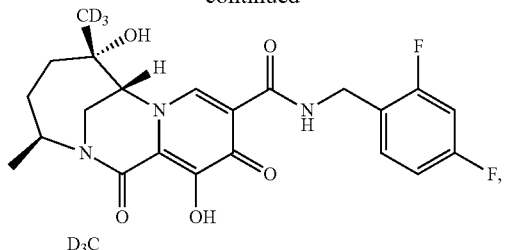
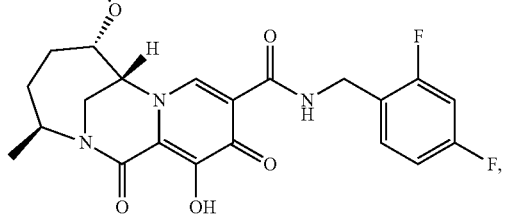
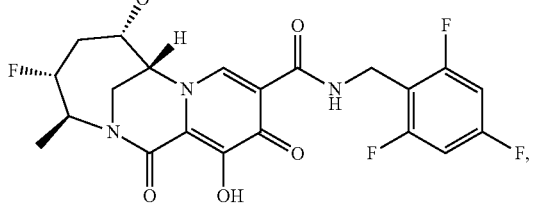
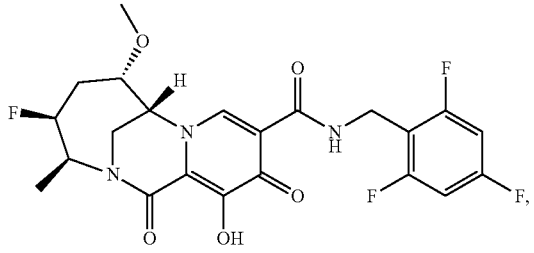
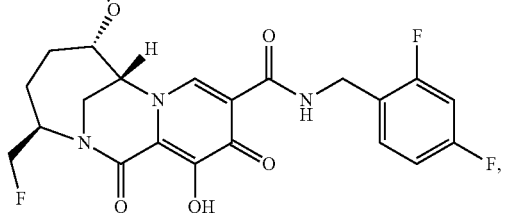
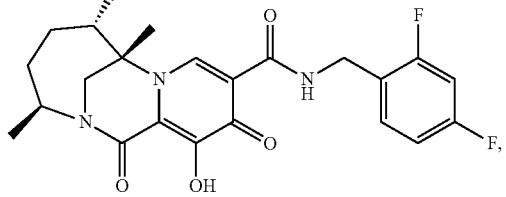
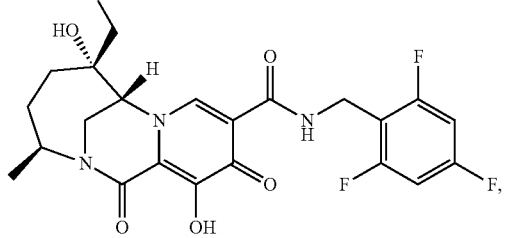

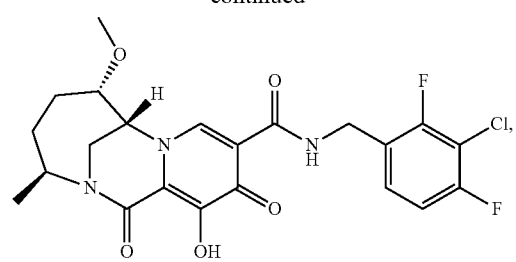
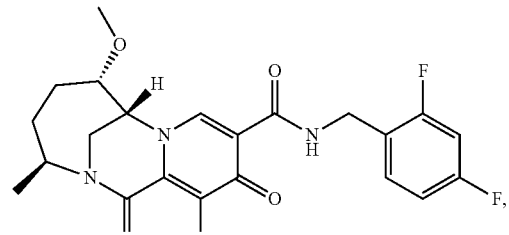
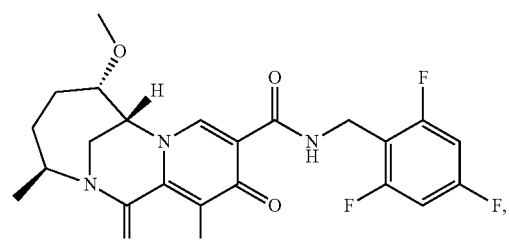
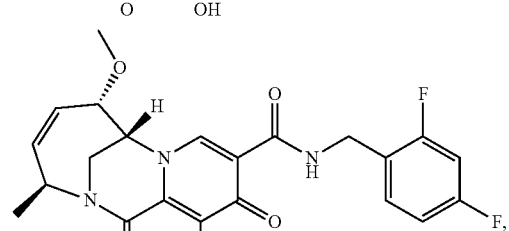
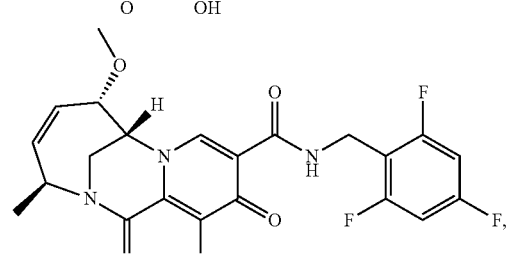
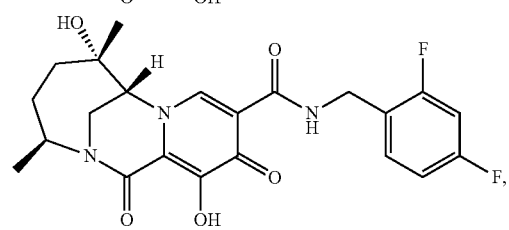
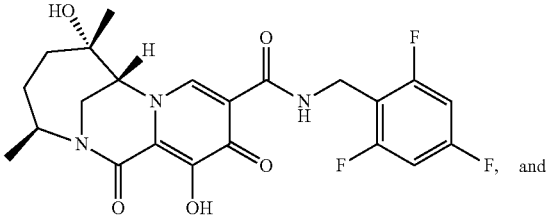
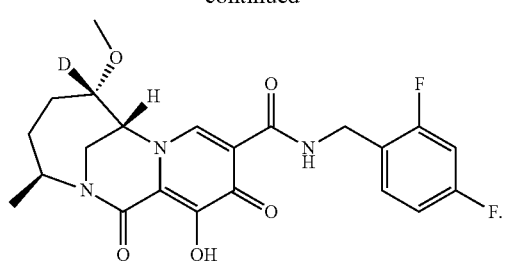
In some embodiments, the compound of Formula I, Id, or II is selected from the group consisting of:
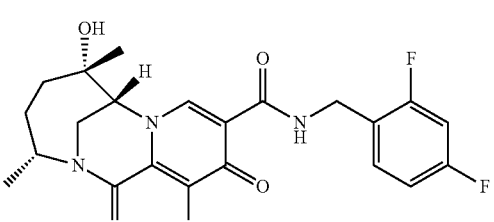
and
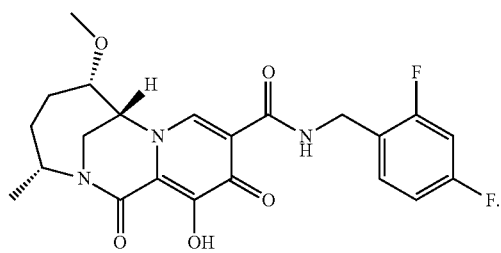
In some embodiments, the compound of Formula I is
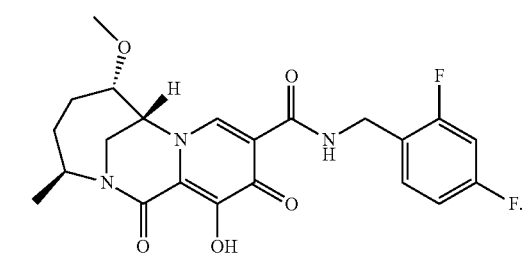 [SMILES: CO[C@H]1CC[C@H](C)N2C[C@H]1n1cc(C(=O)NCc3ccc(F)cc3F)c(=O)c(O)c1C2=O]
In some embodiments, the compound of Formula I is
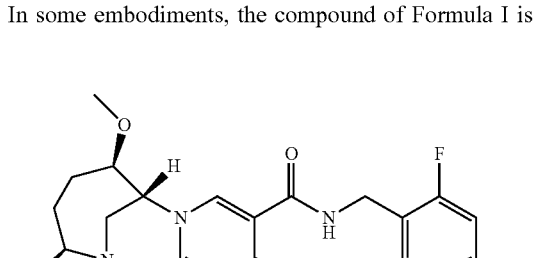
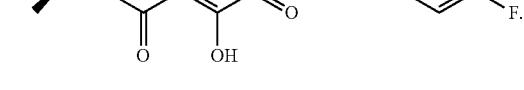

In some embodiments, the compound of Formula I is

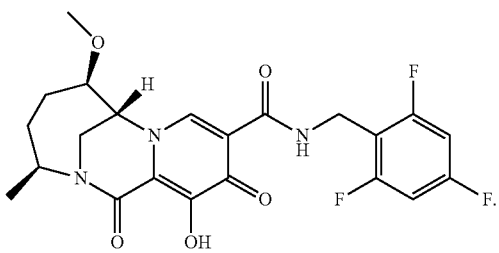 [SMILES: CO[C@@H]1CC[C@H](C)N2C[C@H]1n1cc(C(=O)NCc3c(F)cc(F)cc3F)c(=O)c(O)c1C2=O]

In some embodiments, the compound of Formula I is

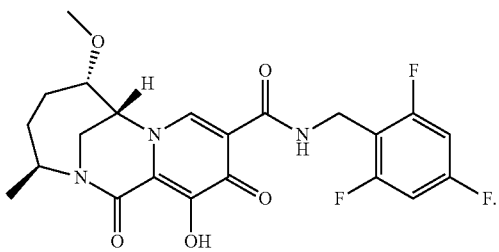 [SMILES: CO[C@H]1CC[C@H](C)N2C[C@H]1n1cc(C(=O)NCc3c(F)cc(F)cc3F)c(=O)c(O)c1C2=O]

In some embodiments, the compound of Formula I is

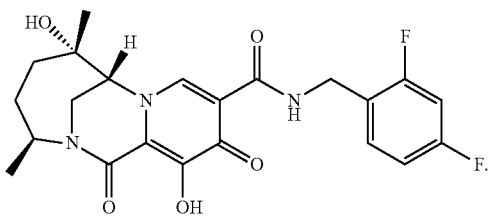

In some embodiments, the compound of Formula I is

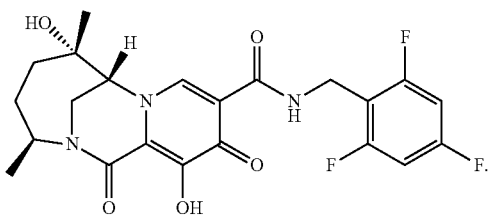 [SMILES: C[C@H]1CC[C@](C)(O)[C@H]2CN1C(=O)c1c(O)c(=O)c(C(=O)NCc3c(F)cc(F)cc3F)cn12]

In some embodiments, the compound of Formula I is

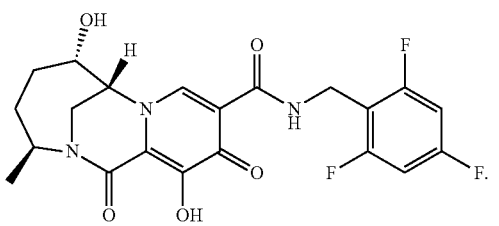 [SMILES: C[C@H]1CC[C@H](O)[C@H]2CN1C(=O)c1c(O)c(=O)c(C(=O)NCc3c(F)cc(F)cc3F)cn12]

In some embodiments, the compound of Formula I is

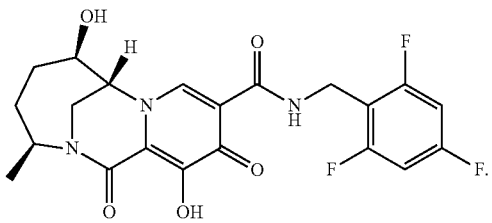 [SMILES: C[C@H]1CC[C@@H](O)[C@H]2CN1C(=O)c1c(O)c(=O)c(C(=O)NCc3c(F)cc(F)cc3F)cn12]

In some embodiments, the compound of Formula I is

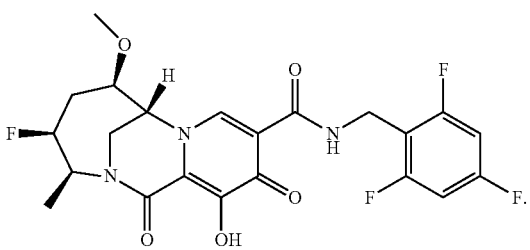 [SMILES: CO[C@@H]1C[C@H](F)[C@H](C)N2C[C@H]1n1cc(C(=O)NCc3c(F)cc(F)cc3F)c(=O)c(O)c1C2=O]

In some embodiments, the compound of Formula I is

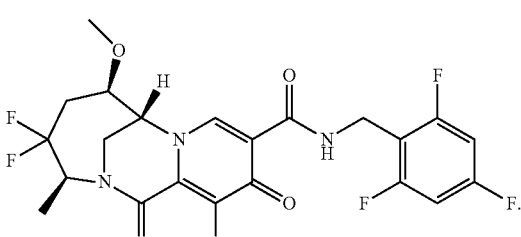

III. COMPOSITIONS AND KITS

Compounds provided herein are usually administered in the form of pharmaceutical compositions. Thus, provided herein are also pharmaceutical compositions that comprise one or more of the compounds provided herein or pharmaceutically acceptable salts, isomer, or a mixture thereof and one or more pharmaceutically acceptable vehicles selected from carriers, adjuvants and excipients. The compounds provided herein may be the sole active ingredient or one of the active ingredients of the pharmaceutical compositions. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In one aspect, provided herein are pharmaceutical compositions comprising a compound provided herein (e.g., a compound of Formula I, Ia, Ib, Ic, Id, or II), or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or a pharmaceutically acceptable salt thereof. In some embodiments, the pharmaceutical compositions further comprise a therapeutically effective amount of the one or more (e.g., one, two, three, four, one or two, one to three, or one to four) additional therapeutic agents, or a pharmaceutically acceptable salt thereof.

The pharmaceutical compositions may be administered in either single or multiple doses. The pharmaceutical compositions may be administered by various methods including, for example, rectal, buccal, intranasal and transdermal routes. In some embodiments, the pharmaceutical compositions may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds provided herein. Administration may be via, for example, capsule or enteric coated tablets. In making the pharmaceutical compositions that include at least one compound provided herein or pharmaceutically acceptable salts, isomer, or a mixture thereof, the active ingredient (such as a compound provided herein) is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose or any combinations thereof. The pharmaceutical compositions can additionally include lubricating agents such as talc, magnesium stearate, and mineral oil; wetting agents; emulsifying and suspending agents; preserving agents such as methyl and propylhydroxy-benzoates; sweetening agents; and flavoring agents; or any combinations thereof.

The pharmaceutical compositions that include at least one compound described herein or pharmaceutically acceptable salts, isomer, or a mixture thereof can be formulated so as to provide quick, sustained or delayed release of the active ingredient (such as a compound provided herein) after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds provided herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with materials such as shellac, cetyl alcohol, and cellulose acetate.

Pharmaceutical compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In one aspect, provided herein are kits that comprise a compound provided herein (e.g., a compound of Formula I, Ia, Ib, Ic, Id, or II), or a pharmaceutically acceptable salt, stereoisomer, prodrug, or solvate thereof, and suitable packaging. In some embodiments, the kit further comprises instructions for use. In some embodiments, the kit comprises a compound provided herein (e.g., a compound of Formula I, Ia, Ib, Ic, Id, or II), or a pharmaceutically acceptable salt, stereoisomer, prodrug, or solvate thereof, and a label and/or instructions for use of the compounds in the treatment of the indications, including the diseases or conditions, described herein.

In some embodiments, the kits further comprise one or more (e.g., one, two, three, four, one or two, one to three, or one to four) additional therapeutic agents, or a pharmaceutically acceptable salt thereof.

In one aspect, provided herein are articles of manufacture that comprise a compound described herein or pharmaceutically acceptable salts, isomer, or a mixture thereof in a suitable container. In some embodiments, the container may be a vial, jar, ampoule, preloaded syringe, or intravenous bag.

IV. METHODS

In one embodiment, methods of treating an HIV (e.g., HIV-1 and/or HIV-2) infection in a human having or at risk of having the infection comprising administering to the human a therapeutically effective amount of a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof, are provided.

In some embodiments, the methods further comprise administering to the human a therapeutically effective amount of one, two, three, or four additional therapeutic agents. In certain embodiments, the additional therapeutic agent or agents are anti-HIV agents. In particular embodiments, the additional therapeutic agent or agents are HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs (broadly neutralizing HIV antibodies), TLR7 agonists, pharmacokinetic enhancers, other drugs for treating HIV, or combinations thereof. In one embodiment, the additional therapeutic agent or agents are abacavir, tenofovir alafenamide, tenofovir disoproxil, N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide, or a pharmaceutically acceptable salt thereof.

In another embodiment, a use of a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof, for treating an HIV (e.g., HIV-1 and/or HIV-2) infection in a human having or at risk of having the infection is provided.

In another embodiment, a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof, for use in medical therapy is provided.

In another embodiment, a compound of Formula I, Ia, Ib, Ic, Id, or II, or a pharmaceutically acceptable salt thereof, or a pharmaceutical composition of Formula I, Ia, Ib, Ic, Id, or II, or pharmaceutically acceptable salt thereof, for use in treating an HIV infection is provided.

In another embodiment, a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof for use in a method of treating an HIV infection in a human having or at risk of having the infection, is provided.

In another embodiment, a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof for use in a method of treating an HIV infection in a human having or at risk of having the infection, is provided wherein said method further comprises administering to the human one, two, three, or four additional therapeutic agents.

In another embodiment, a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof for use in a method of treating an HIV infection in a human having or at risk of having the infection, is provided wherein said method further comprises administering to the human one, two, three, or four additional therapeutic agents selected from the group consisting of HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs, TLR7 agonists, pharmacokinetic enhancers, other drugs for treating HIV, or combinations thereof. In one embodiment, the one, two, three, or four additional therapeutic agents are selected from HIV protease inhibitors, HIV non-nucleoside inhibitors of reverse transcriptase, HIV nucleoside or nucleotide inhibitors of reverse transcriptase, latency reversing agents, HIV capsid inhibitors, HIV bNAbs, TLR7 agonists, and combinations thereof.

In another embodiment, a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof for use in a method of treating an HIV infection in a human having or at risk of having the infection, is provided wherein said method further comprises administering to the human a therapeutically effective amount of tenofovir disoproxil and emtricitabine.

In another embodiment, a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof for use in a method of treating an HIV infection in a human having or at risk of having the infection, is provided wherein said method further comprises administering to the human a therapeutically effective amount of tenofovir alafenamide and emtricitabine.

In another embodiment, a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof for use in a method of treating an HIV infection in a human having or at risk of having the infection, is provided wherein said method further comprises administering to the human a therapeutically effective amount of tenofovir disoproxil.

In another embodiment, a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof for use in a method of treating an HIV infection in a human having or at risk of having the infection, is provided wherein said method further comprises administering to the human a therapeutically effective amount of tenofovir alafenamide.

In another embodiment, a method of using a compound of Formula I, Ia, Ib, Ic, Id, or II in therapy is provided. In particular, a method of treating the proliferation of the HIV virus, treating AIDS, or delaying the onset of AIDS or ARC symptoms in a mammal (e.g., a human) is provided, comprising administering to the mammal a compound of Formula I, Ia, Ib, Ic, Id, or II, or a pharmaceutically acceptable salt thereof, and a pharmaceutically acceptable excipient.

In another embodiment, a composition comprising a compound of Formula I, Ia, Ib, Ic, Id, or II, or pharmaceutically acceptable salt thereof, and a pharmaceutically acceptable excipient, for use in a method of treating the proliferation of the HIV virus, treating AIDS, or delaying the onset of AIDS or ARC symptoms in a mammal (e.g., a human) is provided.

In one embodiment, a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof, is provided for use in preventing HIV infection.

For example, in one embodiment, a compound of Formula I, Ia, Ib, Ic, Id, or II, or a pharmaceutically acceptable salt thereof, or a pharmaceutical composition of a compound of Formula I, Ia, Ib, Ic, Id, or II, or a pharmaceutically acceptable salt thereof, is provided for use in pre-exposure prophylaxis (PrEP), i.e., before the exposure of the individual to the HIV virus to prevent HIV infection from taking hold if the individual is exposed to the virus and/or to keep the virus from establishing a permanent infection and/or to prevent the appearance of symptoms of the disease and/or to prevent the virus from reaching detectable levels in the blood.

In another embodiment, the use of a compound of Formula I, Ia, Ib, Ic, Id, or II, or a pharmaceutically acceptable salt thereof, for the manufacture of a medicament for treating an HIV infection in a human being having or at risk of having the infection is disclosed.

In another embodiment, the use of a compound of Formula I, Ia, Ib, Ic, Id, or II, or a pharmaceutically acceptable salt thereof, as a research tool is disclosed.

In another embodiment, an article of manufacture comprising a composition effective to treat an HIV infection; and packaging material comprising a label which indicates that the composition can be used to treat infection by HIV is disclosed. Exemplary compositions comprise a compound of Formula I, Ia, Ib, Ic, Id, or II, or a pharmaceutically acceptable salt thereof.

In still another embodiment, a method of inhibiting the replication of HIV is disclosed. The method comprises exposing the virus to an effective amount of the compound of Formula I, Ia, Ib, Ic, Id, or II, or a salt thereof, under conditions where replication of HIV is inhibited.

In another embodiment, the use of a compound of Formula I, Ia, Ib, Ic, Id, or II, to inhibit the activity of the HIV integrase enzyme is disclosed.

In another embodiment, the use of a compound of Formula I, Ia, Ib, Ic, Id, or II, or a salt thereof, to inhibit the replication of HIV is disclosed.

V. ADMINISTRATION

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I, Ia, Ib, Ic, Id, or II, or a pharmaceutically acceptable salt or pharmaceutically acceptable tautomer thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a compound of the present disclosure may be adjusted over the course of the treatment, based on the judgment of the administering physician.

The compounds of the present disclosure may be administered to an individual (e.g., a human) in a therapeutically effective amount. In some embodiments, the compound is administered once daily.

The compounds provided herein can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein include from about 0.3 mg to about 30 mg per day, or from about 30 mg to about 300 mg per day, or from about 0.3 µg to about 30 mg per day, or from about 30 µg to about 300 µg per day.

A compound of the present disclosure may be combined with one or more additional therapeutic agents in any dosage amount of the compound of the present disclosure (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I, Ia, Ib, Ic, Id, or II are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present disclosure are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a compound p herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1 mg and 1,000 mg, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, or 1000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein.

The frequency of dosage of the compound of the present disclosure will be determined by the needs of the individual patient and can be, for example, once per day or twice, or more times, per day. Administration of the compound continues for as long as necessary to treat the HBV infection, HIV infection, cancer, hyper-proliferative disease, or any other indication described herein. For example, a compound can be administered to a human being infected with HBV for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

The compounds of the present disclosure or the pharmaceutical compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

VI. COMBINATION THERAPY

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.
Administration of HIV Combination Therapy In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula I, Ia, Ib, Ic, Id, or II is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.
HIV Combination Therapy In the above embodiments, the additional therapeutic agent may be an anti-HIV agent. HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TAL-ENs), cell therapies (such as chimeric antigen receptor T-cell, CAR-T, and engineered T cell receptors, TCR-T, autologous T cell therapies), latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, CD4 modulators, CD4 antagonists, HIV ribonuclease H inhibitors, retrocyclin modulators, CDK-9 inhibitors, CCR5 chemokine antagonists, CCR5 gene modulators, dendritic ICAM-3 grabbing nonintegrin 1 inhibitors, HIV GAG protein inhibitors, HIV POL protein inhibitors, hyaluronidase inhibitors, Nef antagonists, Nef inhibitors, Protease-activated receptor-1 antagonists, TNF alpha ligand inhibitors, PDE4 inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

Other HIV Drugs

Examples of other drugs for treating HIV include acemannan, alisporivir, astodrimer, BanLec, CC-11050, deferiprone, Gamimune, griffithsin, metenkefalin, naltrexone, Prolastin, REP 9, RPI-MN, Vorapaxar, VSSP, Hlviral, SB-728-T, 1,5-dicaffeoylquinic acid, rHIV7-shl-TAR-CCR5RZ, MazF gene therapy, MK-8527, BlockAide, PSC-RANTES, ABX-464, AG-1105, APH-0812, BIT-225, CYT-107, HGTV-43, HPH-116, HS-10234, IMO-3100, IND-02, MK-1376, MK-2048, MK-4250, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, and elsulfavirine (VM-1500).

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500 and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include ceniviroc, CCR5 inhibitors, gp41 inhibitors, CD4 attachment inhibitors, DS-003 (BMS-599793), gp120 inhibitors, and CXCR4 inhibitors.

Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176, BMS-986197, GSK-3640254 and GSK-2838232.

Latency Reversing Agents

Examples of latency reversing agents include histone deacetylase (HDAC) inhibitors, proteasome inhibitors such as velcade, and ixazomib citrate, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), IL-15 modulating antibodies, JQ1, disulfiram, amphotericin B, and ubiquitin inhibitors such as largazole analogs, APH-0812, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, GS-6207 (lenacapvir), AVI-621, AVI-101, AVI-201, AVI-301, and AVI-CAN1-15 series. In some embodiments, the compounds disclosed herein are used in combination with lenacapvir.

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; TL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, recombinant interleukin-15, Xmab-24306, RPI-MN, STING modulators, RIG-I modulators, NOD2 modulators, SB-9200, and IR-103.

Examples of TLR agonists: vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.RO-7020531.

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4 Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bispecific antibodies, trispecific antibodies, multivalent antibodies, bnABs (broadly neutralizing HIV-1 antibodies), BMS-936559, TMB-360, and those targeting HIV gp120 or gp41, antibody-recruiting Molecules targeting HIV, anti-CD63 monoclonal antibodies, CD3 bispecific antibodies, CD16 bispecific antibodies, anti-GB virus C antibodies, anti-GP120/CD4, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66.

Examples of those targeting HIV in such a manner include bavituximab, UB-421, C2F5, 2G12, C4E10, C2F5+C2G12+C4E10, 8ANC195, 3BNC117, 3BNC117-LS, 3BNC60, D1D2, 10-1074, 10-1074-LS, GS-9722, DH411-2, BG18, PGT145, PGT121, PGT122, PGT-151, PGT-133, PGT-135, PGT-128, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PG9, PG16, 8ANC195, 2Dm2m, 4Dm2m, 6Dm2m, VRC-01, VRC-O1-LS, PGDM1400, A32, 7B2, 10E8, 10E8VLS, 3810109, 10E8v4, 10E8.4/iMab, VRC-01/PGDM-1400/10E8v4, IMC-HIV, iMabm36, 10E8v4/PGT121-VRC01, eCD4-Ig, IOMA, CAP256-VRC26.25, DRVIA7, SAR-441236, VRC-07-523, VRC07-52 3LS, VRC-HIVMAB080-00-AB, VRC-HIVMAB060-00-AB, P2G12, and VRC07. Examples of HIV bispecific antibodies include MGD014, TMB-bispecific.

Example of in vivo delivered bnABs such as AAV8-VRC07; mRNA encoding anti-HIV antibody VRC01.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines using viral vectors such as arenavirus, lymphocytic choriomeningitis virus (LCMV), pichinde virus, modified vaccinia Ankara virus (MVA), adenovirus, adeno-associated virus (AAV), vesicular stomatitis virus (VSV) and Chimpanzee adenovirus (ChAd), DNA vaccines, CD4-derived peptide vaccines, vaccine combinations, BG505 SOSIP.664 gp140, rgp120 (AIDSVAX), ALVAC HIV, (vCP1521)/AIDSVAX B/E (gp120) (RV144), monomeric gp120 HIV-1 subtype C vaccine, Remune, ITV-1, Contre Vir, Ad4-Env145NFL, Ad5-ENVA-48, HB-500, DCVax-001 (CDX-2401), Vacc-4x, Vacc-C5, Vacc-CRX, VVX-004, VAC-3S, multiclade DNA recombinant adenovirus-5 (rAd5), rAd5 gag-pol env A/B/C vaccine, Pennvax-G, Pennvax-GP/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140 [delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), Paxvax, EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN55), MVATG-17401, ETV-01, CDX-1401, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, arenavirus vector-based immunotherapies (Vaxwave, TheraT), MVA-BN HIV-1 vaccine regimen, MVA.tHIVconsv4, MVA.tHIVconsv3, UBI HIV gp120, mRNA based prophylactic vaccines, TBL-1203HI, VRC-HIVRGP096-00-VP, VAX-3S, HIV MAG DNA vaccine, HIV Combination Therapy In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

A compound as disclosed herein (e.g., any compound of Formula I, Ia, Ib, Ic, Id, or II) may be combined with one or more additional therapeutic agents in any dosage amount of the compound of Formula I, Ia, Ib, Ic, Id, or II (e.g., from 1 mg to 500 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of Formula I) may be combined with the agents provided herein in any dosage amount of the compound (e.g., from 1 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of Formula I) may be combined with the agents provided herein in any dosage amount of the compound (e.g., from 1 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, one or two, or one to three) additional therapeutic agents are provided.

Birth Control (Contraceptive) Combination Therapy

Therapeutic agents used for birth control (contraceptive) include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Examples of dendritic cell therapy include AGS-004.
Example of CCR5 gene editing drugs such as SB-728T.
Example of CCR5 gene inhibitors such as Cal-1.
C34-CCR5/C34-CXCR4 expressing CD4-positive T cells.
AGT-103-transduced autologous T cell therapy.
AAV-eCD4-Ig gene therapy.

Gene Editors

The genome editing system is selected from the group consisting of: a CRISPR/Cas9 system, a zinc finger nuclease system, a TALEN system, a homing endonucleases system, and a meganuclease system.

Examples of HIV targeting CRISPR/Cas9 systems include EBT-101.

CAR-T Cell Therapy

A population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+ T cell, a CD8+ T cell, or a combination thereof. Cells can be autologous or allogeneic.

Examples of HIV CAR-T include VC-CAR-T, anti-CD4 CART cell therapy, autologous hematopoietic stem cells genetically engineered to express a CD4 CAR and the C46 peptide.

TCR-T Cell Therapy

TCR-T cells are engineered to target HIV derived peptides present on the surface of virus-infected cells.

VII. EXAMPLES

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Intermediate A: (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide

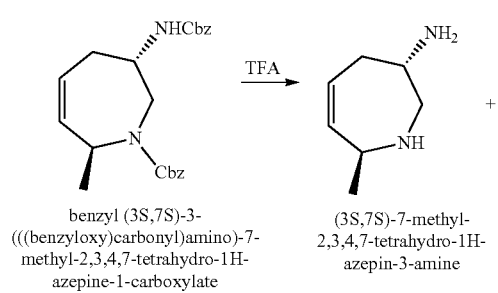

benzyl (3S,7S)-3-(((benzyloxy)carbonyl)amino)-7-methyl-2,3,4,7-tetrahydro-1H-azepine-1-carboxylate (3S,7S)-7-methyl-2,3,4,7-tetrahydro-1H-azepin-3-amine

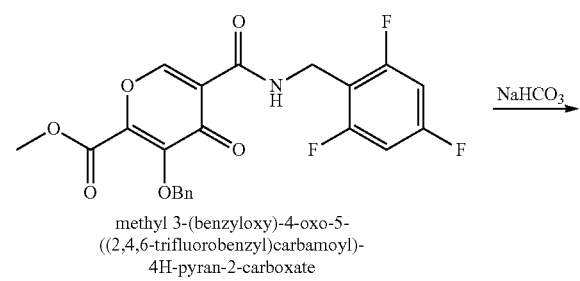

methyl 3-(benzyloxy)-4-oxo-5-((2,4,6-trifluorobenzyl)carbamoyl)-4H-pyran-2-carboxate

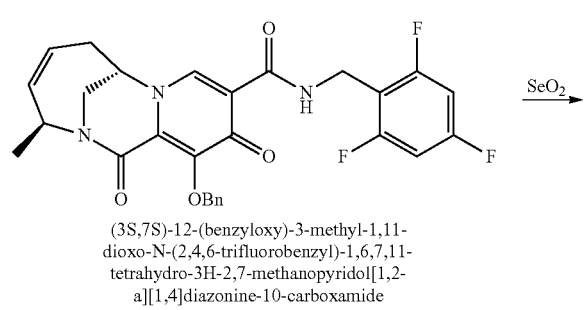

(3S,7S)-12-(benzyloxy)-3-methyl-1,11-dioxo-N-(2,4,6-trifluorobenzyl)-1,6,7,11-tetrahydro-3H-2,7-methanopyridol[1,2-a][1,4]diazonine-10-carboxamide

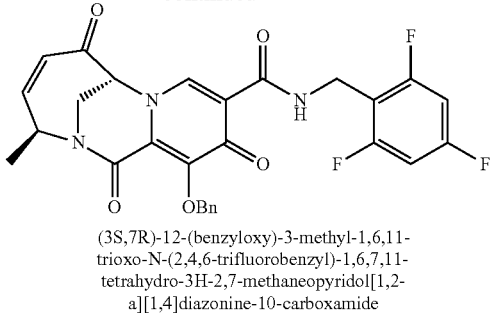

(3S,7R)-12-(benzyloxy)-3-methyl-1,6,11-trioxo-N-(2,4,6-trifluorobenzyl)-1,6,7,11-tetrahydro-3H-2,7-methaneopyridol[1,2-a][1,4]diazonine-10-carboxamide Synthesis of (3S,7S)-7-methyl-2,3,4,7-tetrahydro-1H-azepin-3-amine Trifluoacetic acid (20 mL) was added to benzyl (3S,7S)-3-(((benzyloxy)carbonyl)amino)-7-methyl-2,3,4,7-tetrahydro-1H-azepine-1-carboxylate (6.2 g, 15.7 mmol) and the reaction was heated to 100° C. for 4 hours. The reaction mixture was concentrated down and the crude was used directly in next step.

Synthesis of (3 S,7S)-12-(benzyloxy)-3-methyl-1,11-dioxo-N-(2,4,6-trifluorobenzyl)-1,6,7,11-tetrahydro-3H-2,7-methanopyrido[1,2-a][1,4]diazonine-10-carboxamide Methanol (300 mL) and water (30 mL) were added to methyl 3-(benzyloxy)-4-oxo-5-((2,4,6-trifluorobenzyl)carbamoyl)-4H-pyran-2-carboxylate (6.75 g, 15.7 mmol) and (3S,7S)-7-methyl-2,3,4,7-tetrahydro-1H-azepin-3-amine (the reaction crude from the previous step). At room temperature, NaHCO$_3$ (13.2 g, 157 mmol) was added to the reaction mixture. The reaction was stirred at. room temperature overnight, then heat to 60° C. for 5 hours. The reaction mixture was concentrated down, then added ethyl acetate, washed with saturated ammonium chloride solution. The organic layer was concentrated an d purified via silica chromatograph (eluting with 0-10% MeOH/DCM) to give (3S,7S)-12-(benzyloxy)-3-methyl-1,11-dioxo-N-(2,4,6-trifluorobenzyl)-1,6,7,11-tetrahydro-3H-2,7-methanopyrido[1,2-a][1,4]diazonine-10-carboxamide. MS (m/z) 524.11 [M+H]$^+$.

Synthesis of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide Selenium dioxide (17.4 g, 157 mmol.) was added to (3S,7S)-12-(benzyloxy)-3-methyl-1,11-dioxo-N-(2,4,6-trifluorobenzyl)-1,6,7,11-tetrahydro-3H-2,7-methanopyrido[1,2-a][1,4]diazonine-10-carboxamide (product of previous step, 15.7 mmol) in dioxane (160 mL). Then the reaction was heated to 105° C. overnight. The reaction mixture was cooled down and the solid was filtered off the solid. The filtrate was extracted using ethyl acetate and saturated ammonium chloride solution. The organic layer was concentrated and purified via silica chromatograph (eluting with 40-100% Ethyl acetate/hexane) to give (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide. MS (m/z) 538.095 [M+H]$^+$.

Intermediate B: (3S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide Example 1: (3S,6S,7R)-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

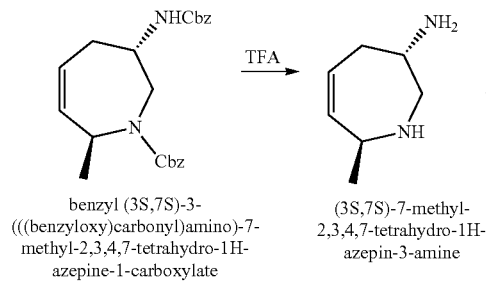

benzyl (3S,7S)-3-(((benzyloxy)carbonyl)amino)-7-methyl-2,3,4,7-tetrahydro-1H-azepine-1-carboxylate (3S,7S)-7-methyl-2,3,4,7-tetrahydro-1H-azepin-3-amine

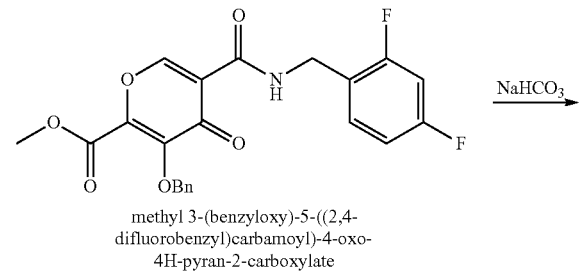

methyl 3-(benzyloxy)-5-((2,4-difluorobenzyl)carbamoyl)-4-oxo-4H-pyran-2-carboxylate

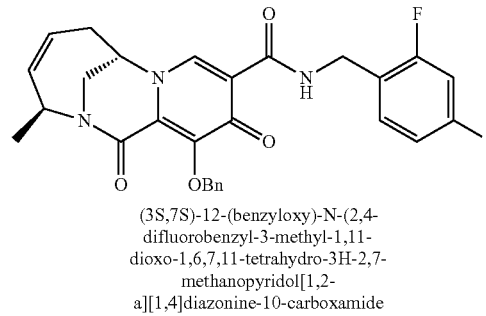

(3S,7S)-12-(benzyloxy)-N-(2,4-difluorobenzyl)-3-methyl-1,11-dioxo-1,6,7,11-tetrahydro-3H-2,7-methanopyrido[1,2-a][1,4]diazonine-10-carboxamide

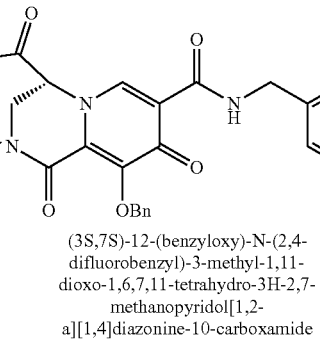

(3S,7S)-12-(benzyloxy)-N-(2,4-difluorobenzyl)-3-methyl-1,11-dioxo-1,6,7,11-tetrahydro-3H-2,7-methanopyridol[1,2-a][1,4]diazonine-10-carboxamide

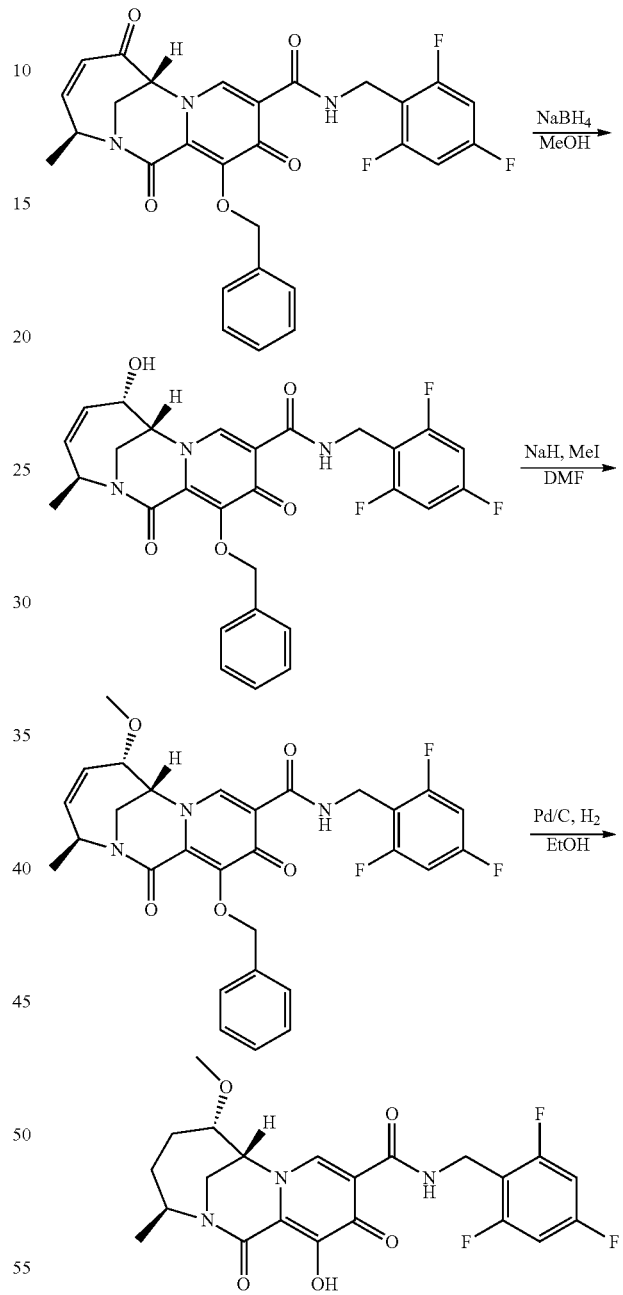

This intermediate was prepared by following the procedure of making (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (intermediate A), except that methyl 3-(benzyloxy)-5-((2,4-difluorobenzyl)carbamoyl)-4-oxo-4H-pyran-2-carboxylate was used in the $2^{nd}$ step. MS (m/z) 520.200 [M+H]$^+$.

Preparation of (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide To a solution of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (intermediate A) (122 mg, 0.227 mmol) in methanol (5 mL)

was added cerium (III) chloride heptahydrate (85 mg, 0.227 mmol). Then to the mixture was added sodium borohydride (2.1 mg, 0.057 mmol) slowly at 0° C. After 5 min, the reaction was quenched by adding sat. NaHCO$_3$ solution and extracted with DCM. The organic phase was separated and concentrated down. The residue was then dissolved in DCM, washed with brine. The organic phase was dried over MgSO$_4$, filtered, concentrated down and further used without purification.

Preparation of (3S,6S,7R)-12-(benzyloxy)-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide To a solution of (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (16 mg, 0.030 mmol) in DMF (1 mL) was added sodium hydride (1.8 mg, 0.045 mmol, 60%) and iodomethane (2.8 uL, 0.045 mmol). The reaction mixture was stirred at room temperature for half an hour. The reaction was quenched by adding sat. NaHCO$_3$, extracted with EtOAc, the organic phase was separated, dried over MgSO$_4$, filtered, concentrated down and to the resulting product was used in next step without further purification.

Preparation of (3S,6S,7R)-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide To a solution of (3S,6S,7R)-12-(benzyloxy)-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (15 mg, 0.018 mmol) in ethanol (1 mL), was added palladium on carbon (10 mg). The reaction was stirred under H$_2$ balloon for half an hour. The reaction mixture was filtered through celite. The filtrated was concentrated down and the residue was purified by reverse phase HPLC chromatography (eluting with 5-100% acetonitrile in water, containing 0.1% TFA) to give the title product. MS (m/z) 466.2 [M+H]$^+$. $^1$H NMR (400 MHz, Methanol-d4) δ 8.34 (s, 1H), 6.98-6.85 (m, 2H), 4.74 (s, 1H), 4.68 (s, 2H), 4.66-4.58 (m, 1H), 3.80-3.69 (m, 2H), 3.55 (d, J=11.8 Hz, 1H), 3.46 (s, 3H), 2.18-1.99 (m, 3H), 1.61-1.49 (m, 1H), 1.28 (d, J=6.7 Hz, 3H), 1.00 (dt, J=14.9, 11.6 Hz, 1H).

Example 2: (3S,6S,7R)-6,12-dihydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide To a solution of (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (10 mg, 0.018 mmol) in ethanol (1 mL), was added palladium on carbon (10 mg). The reaction was stirred under H$_2$ balloon for half an hour. The reaction mixture was filtered through celite. The filtrated was concentrated down and the residue was purified by reverse phase HPLC chromatography (eluting with 5-100% acetonitrile in water, containing 0.1% TFA) to give the title product. MS (m/z) 452.3 [M+H]$^+$. $^1$H NMR (400 MHz, Methanol-d4) δ 8.40 (s, 1H), 6.98-6.86 (m, 2H), 4.68 (s, 2H), 4.67-4.60 (m, 1H), 4.56 (s, 1H), 4.02-3.90 (m, 1H), 3.75 (s, 2H), 2.07 (dt, J=14.5, 7.1 Hz, 1H), 1.81 (ddd, J=14.8, 7.6, 3.8 Hz, 1H), 1.59 (dt, J=15.0, 11.3 Hz, 1H), 1.28 (d, J=6.7 Hz, 3H), 1.19 (dt, J=14.8, 11.7 Hz, 1H).

Example 3: (3S,6S,7R)—N-(2,4-difluorobenzyl)-12-hydroxy-6-methoxy-3-methyl-1,11-dioxo-1,4,5,6,7,11-hexahydro-3H-2,7-methanopyrido[1,2-a][1,4]diazonine-10-carboxamide

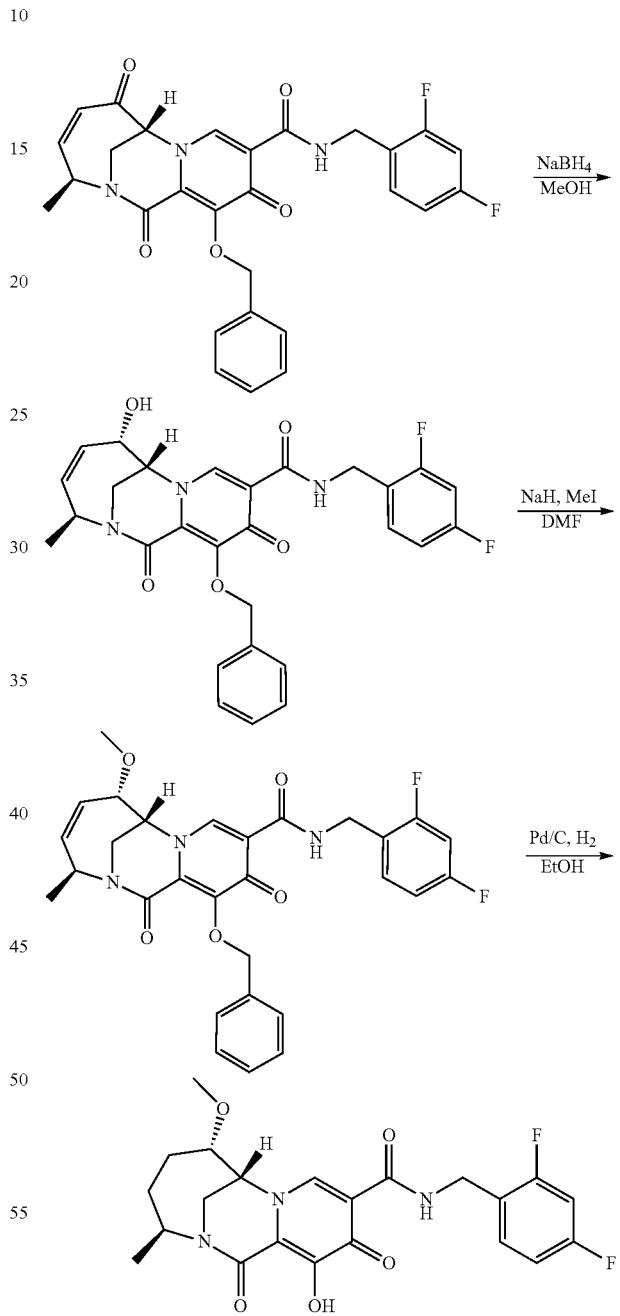

(3S,6S,7R)—N-(2,4-difluorobenzyl)-12-hydroxy-6-methoxy-3-methyl-1,11-dioxo-1,4,5,6,7,11-hexahydro-3H-2,7-methanopyrido[1,2-a][1,4]diazonine-10-carboxamide was made similar to Example 1, except that (3 S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide (intermediate B) was used instead of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (intermediate A). MS (m/z) 448.2 [M+H]$^+$. $^1$H NMR (400 MHz, Methanol-d4) δ 8.37 (s, 1H), 7.45 (q, J=7.8 Hz, 1H), 7.09-6.88 (m, 2H), 4.65 (s, 4H), 3.75 (s, 2H), 3.56 (d, J=11.1 Hz, 1H), 3.46 (s, 3H), 2.18-1.98 (m, 2H), 1.54 (dd, J=25.7, 11.4 Hz, 1H), 1.29 (d, J=6.6 Hz, 3H), 1.01 (q, J=12.1 Hz, 1H).

Example 4: (3S,6R,7R)-12-hydroxy-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide

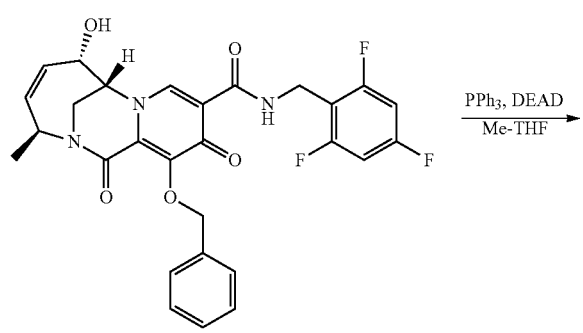

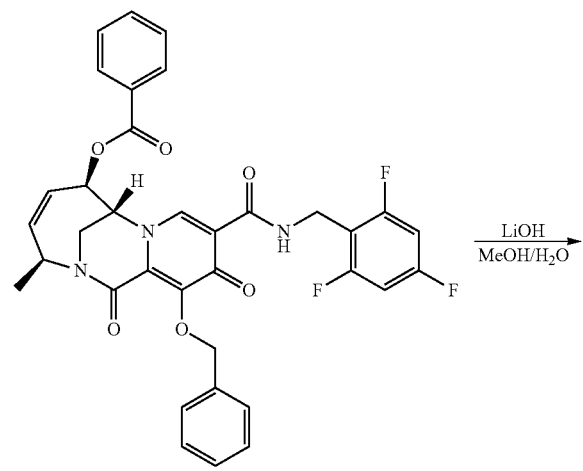

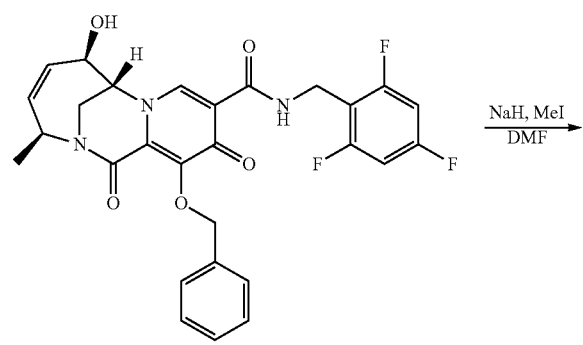

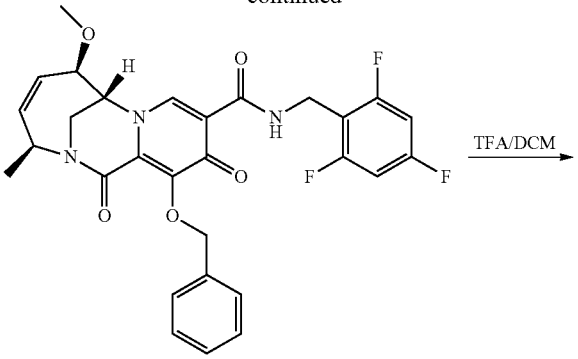

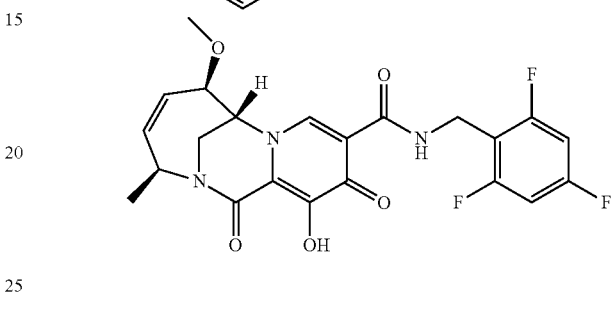

Preparation of (3S,6R,7R)-12-(benzyloxy)-3-methyl-1,11-dioxo-10-((2,4,6-trifluorobenzyl)carbamoyl)-1,6,7,11-tetrahydro-3H-2,7-methanopyrido[1,2-a][1,4]diazonin-6-yl benzoate To a solution of (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (29 mg, 0.054 mmol) in Me-THF (3 mL), was added benzoic acid (16 mg, 0.134 mmol), triphenylphosphine (35 mg, 0.134 mmol) and diisopropyl axodicarboxylate (27.2 mg, 0.134 mmol). The reaction mixture was stirred at room temperature for 3 h. The reaction mixture was diluted with EtOAc, washed with sat. NaHCO$_3$, the organic phase was separated, dried over MgSO$_4$, filtered, concentrated down and purified by silica gel column chromatography (0-100% EtOAc/hexane) to give the title product (30 mg).

Preparation of (3S,6R,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide The reaction mixture of (3S,6R,7R)-12-(benzyloxy)-3-methyl-1,11-dioxo-10-((2,4,6-trifluorobenzyl)carbamoyl)-1,6,7,11-tetrahydro-3H-2,7-methanopyrido[1,2-a][1,4]diazonin-6-yl benzoate (30 mg, 0.047 mmol), LiOH·H$_2$O (5.6 mg, 0.233 mmol) in MeOH (2 mL) and H$_2$O (0.5 mL) was stirred at room temperature overnight. The reaction mixture was concentrated down. The residue was washed with brine, extracted with EtOAc, the organic phase was separated, dried over MgSO$_4$, filtered, concentrated down and used in next step without purification.

Preparation of (3S,6R,7R)-12-(benzyloxy)-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide To a solution of (3S,6R,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (20 mg, 0.037 mmol) in DMF (1 mL) was added sodium hydride (1.8 mg, 0.045 mmol, 60%) and iodomethane (3.5 uL, 0.056 mmol). The reaction mixture was stirred at room temperature for half an hour. The reaction was quenched by adding sat. NaHCO₃, extracted with EtOAc, the organic phase was separated, dried over MgSO₄, filtered, concentrated down and go to next step without purification.

Preparation of (3S,6R,7R)-12-hydroxy-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide The reaction mixture of (3S,6R,7R)-12-(benzyloxy)-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide in DCM (1 mL) and TFA (1 mL) was stirred at rt for 3 h. The reaction mixture was concentrated down. The residue was purified by reverse phase HPLC chromatography (eluting with 5-100% acetonitrile in water, containing 0.1% TFA) to give the title compound. MS (m/z) 464.1 [M+H]⁺. ¹H NMR (400 MHz, Methanol-d4) δ 8.45 (s, 1H), 6.98-6.85 (m, 2H), 5.77 (dt, J=11.8, 2.8 Hz, 1H), 5.56 (ddd, J=11.9, 2.7, 1.7 Hz, 1H), 5.33 (dq, J=7.6, 2.8 Hz, 1H), 4.69 (s, 2H), 4.59 (s, 1H), 4.27 (dq, J=5.7, 3.0 Hz, 1H), 4.11 (d, J=13.7 Hz, 1H), 3.65 (d, J=14.4 Hz, 1H), 3.32 (s, 3H), 1.39 (d, J=7.2 Hz, 3H).

Example 5: (3S,6R,7R)-6,12-dihydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

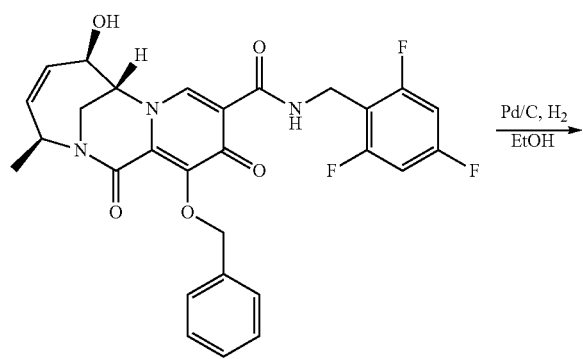

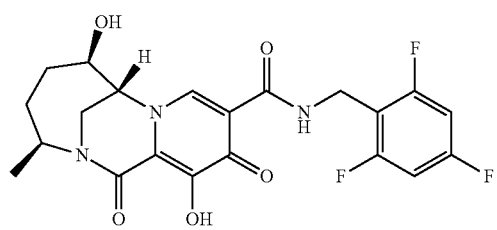

To a solution of (3S,6R,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (10 mg, 0.018 mmol) in ethanol (1 mL), was added palladium on carbon (10 mg). The reaction was stirred under H₂ balloon for half an hour. The reaction mixture was filtered through celite. The filtrated was concentrated down and the residue was purified by reverse phase HPLC chromatography (eluting with 5-100% acetonitrile in water, containing 0.1% TFA) to give the title product. MS (m/z) 452.2 [M+H]⁺. ¹H NMR (400 MHz, Methanol-d4) δ 8.46 (s, 1H), 6.99-6.85 (m, 2H), 4.68 (s, 2H), 4.58 (dt, J=10.7, 6.5 Hz, 1H), 4.40 (s, 1H), 4.04 (d, J=3.9 Hz, 1H), 3.81 (d, J=14.8 Hz, 1H), 3.69 (d, J=14.7 Hz, 1H), 2.01 (dd, J=14.5, 11.3 Hz, 1H), 1.95-1.79 (m, 2H), 1.38-1.30 (m, 1H), 1.29 (d, J=6.6 Hz, 3H).

Example 6: (3S,6R,7R)-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

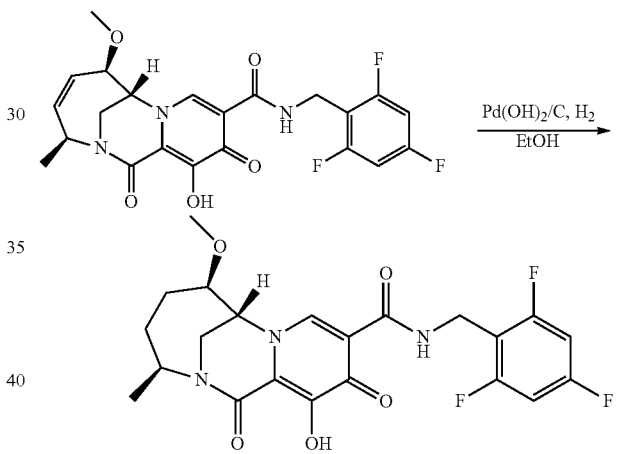

To a solution of (3S,6R,7R)-12-hydroxy-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (Example 4) (18 mg, 0.039 mmol) in EtOH (2 mL) was added Pd(OH)₂/C (10 mg). The reaction mixture was stirred at rt for half an hour with attachment of H₂ balloon. The reaction mixture was filtered through celite, the filtrate was concentrated down and the residue was purified by reverse phase chromatography (eluting with 5-100% acetonitrile in water, containing 0.1% TFA) to give the title product. MS (m/z) 466.2 [M+H]⁺. ¹H NMR (400 MHz, Methanol-d4) δ 8.37 (s, 1H), 7.45 (q, J=7.8 Hz, 1H), 7.09-6.88 (m, 2H), 4.65 (s, 4H), 3.75 (s, 2H), 3.56 (d, J=11.1 Hz, 1H), 3.46 (s, 3H), 2.18-1.98 (m, 2H), 1.54 (dd, J=25.7, 11.4 Hz, 1H), 1.29 (d, J=6.6 Hz, 3H), 1.01 (q, J=12.1 Hz, 1H). 1H NMR (400 MHz, Methanol-d4) δ 8.51 (s, 1H), 6.98-6.85 (m, 2H), 4.68 (s, 2H), 4.66-4.50 (m, 2H), 3.75 (d, J=14.9 Hz, 1H), 3.72-3.60 (m, 2H), 3.48 (s, 3H), 2.09 (dt, J=15.0, 4.6 Hz, 1H), 1.86 (td, J=9.6, 2.7 Hz, 2H), 1.28 (d, J=6.7 Hz, 3H), 1.24-1.15 (m, 1H).

Example 7: (3S,6R,7R)—N-(2,4-difluorobenzyl)-12-hydroxy-6-methoxy-3-methyl-1,11-dioxo-1,6,7,11-tetrahydro-3H-2,7-methanopyrido[1,2-a][1,4]diazonine-10-carboxamide

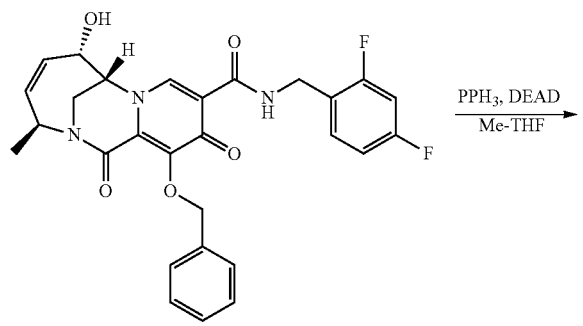

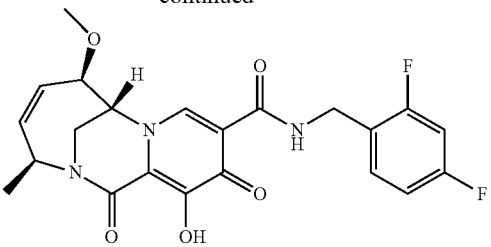

(3S,6R,7R)—N-(2,4-difluorobenzyl)-12-hydroxy-6-methoxy-3-methyl-1,11-dioxo-1,6,7,11-tetrahydro-3H-2,7-methanopyrido[1,2-a][1,4]diazonine-10-carboxamide was prepared in similar method to prepare (3S,6R,7R)-12-hydroxy-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (Example 4) except that (3S,6S,7R)-12-(benzyloxy)-N-(2,4-difluorobenzyl)-6-hydroxy-3-methyl-1,11-dioxo-1,6,7,11-tetrahydro-3H-2,7-methanopyrido[1,2-a][1,4]diazonine-10-carboxamide (see Example 3) was used instead of (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide. MS (m/z) 446.2 [M+H]$^+$. $^1$H NMR (400 MHz, Methanol-d4) δ 8.47 (s, 1H), 7.45 (td, J=8.4, 6.3 Hz, 1H), 7.03-6.90 (m, 2H), 5.77 (dt, J=11.8, 2.8 Hz, 1H), 5.56 (ddd, J=11.8, 2.7, 1.7 Hz, 1H), 5.34 (dq, J=7.4, 2.8 Hz, 1H), 4.67-4.56 (m, 3H), 4.29 (dq, J=5.6, 2.9 Hz, 1H), 4.11 (dd, J=14.4, 3.0 Hz, 1H), 3.65 (d, J=14.2 Hz, 1H), 3.34 (s, 3H), 1.39 (d, J=7.3 Hz, 3H).

Example 8: (3S,6R,7R)-6,12-dihydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

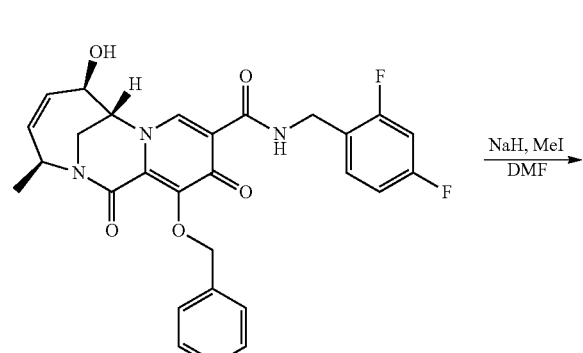

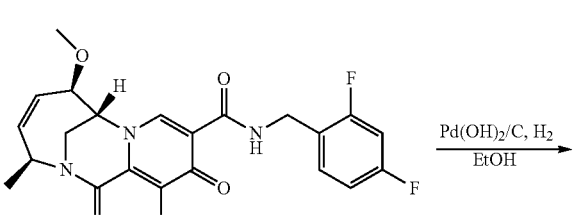

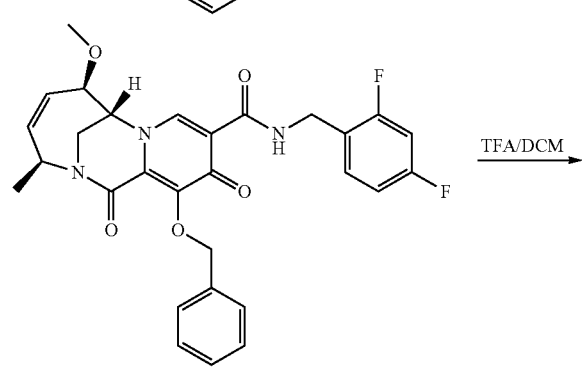

To a solution of (3S,6R,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (Example 7) (20 mg, 0.045 mmol) in EtOH (2 mL) was added Pd(OH)$_2$/C (7 mg). The reaction mixture was stirred at room temperature for half an hour with attachment of H$_2$ balloon. The reaction mixture was filtered through celite, the filtrated was concentrated down and the residue was purified by reverse phase chromatography (eluting with 5-100% acetonitrile in water, containing 0.1% TFA) to give the title product. MS (m/z) 448.3 [M+H]+. 1H NMR (400 MHz, Methanol-d4) δ 8.53 (s, 1H), 7.50-7.40 (m, 1H), 6.97 (dddd, J=12.6, 11.1, 8.9, 2.6 Hz, 2H), 4.65 (s, 2H), 4.62-4.52 (m, 2H), 3.80-3.59 (m, 3H), 3.48 (s, 3H), 2.10 (dt, J=15.1, 4.6 Hz, 1H), 1.85 (tt, J=9.4, 5.2 Hz, 2H), 1.36-1.16 (m, 4H).

Example 9: (3S,6S,7R)—N-(3-chloro-2,4-difluorobenzyl)-12-hydroxy-6-methoxy-3-methyl-1,11-dioxo-1,6,7,11-tetrahydro-3H-2,7-methanopyrido[1,2-a][1,4]diazonine-10-carboxamide

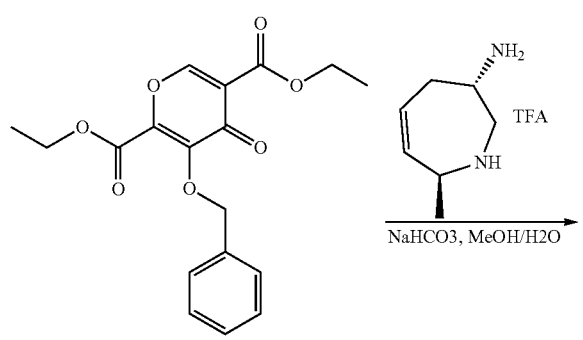

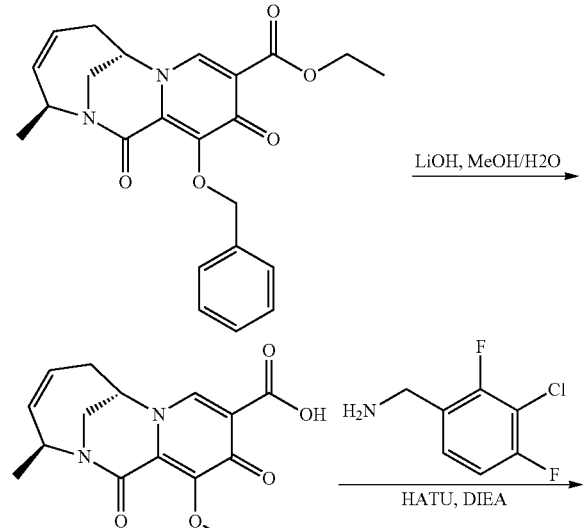

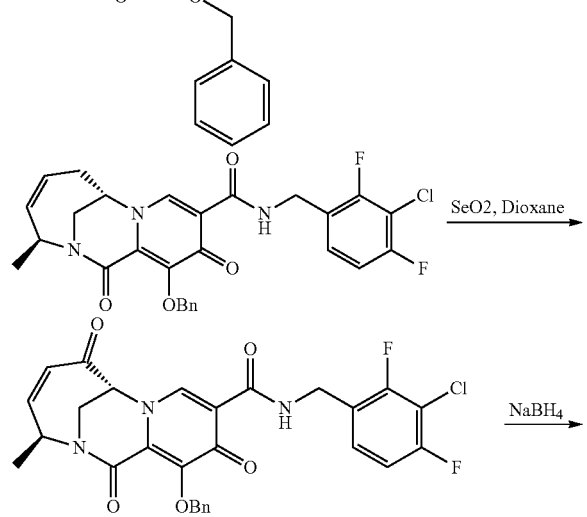

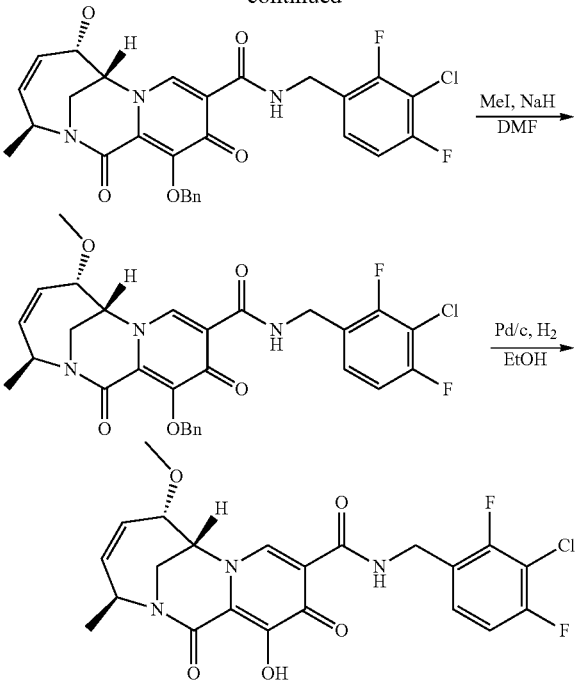

Preparation of (3S,7S)-12-(benzyloxy)-3-methyl-1,11-dioxo-1,6,7,11-tetrahydro-3H-2,7-methanopyrido[1,2-a][1,4]diazonine-10-carboxylic acid A reaction mixture of (3S,7S)-7-methyl-2,3,4,7-tetrahydro-1H-azepin-3-amine (0.39 g, 3.1 mmol), (diethyl 3-(benzyloxy)-4-oxo-4H-pyran-2,5-dicarboxylate (1.07 g, 3.09 mmol) and sodium bicarbonate (2.6 g, 30.9 mmol) in MeOH (10 mL) and water (2 mL) was stirred at rt overnight. Then the reaction mixture was stirred at 60° C. for 8 h. The reaction mixture was cooled and concentrated down. The residue was washed with water, extracted with EtOAc. The organic phase was separated, dried over MgSO4, filtered, concentrated down and purified by silica gel chromatography, eluting by 0-100% hexane/EtOAc to give title compound.

Preparation of (3S,7S)-12-(benzyloxy)-3-methyl-1,11-dioxo-1,6,7,11-tetrahydro-3H-2,7-methanopyrido[1,2-a][1,4]diazonine-10-carboxylic acid A reaction mixture of ethyl (3S,7S)-12-(benzyloxy)-3-methyl-1,11-dioxo-1,6,7,11-tetrahydro-3H-2,7-methanopyrido[1,2-a][1,4]diazonine-10-carboxylate (1.02 g, 2.5 mmol) and sodium hydroxide (2N, 3.75 mL) in MeOH (5 mL) was stirred at 60° C. for 1 h. The reaction mixture is cooled and concentrated down. The residue was dissolved in water, using HCl to adjust the pH to 4, extracted with EtOAc. The organic phase was separated, dried over MgSO4, filtered, concentrated down and used in next reaction without further purification Preparation of (3S,7S)-12-(benzyloxy)-N-(3-chloro-2,4-difluorobenzyl)-3-methyl-1,11-dioxo-1,6,7,11-tetrahydro-3H-2,7-methanopyrido[1,2-a][1,4]diazonine-10-carboxamide To a solution of (3S,7S)-12-(benzyloxy)-3-methyl-1,11-dioxo-1,6,7,11-tetrahydro-3H-2,7-methanopyrido[1,2-a][1, 4]diazonine-10-carboxylic acid (0.88 g, 2.31 mmol) in DCM (10 mL) was added diisopropylethylamine (1.61 mL, 9.25 mmol) and 2-(7-Aza-1H-benzotriazole-1-yl)-1,1,3,3-tetramethyluronium hexafluorophosphate (HATU) (0.88 g, 2.31 mmol) at 0° C. The reaction mixture was stirred at 0° C. for 2 h. The reaction mixture was washed with sat. NaHCO$_3$, extracted with EtOAc, the organic phase was separated, dried over MgSO$_4$, filtered, concentrated down and purified by silica gel chromatography, eluting by 0-100% hexane/ EtOAc to give titled compound.

Preparation of (3S,7R)-12-(benzyloxy)-N-(3-chloro-2,4-difluorobenzyl)-3-methyl-1,6,11-trioxo-1,6,7,11-tetrahydro-3H-2,7-methanopyrido[1,2-a][1,4]diazonine-10-carboxamide The reaction mixture of (3S,7S)-12-(benzyloxy)-N-(3-chloro-2,4-difluorobenzyl)-3-methyl-1,11-dioxo-1,6,7,11-tetrahydro-3H-2,7-methanopyrido[1,2-a][1,4]diazonine-10-carboxamide (0.48 g, 0.89 mmol) and selenium dioxide (0.986 g, 8.9 mmol) in dioxane was stirred at 100° C. overnight. The reaction mixture was cooled down and filtered to remove solid. The filtrate was diluted with EtOAc, washed with sat. NaHCO3. The organic phase was dried over MgSO$_4$, filtered, concentrated down and purified by silica gel chromatography, eluting with 0-100% hexane/ EtOAc to give titled compound.

Preparation of (3S,6S,7R)—N-(3-chloro-2,4-difluorobenzyl)-12-hydroxy-6-methoxy-3-methyl-1,11-dioxo-1,6,7,11-tetrahydro-3H-2,7-methanopyrido[1, 2-a][1,4]diazonine-10-carboxamide (3S,6S,7R)—N-(3-chloro-2,4-difluorobenzyl)-12-hydroxy-6-methoxy-3-methyl-1,11-dioxo-1,6,7,11-tetrahydro-3H-2,7-methanopyrido[1,2-a][1,4]diazonine-10-carboxamide was prepared in similar method to make Example 1, except that (3S,7R)-12-(benzyloxy)-N-(3-chloro-2,4-difluorobenzyl)-3-methyl-1,6,11-trioxo-1,6,7,11-tetrahydro-3H-2,7-methanopyrido[1,2-a][1,4]diazonine-10-carboxamide was used instead of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (intermediate A). MS (m/z) 482.4 [M+H]$^+$. $^1$H NMR (400 MHz, Methanol-d4) δ 8.35 (s, 1H), 7.40 (td, J=8.4, 6.0 Hz, 1H), 7.11 (td, J=8.7, 1.9 Hz, 1H), 4.74 (s, 1H), 4.71-4.57 (m, 3H), 3.83-3.67 (m, 2H), 3.61-3.50 (m, 1H), 3.46 (s, 3H), 2.18-1.98 (m, 3H), 1.54 (dt, J=14.4, 11.2 Hz, 1H), 1.28 (d, J=6.7 Hz, 3H), 1.01 (dt, J=14.9, 11.7 Hz, 1H).

Example 10: (3S,6R,7R)—N-(3-chloro-2,4-difluorobenzyl)-12-hydroxy-6-methoxy-3-methyl-1,11-dioxo-1,6,7,11-tetrahydro-3H-2,7-methanopyrido[1, 2-a][1,4]diazonine-10-carboxamide

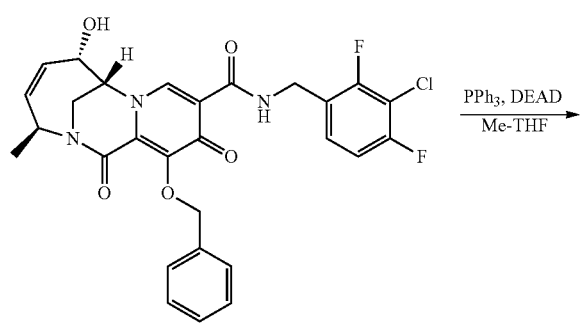

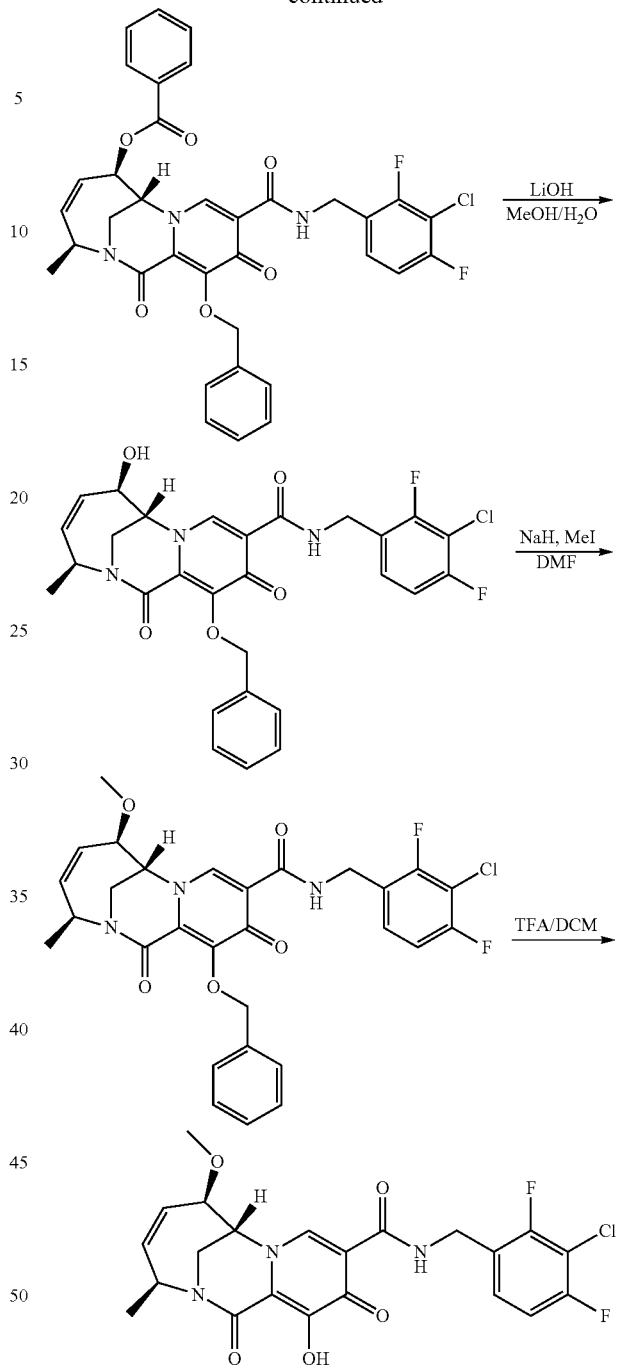

(3S,6R,7R)—N-(3-chloro-2,4-difluorobenzyl)-12-hydroxy-6-methoxy-3-methyl-1,11-dioxo-1,6,7,11-tetrahydro-3H-2,7-methanopyrido[1,2-a][1,4]diazonine-10-carboxamide was prepared in similar method to make Example 4, except that (3S,6S,7R)-12-(benzyloxy)-N-(3-chloro-2,4-difluorobenzyl)-6-hydroxy-3-methyl-1,11-dioxo-1,6,7,11-tetrahydro-3H-2,7-methanopyrido[1,2-a][1,4]diazonine-10-carboxamide was used instead of (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido [1,2-a][1,4]diazonine-10-carboxamide. MS (m/z) 480.2 [M+H]$^+$. $^1$H NMR (400 MHz, Acetonitrile-d3) δ 10.38 (s, 1H), 8.35 (s, 1H), 7.39 (q, J=8.1 Hz, 1H), 7.18-7.04 (m, 1H), 5.72 (dq, J=8.7, 2.8 Hz, 1H), 5.63-5.48 (m, 1H), 5.30 (s, 1H), 4.73-4.60 (m, 3H), 4.46 (s, 1H), 4.27 (s, 1H), 4.01 (dd, J=14.4, 2.9 Hz, 1H), 3.58 (d, J=14.4 Hz, 1H), 3.29 (d, J=4.3 Hz, 3H), 1.34 (d, J=7.3 Hz, 3H).

Example 11. (3S,6S,7R)-12-(benzyloxy)-6-hydroxy-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide

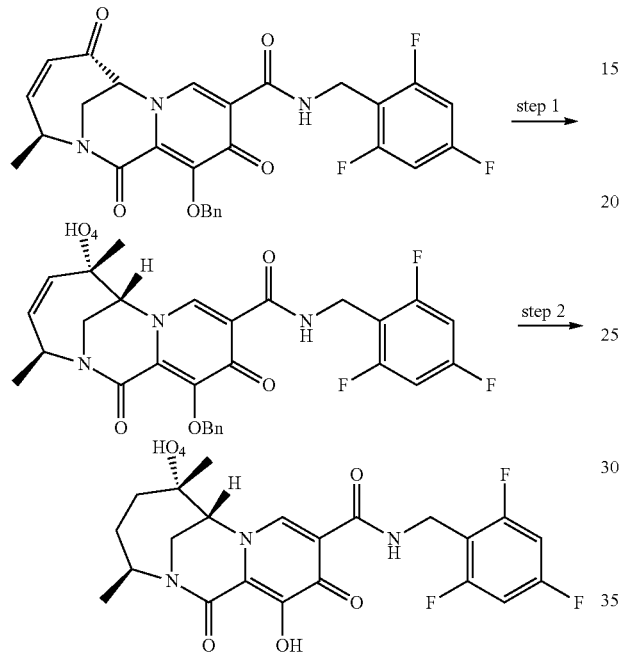

Synthesis of (3S,6S,7R)-6,12-dihydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (132 mg, 0.246 mmol) was dissolved in anhydrous THF (3.0 mL) and the resulting mixture was cooled to −20° C. To this stirred cold mixture was added 3.0 M ether solution of methyl magnesium bromide (0.41 mL, 1.23 mmol). After stirring for 20 minutes, the reaction was quenched with saturated $NH_4Cl$. The mixture was extracted with EtOAc, the organic layer was washed with brine, dried over sodium sulfate, filtered and concentrated. The resulting product was purified by normal phase chromatography (4 g silica gel, 0-100% EtOAc/Hexanes). LCMS-ESI+(m/z): calcd H+ for $C_{29}H_{26}F_3N_3O_5$, Theoretical: 553.18, Found: 553.95. Synthesis of (1R,10S,13S)-6,13-dihydroxy-10,13-dimethyl-5,8-dioxo-N-[(2,4,6-trifluorophenyl)methyl]-2,9-diazatricyclo[7.4.1.02,7]tetradeca-3,6-diene-4-carboxamide:

(3S,6S,7R)-6,12-dihydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (20.0 mg, 0.0361 mmol) was dissolved in MeOH (15.0 mL) at room temperature and treated with 7 mg of 20% $Pd(OH)_2/C$ (50 wt % water). The mixture was degassed and flushed with hydrogen 3 times before it was hydrogenated under hydrogen balloon for overnight. The reaction was then degassed and flushed with nitrogen, filtered through a pad of Celite, concentrated, the resulting residue was redissolved in DMF, filtered and purified by reverse phase HPLC. LCMS-ESI+ (m/z): calcd H+ for $C_{22}H_{22}F_3N_3O_5$, Theoretical: 465.15, Found: 466.24. $^1$H NMR (400 MHz, DMSO-d6) δ 10.95 (s, 1H), 10.46 (t, J=5.8 Hz, 1H), 8.31 (s, 1H), 7.21 (t, J=8.6 Hz, 2H), 4.93 (s, 1H), 4.62-4.41 (m, 3H), 4.26 (s, 1H), 3.66 (d, J=2.5 Hz, 2H), 1.91-1.81 (m, 1H), 1.41 (dd, J=14.6, 7.7 Hz, 2H), 1.34 (s, 3H), 1.17 (d, J=6.6 Hz, 4H).

Example 12: [(3S,6S,7R)—N-(2,4-difluorobenzyl)-6,12-dihydroxy-3,6-dimethyl-1,11-dioxo-1,4,5,6,7,11-hexahydro-3H-2,7-methanopyrido[1,2-a][1,4]diazonine-10-carboxamide]

This compound was prepared by following the same sequence as for the synthesis of Example 11 except in step 1, (3S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide was used instead of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide. Stereochemistry not confirmed. LCMS-ESI+(m/z): calcd H+ for C22H23F2N3O5, Theoretical: 447.16, Found: 448.22. $^1$H NMR (400 MHz, DMSO-d6) δ 10.98 (s, 1H), 10.46 (t, J=6.0 Hz, 1H), 8.34 (s, 1H), 7.40 (td, J=8.7, 6.7 Hz, 1H), 7.25 (ddd, J=10.6, 9.3, 2.6 Hz, 1H), 7.12-7.03 (m, 1H), 5.03-4.83 (m, 1H), 4.56 (d, J=5.9 Hz, 2H), 4.47 (dt, J=12.2, 6.5 Hz, 1H), 4.28 (s, 1H), 3.67 (d, J=3.2 Hz, 2H), 1.87 (dt, J=14.3, 7.1 Hz, 1H), 1.42 (dd, J=14.4, 7.7 Hz, 2H), 1.35 (s, 3H), 1.25-1.12 (m, 4H).

Example 13: Preparation of (3S,6R,7R)-6-chloro-N-(2,4-difluorobenzyl)-12-hydroxy-3-methyl-1,11-dioxo-1,6,7,11-tetrahydro-3H-2,7-methanopyrido[1,2-a][1,4]diazonine-10-carboxamide

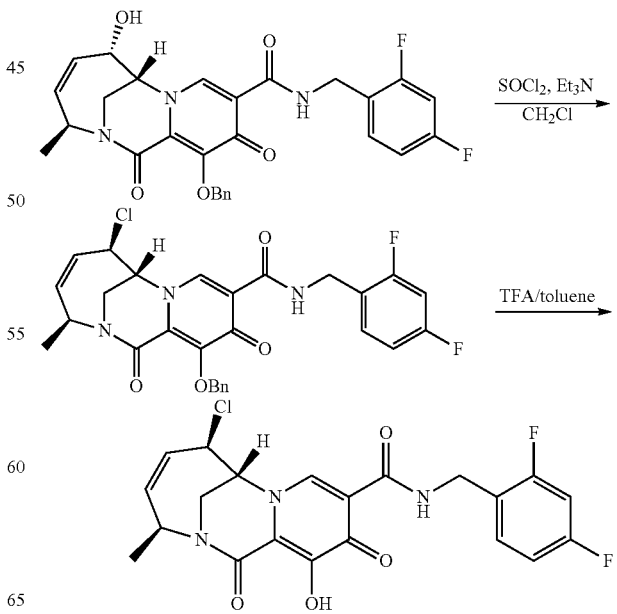

Preparation of (3S,6R,7R)-12-(benzyloxy)-6-chloro-N-(2,4-difluorobenzyl)-3-methyl-1,11-dioxo-1,6,7,11-tetrahydro-3H-2,7-methanopyrido[1,2-a][1,4]diazonine-10-carboxamide To a solution (3S,6S,7R)-12-(benzyloxy)-N-(2,4-difluorobenzyl)-6-hydroxy-3-methyl-1,11-dioxo-1,6,7,11-tetrahydro-3H-2,7-methanopyrido[1,2-a][1,4]diazonine-10-carboxamide (110 mg, 0.211 mmol) in DCM (27 mL) under N₂ was added triethylamine (1.18 mL, 8.44 mmol) and thionyl chloride (0.615 mL, 8.44 mmol). After 5 min, the reaction was quenched by adding sat. NaHCO₃ solution and extracted with DCM. The combined organic layers were washed with brine, dried over Na₂SO₄, filtered, concentrated down and purified by flash column chromatography on silica gel using DCM/MeOH as a solvent system (1:0→95:5→8:2 gradient) to afford (3S,6R,7R)-12-(benzyloxy)-6-chloro-N-(2,4-difluorobenzyl)-3-methyl-1,11-dioxo-1,6,7,11-tetrahydro-3H-2,7-methanopyrido[1,2-a][1,4]diazonine-10-carboxamide as a red/brown solid (111 mg, 98%).

Preparation (3S,6R,7R)-6-chloro-N-(2,4-difluorobenzyl)-12-hydroxy-3-methyl-1,11-dioxo-1,6,7,11-tetrahydro-3H-2,7-methanopyrido[1,2-a][1,4]diazonine-10-carboxamide A solution (3S,6R,7R)-12-(benzyloxy)-6-chloro-N-(2,4-difluorobenzyl)-3-methyl-1,11-dioxo-1,6,7,11-tetrahydro-3H-2,7-methanopyrido[1,2-a][1,4]diazonine-10-carboxamide (63 mg, 0.116 mmol) in toluene/TFA (1:1) (10 mL) was stirred at room temperature for 2.75 h. The reaction was quenched with saturated aqueous sodium bicarbonate until the pH was greater than 7. EtOAc was added and the layers were separated. The aqueous layer was washed with EtOAc. Then combined organic layers were washed with brine, dried over Na₂SO₄, filtered, concentrated down and purified by reverse phase HPLC chromatography (eluting with 5-100% acetonitrile in water, containing 0.1% TFA) to give the title product (34 mg, 65%). MS (m/z) 450.100 [M+H]⁺. 1H NMR (400 MHz, MeOD) δ 8.50 (s, 1H), 7.46-7.40 (m, 1H), 6.99-6.91 (m, 2H), 5.76 (dt, J=11.9, 3.1 Hz, 1H), 5.55 (dt, J=11.9, 2.3 Hz, 1H), 5.35-5.33 (m, 1H), 5.13 (s, 1H), 4.98 (s, 1H), 4.63 (s, 2H), 4.20 (d, J=14.5 Hz, 1H), 3.73 (d, J=14.5 Hz, 1H), 1.39 (d, J=7.3 Hz, 3H).

Example 14: (3S,6S,7R)-6,12-dihydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide

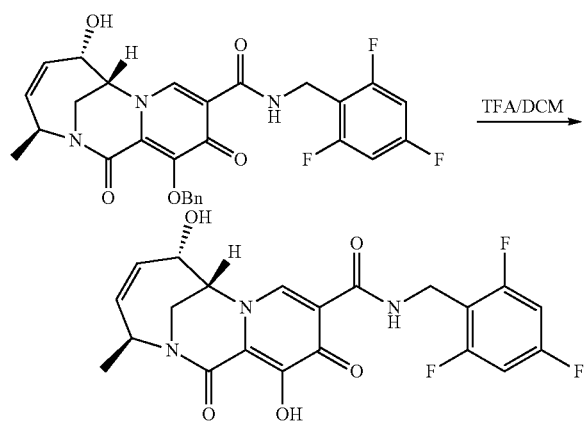

(3S,6S,7R)-6,12-dihydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide was prepared in a similar manner as Example 4 except using (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (prepared according to Example 1) instead of (3S,6R,7R)-12-(benzyloxy)-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide. MS (m/z) 449.1 [M+H]⁺. 1H NMR (400 MHz, MeOD) δ 8.45 (s, 1H), 6.91 (t, J=8.4 Hz, 2H), 5.85 (ddd, J=11.9, 6.1, 2.3 Hz, 1H), 5.63 (dd, J=11.9, 2.7 Hz, 1H), 5.33 (d, J=7.4 Hz, 1H), 4.70 (d, J=7.8 Hz, 2H), 4.4 (m, 1H), 4.05-3.87 (m, 1H), 3.73 (d, J=14.6 Hz, 1H), 3.03 (m, 2H), 1.39 (d, J=7.3 Hz, 3H).

Example 15: Preparation of (1R,10S,13S)-6,13-dihydroxy-10,13-dimethyl-5,8-dioxo-N-[(2,4,6-trifluorophenyl)methyl]-2,9-diazatricyclo[7.4.1.02,7]tetradeca-3,6,11-triene-4-carboxamide

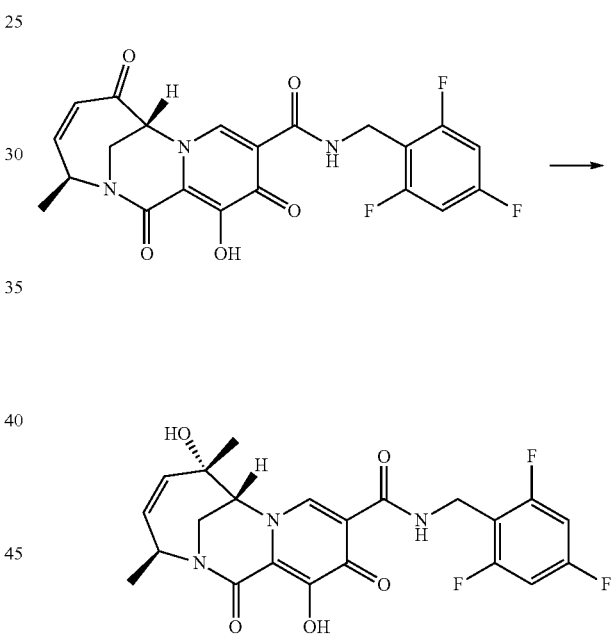

(1R,10S)-6-hydroxy-10-methyl-5,8,13-trioxo-N-[(2,4,6-trifluorophenyl)methyl]-2,9-diazatricyclo[7.4.1.02,7]tetradeca-3,6,11-triene-4-carboxamide (15 mg, 0.0335 mmol) was dissolved in THF (0.5 mL) and cooled to −78° C. To this stirred cold mixture was added 3.0 M MeMgBr in diethylether (0.056 mL, 0.168 mmol) dropwise. The resulting mixture was stirred at −78° C. for 5 minute and then was warmed up to 0° C. for 5 minutes. The reaction was quenched with acetic acid, filtered and purified by reverse phase prep HPLC. LCMS-ESI+(m/z): calcd H+ for C22H20F3N3O5, Theoretical: 463.14, Found: 464.02. 1H NMR (400 MHz, DMSO-d6) δ 10.46 (t, J=5.8 Hz, 1H), 8.36 (s, 1H), 7.25-7.23 (m, 1H), 7.22-7.19 (m, 2H), 5.54 (dd, J=11.9, 2.3 Hz, 1H), 5.39 (dd, J=11.8, 2.6 Hz, 1H), 5.18-5.08 (m, 1H), 4.68 (s, 1H), 4.59-4.55 (m, 3H), 3.86 (dd, J=14.7, 2.6 Hz, 1H), 3.63 (d, J=14.2 Hz, 1H), 1.38 (s, 3H), 1.27 (d, J=7.3 Hz, 3H).

Example 16: (3S,6S,7R)—N-(2,4-difluorobenzyl)-6,12-dihydroxy-3-methyl-1,11-dioxo-1,4,5,6,7,11-hexahydro-3H-2,7-methanopyrido[1,2-a][1,4]diazonine-10-carboxamide Example 17: Preparation of (1R,10S,13S)—N-[(2,4-difluorophenyl)methyl]-6,13-dihydroxy-10,13-dimethyl-5,8-dioxo-2,9-diazatricyclo[7.4.1.02,7]tetradeca-3,6,11-triene-4-carboxamide

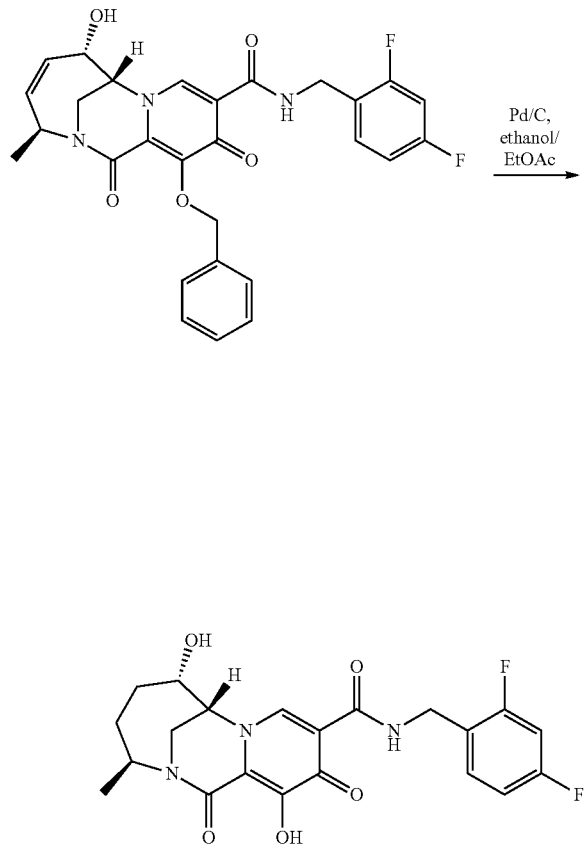

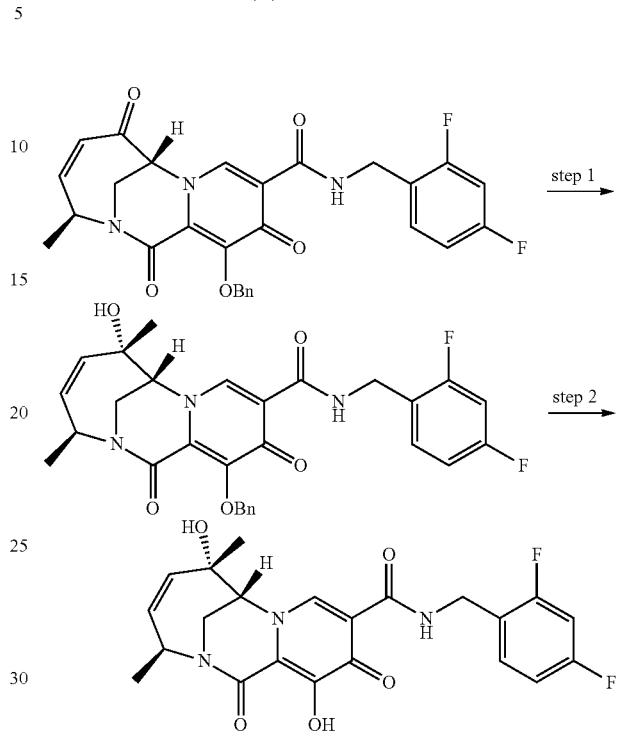

Synthesis of (3S,6S,7R)—N-(2,4-difluorobenzyl)-6,12-dihydroxy-3-methyl-1,11-dioxo-1,4,5,6,7,11-hexahydro-3H-2,7-methanopyrido[1,2-a][1,4]diazonine-10-carboxamide (3S,6S,7R)-12-(benzyloxy)-N-(2,4-difluorobenzyl)-6-hydroxy-3-methyl-1,11-dioxo-1,6,7,11-tetrahydro-3H-2,7-methanopyrido[1,2-a][1,4]diazonine-10-carboxamide (10 mg, 0.019 mmol), was dissolved in 3 mL of ethanol and 3 ml of ethyl acetate and was sparged under an argon atmosphere. Palladium on carbon (10 wt %, wet) E101 NE/W (4.08 mg, 0.0038 mmol) was added. The mixture was sparged under a hydrogen atmosphere (1 atm, balloon) and stirred vigorously for two hours, then sparged under an argon atmosphere. It was filtered through a pad of Celite®. The Celite® was washed with absolute ethanol and the filtrate was concentrated to dryness. The residue was purified by RP-HPLC to afford the title compound. MS (m/z): 434.113 [M+H]+. $^1$H NMR (400 MHz, Methanol-d4) δ 8.43 (s, 1H), 7.56-7.31 (m, 1H), 7.03-6.91 (m, 2H), 4.70-4.55 (m, 4H), 3.95 (dt, J=11.8, 4.4 Hz, 1H), 3.76 (d, J=1.8 Hz, 2H), 2.14-2.01 (m, 1H), 1.82 (ddd, J=14.7, 7.6, 3.8 Hz, 1H), 1.59 (dt, J=15.0, 11.3 Hz, 1H), 1.28 (d, J=6.7 Hz, 3H), 1.27-1.13 (m, 1H).

Step 1: Synthesis of (1R,10S,13S)-6-benzyloxy-N-[(2,4-difluorophenyl)methyl]-13-hydroxy-10,13-dimethyl-5,8-dioxo-2,9-diazatricyclo[7.4.1.02,7]tetradeca-3,6,11-triene-4-carboxamide The compound was prepared by following step 1 for the synthesis of Example 11, except in step 1, (3 S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide was used instead of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide. LCMS-ESI+(m/z): calcd H+ for C29H27F2N3O5, Theoretical: 535.19, Found: 535.94.

Step 2: Synthesis of (1R,10S,13S)—N-[(2,4-difluorophenyl)methyl]-6,13-dihydroxy-10,13-dimethyl-5,8-dioxo-2,9-diazatricyclo[7.4.1.02,7]tetradeca-3,6,11-triene-4-carboxamide (1R,10S,13S)-6-benzyloxy-N-[(2,4-difluorophenyl)methyl]-13-hydroxy-10,13-dimethyl-5,8-dioxo-2,9-diazatricyclo[7.4.1.02,7]tetradeca-3,6,11-triene-4-carboxamide from step 1 (13.0 mg, 0.0243 mmol) was treated with a mixture of DCM (0.2 mL) and TFA (0.2 mL) at room temperature for 4 hrs. The reaction was concentrated, redissolved in DMF, filtered and purified by reverse phase prep HPLC. LCMS-ESI+(m/z): calcd H+ for C22H21F2N3O5, Theoretical: 445.14, Found: 446.04. 1H NMR (400 MHz, Acetone-d6) δ 10.51 (s, 1H), 8.38 (s, 1H), 7.49 (q, J=8.3 Hz, 1H), 7.08-6.95 (m, 2H), 6.25 (s, 1H), 5.74 (dd, J=11.9, 2.5 Hz, 1H), 5.53 (dd, J=11.8, 2.5 Hz, 1H), 5.35-5.23 (m, 1H), 4.79-4.69 (m, 2H), 4.63 (d, J=6.0 Hz, 2H), 4.12 (dd, J=14.7, 2.7 Hz, 1H), 3.85 (dd, J=14.6, 1.8 Hz, 1H), 1.60 (s, 3H), 1.39 (d, J=7.3 Hz, 3H).

Example 18: (3S,6S,7R)-12-hydroxy-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide

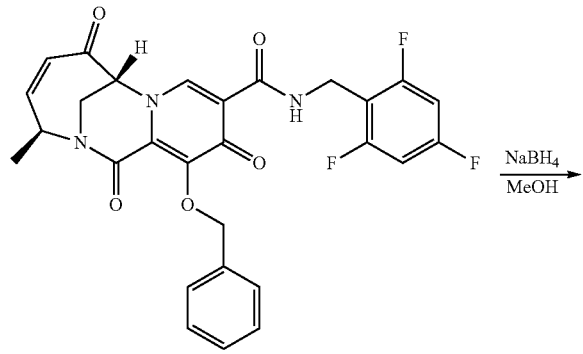

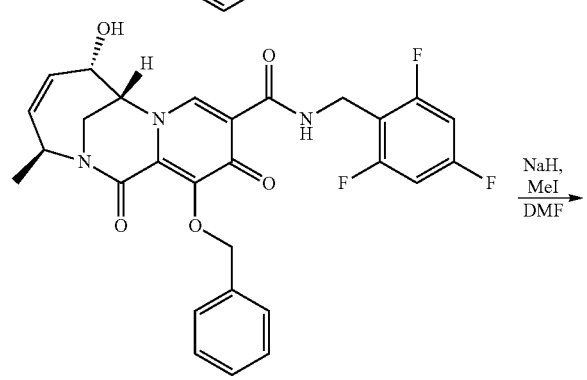

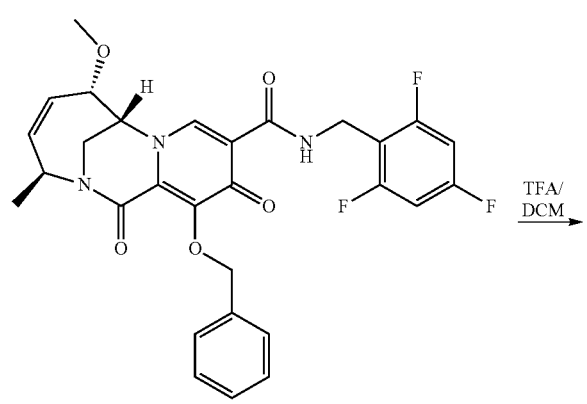

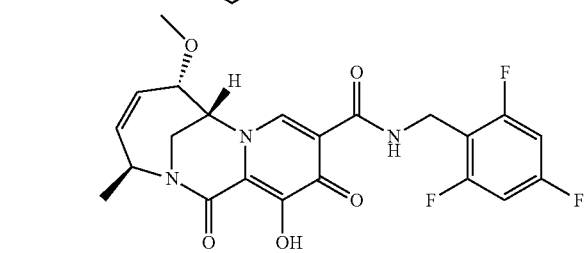

Preparation of (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide To a solution of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (intermediate A) (122 mg, 0.227 mmol) in methanol (5 mL) was added cerium (III) chloride heptahydrate (85 mg, 0.227 mmol). Then to the mixture was added sodium borohydride (2.1 mg, 0.057 mmol) slowly at 0° C. After 5 min, the reaction was quenched by adding saturated NaHCO₃ solution and extracted with DCM. The organic phase was separated and concentrated down. The residue was then dissolved in DCM, washed with brine. The organic phase was dried over MgSO₄, filtered, concentrated down and further used without purification.

Preparation of (3 S,6S,7R)-12-(benzyloxy)-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide To a solution of (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (16 mg, 0.030 mmol) in DMF (1 mL) was added sodium hydride (1.8 mg, 0.045 mmol, 60%) and iodomethane (2.8 uL, 0.045 mmol). The reaction mixture was stirred at room temperature for half an hour. The reaction was quenched by adding saturated NaHCO₃, extracted with EtOAc, the organic phase was separated, dried over MgSO₄, filtered, concentrated down and the resulting product was used in next step without further purification.

Preparation of (3S,6S,7R)-12-hydroxy-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide The reaction mixture of (3S,6S,7R)-12-(benzyloxy)-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (16 mg, 0.029 mmol) in TFA (1 mL) and DCM (1 mL) was stirred at room temperature for 3 h. The reaction mixture was concentrated down and the residue was purified by reverse phase HPLC chromatography (eluting with 5-100% acetonitrile in water, containing 0.1% TFA) to give the title product. MS (m/z) 464.16 [M+H]⁺. ¹H NMR (400 MHz, Methanol-d4) δ 8.47 (s, 1H), 6.98-6.85 (m, 2H), 6.00 (ddd, J=11.6, 6.6, 2.6 Hz, 1H), 5.75 (dd, J=11.6, 2.0 Hz, 1H), 5.27 (qt, J=7.4, 2.4 Hz, 1H), 5.00 (d, J=7.3 Hz, 1H), 4.69 (s, 2H), 4.29 (t, J=7.0 Hz, 1H), 3.96 (dd, J=14.6, 2.5 Hz, 1H), 3.66 (d, J=14.5 Hz, 1H), 3.12 (s, 3H), 1.39 (d, J=7.4 Hz, 3H).

Example 19: (3S,6S,7R)—N-(2,4-difluorobenzyl)-12-hydroxy-6-methoxy-3-methyl-1,11-dioxo-1,6,7,11-tetrahydro-3H-2,7-methanopyrido[1,2-a][1,4]diazonine-10-carboxamide

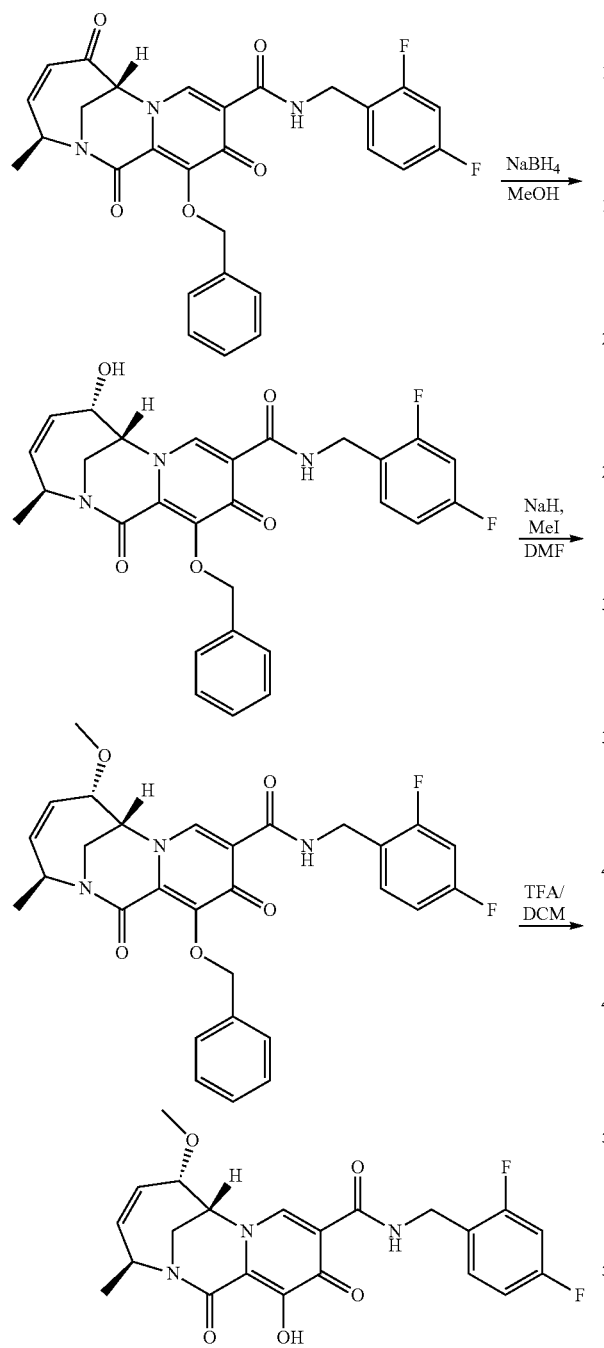

(3S,6S,7R)—N-(2,4-difluorobenzyl)-12-hydroxy-6-methoxy-3-methyl-1,11-dioxo-1,6,7,11-tetrahydro-3H-2,7-methanopyrido[1,2-a][1,4]diazonine-10-carboxamide was made similar to Example 18, except that (3 S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide was used instead of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide. MS (m/z) 446.22 [M+H]+. 1H NMR (400 MHz, Methanol-d4) δ 8.50 (s, 1H), 7.45 (td, J=8.4, 6.3 Hz, 1H), 7.04-6.90 (m, 2H), 6.00 (ddd, J=11.6, 6.6, 2.6 Hz, 1H), 5.76 (dd, J=11.7, 2.0 Hz, 1H), 5.28 (tdt, J=7.4, 4.7, 2.4 Hz, 1H), 5.00 (d, J=6.9 Hz, 1H), 4.65 (s, 2H), 4.29 (t, J=7.0 Hz, 1H), 3.97 (dd, J=14.6, 2.4 Hz, 1H), 3.66 (d, J=14.5 Hz, 1H), 3.13 (s, 3H), 1.39 (d, J=7.3 Hz, 3H).

Example 20: (3S,6S,7R)—N-(2,4-difluorobenzyl)-6,12-dihydroxy-3-methyl-1,11-dioxo-1,6,7,11-tetrahydro-3H-2,7-methanopyrido[1,2-a][1,4]diazonine-10-carboxamide

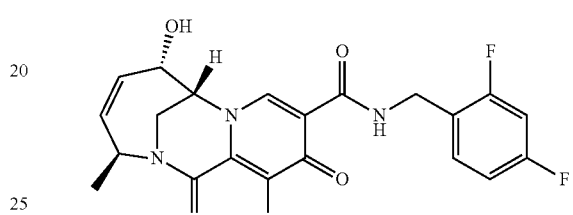

(3S,6S,7R)-12-(benzyloxy)-N-(2,4-difluorobenzyl)-6-hydroxy-3-methyl-1,11-dioxo-1,6,7,11-tetrahydro-3H-2,7-methanopyrido[1,2-a][1,4]diazonine-10-carboxamide (10 mg, 0.19 mmol), prepared according to Example 3, was dissolved in 1 mL of toluene and 1 mL of TFA. It was stirred at room temperature for 1 hour and concentrated to dryness. The residue was purified by RP-HPLC to afford the title compound. MS (m/z): 432.124 [M+H]+. 1H NMR (400 MHz, DMSO-d6) δ 10.49-10.39 (m, 2H), 8.42 (s, 1H), 7.41 (td, J=8.7, 6.6 Hz, 1H), 7.25 (ddd, J=10.5, 9.3, 2.6 Hz, 1H), 7.07 (td, J=8.5, 2.6 Hz, 1H), 5.67 (ddd, J=11.9, 5.6, 2.1 Hz, 1H), 5.57-5.48 (m, 2H), 5.20-5.12 (m, 1H), 4.93 (d, J=7.3 Hz, 1H), 4.58 (dd, J=13.2, 6.2 Hz, 3H), 3.83 (dd, J=14.8, 2.4 Hz, 1H), 3.68 (dd, J=14.7, 2.0 Hz, 1H), 1.28 (d, J=7.3 Hz, 3H).

Example 21: (3S,6S,7R)—N-(2,4-difluorobenzyl)-12-hydroxy-6-methoxy-3-methyl-1,11-dioxo-1,6,7,11-tetrahydro-3H-2,7-methanopyrido[1,2-a][1,4]diazonine-6-d-10-carboxamide

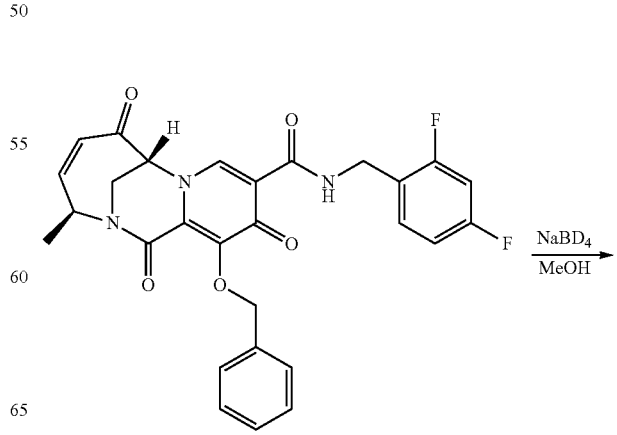

-continued

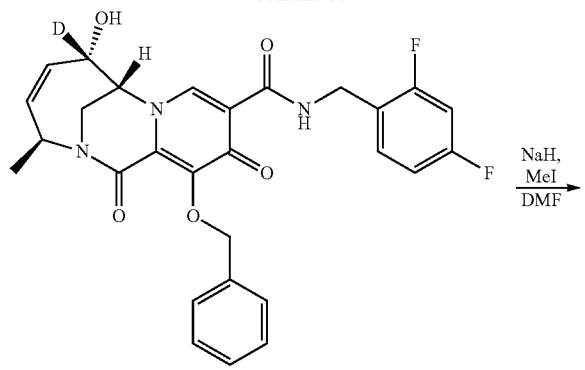

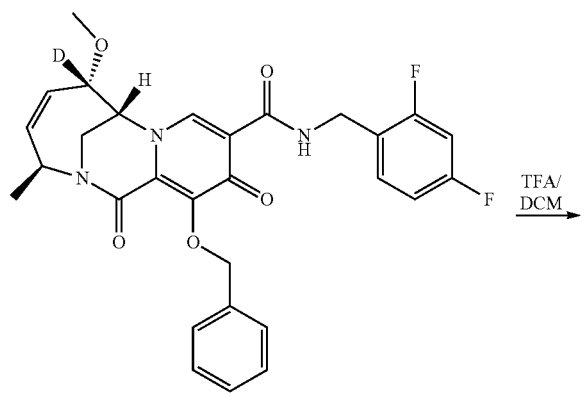

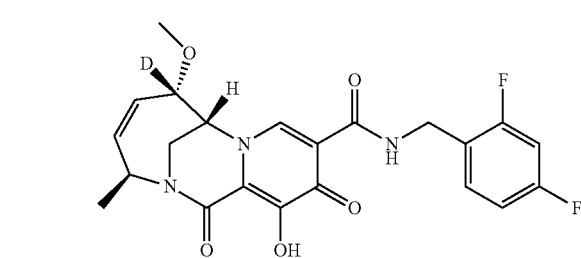

(3S,6S,7R)—N-(2,4-difluorobenzyl)-12-hydroxy-6-methoxy-3-methyl-1,11-dioxo-1,6,7,11-tetrahydro-3H-2,7-methanopyrido[1,2-a][1,4]diazonine-6-d-10-carboxamide was made similar to Example 18, except that sodium borodeuteride was used instead of sodium borohydride and that (3S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide was used instead of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide. MS (m/z) 447.2 [M+H]+. 1H NMR (400 MHz, Methanol-d4) δ 8.50 (s, 1H), 7.45 (td, J=8.4, 6.4 Hz, 1H), 7.04-6.90 (m, 2H), 6.00 (dd, J=11.6, 2.7 Hz, 1H), 5.76 (dd, J=11.6, 2.0 Hz, 1H), 5.28 (dddd, J=9.9, 7.6, 4.9, 2.5 Hz, 1H), 5.00 (s, 1H), 4.65 (s, 2H), 3.96 (dd, J=14.6, 2.7 Hz, 1H), 3.66 (d, J=14.4 Hz, 1H), 3.12 (s, 3H), 1.39 (d, J=7.3 Hz, 3H).

Example 22: (3S,6S,7R)-6-(difluoromethoxy)-12-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide

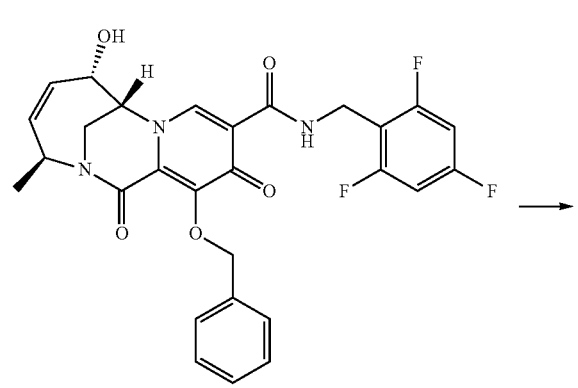

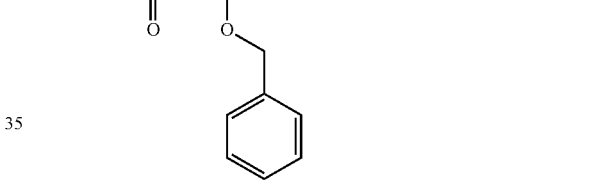

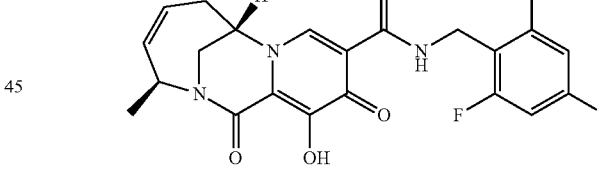

Step 1: Synthesis of (3S,6S,7R)-12-(benzyloxy)-6-(difluoromethoxy)-3-methyl-1,11-dioxo-N-(2,4,6-trifluorobenzyl)-1,6,7,11-tetrahydro-3H-2,7-methanopyrido[1,2-a][1,4]diazonine-10-carboxamide (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (60 mg, 0.11 mmol) was dissolved in 1 mL of acetonitrile, and copper iodide (4.24 mg, 0.022 mmol) was added. The mixture was heated to 50° C., and a solution of 2-fluorosulfonyl-2,2-difluoroacetic acid (0.017 mL, 0.17 mmol) in 1 mL of acetonitrile was added dropwise. The reaction mixture was heated for 10 minutes at 50° C. Then cooled to 0° C., ethyl acetate was added, washed with saturated sodium bicarbonate aqueous solution and brine. The organic layer was separated, dried over magnesium sulfate, filtered and concentrated to dryness. the residue was purified by RP-HPLC to afford the title product. MS (m/z): 590.200 [M+H]+.

Step 2: Synthesis of (3S,6S,7R)-6-(difluoromethoxy)-12-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (3S,6S,7R)-12-(benzyloxy)-6-(difluoromethoxy)-3-methyl-1,11-dioxo-N-(2,4,6-trifluorobenzyl)-1,6,7,11-tetrahydro-3H-2,7-methanopyrido[1,2-a][1,4]diazonine-10-carboxamide (10 mg) was dissolved in 0.5 ml of toluene and 0.5 ml of TFA, stirred at room temperature for 1.5 hour, then removed the solvent and purified by RP-HPLC to afford the title product. MS (m/z): 500.100 [M+H]+. 1H NMR (400 MHz, Methanol-d4) δ 10.54 (s, 1H), 8.46 (s, 1H), 6.92 (t, J=8.4 Hz, 2H), 6.25 (t, J=73.1 Hz, 1H), 5.95-5.86 (m, 1H), 5.79 (dd, J=11.8, 2.3 Hz, 1H), 5.35 (d, J=7.5 Hz, 1H), 5.27 (t, J=7.0 Hz, 1H), 5.10 (d, J=7.5 Hz, 1H), 4.68 (s, 3H), 3.98 (d, J=14.5 Hz, 1H), 3.74 (d, J=14.6 Hz, 1H), 1.41 (d, J=7.3 Hz, 3H).

Example 23: (3S,6S,7R)-12-hydroxy-6-methoxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide

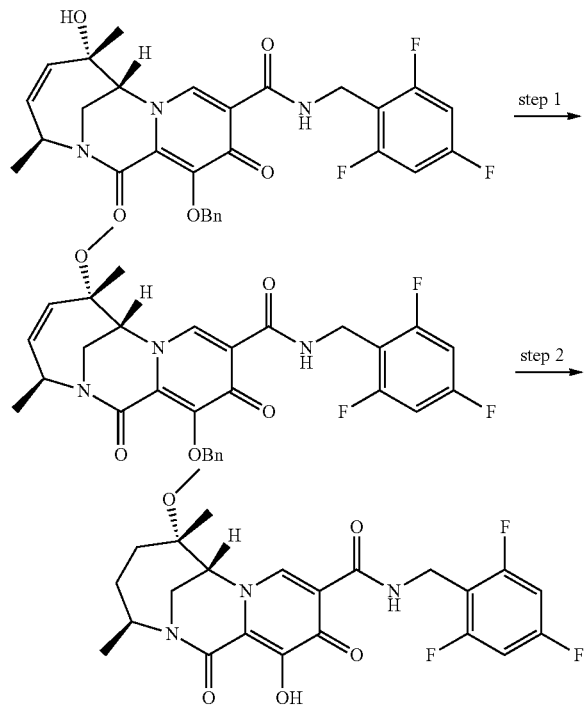

Synthesis of (3S,6S,7R)-12-(benzyloxy)-6-methoxy-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide (3S,6S,7R)-6,12-dihydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (product from Step 1 of Example 11, 25 mg, 0.045 mmol) was dissolved in anhydrous DMF (0.90 mL) and the resulting mixture was cooled to 0° C. To this stirred cold mixture was added 60% sodium hydride in mineral oil (2.6 mg, 0.068 mmol), then iodomethane (10 mg, 0.068 mmol). After stirring for 5 minutes, the reaction was quenched with 10% aqueous citric acid. The mixture was extracted with EtOAc, the organic layer was washed with water, then saturated aqueous sodium bicarbonate then brine, dried over magnesium sulfate, filtered and concentrated. Flash column chromatography (silica gel, EtOAc/Hexane) yielded the product (stereochemistry assignment tentative). 1H NMR (400 MHz, Chloroform-d) δ 10.47 (s, 1H), 8.35 (s, 1H), 7.59-7.53 (m, 2H), 7.37-7.27 (m, 3H), 6.66 (dd, J=8.8, 7.5 Hz, 2H), 5.63 (dd, J=11.6, 1.8 Hz, 1H), 5.52-5.41 (m, 2H), 5.39-5.29 (m, 1H), 5.21 (d, J=10.3 Hz, 1H), 4.66 (d, J=5.4 Hz, 2H), 4.11 (s, 1H), 3.78 (dd, J=14.5, 2.9 Hz, 1H), 3.27 (dd, J=14.5, 1.3 Hz, 1H), 3.00 (s, 3H), 1.45 (s, 3H), 1.29 (d, J=7.4 Hz, 3H). LCMS-ESI+(m/z): calcd H+ for $C_{30}H_{28}F_3N_3O_5$, Theoretical: 568.21, Found: 568.19.

Synthesis of (3S,6S,7R)-12-hydroxy-6-methoxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (3S,6S,7R)-12-(benzyloxy)-6-methoxy-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide (20.0 mg, 0.035 mmol) was dissolved in EtOH (1.0 mL) at room temperature and treated with 1.2 mg of 20% Pd(OH)$_2$/C (50 wt % water). The mixture was degassed and flushed with hydrogen 3 times, then stirred under hydrogen atmosphere for 45 min. The reaction was then degassed and flushed with nitrogen, filtered through a pad of Celite, concentrated, the resulting residue was purified by flash column chromatography (silica gel, dichloromethane/methanol) to yield the product (stereochemistry assignment tentative). 1H NMR (400 MHz, Chloroform-d) δ 10.48 (s, 1H), 6.65 (dd, J=8.8, 7.5 Hz, 2H), 4.75-4.58 (m, 3H), 3.67 (dd, J=15.3, 3.0 Hz, 1H), 3.44 (d, J=15.2 Hz, 1H), 3.12 (s, 3H), 2.13-2.01 (m, 1H), 1.91 (dd, J=14.8, 7.7 Hz, 1H), 1.41 (s, 3H), 1.36-1.28 (m, 1H), 1.26 (d, J=6.7 Hz, 3H), 1.24-1.06 (m, 2H). LCMS-ESI+(m/z): calcd H+ for $C_{23}H_{24}F_3N_3O_5$, Theoretical: 480.18, Found: 480.30.

Example 24: Synthesis of (3S,6S,7R)-12-hydroxy-6-methoxy-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide

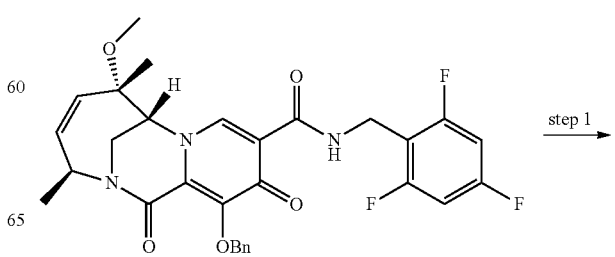

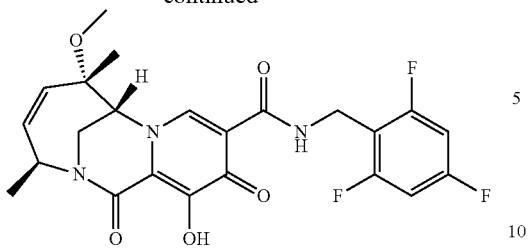

(3S,6S,7R)-12-(benzyloxy)-6-methoxy-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide (from Step 1 of Example 23, 16 mg, 0.028 mmol) was dissolved in 1:1 toluene:trifluoroacetic acid (1.16 mL). The resulting solution was stirred at 20° C. for 8 hr, then allowed to stand at 0° C. for 12 hr. The solution was diluted with acetonitrile and concentrated in vacuo, and the resulting crude was purified by flash column chromatography (silica gel, dichloromethane/methanol) to yield the product (stereochemistry assignment tentative). 1H NMR (400 MHz, Chloroform-d) δ 10.36 (s, 1H), 8.32 (s, 1H), 6.65 (dd, J=8.7, 7.5 Hz, 2H), 5.64 (dd, J=11.6, 1.8 Hz, 1H), 5.53 (dd, J=11.6, 2.7 Hz, 1H), 5.29-5.20 (m, 1H), 4.77-4.55 (m, 2H), 4.23 (s, 1H), 3.93 (dd, J=14.3, 3.0 Hz, 1H), 3.54 (dd, J=14.3, 1.3 Hz, 1H), 2.97 (s, 3H), 1.45 (s, 3H), 1.36 (d, J=7.4 Hz, 3H). LCMS-ESI+(m/z): calcd H+ for $C_{23}H_{22}F_3N_3O_5$, Theoretical: 478.16, Found: 478.25.

Example 25: Preparation of (3S,6S,7R)-6-ethoxy-12-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide

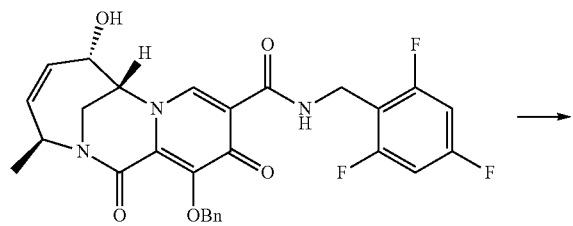

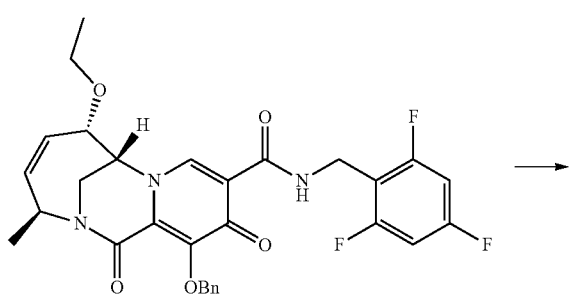

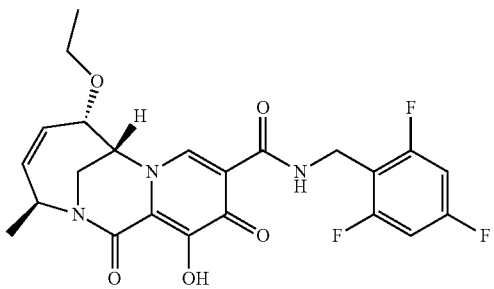

Synthesis of (3S,6S,7R)-12-(benzyloxy)-6-ethoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide Dissolve (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (24 mg, 0.04 mmol) in 2 mL anhydrous DMF, cool to 0° C., NaH (1.5 eq.) was added, followed by EtI (1.2 eq.). After 10 minutes, the reaction was complete. A drop of water was added to quench the reaction. The crude reaction was purified via preparative HPLC, eluting 10-60% acetonitrile (0.1% TFA) in water (0.1% TFA) to give (3S,6S,7R)-12-(benzyloxy)-6-ethoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide. MS (m/z) 568.24 [M+H]+.

Synthesis of (3S,6S,7R)-6-ethoxy-12-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide At room temperature (3S,6S,7R)-12-(benzyloxy)-6-ethoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (5 mg) was dissolved in toluene (0.5 mL), TFA (0.5 mL) was added. The reaction was stirred at room temperature for one hour. The reaction mixture was concentrated down, purified via preparative HPLC, eluting 10-60% acetonitrile (0.1% TFA) in water (0.1% TFA). Combined fractions were freeze-dried to afford the title compound. MS (m/z) 478.32 [M+H]+. 1H NMR (400 MHz, Acetonitrile-d3) δ 8.44 (d, J=22.1 Hz, 1H), 7.00-6.81 (m, 1H), 6.73 (t, J=8.5 Hz, 1H), 6.02-5.84 (m, 1H), 5.79-5.60 (m, 1H), 5.24 (d, J=7.9 Hz, 1H), 5.03 (dd, J=42.6, 7.4 Hz, 1H), 4.82 (dd, J=15.0, 6.8 Hz, 1H), 4.70-4.58 (m, 1H), 4.52 (d, J=12.9 Hz, 1H), 4.44-4.29 (m, 1H), 3.81 (t, J=12.5 Hz, 1H), 3.70-3.54 (m, 1H), 3.41 (p, J=6.9 Hz, 1H), 1.43-1.24 (m, 3H), 0.92-0.68 (m, 3H).

Example 26: Preparation of (3S,6S,7R)-6-ethoxy-12-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

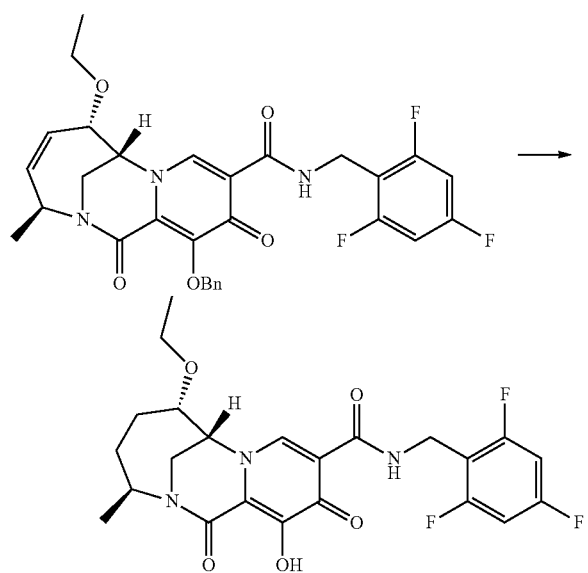

Dissolved (3S,6S,7R)-12-(benzyloxy)-6-ethoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (7 mg) in 2 mL ethanol and 2 mL ethyl acetate. 2 mg 10% Pd/C was added and hydrogen balloon was applied. After 2 hours, the catalyst was filtered off through celite. The filtrate was concentrated down. The crude reaction was purified via preparative HPLC, eluting 10-60% acetonitrile (0.1% TFA) in water (0.1% TFA) to give (3S,6S,7R)-6-ethoxy-12-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide. MS (m/z) 480.27 [M+H]+. 1H NMR (400 MHz, Acetonitrile-d3) δ 8.46-8.26 (m, 1H), 6.87 (t, J=8.5 Hz, 1H), 6.69 (t, J=8.5 Hz, 1H), 4.97-4.38 (m, 4H), 3.86-3.49 (m, 5H), 1.87 (m, 2H), 1.44 (d, J=17.7 Hz, 2H), 1.25-1.08 (m, 3H), 1.08-0.82 (m, 3H).

Example 27: (3S,6S,7R)-6-(difluoromethoxy)-12-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

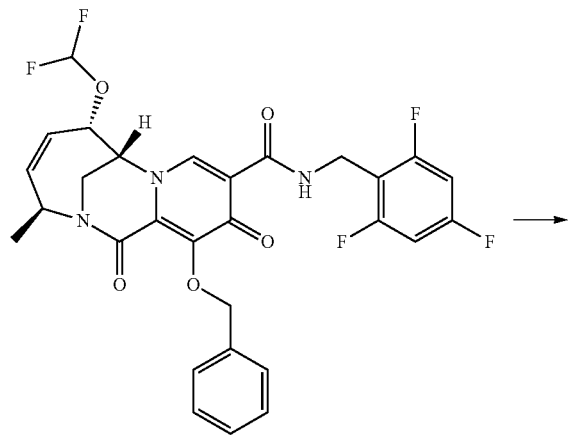

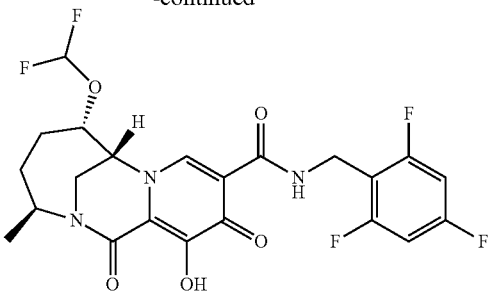

Prepared in a manner similar to (3S,6S,7R)—N-(2,4-difluorobenzyl)-6,12-dihydroxy-3-methyl-1,11-dioxo-1,4,5,6,7,11-hexahydro-3H-2,7-methanopyrido[1,2-a][1,4]diazonine-10-carboxamide (Example 16) except using (3S,6S,7R)-12-(benzyloxy)-6-(difluoromethoxy)-3-methyl-1,11-dioxo-N-(2,4,6-trifluorobenzyl)-1,6,7,11-tetrahydro-3H-2,7-methanopyrido[1,2-a][1,4]diazonine-10-carboxamide (prepared according to Example 22) instead of (3S,6S,7R)-12-(benzyloxy)-N-(2,4-difluorobenzyl)-6-hydroxy-3-methyl-1,11-dioxo-1,6,7,11-tetrahydro-3H-2,7-methanopyrido[1,2-a][1,4]diazonine-10-carboxamide. MS (m/z): 502.137 [M+H]+. 1H NMR (400 MHz, Methanol-d4) δ 10.56 (s, 1H), 8.35 (s, 1H), 6.92 (t, J=8.4 Hz, 2H), 6.58 (t, J=73.8 Hz, 1H), 4.79-4.44 (m, 5H), 3.81 (s, 2H), 2.14 (dt, J=14.7, 7.2 Hz, 1H), 2.02-1.81 (m, 1H), 1.74-1.60 (m, 1H), 1.45-1.30 (m, 1H), 1.29 (d, J=6.7 Hz, 3H).

Example 28: Preparation of (3S,6S,7R)-6-ethyl-6,12-dihydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

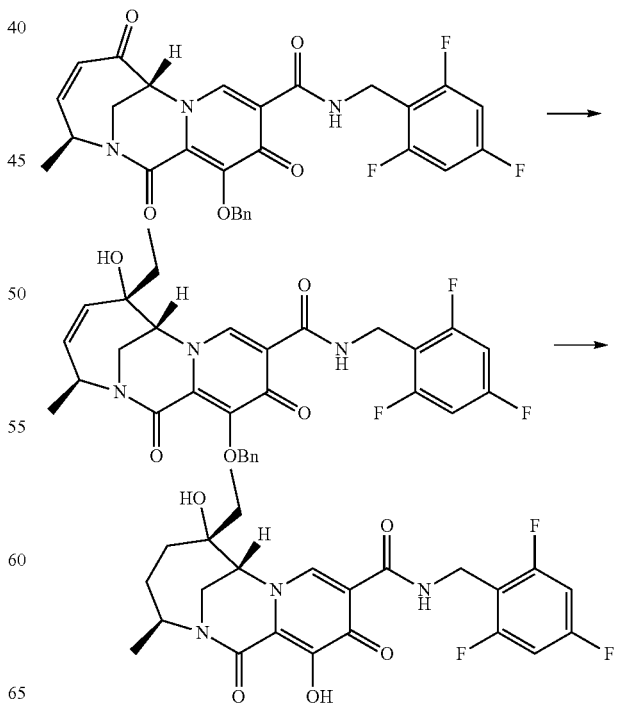

Synthesis of (3S,6S,7R)-12-(benzyloxy)-6-ethyl-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide Dissolved (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (43 mg, 0.08 mmol) is 2 mL anhydrous THF. The mixture was cooled to 0° C. and EtMgBr (3.4 M, 3 eq., 0.07 mL) was added. The reaction was kept at 0° C. for one hour. A drop of water was added to quench the reaction. The reaction crude was filtered and purified via preparative HPLC, eluting 10-60% acetonitrile (0.1% TFA) in water (0.1% TFA) to give (3S,6S,7R)-12-(benzyloxy)-6-ethyl-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide. MS (m/z) 568.21 [M+H]$^+$.

Synthesis of (3S,6S,7R)-6-ethyl-6,12-dihydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide At room temperature (3S,6S,7R)-12-(benzyloxy)-6-ethyl-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (3 mg) was dissolved in in 2 mL ethanol and 2 mL ethyl acetate. Then 2 mg 10% Pd/C was added and hydrogen balloon was applied. After 2 hours, filtered off the catalyst through celite. The filtrate was concentrated down. The reaction crude was purified via preparative HPLC, eluting 10-60% acetonitrile (0.1% TFA) in water (0.1% TFA) to give the title compound. MS (m/z) 480.20 [M+H]$^+$. 1H NMR (400 MHz, Acetonitrile-d3) δ 10.44 (s, 1H), 8.27 (s, 1H), 6.87 (t, J=8.6 Hz, 2H), 6.69 (d, J=7.5 Hz, 1H), 4.79-4.51 (m, 2H), 4.06 (m, 1H), 3.76-3.48 (m, 3H), 1.90-1.74 (m, 2H), 1.65 (td, J=14.8, 7.5 Hz, 2H), 1.49-1.32 (m, 1H), 1.32-1.09 (m, 4H), 0.96 (t, J=7.2 Hz, 3H).

Example 29: Synthesis of (1R,10S,13S)-6,13-dihydroxy-10-methyl-5,8-dioxo-13-(trideuteriomethyl)-N-[(2,4,6-trifluorophenyl)methyl]-2,9-diazatricyclo[7.4.1.02,7]tetradeca-3,6,11-triene-4-carboxamide

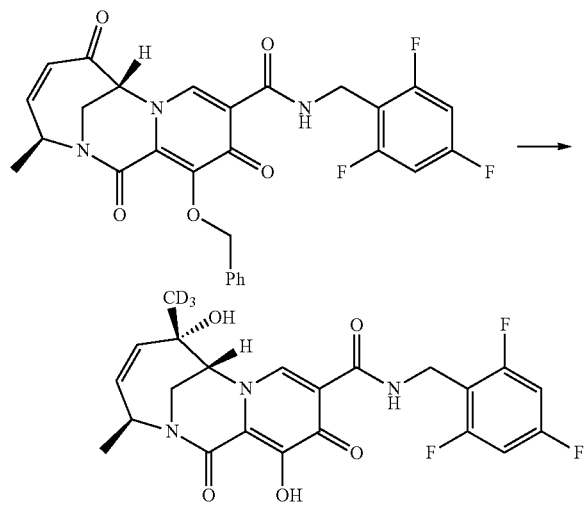

To a cold solution of (1R,10S)-6-benzyloxy-10-methyl-5,8,13-trioxo-N-[(2,4,6-trifluorophenyl)methyl]-2,9-diazatricyclo[7.4.1.02,7]tetradeca-3,6,11-triene-4-carboxamide (50 mg, 0.093 mmol) in THF (1.0 mL) at 0° C. was added 1.0 M CD3MgI in diethylether (0.279 mmol, 0.279 mL). The reaction was stirred at 0° C. for 30 minutes before it was quenched with ice and methanol. The reaction was then concentrated, redissolved in DMF, filtered and purified by reverse phase prep HPLC. (LCMS-ESI+(m/z): calcd H+ for C22H17D3F3N3O5, Theoretical: 466.15, Found: 467.35. 1H NMR (400 MHz, DMSO-d6) δ 10.46 (t, J=5.8 Hz, 1H), 8.36 (s, 1H), 7.21 (t, J=8.6 Hz, 2H), 5.54 (dd, J=11.8, 2.3 Hz, 1H), 5.39 (dd, J=11.8, 2.6 Hz, 1H), 5.32 (s, 1H), 5.13 (dt, J=7.3, 2.6 Hz, 1H), 4.67 (d, J=2.3 Hz, 1H), 4.59 (dt, J=11.3, 6.0 Hz, 2H), 3.86 (dd, J=14.8, 2.6 Hz, 1H), 3.63 (dd, J=14.8, 1.9 Hz, 1H), 1.27 (d, J=7.3 Hz, 3H).

Example 30: Synthesis of (1R,10S,13S)—N-[(2,4-difluorophenyl)methyl]-6,13-dihydroxy-10-methyl-5,8-dioxo-13-(trideuteriomethyl)-2,9-diazatricyclo[7.4.1.02,7]tetradeca-3,6,11-triene-4-carboxamide

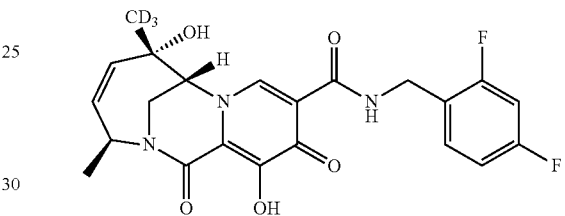

The title compound was prepared following the same method for the synthesis of Example 29 except (1R,10S)-6-benzyloxy-N-[(2,4-difluorophenyl)methyl]-10-methyl-5,8,13-trioxo-2,9-diazatricyclo[7.4.1.02,7]tetradeca-3,6,11-triene-4-carboxamide was used instead of (1R,10S)-6-benzyloxy-10-methyl-5,8,13-trioxo-N-[(2,4,6-trifluorophenyl)methyl]-2,9-diazatricyclo[7.4.1.02,7]tetradeca-3,6,11-triene-4-carboxamide. LCMS-ESI+(m/z): calcd H+ for C22H18D3F2N3O5, Theoretical: 448.16, Found: 449.23. 1H NMR (400 MHz, DMSO-d6) δ 10.44 (t, J=5.9 Hz, 1H), 8.38 (s, 1H), 7.42 (td, J=8.7, 6.6 Hz, 1H), 7.25 (ddd, J=11.9, 9.3, 2.6 Hz, 1H), 7.08 (td, J=8.5, 2.7 Hz, 1H), 5.54 (dd, J=11.9, 2.3 Hz, 1H), 5.40 (dd, J=11.9, 2.6 Hz, 2H), 5.13 (dt, J=7.1, 2.3 Hz, 1H), 4.70 (d, J=2.2 Hz, 1H), 4.56 (d, J=5.9 Hz, 2H), 3.87 (dd, J=14.7, 2.7 Hz, 1H), 3.65 (dd, J=14.7, 1.9 Hz, 1H), 1.28 (d, J=7.3 Hz, 3H).

Example 31: Synthesis of (1R,10S,13S)—N-[(2,4-difluorophenyl)methyl]-6,13-dihydroxy-10-methyl-5,8-dioxo-13-(trideuteriomethyl)-2,9-diazatricyclo[7.4.1.02,7]tetradeca-3,6-diene-4-carboxamide

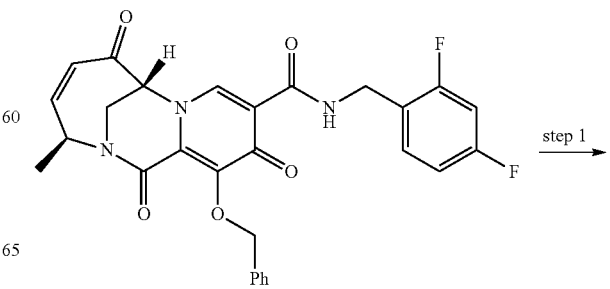

step 1

93

-continued

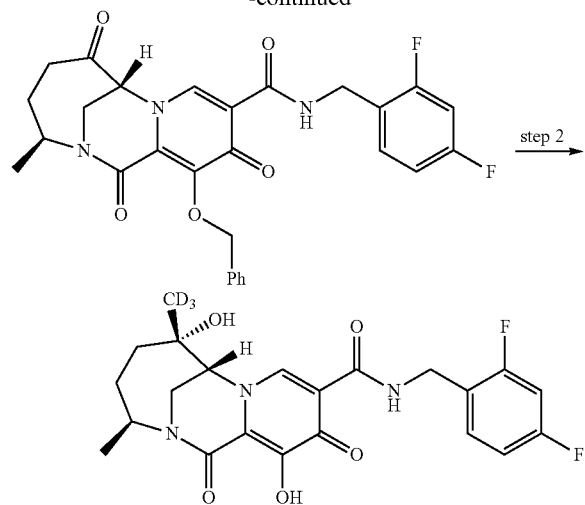

Step 1: Synthesis of (1R,10S)-6-benzyloxy-N-[(2,4-difluorophenyl)methyl]-10-methyl-5,8,13-trioxo-2,9-diazatricyclo[7.4.1.0²,⁷]tetradeca-3,6-diene-4-carboxamide To a solution of (1R,10S)-6-benzyloxy-N-[(2,4-difluorophenyl)methyl]-10-methyl-5,8,13-trioxo-2,9-diazatricyclo [7.4.1.02,7]tetradeca-3,6,11-triene-4-carboxamide (215 mg, 0.41 mmol) in EtOH (50 mL) at room temperature was added 20% Pd(OH)2/C (50 mg, 50 wt % water). The resulting suspension was degassed, flushed with nitrogen three times, then it was degassed and flushed with hydrogen three times before it was hydrogenated under hydrogen balloon for 3 hours. The reaction was then degassed and flushed with nitrogen and filtered through a pad of Celite. The filtrate was concentrated, and dried over the vacuum line. The residue was then dissolved in DMF (4.0 mL) and treated with potassium carbonate (171 mg, 1.24 mmol) and benzyl bromide (212 mg, 1.24 mmol) at room temperature for overnight. The reaction was then diluted with EtOAc, washed with water, then brine, dried over sodium sulfate, filtered and concentrated, purified by normal phase chromatography.

Step 2: Synthesis of (1R,10S,13S)—N-[(2,4-difluorophenyl)methyl]-6,13-dihydroxy-10-methyl-5,8-dioxo-13-(trideuteriomethyl)-2,9-diazatricyclo [7.4.1.02,7]tetradeca-3,6-diene-4-carboxamide The compound was prepared by following the synthesis of Example 29 except (1R,10S)-6-benzyloxy-N-[(2,4-difluorophenyl)methyl]-10-methyl-5,8,13-trioxo-2,9-diazatricyclo[7.4.1.02,7]tetradeca-3,6-diene-4-carboxamide was used instead of (1R,10S)-6-benzyloxy-10-methyl-5,8,13-trioxo-N-[(2,4,6-trifluorophenyl)methyl]-2,9-diazatricyclo [7.4.1.02,7]tetradeca-3,6,11-triene-4-carboxamide. LCMS-ESI+(m/z): calcd H+ for C22H20D3F2N3O5, Theoretical: 450.18, Found: 451.28. 1H NMR (400 MHz, DMSO-d6) δ 10.98 (s, 1H), 10.46 (t, J=6.0 Hz, 1H), 8.34 (s, 1H), 7.40 (td, J=8.7, 6.6 Hz, 1H), 7.25 (ddd, J=10.5, 9.3, 2.6 Hz, 1H), 7.07 (td, J=8.5, 2.6 Hz, 1H), 4.93 (s, 1H), 4.56 (d, J=5.9 Hz, 2H), 4.47 (dt, J=10.4, 6.5 Hz, 1H), 4.28 (s, 1H), 3.67 (t, J=2.5 Hz, 2H), 1.87 (dt, J=14.4, 7.0 Hz, 1H), 1.52-1.34 (m, 2H), 1.17 (t, J=7.6 Hz, 4H).

94

Example 32: Synthesis of (3S,6R,7R)-6,12-dihydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide

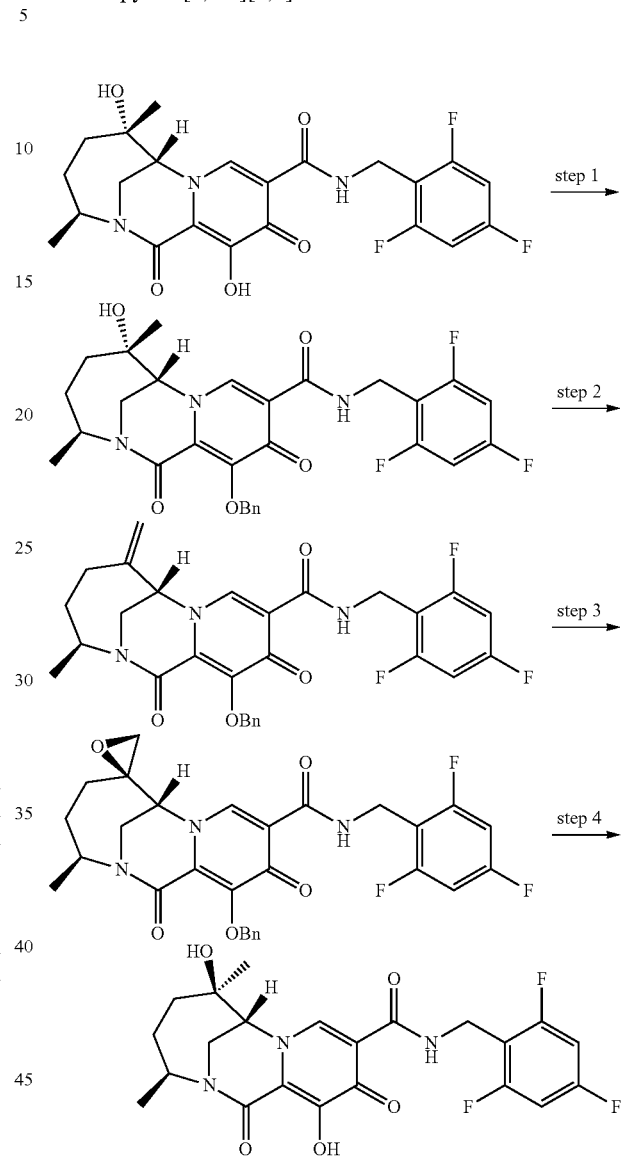

Synthesis of (3S,6S,7R)-12-(benzyloxy)-6-hydroxy-3,6-dimethyl-1,11-dioxo-N-(2,4,6-trifluorobenzyl)-1, 4,5,6,7,11-hexahydro-3H-2,7-methanopyrido[1,2-a] [1,4]diazonine-10-carboxamide To ((1R,10S,13S)-6,13-dihydroxy-10,13-dimethyl-5,8-dioxo-N-[(2,4,6-trifluorophenyl)methyl]-2,9-diazatricyclo [7.4.1.02,7]tetradeca-3,6-diene-4-carboxamide (Example 11, 165 mg, 0.355 mmol) was added DMF (7.0 mL), then potassium carbonate, then benzyl bromide. The mixture was stirred at 20° C. for 4 hr. The reaction was extracted with EtOAc, the organic layer was washed with water, then brine, dried over magnesium sulfate, filtered and concentrated. Flash column chromatography (silica gel, EtOAc/Hexane) yielded the product (stereochemistry assignment tentative). 1H NMR (400 MHz, Chloroform-d) δ 10.40 (t, J=5.6 Hz, 1H), 8.46 (s, 1H), 7.59-7.49 (m, 2H), 7.39-7.27 (m, 3H), 6.62 (dd, J=8.8, 7.4 Hz, 2H), 5.28 (d, J=10.3 Hz, 1H), 5.15 (d, J=10.3 Hz, 1H), 4.78 (dt, J=10.5, 6.7 Hz, 1H), 4.57 (dd, J=14.5, 5.7 Hz, 1H), 4.49 (dd, J=14.5, 5.4 Hz, 1H), 4.38 (s, 1H), 4.03 (s, 1H), 3.26 (dd, J=15.3, 3.0 Hz, 1H), 3.06 (dd, J=15.0, 1.5 Hz, 1H), 1.98 (dt, J=13.4, 6.8 Hz, 1H), 1.62-1.47 (m, 2H), 1.39 (s, 3H), 1.15 (d, J=6.7 Hz, 3H). LCMS-ESI+ (m/z): calcd H+ for $C_{23}H_{22}F_3N_3O_5$, Theoretical: 556.21, Found: 556.20.

Synthesis of (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide (3S,6S,7R)-12-(benzyloxy)-6-hydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (82 mg, 0.148 mmol) was dissolved in toluene (4.1 mL), then Martin sulfurane (506 mg, 0.75 mmol) was added. The mixture was stirred at 20° C. for 1 hr. The reaction mixture was purified directly by flash column chromatography (silica gel, EtOAc/Hexane) to yield the product. 1H NMR (400 MHz, Chloroform-d) δ 10.43 (t, J=5.8 Hz, 1H), 8.47 (s, 1H), 7.64-7.53 (m, 2H), 7.42-7.30 (m, 3H), 6.68 (dd, J=8.7, 7.5 Hz, 2H), 5.56 (d, J=10.2 Hz, 1H), 5.31 (s, 1H), 5.21-5.11 (m, 2H), 4.86 (dp, J=10.2, 6.7 Hz, 1H), 4.68 (d, J=5.7 Hz, 2H), 4.60 (s, 1H), 3.52 (dd, J=14.9, 2.6 Hz, 1H), 3.44 (dd, J=14.9, 1.9 Hz, 1H), 2.36 (dd, J=14.9, 7.3 Hz, 1H), 2.22 (dt, J=14.2, 7.0 Hz, 1H), 2.02-1.92 (m, 1H), 1.35 (dt, J=14.5, 10.8 Hz, 1H), 1.22 (d, J=6.8 Hz, 3H). LCMS-ESI+(m/z): calcd H+ for $C_{29}H_{26}F_3N_3O_4$, Theoretical: 538.20, Found: 538.16.

Synthesis of (2R,3'S,7'R)-12'-(benzyloxy)-3'-methyl-1',11'-dioxo-N-(2,4,6-trifluorobenzyl)-1',4',5',11'-tetrahydro-3'H,7'H-spiro[oxirane-2,6'-[2,7]methanopyrido[1,2-a][1,4]diazonine]-10'-carboxamide (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide (30 mg, 0.0558 mmol) was dissolved in dichloromethane (3.0 mL), then 3-chloroperoxybenzoic acid (88 mg, 0.391 mmol) was added. The mixture was stirred in a metal heating block at 45° C. for 48 hr. The reaction mixture was diluted with more dichloromethane, then the organic phase was washed with 2 N aqueous sodium hydroxide, then brine. The combined aqueous phases were extracted with additional dichloromethane. The combined organic phases were dried over magnesium sulfate, filtered and concentrated. Flash column chromatography (silica gel, EtOAc/Hexane) yielded the product (stereochemistry assignment tentative). 1H NMR (400 MHz, Chloroform-d) δ 10.33 (s, 1H), 8.33 (s, 1H), 7.61-7.51 (m, 2H), 7.32 (dd, J=12.1, 7.2 Hz, 3H), 6.67 (t, J=8.1 Hz, 2H), 5.54 (d, J=10.2 Hz, 1H), 5.17 (d, J=10.2 Hz, 1H), 4.90 (dt, J=10.7, 6.6 Hz, 1H), 4.66 (dd, J=5.6, 3.1 Hz, 2H), 3.64 (dd, J=14.9, 1.8 Hz, 1H), 3.52 (s, 1H), 3.44 (dd, J=15.1, 2.5 Hz, 1H), 3.21 (d, J=3.7 Hz, 1H), 2.79 (d, J=3.7 Hz, 1H), 2.07-1.98 (m, 1H), 1.79 (ddd, J=39.5, 15.0, 11.6 Hz, 2H), 1.24 (d, J=6.8 Hz, 3H). LCMS-ESI+(m/z): calcd H+ for $C_{29}H_{26}F_3N_3O_5$, Theoretical: 554.19, Found: 554.21.

Synthesis of (3S,6R,7R)-6,12-dihydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide ((2R,3'S,7'R)-12'-(benzyloxy)-3'-methyl-1',11'-dioxo-N-(2,4,6-trifluorobenzyl)-1',4',5',11'-tetrahydro-3'H,7'H-spiro[oxirane-2,6'-[2,7]methanopyrido[1,2-a][1,4]diazonine]-10'-carboxamide (4 mg, 0.007 mmol) was dissolved in ethanol (0.5 mL), then ammonium formate (23 mg, 0.36 mmol) was added, followed by 10% palladium on carbon (1.54 mg, 0.0015 mmol). The mixture was stirred in a metal heating block at 70° C. for 12 hr. The reaction mixture was diluted with 1:1 DMF:water, filtered, and purified by reverse-phase HPLC (acetonitrile/water, 0.1% trifluoroacetic acid) to yield the product (stereochemistry assignment tentative). 1H NMR (400 MHz, DMSO-d6) δ 11.00 (s, 1H), 10.45-10.33 (m, 1H), 8.35 (s, 1H), 7.21 (t, J=8.8 Hz, 2H), 5.16 (s, 1H), 4.56 (d, J=5.5 Hz, 2H), 4.48 (s, 1H), 4.27 (s, 1H), 3.70 (d, J=14.9 Hz, 1H), 3.60 (d, J=14.7 Hz, 1H), 1.87-1.75 (m, 2H), 1.75-1.65 (m, 1H), 1.52 (dd, J=16.0, 6.6 Hz, 1H), 1.16 (d, J=7.0 Hz, 3H), 1.02 (s, 3H). LCMS-ESI+ (m/z): calcd H+ for $C_{22}H_{22}F_3N_3O_5$, Theoretical: 466.16, Found: 466.27.

Example 33: Synthesis of (1R,10S,13R)—N-[(2,4-difluorophenyl)methyl]-6,13-dihydroxy-10,13-dimethyl-5,8-dioxo-2,9-diazatricyclo[7.4.1.02,7]tetradeca-3,6-diene-4-carboxamide

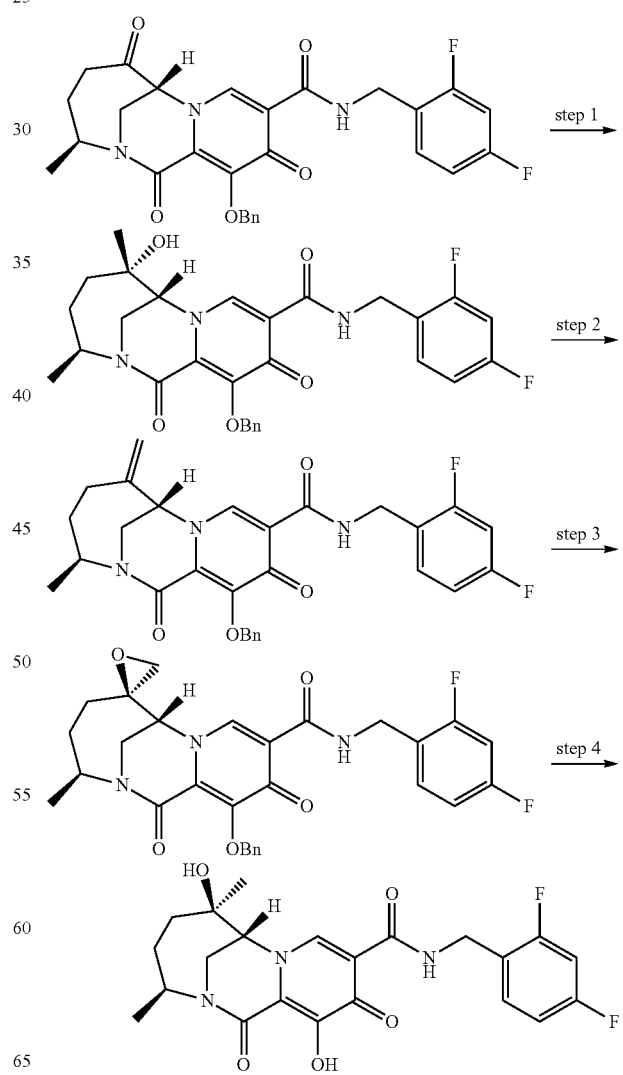

Step 1: Synthesis of (1R,10S)-6-benzyloxy-N-[(2,4-difluorophenyl)methyl]-13-hydroxy-10,13-dimethyl-5,8-dioxo-2,9-diazatricyclo[7.4.1.02,7]tetradeca-3,6-diene-4-carboxamide (1R,10S)-6-benzyloxy-N-[(2,4-difluorophenyl)methyl]-10-methyl-5,8,13-trioxo-2,9-diazatricyclo[7.4.1.02,7]tetradeca-3,6-diene-4-carboxamide (200 mg, 0.384 mmol) was dissolved in THF (4.0 mL) and cooled to 0° C. To this cold mixture was added 3.0 M MeMgBr in Et$_2$O (0.38 mL, 1.15 mmol) dropwise. The reaction was stirred at 0° C. for 20 minutes before it was quenched with ice water. The mixture was then diluted with EtOAc, washed with saturated ammonium chloride, brine, dried over sodium sulfate, filtered and concentrated, purified by normal phase chromatography. LCMS-ESI+(m/z): calcd H+ for C29H29F2N3O5, Theoretical: 537.21, Found: 538.17.

Step 2: Synthesis of (1S,10S)-6-benzyloxy-N-[(2,4-difluorophenyl)methyl]-10-methyl-13-methylene-5,8-dioxo-2,9-diazatricyclo[7.4.1.02,7]tetradeca-3,6-diene-4-carboxamide (1R,10S)-6-benzyloxy-N-[(2,4-difluorophenyl)methyl]-13-hydroxy-10,13-dimethyl-5,8-dioxo-2,9-diazatricyclo[7.4.1.02,7]tetradeca-3,6-diene-4-carboxamide (81 mg, 0.151 mmol) was dissolved in Toluene (3.0 mL) at room temperature and treated with martin sulfurane dehydration reagent (507 mg, 0.753 mmol) for 20 min. the reaction was concentrated and purified by normal phase chromatography. LCMS-ESI+(m/z): calcd H+ for C29H27F2N3O4, Theoretical: 519.20, Found: 520.22.

Step 3: Synthesis of (1R,10S,13R)-6-benzyloxy-N-[(2,4-difluorophenyl)methyl]-10-methyl-5,8-dioxo-spiro[2,9-diazatricyclo[7.4.1.02,7]tetradeca-3,6-diene-13,2'-oxirane]-4-carboxamide (1S,10S)-6-benzyloxy-N-[(2,4-difluorophenyl)methyl]-10-methyl-13-methylene-5,8-dioxo-2,9-diazatricyclo[7.4.1.02,7]tetradeca-3,6-diene-4-carboxamide (57 mg, 0.11 mmol) was dissolved in DCE (2.0 mL) and treated with MCPBA (56.8 mg, 0.329 mmol) at 60° C. for 3 hours. The reaction was cooled to room temperature, diluted with DCM, mixed with 1:1 mixture of 1 N sodium thiosulfate and saturated sodium bicarbonate, stirred vigorously for 10 minutes. Layers were separated. The organic layer was washed with brine, dried over sodium sulfate, filtered and concentrated, purified by normal phase chromatography. LCMS-ESI+(m/z): calcd H+ for C29H27F2N3O5, Theoretical: 535.19, Found: 536.17.

Step 4: Synthesis of (1R,10S,13R)—N-[(2,4-difluorophenyl)methyl]-6,13-dihydroxy-10,13-dimethyl-5,8-dioxo-2,9-diazatricyclo[7.4.1.02,7]tetradeca-3,6-diene-4-carboxamide (1R,10S,13R)-6-benzyloxy-N-[(2,4-difluorophenyl)methyl]-10-methyl-5,8-dioxo-spiro[2,9-diazatricyclo[7.4.1.02,7]tetradeca-3,6-diene-13,2'-oxirane]-4-carboxamide (10 mg, 0.0187 mmol) was dissolved in EtOH (0.5 mL), treated with ammonium formate (59 mg, 0.934 mmol) and 10% Pd/C (3.97 mg). The resulting mixture was degassed and flushed with nitrogen three times and then heated at 70° C. for 3 hours under nitrogen. The reaction was then cooled to room temperature, filtered and concentrated, redissolved in DMF, filtered and purified by reverse phase prep HPLC.

LCMS-ESI+(m/z): calcd H+ for C22H23F2N3O5, Theoretical: 447.16, Found: 448.256. 1H NMR (400 MHz, DMSO-d6) δ 11.04 (s, 1H), 10.37 (t, J=6.0 Hz, 1H), 8.38 (s, 1H), 7.41 (td, J=8.6, 6.5 Hz, 1H), 7.34-7.18 (m, 1H), 7.08 (td, J=8.6, 2.7 Hz, 1H), 5.16 (s, 1H), 4.52 (dt, J=22.6, 6.3 Hz, 3H), 4.30 (s, 1H), 3.75-3.61 (m, 2H), 1.92-1.64 (m, 2H), 1.53 (dd, J=15.3, 6.7 Hz, 1H), 1.17 (d, J=6.7 Hz, 4H), 1.03 (s, 3H).

Example 34: (3S,6S,7R)—N-(2,4-difluorobenzyl)-12-hydroxy-6-(methoxy-d3)-3-methyl-1,11-dioxo-1,4,5,6,7,11-hexahydro-3H-2,7-methanopyrido[1,2-a][1,4]diazonine-10-carboxamide

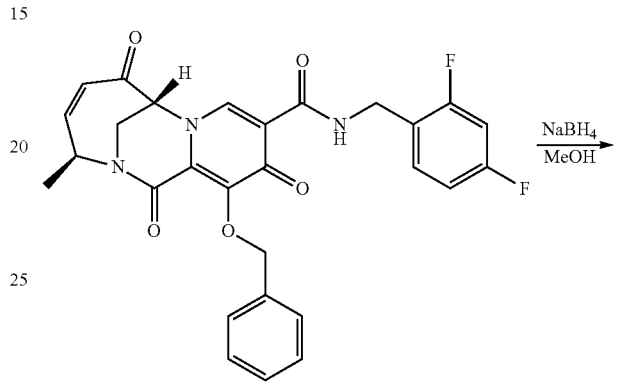

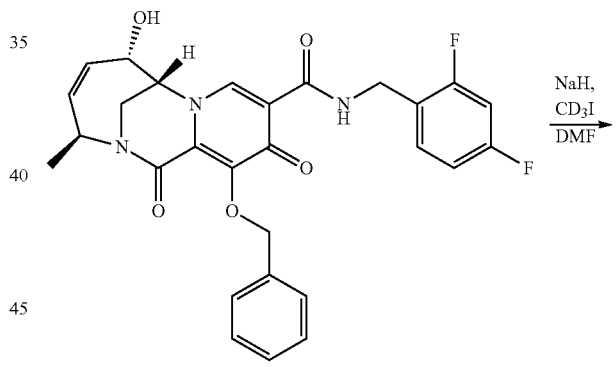

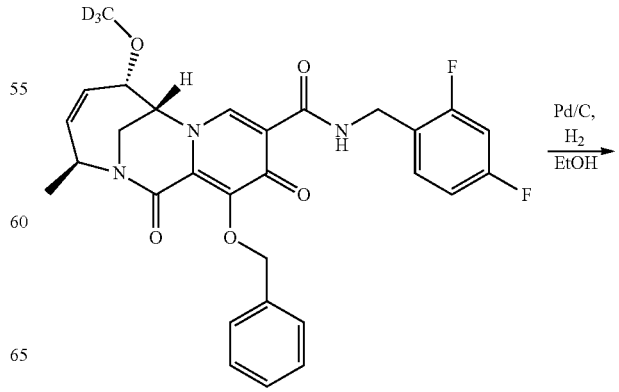

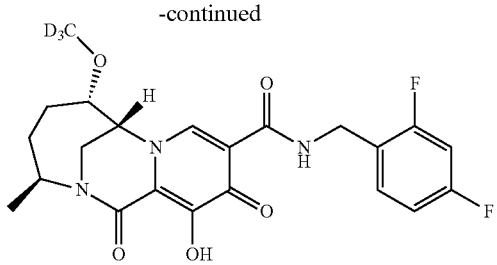

Preparation of (3S,6S,7R)-12-(benzyloxy)-N-(2,4-difluorobenzyl)-6-(methoxy-d3)-3-methyl-1,11-dioxo-1,6,7,11-tetrahydro-3H-2,7-methanopyrido[1,2-a][1,4]diazonine-10-carboxamide (3S,6S,7R)-12-(benzyloxy)-N-(2,4-difluorobenzyl)-6-(methoxy-d3)-3-methyl-1,11-dioxo-1,6,7,11-tetrahydro-3H-2,7-methanopyrido[1,2-a][1,4]diazonine-10-carboxamide was made similar to (3 S,6S,7R)-12-(benzyloxy)-N-(2,4-difluorobenzyl)-6-methoxy-3-methyl-1,11-dioxo-1,6,7,11-tetrahydro-3H-2,7-methanopyrido[1,2-a][1,4]diazonine-10-carboxamide in Example 18, except that iodomethane-d3 was used instead of iodomethane and that (3S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide was used instead of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide.

Preparation of (3S,6S,7R)—N-(2,4-difluorobenzyl)-12-hydroxy-6-(methoxy-d3)-3-methyl-1,11-dioxo-1,4,5,6,7,11-hexahydro-3H-2,7-methanopyrido[1,2-a][1,4]diazonine-10-carboxamide To a solution of (3S,6S,7R)-12-(benzyloxy)-N-(2,4-difluorobenzyl)-6-(methoxy-d3)-3-methyl-1,11-dioxo-1,6,7,11-tetrahydro-3H-2,7-methanopyrido[1,2-a][1,4]diazonine-10-carboxamide (35 mg, 0.065 mmol) in EtOH (3 mL) was added Pd/C (10 mg). The reaction mixture was stirred at room temperature under H2 balloon. After the reaction was finished, the reaction mixture was filtered through celite, the filtrate was concentrated down and the residue was purified by reverse phase chromatography (eluting with 5-100% acetonitrile in water, containing 0.1% TFA) to give the title compound. MS (m/z) 451.2 [M+H]+. ¹H NMR (400 MHz, Methanol-d4) δ 8.36 (s, 1H), 7.45 (q, J=8.3 Hz, 1H), 7.04-6.85 (m, 2H), 4.80-4.53 (m, 4H), 3.94-3.64 (m, 2H), 3.55 (d, J=11.7 Hz, 1H), 2.19-1.96 (m, 2H), 1.54 (dt, J=14.5, 11.2 Hz, 1H), 1.28 (d, J=6.7 Hz, 3H), 1.01 (dt, J=14.8, 11.6 Hz, 1H).

Example 35: Synthesis of (1R,10R,13S)—N-[(2,4-difluorophenyl)methyl]-6,13-dihydroxy-10,13-dimethyl-5,8-dioxo-2,9-diazatricyclo[7.4.1.02,7]tetradeca-3,6-diene-4-carboxamide

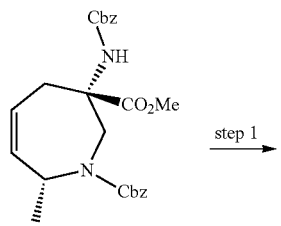

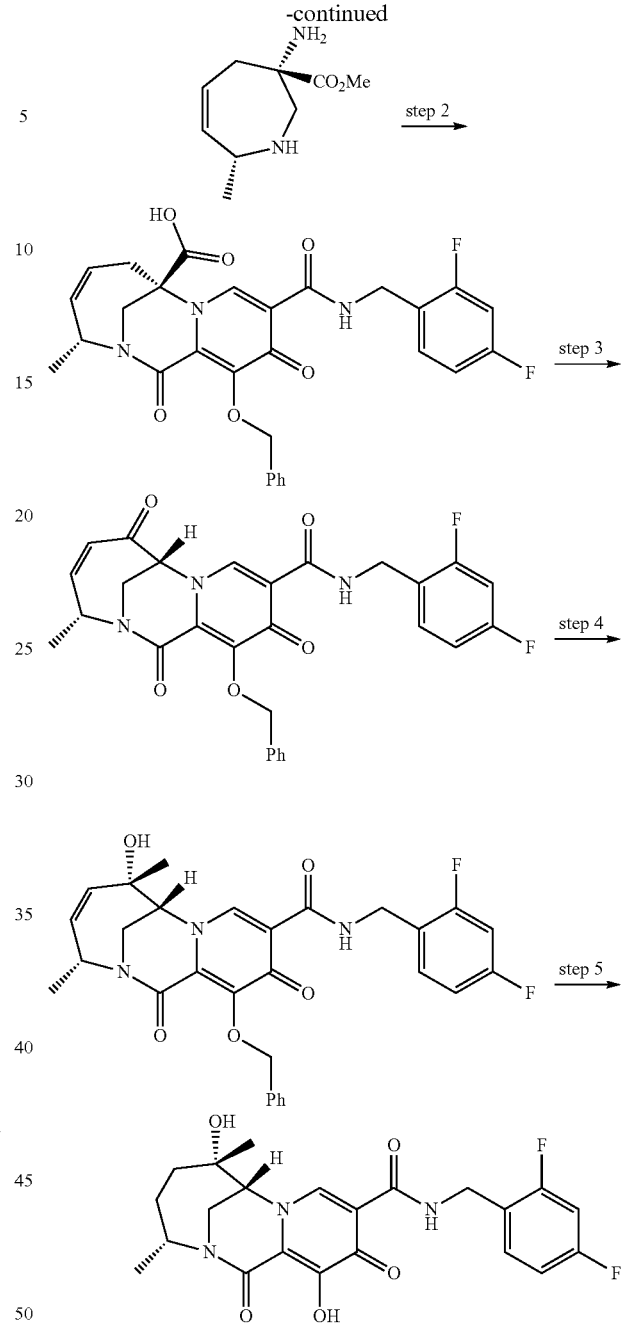

Step 1: Synthesis of methyl (3S,7R)-3-amino-7-methyl-1,2,4,7-tetrahydroazepine-3-carboxylate; 2,2,2-trifluoroacetic acid O1-benzyl O3-methyl (3S,7R)-3-(benzyloxycarbonylamino)-7-methyl-4,7-dihydro-2H-azepine-1,3-dicarboxylate (1.2 g, 2.65 mmol) was mixed with TFA (10.0 mL). The resulting mixture was sealed and heated at 100° C. for 4 hours. The reaction was cooled to room temperature and concentrated, the residue was coevaporated with EtOAc for 4 times to give desired product, which was used directly in next step. LCMS-ESI+(m/z): calcd H+ for C9H16N2O2, Theoretical: 184.12, Found: 185.01.

Step 2: Synthesis of (1S,10R)-6-benzyloxy-4-[(2,4-difluorophenyl)methylcarbamoyl]-10-methyl-5,8-dioxo-2,9-diazatricyclo[7.4.1.02,7]tetradeca-3,6,11-triene-1-carboxylic acid The residue from previous step (2.36 g, 5.72 mmol) and methyl 3-benzyloxy-4-oxo-5-[(2,4,6-trifluorophenyl)methylcarbamoyl]pyran-2-carboxylate (1.08 g, 2.52 mmol) was suspended in a mixture of THF (6.0 mL), ethanol (1.0 mL) and triethylamine (5.36 g, 53 mmol). The resulting mixture was heated at 40° C. for overnight. The reaction was cooled to room temperature. The residue was partitioned between EtOAc and water, organic layer was washed with 10% citric acid, water, brine, dried over sodium sulfate, filtered, concentrated and purified by normal phase chromatography. LCMS-ESI+(m/z): calcd H+ for C29H25F2N3O6, Theoretical: 549.17, Found: 550.10.

Step 3: Synthesis of (1R,10R)-6-benzyloxy-N-[(2,4-difluorophenyl)methyl]-10-methyl-5,8,13-trioxo-2,9-diazatricyclo[7.4.1.02,7]tetradeca-3,6,11-triene-4-carboxamide (1S,10R)-6-benzyloxy-4-[(2,4-difluorophenyl)methylcarbamoyl]-10-methyl-5,8-dioxo-2,9-diazatricyclo[7.4.1.02,7]tetradeca-3,6,11-triene-1-carboxylic acid (470 mg, 0.855 mmol) was dissolved in 1,4-dioxane (8.0 mL) and treated with Selenium dioxide (753 mg, 6.84 mmol) at 100° C. for 8 hours. The reaction was cooled to room temperature, filtered and concentrated, purified by normal phase chromatography. LCMS-ESI+(m/z): calcd H+ for C29H23F2N3O6, Theoretical: 519.16, Found: 520.04.

Step 4: synthesis of (1R,10R,13S)-6-benzyloxy-N-[(2,4-difluorophenyl)methyl]-13-hydroxy-10,13-dimethyl-5,8-dioxo-2,9-diazatricyclo[7.4.1.02,7]tetradeca-3,6,11-triene-4-carboxamide The compound was prepared following Step 1 of the preparation of Example 17 except (1R,10R)-6-benzyloxy-N-[(2,4-difluorophenyl)methyl]-10-methyl-5,8,13-trioxo-2,9-diazatricyclo[7.4.1.02,7]tetradeca-3,6,11-triene-4-carboxamide was used instead of (1R,10S)-6-benzyloxy-N-[(2,4-difluorophenyl)methyl]-10-methyl-5,8,13-trioxo-2,9-diazatricyclo[7.4.1.02,7]tetradeca-3,6,11-triene-4-carboxamide. LCMS-ESI+(m/z): calcd H+ for C29H27F2N3O5, Theoretical: 535.19, Found: 536.13. Stereochemistry at C13 not confirmed.

Step 5: Synthesis of (1R,10R,13S)—N-[(2,4-difluorophenyl)methyl]-6,13-dihydroxy-10,13-dimethyl-5,8-dioxo-2,9-diazatricyclo[7.4.1.02,7]tetradeca-3,6-diene-4-carboxamide (1R,10R,13S)-6-benzyloxy-N-[(2,4-difluorophenyl)methyl]-13-hydroxy-10,13-dimethyl-5,8-dioxo-2,9-diazatricyclo[7.4.1.02,7]tetradeca-3,6,11-triene-4-carboxamide (40 mg, 0.0747 mmol) was dissolved in EtOH (10 mL) at room temperature. To this mixture was added 10% Pd/C (30 mg) and ammonium formate (235 mg, 3.73 mmol). The resulting mixture was degassed and flushed with nitrogen then it was heated at 70° C. for 1 hr. The reaction was cooled to room temperature, filtered, concentrated and purified by reverse phase prep HPLC. Stereochemistry at C13 not confirmed. LCMS-ESI+(m/z): calcd H+ for C22H23F2N3O5, Theoretical: 447.16, Found: 448.23. 1H NMR (400 MHz, Acetone-d6) δ 11.11 (s, 1H), 10.55 (s, 1H), 8.32 (s, 1H), 7.53-7.44 (m, 1H), 7.08-6.96 (m, 2H), 4.62 (t, J=4.5 Hz, 2H), 4.53-4.46 (m, 1H), 4.08 (dd, J=15.2, 2.1 Hz, 1H), 3.83 (dd, J=15.1, 2.5 Hz, 1H), 3.73 (dt, J=14.5, 7.0 Hz, 1H), 2.18 (q, J=5.6, 5.0 Hz, 1H), 2.05-1.89 (m, 3H), 1.87-1.77 (m, 1H), 1.74 (d, J=7.1 Hz, 3H), 1.55 (s, 3H).

Intermediate C: (3S,7S)-12-(benzyloxy)-3-methyl-1,4,11-trioxo-N-(2,4,6-trifluorobenzyl)-1,4,7,11-tetrahydro-3H-2,7-methanopyrido[1,2-a][1,4]diazonine-10-carboxamide

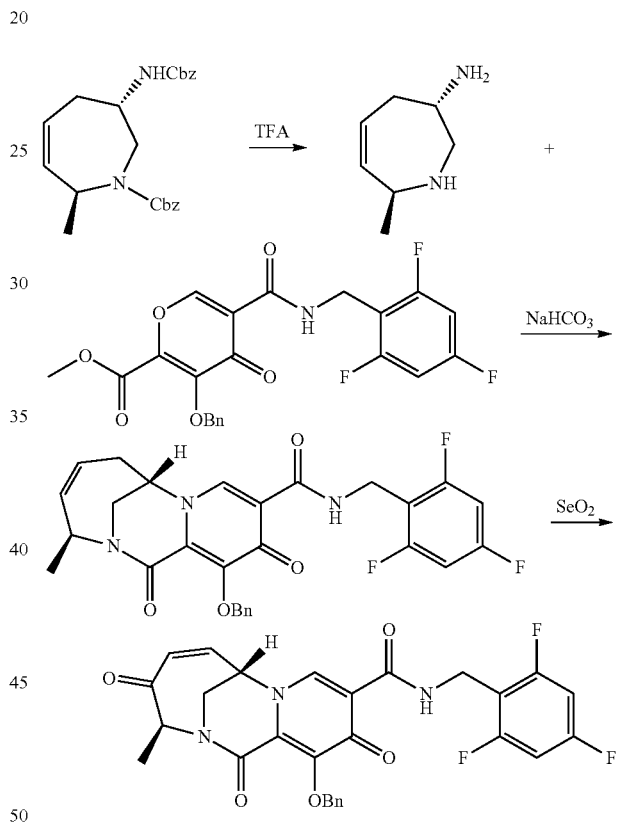

(3S,7S)-12-(benzyloxy)-3-methyl-1,4,11-trioxo-N-(2,4,6-trifluorobenzyl)-1,4,7,11-tetrahydro-3H-2,7-methanopyrido[1,2-a][1,4]diazonine-10-carboxamide (Intermediate C) was synthesized in the same manner as for Intermediate A, and was isolated as an additional product from the identical reaction conditions. 1H NMR (400 MHz, Chloroform-d) δ 10.41 (t, J=5.8 Hz, 1H), 8.66 (s, 1H), 7.58-7.46 (m, 2H), 7.41-7.27 (m, 3H), 6.76-6.56 (m, 2H), 6.31 (d, J=12.4 Hz, 1H), 6.11 (d, J=12.2 Hz, 1H), 5.50 (d, J=10.2 Hz, 1H), 5.28 (q, J=7.0 Hz, 1H), 5.15 (d, J=10.2 Hz, 1H), 4.98 (s, 1H), 4.66 (d, J=5.7 Hz, 2H), 3.75 (d, J=15.0 Hz, 1H), 3.50 (d, J=14.9 Hz, 1H), 1.46 (d, J=7.0 Hz, 3H). LCMS-ESI+ (m/z): calcd H+ for $C_{28}H_{22}F_3N_3O_5$, Theoretical: 538.16, Found: 538.10.

Example 36: Synthesis of (3S,6R,7R)-4,4-difluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

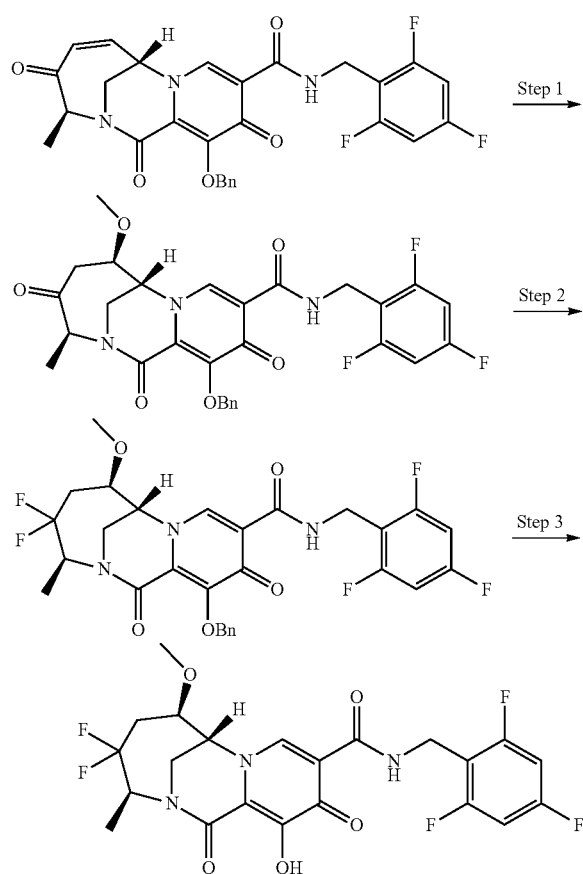

Step 1: Synthesis of (3S,6R,7R)-12-(benzyloxy)-6-methoxy-3-methyl-1,4,11-trioxo-N-(2,4,6-trifluorobenzyl)-1,4,5,6,7,11-hexahydro-3H-2,7-methanopyrido[1,2-a][1,4]diazonine-10-carboxamide To (3S,7S)-12-(benzyloxy)-3-methyl-1,4,11-trioxo-N-(2,4,6-trifluorobenzyl)-1,4,7,11-tetrahydro-3H-2,7-methanopyrido[1,2-a][1,4]diazonine-10-carboxamide (Intermediate C, 50 mg, 0.093 mmol) was added triethylamine hydrochloride (12.8 mg, 0.093 mmol), then methanol (2.0 mL), then water (0.5 mL), then triethylamine (30 μL, 0.214 mmol), then potassium cyanide (6.0 mg, 0.093 mmol). The reaction was stirred in metal heating block at 60° C. for 1 hr. The reaction was partitioned between EtOAc, 10% aqueous sodium carbonate. The organic phase was washed with saturated aqueous ammonium chloride, then brine. The aqueous $Na_2CO_3$ phase was extracted with more ethyl acetate. The combined organic phases were dried over $MgSO_4$, filtered, concentrated in vacuo. Flash column chromatography (silica gel, EtOAc/Hexane) yielded the product (stereochemistry assignment tentative). 1H NMR (400 MHz, Chloroform-d) δ 10.27 (t, J=6.0 Hz, 1H), 8.52 (s, 1H), 7.61-7.48 (m, 2H), 7.46-7.29 (m, 3H), 6.67 (dd, J=8.7, 7.5 Hz, 2H), 5.57 (d, J=10.3 Hz, 1H), 5.16 (d, J=10.3 Hz, 1H), 5.10 (d, J=7.0 Hz, 1H), 4.67 (dd, J=5.7, 3.6 Hz, 2H), 4.24 (s, 1H), 3.80 (t, J=4.1 Hz, 1H), 3.55 (dt, J=15.3, 1.8 Hz, 1H), 3.48 (s, 3H), 3.45 (dd, J=15.2, 1.8 Hz, 1H), 2.91 (dd, J=13.6, 5.7 Hz, 1H), 2.70 (dd, J=13.5, 1.6 Hz, 1H), 1.36 (d, J=7.0 Hz, 3H). LCMS-ESI+(m/z): calcd H+ for $C_{29}H_{26}F_3N_3O_6$, Theoretical: 570.18, Found: 570.13.

Step 2: Synthesis of (3S,6R,7R)-12-(benzyloxy)-4,4-difluoro-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide To ((1R,10S,13S)-6,13-dihydroxy-10,13-dimethyl-5,8-dioxo-N-[(2,4,6-trifluorophenyl)methyl]-2,9-diazatricyclo [7.4.1.02,7]tetradeca-3,6-diene-4-carboxamide (50 mg, 0.355 mmol) was added DCM (0.88 mL), then 2.7 M solution in toluene of Deoxo-Fluor (3.25 mL, 8.8 mmol). The mixture was stirred at 20° C. for 60 hr. The reaction was quenched by slow addition into ice-cold 10% aqueous potassium carbonate, then extracted with EtOAc. The organic layer was washed with saturated aqueous ammonium chloride, then brine, dried over magnesium sulfate, filtered and concentrated. Flash column chromatography (silica gel, EtOAc/Hexane) yielded the product (stereochemistry assignment tentative). LCMS-ESI+(m/z): calcd H+ for $C_{29}H_{26}F_5N_3O_5$, Theoretical: 592.19, Found: 592.11.

Step 3: Synthesis of (3S,6R,7R)-4,4-difluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (3S,6R,7R)-12-(benzyloxy)-4,4-difluoro-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (30 mg) was dissolved in 1:1 toluene: trifluoroacetic acid (2.2 mL). The resulting solution was stirred at 60° C. for 30 min. The solution was diluted with acetonitrile and concentrated in vacuo, and the resulting crude was purified by reverse-phase preparative HPLC (acetonitrile/water, 0.1% trifluoroacetic acid). Crude residue was further washed with a minimal amount of dichloromethane to yield the product (stereochemistry assignment tentative). 1H NMR (400 MHz, Acetonitrile-d3) δ 10.29 (s, 1H), 8.39 (s, 1H), 6.88 (dd, J=9.2, 8.1 Hz, 2H), 4.95 (dt, J=13.8, 7.0 Hz, 1H), 4.63 (d, J=5.9 Hz, 2H), 4.49 (d, J=2.9 Hz, 1H), 3.91 (dd, J=15.4, 2.6 Hz, 1H), 3.75-3.61 (m, 2H), 3.38 (s, 3H), 2.58 (ddd, J=27.6, 15.6, 8.5 Hz, 1H), 2.36-2.21 (m, 1H), 1.39 (dd, J=7.2, 2.8 Hz, 3H). LCMS-ESI+(m/z): calcd H+ for $C_{22}H_{20}F5N_3O_5$, Theoretical: 502.14, Found: 502.24.

Example 37: (3S,4S,6R,7R)-4-fluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

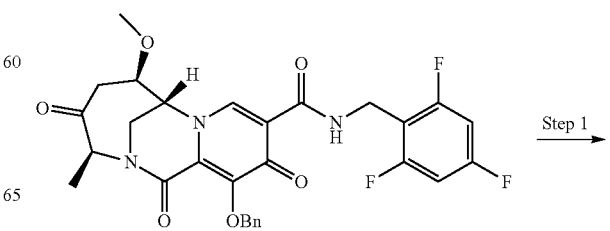

Step 1

-continued

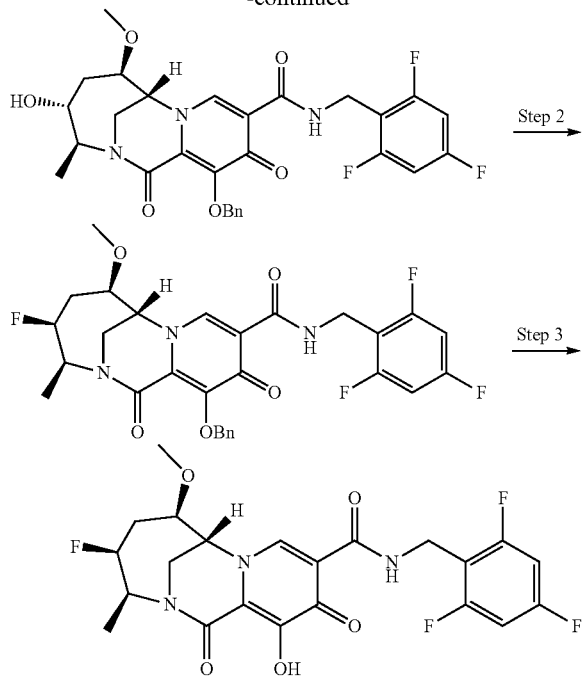

Step 1: Synthesis of (3S,4R,6R,7R)-12-(benzyloxy)-4-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide A mixture of (3S,6R,7R)-12-(benzyloxy)-6-methoxy-3-methyl-1,4,11-trioxo-N-(2,4,6-trifluorobenzyl)-1,4,5,6,7,11-hexahydro-3H-2,7-methanopyrido[1,2-a][1,4]diazonine-10-carboxamide (770.8 mg, 1.35 mmol), prepared according to Example 36, in methanol (30 mL) was stirred at 0° C. and NaBH4 (57.7 mg, 1.53 mmol) was added. After 3 min, THF (~10 mL) was to dissolve the insoluble material. The reaction mixture was concentrated, and the residue was dissolved in ethyl acetate (~50 mL) and saturated NaHCO3 (~25 mL) and water (~25 mL). After separation of two layers, the aqueous fraction was extracted with ethyl acetate (~50 mL). The two organic fractions were washed with brine, combined, dried (MgSO4), and concentrated. The residue was purified by column chromatography on silica gel (80 g column) eluting 0-10% methanol in CH2Cl2 to get (3S,4R,6R,7R)-12-(benzyloxy)-4-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide. ES/MS m/z: calculated for C29H29F3N3O6 (M+H): 572.20, found: 572.20.

Step 2: Synthesis of (3S,4S,6R,7R)-12-(benzyloxy)-4-fluoro-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide A solution of (3S,4R,6R,7R)-12-(benzyloxy)-4-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (811.2 mg, 1.42 mmol) in CH2Cl2 (14 mL) was stirred at 0° C. as 2.7 M Deoxo-Fluor (bis(2-methoxyethyl)aminosulfur trifluoride) solution in toluene (1.39 mL, 3.75 mmol) was added. After 30 min, the reaction mixture was stirred at room temperature overnight. The reaction mixture was cooled and stirred at 0° C. as saturated NaHCO3 (~40 mL) was added. After water was added (~40 mL). the product was extracted with ethyl acetate (~70 mL×2). After the extracts were washed with brine (~70 mL×1), the combined organic fractions were dried (MgSO4). The residue was purified by column chromatography on silica gel (80 g column) eluting 50-100% ethyl acetate in hexane to get (3S,4S,6R,7R)-12-(benzyloxy)-4-fluoro-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide: ES/MS m/z: calculated for C29H28F4N3O5 (M+H): 574.20, found: 574.30.

Step 3: Synthesis of (3S,4S,6R,7R)-4-fluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (3S,4S,6R,7R)-12-(benzyloxy)-4-fluoro-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (556.5 mg, 0.970 mmol) was dissolved in toluene (0.25 mL) and trifluoroacetic acid (10 mL). The resulting mixture was stirred at room temperature for 1 h and at 60° C. for 1 h. The reaction mixture was concentrated, and the residue was dissolved in ethyl acetate (~25 mL) before washed with saturated NaHCO3 (~25 mL). After separating two layers, the aqueous fraction was extracted with ethyl acetate (~25 mL). The organic fractions were washed with brine, combined, dried (MgSO4), and concentrated. The residue was purified by column chromatography on silica gel (50 g column) eluting 0-10% methanol in CH2Cl2 to get the product. The impure product was purified again using column chromatography on silica gel (40 g column) eluting 0-10% methanol in ethyl acetate to get (3S,4S,6R,7R)-4-fluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide: 1H NMR (400 MHz, Acetonitrile-d3) δ 10.62 (s, 1H), 10.31 (t, J=6.0 Hz, 1H), 8.37 (s, 1H), 6.84 (t, J=8.5 Hz, 2H), 5.01-4.70 (m, 2H), 4.60 (d, J=5.9 Hz, 2H), 4.48 (q, J=2.4 Hz, 1H), 3.91 (dd, J=15.1, 2.3 Hz, 1H), 3.73-3.57 (m, 2H), 3.37 (s, 3H), 2.53 (ddd, J=15.3, 8.4, 6.5 Hz, 1H), 1.85-1.65 (m, 1H), 1.33 (dd, J=7.1, 2.7 Hz, 3H); 19F NMR (376 MHz, Acetonitrile-d3) δ -111.21 (ddd, J=15.3, 9.1, 6.1 Hz), -113.91 (t, J=7.0 Hz), -193.86 (ddd, J=46.9, 31.9, 16.7 Hz); ES/MS m/z: calculated for C22H22F4N3O5 (M+H): 484.15, found: 484.20.

Example 38: (3S,4R,6R,7R)-4-fluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

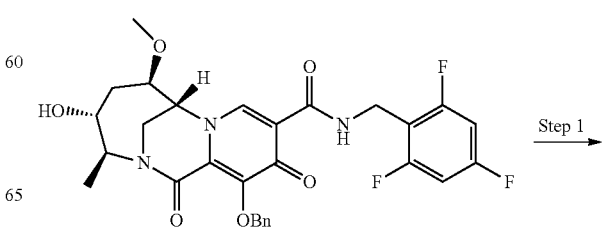

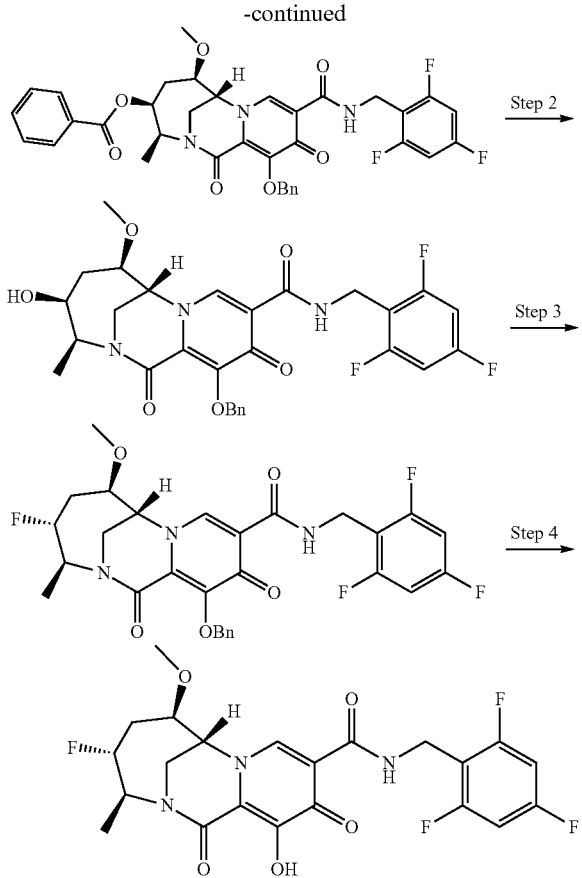

Step 1: Synthesis of (3S,4S,6R,7R)-12-(benzyloxy)-6-methoxy-3-methyl-1,11-dioxo-10-((2,4,6-trifluorobenzyl)carbamoyl)-1,4,5,6,7,11-hexahydro-3H-2,7-methanopyrido[1,2-a][1,4]diazonin-4-yl benzoate To (3S,4R,6R,7R)-12-(benzyloxy)-4-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (prepared according to Example 37, 45 mg, 0.079 mmol) was added 2-methyltetrahydrofuran (1.6 mL), then triphenylphosphine (54 mg, 0.205 mmol), then benzoic acid (25 mg, 0.205 mmol), then diisopropylazodicarboxylate (41 mg, 0.205 mmol). The reaction was stirred at 20° C. for 1.5 hr. Then the reaction was diluted with dichloromethane and concentrated in vacuo. Flash column chromatography (silica gel, EtOAc/hexane) yielded the product (stereochemistry assignment tentative). LCMS-ESI+(m/z): calcd H+ for $C_{36}H_{32}F_3N_3O_7$, Theoretical: 676.23, Found: 676.13.

Step 2: Synthesis of (3S,4S,6R,7R)-12-(benzyloxy)-4-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide To (3S,4S,6R,7R)-12-(benzyloxy)-6-methoxy-3-methyl-1,11-dioxo-10-((2,4,6-trifluorobenzyl)carbamoyl)-1,4,5,6,7,11-hexahydro-3H-2,7-methanopyrido[1,2-a][1,4]diazonin-4-yl benzoate (65 mg, 0.0962 mmol) was added methanol (2 mL), then THF (2 mL), then water (0.5 mL), then lithium hydroxide monohydrate (40 mg, 0.962 mmol). The reaction was stirred at 20° C. for 1.5 hr. Then the reaction was partitioned between ethyl acetate and saturated aqueous sodium bicarbonate. The organic phase was washed with brine, dried over MgSO4, filtered, concentrated in vacuo. Flash column chromatography (silica gel, EtOAc/hexane) yielded the product (stereochemistry assignment tentative). 1H NMR (400 MHz, Chloroform-d) δ 10.35 (t, J=5.8 Hz, 1H), 8.46 (s, 1H), 7.57-7.48 (m, 2H), 7.34 (d, J=6.6 Hz, 3H), 6.72-6.61 (m, 2H), 5.50 (d, J=10.3 Hz, 1H), 5.13 (d, J=10.3 Hz, 1H), 4.74-4.59 (m, 2H), 4.53-4.43 (m, 1H), 4.12 (d, J=7.0 Hz, 1H), 3.86 (t, J=9.3 Hz, 1H), 3.64-3.57 (m, 1H), 3.45 (s, 3H), 3.45-3.38 (m, 1H), 3.36-3.27 (m, 1H), 2.18-2.10 (m, 1H), 1.76 (ddd, J=15.4, 10.6, 1.5 Hz, 1H), 1.34 (d, J=6.8 Hz, 3H). LCMS-ESI+(m/z): calcd H+ for $C_{29}H_{28}F_3N_3O_6$, Theoretical: 572.20, Found 572.16.

Step 3: Synthesis of (3S,4R,6R,7R)-12-(benzyloxy)-4-fluoro-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide To (3S,4S,6R,7R)-12-(benzyloxy)-4-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (13 mg, 0.0227 mmol) was added DCM (1.3 mL), then 2.7 M solution in toluene of Deoxo-Fluor (0.020 mL, 0.0546 mmol). The mixture was stirred at 20° C. for 1.5 hr. The reaction was quenched by slow addition into ice-cold 10% aqueous potassium carbonate, then extracted with EtOAc. The organic layer was washed with saturated aqueous ammonium chloride, then brine, dried over magnesium sulfate, filtered and concentrated. Preparative thin-layer chromatography (silica gel, EtOAc) yielded the product (stereochemistry assignment tentative). 1H NMR (400 MHz, Chloroform-d) δ 10.35 (t, J=5.7 Hz, 1H), 8.50 (s, 1H), 7.61-7.46 (m, 2H), 7.44-7.27 (m, 3H), 6.67 (dd, J=8.7, 7.5 Hz, 2H), 5.54 (d, J=10.3 Hz, 1H), 5.13 (d, J=10.3 Hz, 1H), 4.93-4.85 (m, 1H), 4.67 (d, J=5.6 Hz, 2H), 4.28 (d, J=2.2 Hz, 1H), 3.87 (dd, J=15.0, 2.1 Hz, 1H), 3.70 (s, 1H), 3.45 (s, 3H), 3.42-3.36 (m, 1H), 2.63 (dt, J=15.9, 6.3 Hz, 1H), 1.78-1.68 (m, 1H), 1.63 (dd, J=15.8, 2.8 Hz, 1H), 1.34 (dd, J=6.8, 2.6 Hz, 3H). LCMS-ESI+(m/z): calcd H+ for $C_{29}H_{27}F_4N_3O_5$, Theoretical: 574.20, Found: 574.14.

Step 4: Synthesis of (3S,4R,6R,7R)-4-fluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (3S,4R,6R,7R)-12-(benzyloxy)-4-fluoro-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (7 mg) was dissolved in 1:1 toluene:trifluoroacetic acid (0.48 mL). The resulting solution was stirred at 60° C. for 30 min. The solution was diluted with acetonitrile and concentrated in vacuo, and the resulting crude was purified by reverse-phase preparative HPLC (acetonitrile/water, 0.1% trifluoroacetic acid) to yield the product (stereochemistry assignment tentative). 1H NMR (400 MHz, Acetonitrile-d3) δ 10.31 (s, 1H), 8.37 (s, 1H), 6.85 (dd, J=9.1, 8.0 Hz, 2H), 5.00-4.73 (m, 2H), 4.60 (d, J=5.7 Hz, 2H), 4.48 (d, J=2.5 Hz, 1H), 3.91 (dd, J=15.1, 2.3 Hz, 1H), 3.65 (d, J=8.1 Hz, 1H), 3.63 (s, 1H), 3.37 (s, 3H), 2.53 (ddd, J=15.3, 8.2, 6.4 Hz, 1H), 1.86-1.66 (m, 1H), 1.33 (dd, J=7.1, 2.7 Hz, 3H). LCMS-ESI+(m/z): calcd H+ for $C_{22}H_{21}F_4N_3O_5$, Theoretical: 484.15, Found: 484.23.

Example 39: (3S,4R,6S,7R)-4-fluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

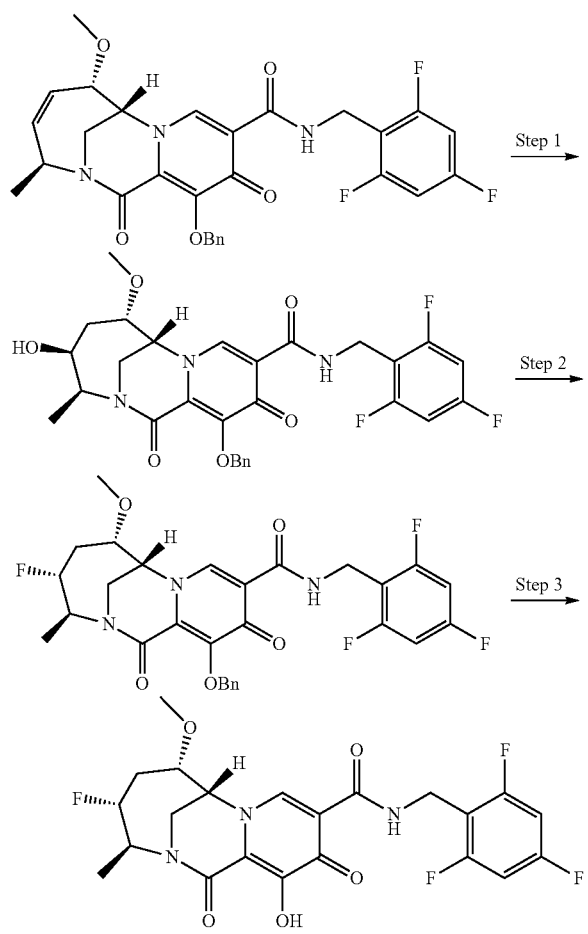

Step 1: Synthesis of ((3S,4S,6S,7R)-12-(benzyloxy)-4-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide To (3S,6S,7R)-12-(benzyloxy)-6-methoxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (from Step 2 for Example 1, 50 mg, 0.0903 mmol) was added isopropanol (2.5 mL), then phenylsilane (20 mg, 0.181 mmol), then benzoic acid (25 mg, 0.205 mmol), then tris(2,2,6,6-tetramethyl-3,5-heptanedionato)manganese(III) (1.6 mg, 0.0027 mmol). The reaction was cycled between vacuum and oxygen three times, then stirred vigorously under oxygen at 20° C. for 45 min, then more tris(2,2,6,6-tetramethyl-3,5-heptanedionato)manganese(III) (0.5 mg, 0.0009 mmol) was added. The reaction was stirred vigorously under oxygen at 20° C. for 45 min. Then 1 N aqueous sodium thiosulfate was added, and the phases mixed for 60 min. Then the reaction was extracted with ethyl acetate. The organic phase was washed with brine, dried over MgSO4, filtered, concentrated in vacuo. Flash column chromatography (silica gel, EtOAc/hexane) yielded the product as the major diastereomer (stereochemistry assignment tentative). 1H NMR (400 MHz, Chloroform-d) δ 10.43 (s, 1H), 8.48 (s, 1H), 7.66-7.50 (m, 2H), 7.46-7.27 (m, 3H), 6.66 (t, J=8.1 Hz, 2H), 5.42 (d, J=10.3 Hz, 1H), 5.14 (d, J=10.3 Hz, 1H), 4.72-4.59 (m, 2H), 4.54 (q, J=7.2 Hz, 1H), 4.40 (s, 1H), 3.52-3.28 (m, 3H), 3.41 (s, 3H), 3.12 (d, J=15.3 Hz, 1H), 2.06 (d, J=13.2 Hz, 1H), 1.72-1.57 (m, 1H), 1.33 (d, J=6.7 Hz, 3H). LCMS-ESI+(m/z): calcd H+ for $C_{29}H_{28}F_3N_3O_6$, Theoretical: 572.20, Found: 572.02.

Steps 2-3: Synthesis of (3S,4R,6S,7R)-4-fluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (3S,4R,6S,7R)-4-fluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide was synthesized in a manner similar to Example 38, starting with (3S,4S,6S,7R)-12-(benzyloxy)-4-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide. 1H NMR (400 MHz, Acetonitrile-d3) δ 10.33 (s, 1H), 8.27 (s, 1H), 6.84 (t, J=8.5 Hz, 2H), 5.03 (ddd, J=48.0, 7.1, 4.9 Hz, 1H), 4.79-4.63 (m, 2H), 4.60 (d, J=5.8 Hz, 2H), 3.90 (ddd, J=11.8, 5.1, 3.7 Hz, 1H), 3.74 (dt, J=15.1, 2.6 Hz, 1H), 3.61 (d, J=15.2 Hz, 1H), 3.42 (s, 3H), 2.51 (ddd, J=15.3, 7.3, 3.6 Hz, 1H), 1.45-1.35 (m, 1H), 1.33 (dd, J=7.1, 2.3 Hz, 3H). LCMS-ESI+(m/z): calcd H+ for $C_{22}H_{21}F_4N_3O_5$, Theoretical: 484.15, Found: 484.11.

Example 40: (3S,4S,6S,7R)-4-fluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

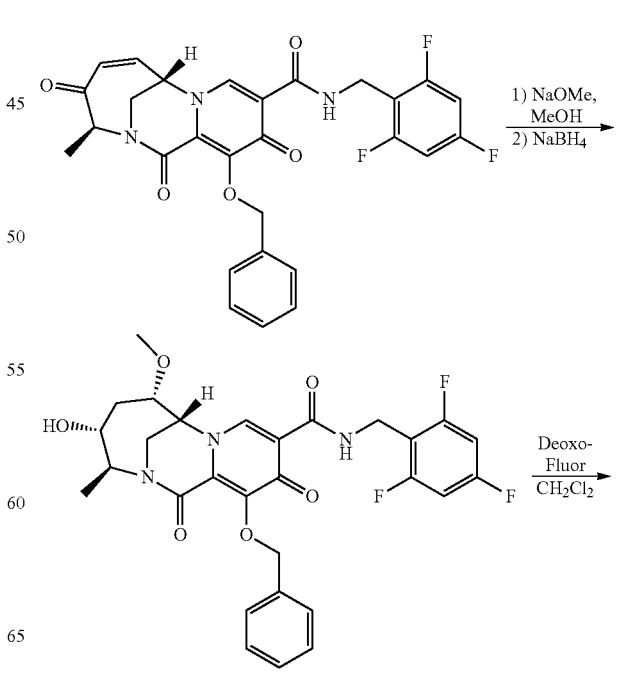

-continued

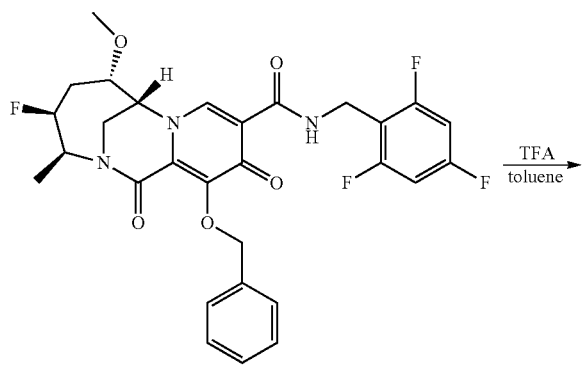

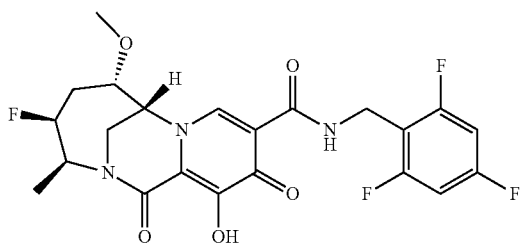

Step 1: Synthesis of (3S,4R,6S,7R)-12-(benzyloxy)-4-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide To a mixture of Intermediate C (706.9 mg, 1.32 mmol) in methanol (10 mL) was added 0.5 M sodium methoxide (3 mL, 1.5 mmol) at rt. The reaction mixture was stirred in at 50° C. After 2 h, the reaction mixture was stirred at 0° C. and added 4 N HCl in dioxane (0.375 mL, 1.5 mmol): ES/MS m/z: calculated for C29H27F3N3O6 (M+H): 570.19, found: 570.30.

The above solution was stirred at 0° C. as NaBH4 (157 mg, 4.15 mmol) was added. After 30 min at 0° C., the reaction mixture was concentrated, and the residue was dissolved in saturated NaHCO3 before the product was extracted with ethyl acetate (×2). After the organic extracts were washed with brine (×1), the organic fractions were combined, dried (MgSO4), and concentrated. The residue was purified by repeated column chromatography on silica gel (80 g column) eluting 0-5% methanol in CH2Cl2, and preparative HPLC (column, Gemini 5 um C18 110A, LC column 100×30 mm) eluting 23-90% acetonitrile (0.1% TFA) in water (0.1% TFA) over 20 min. After the combined fractions were neutralized by adding saturated NaHCO3 (~1 mL), the solution was concentrated to remove most of acetonitrile. The resulting aqueous mixture was extracted with EA (~25 mL×2), and the extracts were washed with brine (×1) combined, dried (MgSO4), and concentrated to get (3S,4R,6S,7R)-12-(benzyloxy)-4-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide. ES/MS m/z: calculated for C29H29F3N3O6 (M+H): 572.20, found: 572.27.

Step 2: Synthesis of (3S,4S,6S,7R)-12-(benzyloxy)-4-fluoro-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide A solution of (3S,4R,6S,7R)-12-(benzyloxy)-4-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (81.8 mg, 0.143 mmol) in CH2Cl2 (2 mL) was stirred at 0° C. as 2.7 M bis(2-methoxyethyl)aminosulfur trifluoride solution in toluene (0.14 mL, 0.378 mmol) was added. After 30 min, the reaction mixture was stirred at room temperature for 2.5 h and cooled to 0° C. as saturated NaHCO3 (10 mL) was added. After water was added (20 mL). The product was extracted with ethyl acetate (25 mL×2). After the extracts were combined, it was dried (MgSO4) and concentrated. The residue was purified by column chromatography on silica gel (12 g column used) eluting 20-100% EA in hexane to get (3S,4S,6S,7R)-12-(benzyloxy)-4-fluoro-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide: ES/MS m/z: calculated for C29H28F4N3O5 (M+H): 574.20, found: 574.30.

Step 3: Synthesis of (3S,4S,6S,7R)-4-fluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (3S,4S,6S,7R)-12-(benzyloxy)-4-fluoro-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (50.3 mg, 0.0877 mmol) was dissolved in toluene (0.02 mL) and trifluoroacetic acid (2 mL). After stirring at room temperature for 1 h, the reaction mixture was concentrated completely, and the residue was purified by preparative HPLC (2 injections; column, Gemini Sum C18 110A, LC column 100×30 mm) eluting 20-65% acetonitrile (0.1% TFA) in water (0.1% TFA) over 20 min. The combined fractions were neutralized by addition of saturated NaHCO3 (~1 mL) before concentration to remove most of acetonitrile. The concentrated solution was extracted with ethyl acetate (~20 mL×2). The extracted fractions were washed with brine (×1), combined, dried (MgSO4), concentrated, and dried in vacuum to obtain (3S,4S,6S,7R)-4-fluoro-12-hydroxy-6-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide. 1H NMR (400 MHz, Chloroform-d) δ 10.39 (s, 1H), 10.19 (s, 1H), 8.44 (s, 1H), 6.74-6.59 (m, 2H), 4.97 (dt, J=46.8, 6.4 Hz, 1H), 4.82 (dp, J=19.9, 6.8 Hz, 1H), 4.74-4.59 (m, 2H), 4.39 (d, J=2.4 Hz, 1H), 4.02 (dd, J=14.7, 2.1 Hz, 1H), 3.73-3.58 (m, 2H), 3.45 (s, 3H), 2.68 (ddd, J=16.0, 7.5, 5.1 Hz, 1H), 1.73-1.55 (m, 1H), 1.41 (dd, J=7.1, 2.6 Hz, 3H); 19F NMR (376 MHz, Acetonitrile-d3) 6-111.29 (q, J=7.8, 7.3 Hz), −113.92 (t, J=7.1 Hz), −200.03−200.69 (m); ES/MS m/z: calculated for C22H22F4N3O5 (M+H): 484.15, found: 484.20.

Example 41: (3R,6S,7R)—N-(2,4-difluorobenzyl)-3-(fluoromethyl)-12-hydroxy-6-methoxy-1,11-dioxo-1,4,5,6,7,11-hexahydro-3H-2,7-methanopyrido[1,2-a][1,4]diazonine-10-carboxamide
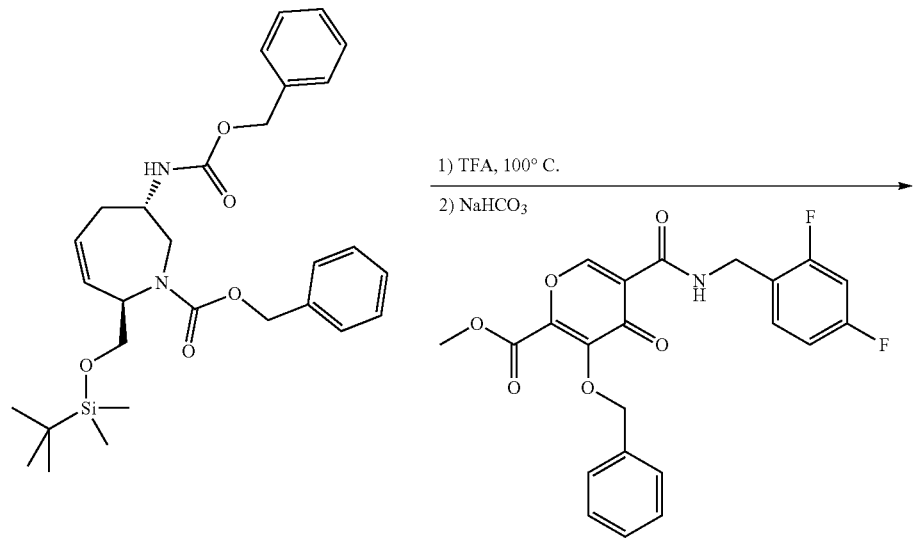
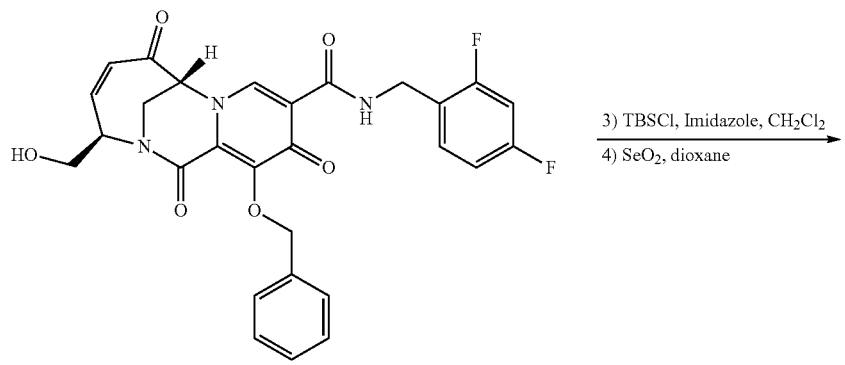
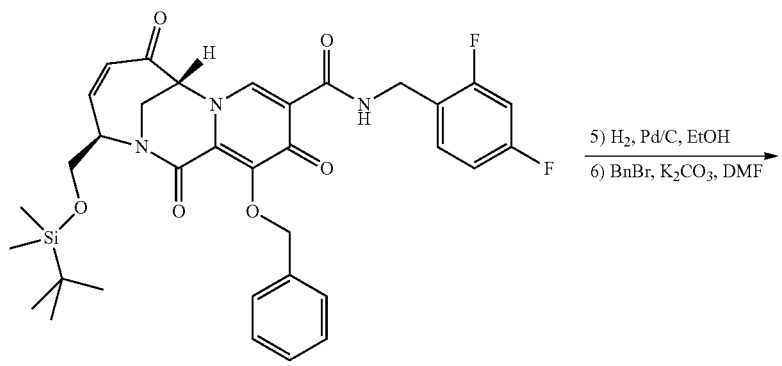

-continued

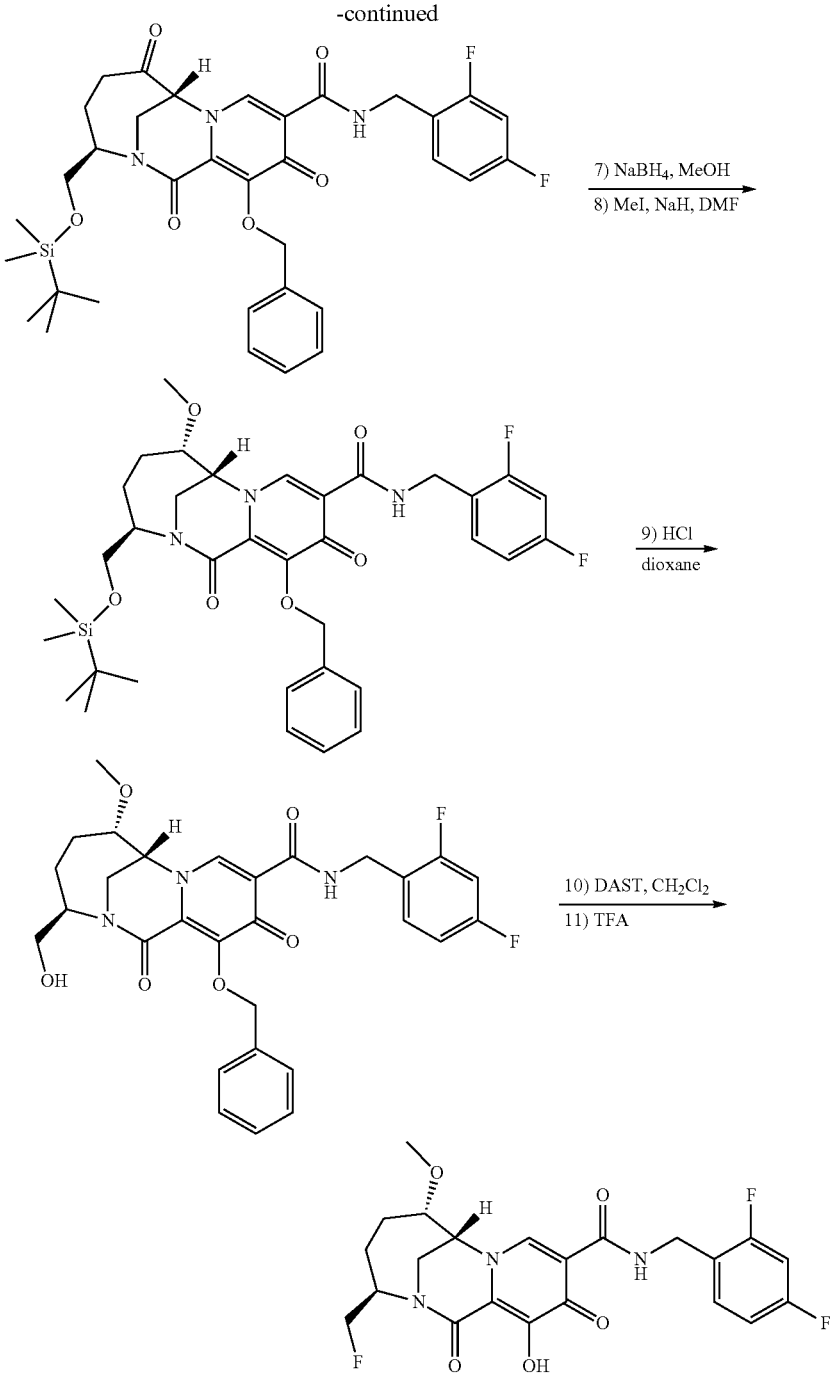

7) NaBH₄, MeOH
8) MeI, NaH, DMF

9) HCl
dioxane

10) DAST, CH₂Cl₂
11) TFA

Steps 1-2: Synthesis of (3R,7S)-12-(benzyloxy)-N-(2,4-difluorobenzyl)-3-(hydroxymethyl)-1,11-dioxo-1,6,7,11-tetrahydro-3H-2,7-methanopyrido[1,2-a][1,4]diazonine-10-carboxamide (3R,7S)-12-(benzyloxy)-N-(2,4-difluorobenzyl)-3-(hydroxymethyl)-1,11-dioxo-1,6,7,11-tetrahydro-3H-2,7-methanopyrido[1,2-a][1,4]diazonine-10-carboxamide was prepared by following the procedure of making Intermediate B, except that Benzyl (3S,7R)-3-(((benzyloxy)carbonyl)amino)-7-((((tert-butyldimethylsilyl)oxy)methyl)-2,3,4,7-tetrahydro-1H-azepine-1-carboxylate was used in the 1st step. ES/MS m/z: calculated for C28H26F2N3O5 (M+H): 522.18, found: 522.20.

Steps 3-4: Synthesis of (3R,7R)-12-(benzyloxy)-3-(((tert-butyldimethylsilyl)oxy)methyl)-N-(2,4-difluorobenzyl)-1,6,11-trioxo-1,6,7,11-tetrahydro-3H-2,7-methanopyrido[1,2-a][1,4]diazonine-10-carboxamide To a solution of (3R,7S)-12-(benzyloxy)-N-(2,4-difluorobenzyl)-3-(hydroxymethyl)-1,11-dioxo-1,6,7,11-tetrahydro-3H-2,7-methanopyrido[1,2-a][1,4]diazonine-10-carboxamide (2971.9 mg, 5.70 mmol) and imidazole (601.0 mg, 8.83 mmol) in CH2Cl2 (45 mL) was added tert-butyldimethylsilyl chloride (1039.7 mg, 6.90 mmol) at room temperature and the resulting solution was stirred at rt. After 16 h, the reaction mixture was diluted with CH2Cl2, washed with water (×1), and the two layers were separated. After the aqueous fraction was extracted with ethyl acetate (×1), the organic fractions were combined, dried (MgSO4), and concentrated. The residue was purified by column chromatography on silica gel (120 g column) eluting 0-100% ethyl acetate in hexane to get (3R,7S)-12-(benzyloxy)-3-(((tert-butyldimethylsilyl)oxy)methyl)-N-(2,4-difluorobenzyl)-1,11-dioxo-1,6,7,11-tetrahydro-3H-2,7-methanopyrido[1,2-a][1,4]diazonine-10-carboxamide. ES/MS m/z: calculated for C34H40F2N3O5Si (M+H): 636.27, found: 636.30.

(3R,7R)-12-(benzyloxy)-3-(((tert-butyldimethylsilyl)oxy)methyl)-N-(2,4-difluorobenzyl)-1,6,11-trioxo-1,6,7,11-tetrahydro-3H-2,7-methanopyrido[1,2-a][1,4]diazonine-10-carboxamide was prepared by following the procedure of making Intermediate B, except that (3R,7S)-12-(benzyloxy)-3-(((tert-butyldimethylsilyl)oxy)methyl)-N-(2,4-difluorobenzyl)-1,11-dioxo-1,6,7,11-tetrahydro-3H-2,7-methanopyrido[1,2-a][1,4]diazonine-10-carboxamide was used. ES/MS m/z: calculated for C34H38F2N3O6Si (M+H): 650.25, found: 650.30.

Steps 5-6: Synthesis of (3R,7R)-12-(benzyloxy)-3-(((tert-butyldimethylsilyl)oxy)methyl)-N-(2,4-difluorobenzyl)-1,6,11-trioxo-1,4,5,6,7,11-hexahydro-3H-2,7-methanopyrido[1,2-a][1,4]diazonine-10-carboxamide A mixture of (3R,7R)-12-(benzyloxy)-3-(((tert-butyldimethylsilyl)oxy)methyl)-N-(2,4-difluorobenzyl)-1,6,11-trioxo-1,6,7,11-tetrahydro-3H-2,7-methanopyrido[1,2-a][1,4]diazonine-10-carboxamide (1420.6 mg, 2.19 mmol) and 10% palladium on carbon (151.3 mg) in ethanol (30 mL) was stirred under H2 atmosphere at rt. After 2 h, the reaction mixture was filtered, and the filtrate was concentrated and dried in vacuum for 30 min. ES/MS m/z: calculated for C29H40F2N3O7Si (M+EtOH+H): 608.26, found: 608.30.

The above residue and potassium carbonate (614.5 mg, 4.45 mmol) in DMF (13 mL) was stirred at room temperature when benzyl bromide (0.35 mL, 2.94 mmol) was added. After stirring at room temperature overnight, the reaction mixture was diluted with water (~30 mL) and the product was extracted with ethyl acetate (×2). After the extracts were washed with water (×1), combined, dried (MgSO4), and concentrated. The residue was purified by column chromatography on silica gel (40 g column) eluting 0-10% methanol in CH2Cl2 to get (3R,7R)-12-(benzyloxy)-3-(((tert-butyldimethylsilyl)oxy)methyl)-N-(2,4-difluorobenzyl)-1,6,11-trioxo-1,4,5,6,7,11-hexahydro-3H-2,7-methanopyrido[1,2-a][1,4]diazonine-10-carboxamide: ES/MS m/z: calculated for C34H42F2N3O7Si (M+H2O+H): 670.28, found: 670.30; calculated for C35H44F2N3O7Si (M+MeOH+H): 684.29, found: 684.40.

Steps 7-8: Synthesis of (3R,6S,7R)-12-(benzyloxy)-3-(((tert-butyldimethylsilyl)oxy)methyl)-N-(2,4-difluorobenzyl)-6-methoxy-1,11-dioxo-1,4,5,6,7,11-hexahydro-3H-2,7-methanopyrido[1,2-a][1,4]diazonine-10-carboxamide A solution of (3R,7R)-12-(benzyloxy)-3-(((tert-butyldimethylsilyl)oxy)methyl)-N-(2,4-difluorobenzyl)-1,6,11-trioxo-1,4,5,6,7,11-hexahydro-3H-2,7-methanopyrido[1,2-a][1,4]diazonine-10-carboxamide (1234.0 mg, 1.89 mmol) in methanol (18 mL) was stirred at 0° C. as NaBH4 (156.2 mg, 4.13 mmol) was added. After 1 h at 0° C., the reaction mixture was concentrated, and the residue was dissolved in water before extraction with EtOAc (×2). The combined extracts were dried (MgSO4), and concentrated. The residue was purified by column chromatography on silica gel (80 g column) eluting 0-10% methanol in CH2Cl2 to get (3R,6S,7R)-12-(benzyloxy)-3-(((tert-butyldimethylsilyl)oxy)methyl)-N-(2,4-difluorobenzyl)-6-hydroxy-1,11-dioxo-1,4,5,6,7,11-hexahydro-3H-2,7-methanopyrido[1,2-a][1,4]diazonine-10-carboxamide. ES/MS m/z: calculated for C34H42F2N3O6Si (M+H): 654.28, found: 654.30.

A solution of the above product (221.3 mg, 0.338 mmol) in DMF (2.25 mL) was stirred at 0° C. as 60% sodium hydride dispersion (19.1 mg, 0.498 mmol) was added. After 20 min at 0° C., a solution of iodomethane (0.021 mL, 0.337 mmol) was added. After 1 h at 0° C., additional iodomethane (0.021 mL, 0.337 mmol) to the reaction mixture. After ~1 h at 0° C., the reaction mixture was diluted with saturated NH4Cl and the product was extracted with ethyl acetate (×2). After the extracts were washed with water (×1), the organic fractions were combined, dried (MgSO4), and concentrated. The residue was purified by column chromatography on silica gel (120 g column) eluting 0-10% methanol in CH2Cl2. The fractions containing product were combined and concentrated and the residue was purified again by column chromatography on silica gel (24 g column) eluting 20-100% ethyl acetate in hexane to get a mixture the reactant and (3R,6S,7R)-12-(benzyloxy)-3-(((tert-butyldimethylsilyl)oxy)methyl)-N-(2,4-difluorobenzyl)-6-methoxy-1,11-dioxo-1,4,5,6,7,11-hexahydro-3H-2,7-methanopyrido[1,2-a][1,4]diazonine-10-carboxamide. ES/MS m/z: calculated for C35H44F2N3O6Si (M+H): 668.30, found: 668.30.

Step 9: Synthesis of (3R,6S,7R)-12-(benzyloxy)-N-(2,4-difluorobenzyl)-3-(hydroxymethyl)-6-methoxy-1,11-dioxo-1,4,5,6,7,11-hexahydro-3H-2,7-methanopyrido[1,2-a][1,4]diazonine-10-carboxamide (3R,6S,7R)-12-(benzyloxy)-3-(((tert-butyldimethylsilyl)oxy)methyl)-N-(2,4-difluorobenzyl)-6-methoxy-1,11-dioxo-1,4,5,6,7,11-hexahydro-3H-2,7-methanopyrido[1,2-a][1,4]diazonine-10-carboxamide (333 mg, 0.494 mmol) from above was dissolved in 4 N HCl in dioxane (3 mL) in 0° C. bath and stirred at 0° C. for 30 min. The reaction mixture was concentrated, and the residue was purified by column chromatography on silica gel (24 g column) eluting 0-15% methanol in CH2Cl2 to get (3R,6S,7R)-12-(benzyloxy)-N-(2,4-difluorobenzyl)-3-(hydroxymethyl)-6-methoxy-1,11-dioxo-1,4,5,6,7,11-hexahydro-3H-2,7-methanopyrido[1,2-a][1,4]diazonine-10-carboxamide. ES/MS m/z: calculated for C28H28F2N3O6 (M+H): 554.21, found: 554.30.

Steps 10-11: Synthesis of (3R,6S,7R)—N-(2,4-difluorobenzyl)-3-(fluoromethyl)-12-hydroxy-6-methoxy-1,11-dioxo-1,4,5,6,7,11-hexahydro-3H-2,7-methanopyrido[1,2-a][1,4]diazonine-10-carboxamide A solution of (3R,6S,7R)-12-(benzyloxy)-N-(2,4-difluorobenzyl)-3-(hydroxymethyl)-6-methoxy-1,11-dioxo-1,4,5,6,7,11-hexahydro-3H-2,7-methanopyrido[1,2-a][1,4]diazonine-10-carboxamide (50.3 mg, 0.0909 mmol) in CH2Cl2 (2.5 mL) was stirred at 0° C. as (diethylamino)sulfur trifluoride (0.05 mL, 0.378 mmol) was added. After 30 min, the reaction mixture was stirred at room temperature overnight.

The reaction mixture was stirred at 0° C. and added saturated NaHCO3 (5 mL). After the mixture was diluted with water (20 mL), the product was extracted with CH2Cl2 (2×20 mL). The combined extracts were dried (MgSO4), and concentrated to get the crude product, (3R,6S,7R)-12-(benzyloxy)-N-(2,4-difluorobenzyl)-3-(fluoromethyl)-6-methoxy-1,11-dioxo-1,4,5,6,7,11-hexahydro-3H-2,7-methanopyrido[1,2-a][1,4]diazonine-10-carboxamide. ES/MS m/z: calculated for C29H29F3N3O5 (M+H): 556.21, found: 556.30.

The crude fluorinated product was dissolved in trifluoroacetic acid (3 mL) and stirred at room temperature for 1.5 h. The reaction mixture was concentrated and the residue was purified by preparative HPLC (column, Gemini Sum C18 110A, LC column 100×30 mm) eluting 15-70% acetonitrile (0.1% TFA) in water (0.1% TFA) over 20 min to get (3R,6S,7R)—N-(2,4-difluorobenzyl)-3-(fluoromethyl)-12-hydroxy-6-methoxy-1,11-dioxo-1,4,5,6,7,11-hexahydro-3H-2,7-methanopyrido[1,2-a][1,4]diazonine-10-carboxamide. 1H NMR (400 MHz, Chloroform-d) δ 10.49 (t, J=5.9 Hz, 1H), 9.63 (s, 2H), 8.44 (s, 1H), 7.36 (td, J=8.6, 6.6 Hz, 1H), 6.87-6.74 (m, 2H), 4.84-4.67 (m, 1H), 4.67-4.62 (m, 3H), 4.62-4.50 (m, 1H), 4.48 (dd, J=5.7, 2.8 Hz, 1H), 3.86 (dd, J=15.5, 3.1 Hz, 1H), 3.74 (dt, J=15.5, 1.3 Hz, 1H), 3.50-3.42 (m, 1H), 3.41 (s, 3H), 2.20-2.01 (m, 2H), 1.98-1.79 (m, 1H), 1.14 (dt, J=13.9, 11.6 Hz, 1H); 19F NMR (376 MHz, Chloroform-d) δ−76.43, −111.94 (p, J=7.8 Hz), −114.64-−114.87 (m); ES/MS m/z: calculated for C22H23F3N3O5 (M+H): 466.16, found: 466.20.

Example 42: (3R,6S,7R)—N-(2,4-difluorobenzyl)-12-hydroxy-6-methoxy-3-methyl-1,11-dioxo-1,4,5,6,7,11-hexahydro-3H-2,7-methanopyrido[1,2-a][1,4]diazonine-10-carboxamide

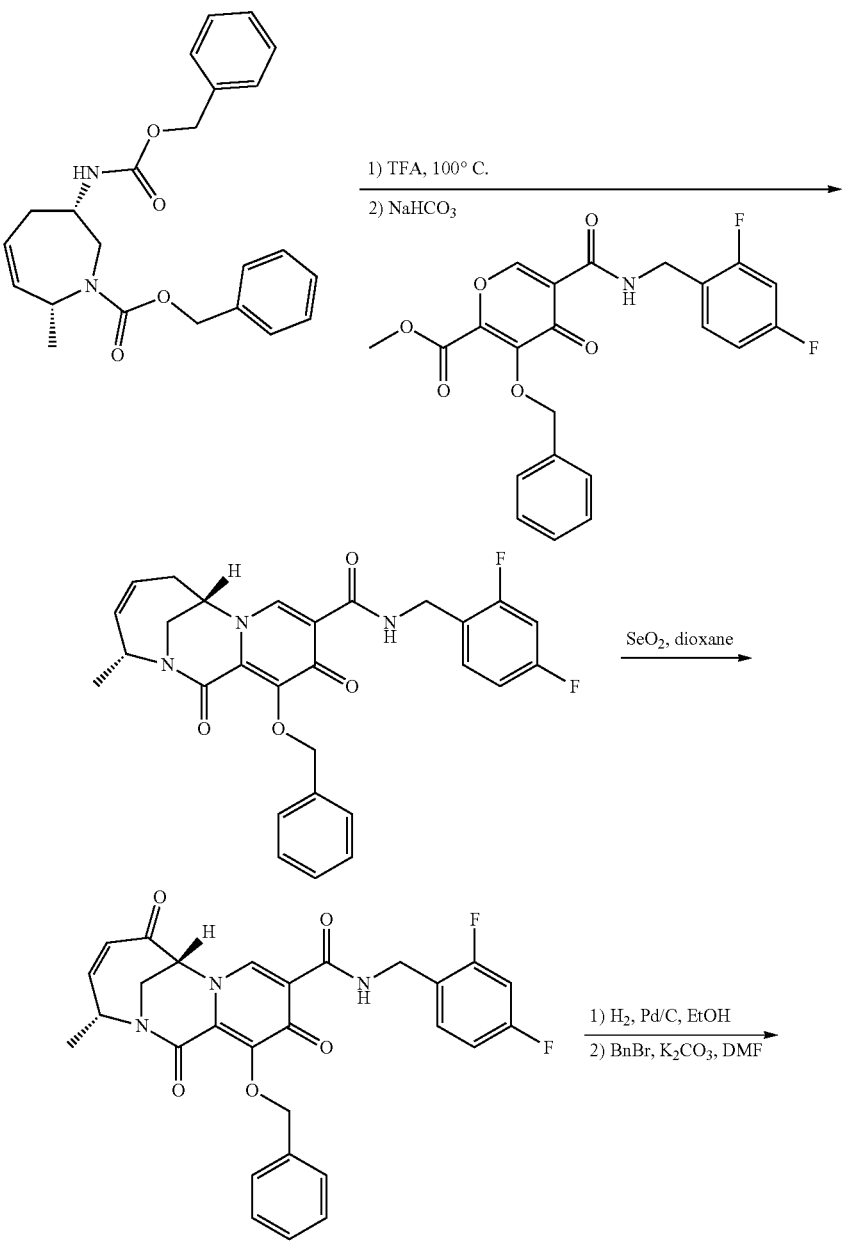

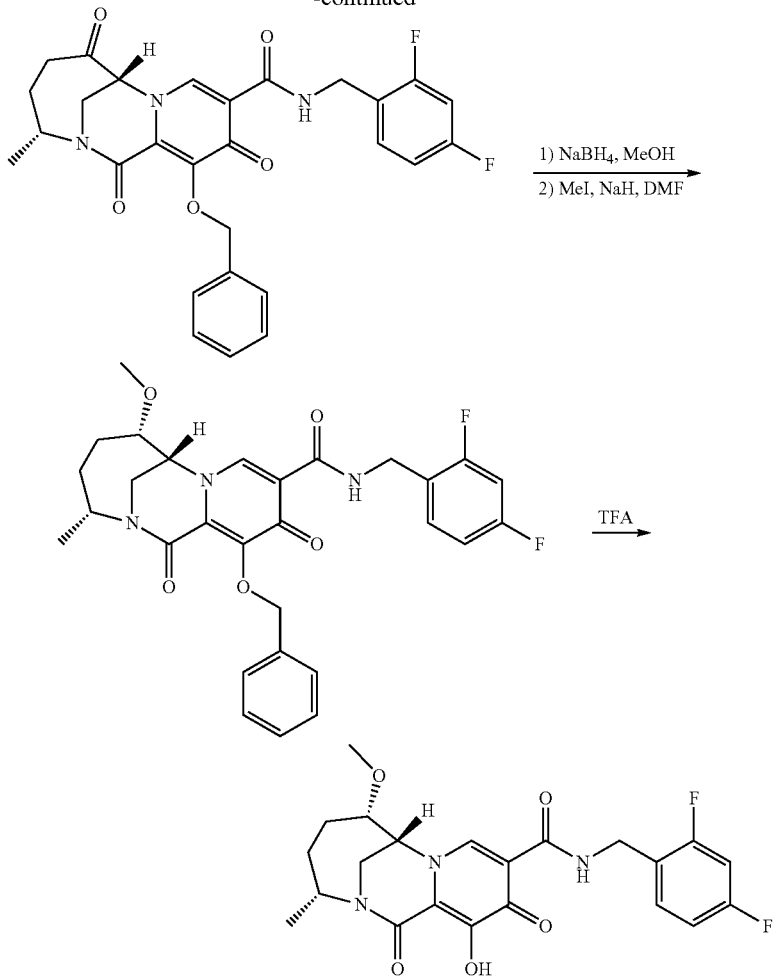

Steps 1-2: Synthesis of (3R,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide (3R,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide was prepared by following the procedure of making Intermediate B, except that benzyl (3S,7R)-3-(((benzyloxy)carbonyl)amino)-7-methyl-2,3,4,7-tetrahydro-1H-azepine-1-carboxylate was used in the 1st step. ES/MS m/z: calculated for C28H24F2N3O5 (M+H): 520.17, found: 520.20.

Step 3: Synthesis of (3R,7R)-12-(benzyloxy)-N-(2,4-difluorobenzyl)-3-methyl-1,6,11-trioxo-1,4,5,6,7,11-hexahydro-3H-2,7-methanopyrido[1,2-a][1,4]diazonine-10-carboxamide A mixture of (3R,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide (0.637 mmol) and 10% palladium on carbon (70 mg) in ethanol (10 mL) was stirred under H2 atmosphere at room temperature for 4 h. The reaction mixture was filtered, and the filtrate was concentrated and dried in vacuum for 30 min. The residue and potassium carbonate (179.0 mg, 1.3 mmol) in DMF (3.8 mL) was stirred at room temperature when benzyl bromide (0.1 mg, 0.841 mmol) was added. After overnight, the reaction mixture was diluted with water (30 mL) and the product was extracted with ethyl acetate (×2). After the extracts were washed with water (×1), combined, dried (MgSO4), and concentrated. The residue was purified by column chromatography on silica gel (40 g column) eluting 20-100% ethyl acetate in hexane to get (3R,7R)-12-(benzyloxy)-N-(2,4-difluorobenzyl)-3-methyl-1,6,11-trioxo-1,4,5,6,7,11-hexahydro-3H-2,7-methanopyrido[1,2-a][1,4]diazonine-10-carboxamide. ES/MS m/z: calculated for C28H26F2N3O5 (M+H): 522.18, found: 522.20.

Step 4: Synthesis of (3R,6S,7R)-12-(benzyloxy)-N-(2,4-difluorobenzyl)-6-methoxy-3-methyl-1,11-dioxo-1,4,5,6,7,11-hexahydro-3H-2,7-methanopyrido[1,2-a][1,4]diazonine-10-carboxamide A solution of (3R,7R)-12-(benzyloxy)-N-(2,4-difluorobenzyl)-3-methyl-1,6,11-trioxo-1,4,5,6,7,11-hexahydro-3H-2,7-methanopyrido[1,2-a][1,4]diazonine-10-carboxamide (125.1 mg, 0.24 mmol) in methanol (3 mL) was stirred at 0° C. as NaBH4 (28.9 mg, 0.764 mmol) was added. After 1 h at 0° C., the reaction mixture was concentrated, and the residue was dissolved in water (~30 mL) before extraction with ethyl acetate (20 mL×2). The combined extracts were dried (MgSO4), and concentrated. The residue was purified by column chromatography on silica gel (24 g column) eluting 0-20% methanol in CH2Cl2 to get (3R,6S,7R)-12-(benzyloxy)-N-(2,4-difluorobenzyl)-6-hydroxy-3-methyl-1,11-dioxo-1,4,5,6,7,11-hexahydro-3H-2,7-methanopyrido[1,2-a][1,4]diazonine-10-carboxamide: ES/MS m/z: calculated for C28H28F2N3O5 (M+H): 524.20, found: 524.30.

A solution of the above alcohol (73.2 mg, 0.140 mmol) in DMF (1.5 mL) was stirred at 0° C. as 60% sodium hydride dispersion (10.5 mg, 0.274 mmol) was added After 20 min at 0° C., a solution of iodomethane (0.0104 mL 0.168 mmol), 0.21 mL, 0.337 mmol) was added. After 1 h at 0° C., After the reaction mixture was diluted with saturated NaHCO3 solution, the product was extracted with ethyl acetate (×2), and the combined extracts were dried (MgSO4) and concentrated. The residue was purified by preparative HPLC (column, Gemini Sum C18 110A, LC column 100×30 mm) eluting 20-100% acetonitrile (0.1% TFA) in water (0.1% TFA) over 30 min to get (3R,6S,7R)-12-(benzyloxy)-N-(2,4-difluorobenzyl)-6-methoxy-3-methyl-1,11-dioxo-1,4,5,6,7,11-hexahydro-3H-2,7-methanopyrido[1,2-a][1,4]diazonine-10-carboxamide. ES/MS m/z: calculated for C29H30F2N3O5 (M+H): 538.22, found: 538.30.

Step 5: Synthesis of (3R,6S,7R)—N-(2,4-difluorobenzyl)-12-hydroxy-6-methoxy-3-methyl-1,11-dioxo-1,4,5,6,7,11-hexahydro-3H-2,7-methanopyrido[1,2-a][1,4]diazonine-10-carboxamide (3R,6S,7R)-12-(benzyloxy)-N-(2,4-difluorobenzyl)-6-methoxy-3-methyl-1,11-dioxo-1,4,5,6,7,11-hexahydro-3H-2,7-methanopyrido[1,2-a][1,4]diazonine-10-carboxamide (3.1 mg, 5.77 umol) was dissolved in trifluoroacetic acid (1 mL) and stirred at room temperature for 1.5 h. The reaction mixture was concentrated and the residue was purified by preparative HPLC (column, Gemini Sum C18 110A, LC column 100×30 mm) eluting 15-70% acetonitrile (0.1% TFA) in water (0.1% TFA) over 20 min to get (3R,6S,7R)—N-(2,4-difluorobenzyl)-12-hydroxy-6-methoxy-3-methyl-1,11-dioxo-1,4,5,6,7,11-hexahydro-3H-2,7-methanopyrido[1,2-a][1,4]diazonine-10-carboxamide. 1H NMR (400 MHz, Acetonitrile-d3) δ 10.41 (s, 1H), 8.29 (s, 1H), 7.41 (q, J=8.2 Hz, 1H), 7.04-6.85 (m, 2H), 4.63 (d, J=5.7 Hz, 1H), 4.60-4.51 (m, 2H), 3.87 (dd, J=15.0, 2.1 Hz, 1H), 3.76 (td, J=5.9, 2.9 Hz, 1H), 3.57 (h, J=7.0 Hz, 1H), 3.45 (dd, J=15.0, 2.1 Hz, 1H), 3.24 (s, 3H), 1.92-1.74 (m, 3H), 1.67 (d, J=7.2 Hz, 4H); 19F NMR (376 MHz, Acetonitrile-d3) δ–77.29, –114.23 (p, J=7.4 Hz), –116.68 (q, J=8.8, 8.2 Hz); ES/MS m/z: calculated for C22H24F2N3O5 (M+H): 448.17, found: 448.22.

Example 43: Preparation of (3S,6S,7R)—N-(2,4-difluorobenzyl)-6,12-dihydroxy-3,7-dimethyl-1,11-dioxo-1,4,5,6,7,11-hexahydro-3H-2,7-methanopyrido[1,2-a][1,4]diazonine-10-carboxamide

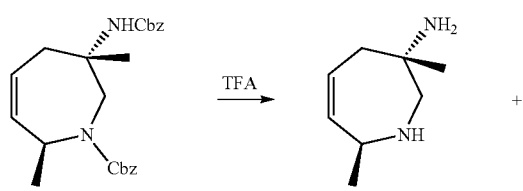

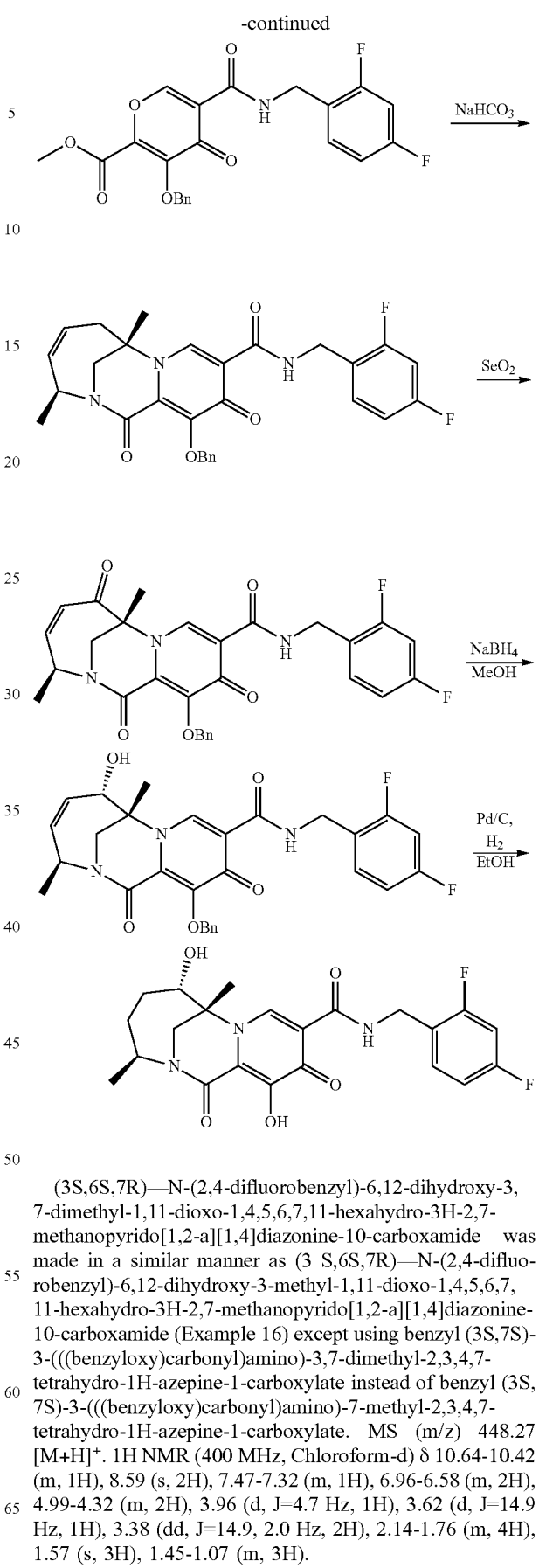

(3S,6S,7R)—N-(2,4-difluorobenzyl)-6,12-dihydroxy-3,7-dimethyl-1,11-dioxo-1,4,5,6,7,11-hexahydro-3H-2,7-methanopyrido[1,2-a][1,4]diazonine-10-carboxamide was made in a similar manner as (3 S,6S,7R)—N-(2,4-difluorobenzyl)-6,12-dihydroxy-3-methyl-1,11-dioxo-1,4,5,6,7,11-hexahydro-3H-2,7-methanopyrido[1,2-a][1,4]diazonine-10-carboxamide (Example 16) except using benzyl (3S,7S)-3-(((benzyloxy)carbonyl)amino)-3,7-dimethyl-2,3,4,7-tetrahydro-1H-azepine-1-carboxylate instead of benzyl (3S,7S)-3-(((benzyloxy)carbonyl)amino)-7-methyl-2,3,4,7-tetrahydro-1H-azepine-1-carboxylate. MS (m/z) 448.27 [M+H]+. 1H NMR (400 MHz, Chloroform-d) δ 10.64-10.42 (m, 1H), 8.59 (s, 2H), 7.47-7.32 (m, 1H), 6.96-6.58 (m, 2H), 4.99-4.32 (m, 2H), 3.96 (d, J=4.7 Hz, 1H), 3.62 (d, J=14.9 Hz, 1H), 3.38 (dd, J=14.9, 2.0 Hz, 2H), 2.14-1.76 (m, 4H), 1.57 (s, 3H), 1.45-1.07 (m, 3H).

Example 44: (3S,6S,7R)-6-(fluoromethyl)-6,12-dihydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide

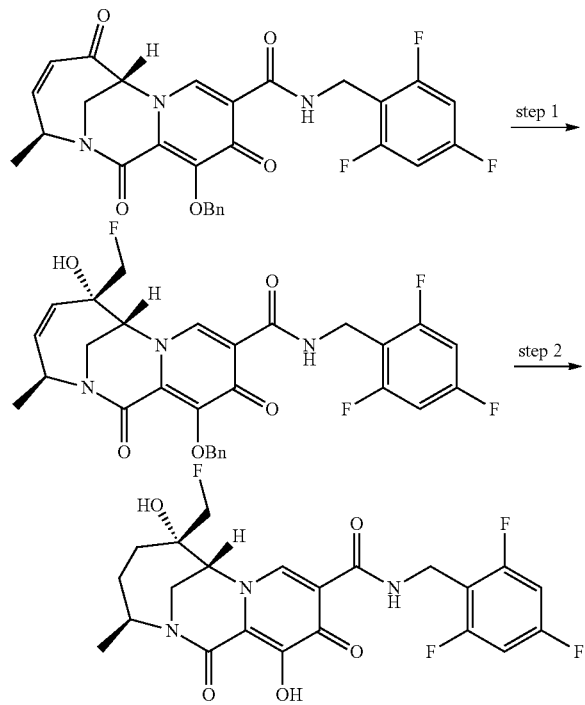

Step 1: Synthesis of (3S,6S,7R)-12-(benzyloxy)-6-(fluoromethyl)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide To a stirred solution of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (220 mg, 0.409 mmol) in dry mixture of THF:Et$_2$O (12 ml, 1:1, v/v) cooled at −78° C., fluoroiodomethane (164 mg, 2.5 eq.) was added. Then, a solution of MeLi—LiBr complex (1.5 M, in Et2O, 2 eq.) was added dropwise. After stirring for 5 min at −78° C., the reaction mixture was quenched with saturated aqueous NH$_4$Cl (1 ml). The mixture was poured into water (50 ml) and extracted with EtOAc. The organic layer was dried with MgSO$_4$, filtered and concentrated under vacuum. Flash chromatography on the crude afforded (3S,6S,7R)-12-(benzyloxy)-6-(fluoromethyl)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide. MS (m/z) 572.157[M+H]$^+$.

Step 2: Synthesis of (3S,6S,7R)-6-(fluoromethyl)-6,12-dihydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (3S,6S,7R)-12-(benzyloxy)-6-(fluoromethyl)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (5.8 mg, 0.0102 mmol) was dissolved in MeOH (5.0 mL) at room temperature and treated with 2 mg of 20% Pd(OH)$_2$/C (50 wt % water). The mixture was degassed and flushed with hydrogen 3 times before it was hydrogenated under hydrogen balloon for overnight. The reaction was then degassed and flushed with nitrogen, filtered through a pad of Celite, concentrated, the resulting residue was redissolved in DMF, filtered and purified by reverse phase HPLC. MS (m/z) 484.227 [M+H]$^+$. 1H NMR (400 MHz, Chloroform-d) δ 11.12 (s, 1H), 10.22 (t, J=5.7 Hz, 1H), 8.35 (s, 1H), 6.65 (dd, J=8.7, 7.5 Hz, 2H), 4.81-4.60 (m, 4H), 4.60-4.49 (m, 1H), 4.45 (dd, J=14.5, 5.1 Hz, 1H), 4.26 (s, 1H), 3.79-3.62 (m, 2H), 2.15-2.05 (m, 1H), 2.00-1.92 (m, 1H), 1.80 (s, 1H), 1.65 (s, 1H), 1.29 (d, J=6.8 Hz, 3H).

Example 45: Preparation (3S,4S,7R,8R)—N-(2,4-difluorobenzyl)-13-hydroxy-3-methyl-1,12-dioxo-1,4,5,7,8,12-hexahydro-3H-2,8:4,7-dimethanopyrido[1,2-d][1,4,7]oxadiazecine-11-carboxamide

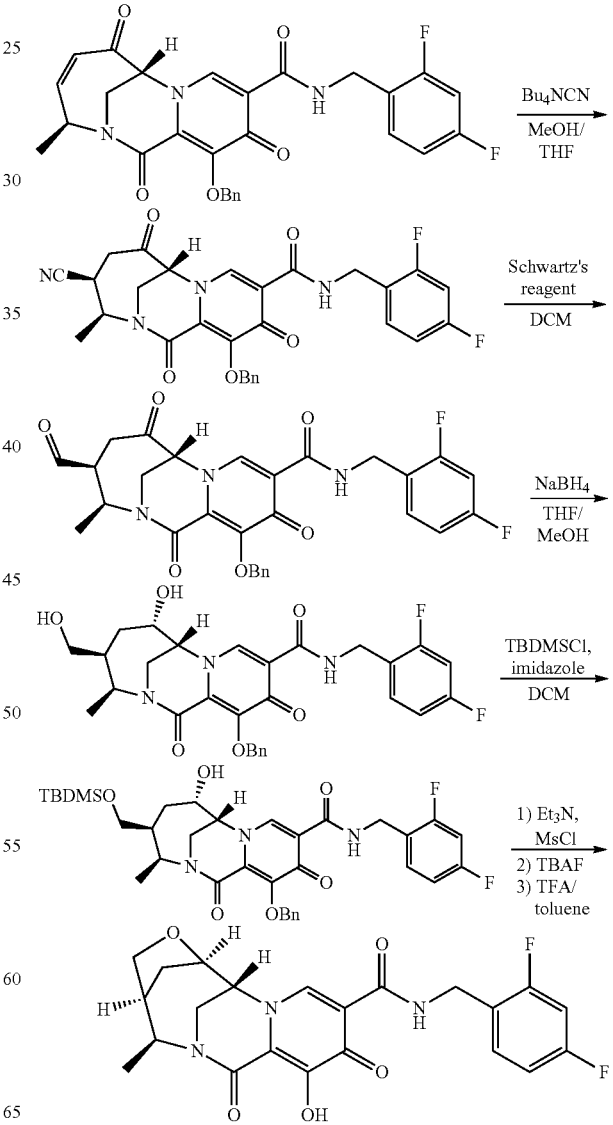

Step 1: Preparation of (3S,4S,7R)-12-(benzyloxy)-4-cyano-N-(2,4-difluorobenzyl)-3-methyl-1,6,11-trioxo-1,4,5,6,7,11-hexahydro-3H-2,7-methanopyrido[1,2-a][1,4]diazonine-10-carboxamide To a solution of (3S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide (512 mg, 0.985 mmol, 1 Eq) in THF/MeOH (1:1) (18 mL) was added tetrabutylammonium cyanide (397 mg, 1.48 mmol, 1.5 Eq) and the resulting solution was stirred at room temperature for 2 days. EtOAc (20 mL) was added and the resulting mixture was washed with saturated aqueous sodium carbonate and brine. The organic layer was dried over sodium sulfate, filtered and concentrated in vacuo. The resulting residue was purified by flash column chromatography on silica gel using a gradient of MeOH in DCM (0 to 10%) to afford the desired product as a mixture of the parent ketone as well as the ketone hydrate and hemiketal with methanol. The stereochemistry at the position alpha to the cyano group was assigned by 2D NMR spectroscopy using Nuclear Overhauser Effect correlation of the diol product obtained after step 3.

Step 2: Preparation of (3S,4S,7R)-12-(benzyloxy)-N-(2,4-difluorobenzyl)-4-formyl-3-methyl-1,6,11-trioxo-1,4,5,6,7,11-hexahydro-3H-2,7-methanopyrido[1,2-a][1,4]diazonine-10-carboxamide A solution of (3S,4S,7R)-12-(benzyloxy)-4-cyano-N-(2,4-difluorobenzyl)-3-methyl-1,6,11-trioxo-1,4,5,6,7,11-hexahydro-3H-2,7-methanopyrido[1,2-a][1,4]diazonine-10-carboxamide (179 mg, 0.317 mmol, 1 Eq) in DCM (5 mL) was cooled to 0° C. under $N_2$. Bis(cyclopentadienyl)zirconium(IV) chloride hydride (Schwartz's reagent, 425 mg, 0.159 mmol, 5 Eq.) was added and the resulting mixture was stirred for 1 h at 0° C. and then 15 minutes at rt. Water was added and the mixture was extracted 3× with DCM. The combined organic layers were dried over sodium sulfate, filtered and concentrated in vacuo. The resulting residue was filtered through a plug of silica to remove any Zr species using a gradient of MeOH in DCM (0 to 20%) to afford the desired product as a mixture of the parent carbonyl as well as carbonyl hydrates, hemiketals with MeOH and overreduction products. The mixture was use directly in Step 3 below.

Step 3: Preparation of (3S,4S,6S,7R)-12-(benzyloxy)-N-(2,4-difluorobenzyl)-6-hydroxy-4-(hydroxymethyl)-3-methyl-1,11-dioxo-1,4,5,6,7,11-hexahydro-3H-2,7-methanopyrido[1,2-a][1,4]diazonine-10-carboxamide To a solution of the product mixture from Step 2 (above) (169 mg, 0.298 mmol, 1 Eq) in THF/MeOH (1:1) (12 mL) at 0° C. was added sodium borohydride (22.5 mg, 0.596 mmol, 2 Eq) and the resulting mixture was stirred for 10 minutes at room temperature then concentrated in vacuo. Water was added and the pH was adjusted to ~5 by addition of dilute acetic acid. The mixture was extracted twice with DCM and the combined organic layers were washed with brine, dried over sodium sulfate, filtered and concentrated in vacuo. The resulting residue was purified by reverse phase preparative high performance liquid chromatography using a gradient of MeCN in $H_2O$ (40% to 80% with 0.1% TFA) to afford the desired product.

Step 4: Preparation of (3S,4S,6S,7R)-12-(benzyloxy)-4-(((tert-butyldimethylsilyl)oxy)methyl)-N-(2,4-difluorobenzyl)-6-hydroxy-3-methyl-1,11-dioxo-1,4,5,6,7,11-hexahydro-3H-2,7-methanopyrido[1,2-a][1,4]diazonine-10-carboxamide To a solution of (3S,4S,6S,7R)-12-(benzyloxy)-N-(2,4-difluorobenzyl)-6-hydroxy-4-(hydroxymethyl)-3-methyl-1,11-dioxo-1,4,5,6,7,11-hexahydro-3H-2,7-methanopyrido[1,2-a][1,4]diazonine-10-carboxamide (15 mg, 0.027 mmol, 1 Eq) in DMF (1.0 mL) was added tert-butylchlorodimethylsilane (22.7 mg, 0.135 mmol, 5 Eq) and imidazole (10 mg, 0.149 mmol, 5.5 Eq) and the resulting mixture was stirred for 30 minutes at 60° C. The reaction mixture was partitioned between water and EtOAc and the layers were separated. The aqueous layer was extracted twice with EtOAc and the combined organic layers were dried over sodium sulfate, filtered and concentrated in vacuo. The residue was used directly in Step 5 without further purification.

Step 5: Preparation of (3S,4S,7R,8R)—N-(2,4-difluorobenzyl)-13-hydroxy-3-methyl-1,12-dioxo-1,4,5,7,8,12-hexahydro-3H-2,8:4,7-dimethanopyrido[1,2-d][1,4,7]oxadiazecine-11-carboxamide To a solution of the crude residue from step 5 (assumed to be 0.0271 mmol, 1 Eq) in DCM (6 mL) was added triethylamine (22.7 uL, 0.163 mmol, 6 Eq) and MsCl (6.29 uL, 0.0813 mmol, 3 Eq) under $N_2$ atmosphere and the resulting solution was stirred at room temperature for 5 minutes. Tetrabutylammonium fluoride (1.0 M in THF, 0.569 mL, 0.569 mmol, 21 Eq) was added directly to the reaction and the resulting solution was stirred in a sealed vial at 45° C. for 2 days. The reaction mixture was concentrated in vacuo and partitioned between water and EtOAc. The layers were separated and the aqueous layer was extracted with EtOAc. The combined organic layers were washed with brine, dried over sodium sulfate, filtered and concentrated in vacuo. The resulting residue was taken up into TFA/toluene (1:1) (2 mL) and stirred at room temperature for 4 h. The reaction mixture was concentrated in vacuo and purified by reverse phase preparative high performance liquid chromatography using a gradient of MeCN in $H_2O$ (10% to 90% with 0.1% TFA) and normal phase silica gel column chromatography using a gradient of MeOH in DCM (0 to 20%) to afford the desired compound. MS (m/z) 446.200 [M+H]+ $^1$H NMR (400 MHz, $CD_3CN$) δ 10.63 (s, 1H), 10.32 (s, 1H), 8.43 (s, 1H), 7.40 (td, J=8.8, 6.5 Hz, 1H), 7.00-6.88 (m, 2H), 4.65 (p, J=6.9 Hz, 1H), 4.57 (d, J=6.0 Hz, 2H), 4.54-4.47 (m, 1H), 4.31 (dt, J=4.9, 2.3 Hz, 1H), 4.23 (dd, J=9.9, 1.5 Hz, 1H), 3.85 (dd, J=10.0, 7.5 Hz, 1H), 3.60-3.38 (m, 2H), 2.71 (q, J=6.2 Hz, 1H), 2.02 (dt, J=14.7, 7.4 Hz, 1H), 1.59 (d, J=14.7 Hz, 1H), 1.28 (d, J=7.1 Hz, 3H).

Example 46: (3S,6S,7R)—N-(2,4-difluorobenzyl)-12-hydroxy-6-methoxy-3-methyl-1,11-dioxo-1,6,7,11-tetrahydro-3H-2,7-methanopyrido[1,2-a][1,4]diazonine-6-d-10-carboxamide

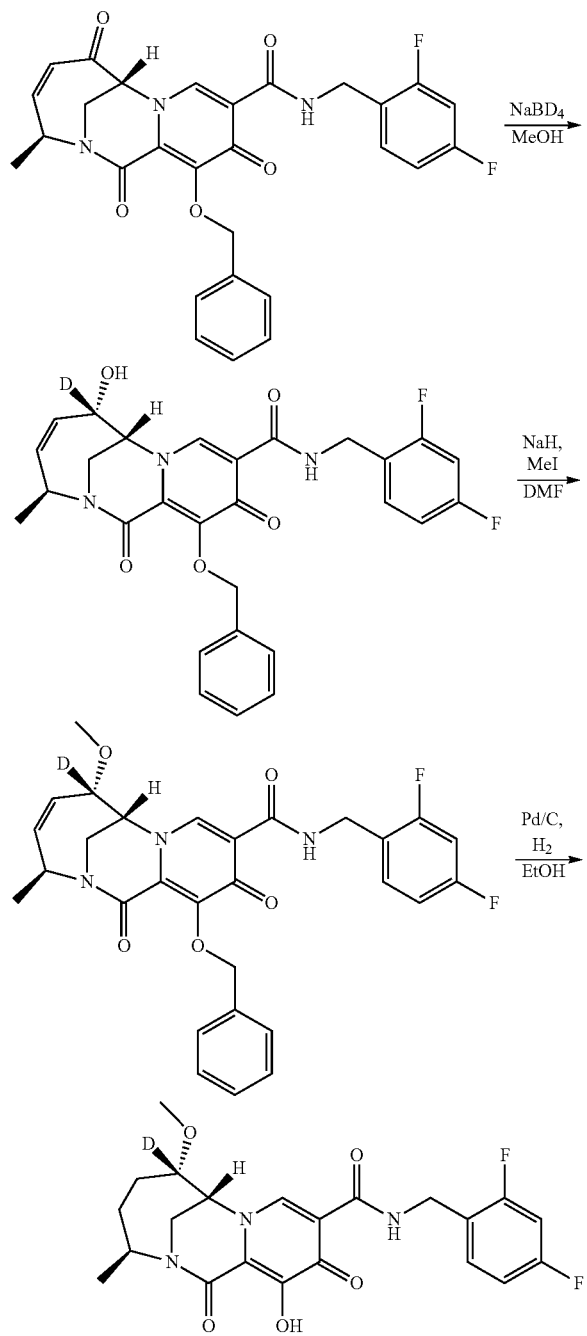

Step 1: Preparation of (3S,6S,7R)-12-(benzyloxy)-N-(2,4-difluorobenzyl)-6-hydroxy-3-methyl-1,11-dioxo-1,6,7,11-tetrahydro-3H-2,7-methanopyrido[1,2-a][1,4]diazonine-6-d-10-carboxamide To a solution of (3S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide (100 mg, 0.192 mmol) in MeOH (5 mL) was added cerium (III) chloride heptahydrate (717 mg, 0.192 mmol). Then to the mixture was added sodium borodeuteride (4 mg, 0.096 mol) slowly. The reaction mixture was stirred at 0° C. After the reaction was finished, the reaction was quenched by adding sat. NaHCO3, extracted with DCM, the organic phase was separated and dried over MgSO4. Then the separated organic phase was filtered, concentrated down and used in next step without purification.

Step 2: Preparation of (3S,6S,7R)-12-(benzyloxy)-N-(2,4-difluorobenzyl)-6-methoxy-3-methyl-1,11-dioxo-1,6,7,11-tetrahydro-3H-2,7-methanopyrido[1,2-a][1,4]diazonine-6-d-10-carboxamide To a solution of (3S,6S,7R)-12-(benzyloxy)-N-(2,4-difluorobenzyl)-6-hydroxy-3-methyl-1,11-dioxo-1,6,7,11-tetrahydro-3H-2,7-methanopyrido[1,2-a][1,4]diazonine-6-d-10-carboxamide (90 mg, 0.172 mmol) in DMF (3 mL) was added sodium hydride (8.3 mg, 0.21 mmol, 60%) and iodomethane (12.9 uL, 0.21 mmol). The reaction mixture was stirred at 0° C. for 0.5 h. The reaction was quenched by adding sat. NaHCO3, extracted with EtOAc, the organic phase was separated, dried over MgSO$_4$, filtered, concentrated down and the resulting product was used in next step without further purification.

Step 3: Preparation of (3S,6S,7R)—N-(2,4-difluorobenzyl)-12-hydroxy-6-methoxy-3-methyl-1,11-dioxo-1,6,7,11-tetrahydro-3H-2,7-methanopyrido[1,2-a][1,4]diazonine-6-d-10-carboxamide To a solution of (3S,6S,7R)-12-(benzyloxy)-N-(2,4-difluorobenzyl)-6-methoxy-3-methyl-1,11-dioxo-1,6,7,11-tetrahydro-3H-2,7-methanopyrido[1,2-a][1,4]diazonine-6-d-10-carboxamide (60 mg, 0.112 mmol) in EtOH (3 mL) was added Pd/C (38 mg). The reaction mixture was stirred at rt with H2 balloon attached. After the reaction was finished, the reaction mixture was filtered through celite. The filtrate was concentrated down and the residue was purified by reverse phase HPLC, eluting with 4-100% ACN in water, containing 0.1% TFA, to afford the title compound. MS (m/z) 449.2 [M+H]$^+$. 1H NMR (400 MHz, Methanol-d4) δ 8.36 (s, 1H), 7.44 (td, J=8.4, 6.3 Hz, 1H), 7.03-6.90 (m, 2H), 4.89 (s, 1H), 4.73 (s, 1H), 4.69-4.57 (m, 3H), 3.83-3.68 (m, 2H), 3.46 (s, 3H), 2.18-1.97 (m, 2H), 1.54 (dt, J=14.6, 11.3 Hz, 1H), 1.28 (d, J=6.7 Hz, 3H), 1.00 (dd, J=14.7, 11.6 Hz, 1H).

Example 47: HIV MT-4 Antiviral and Cytotoxicity Assay

Antiviral Assay in MT-4 Cells

Compounds were tested in a high-throughput 384-well assay format for their ability to inhibit the replication of HIV-1 (IIIB) in MT-4 cells. Compounds were serially diluted (1:3) in DMSO on 384-well polypropylene plates and further diluted 200-fold into complete RPMI media (10% FBS, 1% P/S) using the Biotek Micro Flow and Labcyte ECHO acoustic dispenser. Each plate contained up to 8 test compounds, with negative (No Drug Control) and 5 μM AZT positive controls. MT-4 cells were pre-infected with 10 μL of either RPMI (mock-infected) or a fresh 1:250 dilution of HIV-1 IIIB concentrated virus stock. Infected and uninfected MT-4 cells were further diluted in complete RPMI media and added to each plate using a Micro Flow dispenser. After 5 days incubation in a humidified and temperature controlled incubator (37° C.), Cell Titer Glo (Promega) was added to the assay plates and chemiluminescence read using an Envision plate-reader. $EC_{50}$ values were defined as the compound concentration that causes a 50% decrease in luminescence signal, and were calculated using a sigmoidal dose-response model to generate curve fits.

Cytotoxicity Assay in MT-4 Cells

Assays were performed as above except uninfected MT-4 cells were added to each well containing test compound. In addition, 10 μM puromycin was added to the last column of each assay plate to assess a base level of cytotoxicity.

Example 48: HIV MT-4 Serum Shift Antiviral Reporter Assay

To quantify the amount of protein binding to human serum, compounds were serially diluted (1:3) in DMSO and acoustically transferred onto 384-well assay plates via a Labcyte ECHO robot. Each plate contained up to 8 test compounds, including negative and positive controls, (DMSO, 5 μM AZT respectively). Assay plates were prepared in duplicate, and tested in either CCM (cell culture media) or HS/CCM (human serum/cell culture media). MT-4 cells were first pre-infected with pLai RLuc reporter virus for 2 h at 37° C., then further diluted in either CCM (RPMI media, 10% FBS, 1% P/S) or HS/CCM (RPMI media, 10% FBS, 50% HS, 1% P/S), and subsequently added to each plate using a Biotek Micro Flow dispenser. After a 72-h incubation in a humidified and temperature controlled incubator (37° C.), *Renilla* Glo (Promega) was added to all assay plates and chemiluminescence read using an Envision plate-reader. $EC_{50}$ values were defined as the compound concentration that causes a 50% decrease in luminescence signal, and were calculated using a sigmoidal dose-response model to generate curve fits. To determine the amount of protein binding, $EC_{50}$ fold shifts (or $EC_{50}$ shifts) were calculated by dividing $EC_{50}$ (HS/CCM)/$EC_{50}$ (CCM).

Compounds of the present disclosure demonstrate antiviral activity in this assay as depicted in Table 1 below. Accordingly, the compounds of the embodiments disclosed herein may be useful for treating the proliferation of the HIV virus, treating AIDS, or delaying the onset of AIDS or ARC symptoms.

Example 49: High Throughput Microsomal Stability Assay

Metabolic stability of compounds was assessed using Human, or Rat Liver Microsomal assays (Corning). In this assay, 10 nL compounds at concentration of 1 mM in 100% DMSO were dispensed into 384-well polypropylene plates using the Echo 550 acoustic liquid dispenser (Labcyte®). Each plate contained 384 wells with a single test compound in each well.

A solution of human (Corning® Gentest™ Human Mixed Pooled Microsomes), or rat (Corning® Gentest™ Rat [Sprague-Dawley] Pooled Liver Microsomes) liver microsomes at 2 mg/ml in 100 mM $K_2HPO_4/KH_2PO_4$ pH 7.4 with Alamethicin from *Trichoderma viride* (Sigma-Aldrich) 0.0225 mg/ml were incubated on ice for 15 minutes. 5 uL of this solution was added to individual wells following 15 minute incubation at room temperature; and supplemented with 5 uL NADPH Regenerating Solution of cofactors (Corning® Gentest™ UGT Reaction Mix) containing 100 mM $K_2HPO_4/KH_2PO_4$ pH 7.4, 2.6 mM NADP+, 6.6 mM glucose-6-phosphate, 6.6 mM $MgCl_2$, 0.8 U/mL glucose-6-phosphate dehydrogenase, 0.1 mM Sodium Citrate, 6.8 mM uridine diphosphate-glucuronic acid. Final concentration of analyte compounds at the beginning of the reaction was 1 uM. The reactions were incubated at 37° C. and time points of 0, 5, 15, 30, 40, 50, 60, and 70 minutes were collected for further analysis. Background data were collected using reactions without analyte compounds.

Upon collection of the reaction time points, samples were quenched with 30 uL of a solution of 72% acetonitrile, 8% methanol, 0.1% formic acid, 19.9% water, and internal standard (IS). Reaction plates were span in a centrifuge at speed of 4,000 rcf for 30 minutes and 4° C., following a dilution of the 10 uL quenched reaction into 40 uL de-ionized water, yielding assay plates.

Assay plates were analyzed using solid-state extraction coupled with quadrupole time-of-flight mass spectrometer, using Agilent QToF 6530 RapidFire 360 system, with C4 type A solid state cartridges. Analysis was performed in either positive or negative ionization modes. Mobile phases contained 0.1% formic acid in water for loading analytes onto solid state extraction cartridges, and 0.1% formic acid in acetonitrile for elution into mass spectrometer in positive ionization mode, or 0.1% acetic acid in water for loading and 0.1% acetic acid in acetonitrile for extraction in negative ionization mode. Peak-area ratios of integrated counts for individual compounds to IS were plotted as semi-logarithmic chart of log vs time. Initial, linear portion of decay was fitted to a linear regression equation to derive half time of a compound decay.

Pharmacological parameters for an analyte compound metabolism were calculated using the following equations:

| Parameter | Equation |
| --- | --- |
| Half Life | $T_{1/2} = \dfrac{\mathrm{Ln}(2)}{-1 * \mathrm{Slope}}$ |
| Intrinsic Clearance (in vitro) | $Cl_{int,in\,vitro} = \dfrac{\ln 2}{T_{1/2} - \mathrm{Conc}}$ |
| Intrinsic Clearance | $Cl_{int} = \dfrac{Cl_{int,in\,vitro} - \mathrm{Liver\,Mass} * \mathrm{Yield}}{\mathrm{Body\,Weight}}$ |
| Predicted Hepatic Clearance | $Cl = \dfrac{Cl_{int} * Q_H}{Cl_{int} + Q_H}$ |
| Hepatic Extraction | $E = \dfrac{Cl}{Q_H} * 100\%$ |

Where.
Calculation of In Vitro Intrinsic Clearance $$CL_{int,\,in\,vitro} = \dfrac{\ln 2}{\text{Half-Life} * \text{Concentration}}$$

Concentration refers to the protein concentration (mg/mL) in the reaction.

| System | Concentration |
| --- | --- |
| "Mixed cofactor" Hepatic microsomes (+UDPGA + NADPH) | 1.0 mg protein/mL |

Calculation of In Vivo Intrinsic Clearance

This scales the in vitro intrinsic clearance up to the value that would be predicted for the entire mass of liver tissue (but with no restriction by blood flow). The value depends upon the size of the liver (species-dependent) and the yield of microsomal protein as appropriate (assumed to be species-independent).

$$CL_{int} = \frac{CL_{int,\,in\,vitro} * \text{Liver mass} * \text{Yield}}{\text{Body weight}}$$

| Matrix | Yield |
|---|---|
| Microsomal fraction | 45 mg/g liver |

| Species | Body weight kg | Liver weight g |
|---|---|---|
| Human | 70 | 1800 |

Calculation of Predicted Clearance

Hepatic clearance will depend upon the inter-relationship of intrinsic clearance and hepatic blood flow and can be predicted from in vitro data using a variety of approaches.

$$CL = \frac{CL_{in} * Q_H}{CL_{int} + Q_H}$$

| Species | Hepatic blood flow L/hr/kg |
|---|---|
| Human | 1.3 |

Calculation of Hepatic Extraction

This is simply the predicted clearance expressed as a proportion of hepatic blood flow.

$$E = CL/Q_H * 100\%$$

Intrinsic clearance of the instant compounds, as well as for reference compounds A-F, were calculated following the procedure above. The results of these compounds are shown in Table 2 below. As seen, the instant compounds are 1.5 to 3.6 times more stable than the Reference compounds A-F.

TABLE 1

| | MT4 EC$_{50}$ (nM) | CC$_{50}$ (nM) | RLUC CCM (nM) | RLUC 50% HS (nM) | RLUC Shift | HLM stability L/h/Kg |
|---|---|---|---|---|---|---|
| 1 | 1.5 | 34798 | 0.55 | 23 | 43 | 0.21 |
| 2 | 1.8 | 50000 | 0.53 | 40 | 76 | 0.15 |
| 3 | 1.5 | 16498 | 0.42 | 13 | 30 | 0.15 |
| 4 | 1.1 | 11167 | 0.34 | 7.5 | 22 | 0.14 |
| 5 | 1.8 | 50000 | 0.71 | 17 | 24 | 0.20 |
| 6 | 1.4 | 13013 | 0.50 | 87 | 174 | 0.29 |
| 7 | 1.2 | 9906 | 0.29 | 4.8 | 16 | 0.20 |
| 8 | 1.4 | 10671 | 0.34 | 34 | 100 | 0.22 |
| 9 | 1.0 | 4272 | 0.42 | 30 | 72 | 0.48 |
| 10 | 1.2 | 4015 | 0.28 | 22 | 79 | 0.40 |
| 11 | 1.5 | 38651 | 0.84 | 72 | 86 | 0.25 |
| 12 | 1.4 | 41294 | 0.61 | 47 | 76 | 0.15 |
| 13 | 1.5 | 15605 | 0.55 | 22 | 41 | 0.26 |
| 14 | 4.2 | 50000 | | | | 0.16 |
| 15 | 7.9 | 28431 | 1.64 | 47 | 29 | 0.19 |
| 16 | 2.6 | 41407 | 1.14 | 52 | 46 | 0.11 |
| 17 | 3.0 | 31379 | 1.33 | 34 | 26 | 0.17 |
| 18 | 1.4 | 13441 | 0.55 | 5.3 | 10 | 0.73 |
| 19 | 1.1 | 20000 | 0.38 | 2.4 | 6 | 0.47 |
| 20 | 2.8 | 30009 | | | | 0.11 |
| 21 | 1.8 | 19331 | 0.52 | 3.4 | 7 | 0.37 |
| 22 | 1.7 | 8914.7 | | | | 0.84 |
| 23 | 2.2 | 9790.3 | 0.47 | 22 | 47 | 0.7 |
| 24 | 2.2 | 11101 | | | | 0.69 |
| 25 | 4.1 | 43655 | 0.82 | 15 | 18 | 0.58 |
| 26 | 4.4 | 44336 | 0.92 | 212 | 231 | 0.22 |
| 27 | 1.1 | 13601 | 0.35 | 28 | 80 | 0.88 |
| 28 | 4.1 | 24443 | 0.96 | 39 | 40 | 0.34 |
| 29 | 2.0 | 12998 | 0.74 | 23 | 30 | 0.11 |
| 30 | 2.1 | 7478.2 | | | | 0.11 |
| 31 | 2.1 | 8226.7 | 0.36 | 16 | 45 | 0.18 |
| 32 | 1.9 | 34620 | 0.43 | 3.9 | 9 | 0.54 |
| 33 | 2.1 | 22780 | 0.36 | 9.4 | 26 | 0.35 |
| 34 | 0.9 | 15134 | 0.42 | 20 | 47 | 0.25 |
| 35 | 3.2 | 11712 | 1.45 | 4.3 | 3 | 0.62 |
| 36 | 2.6 | 27314 | 0.33 | 14 | 43 | 0.2 |
| 37 | 1.4 | 14802 | 0.65 | 191 | 294 | 0.17 |
| 38 | 1.8 | 25460 | 0.34 | 101 | 298 | 0.19 |
| 39 | 1.5 | 11708 | 1.5 | 257 | 171 | 0.28 |
| 40 | 1.1 | 19598 | 2.87 | 450 | 157 | 0.28 |
| 41 | 1.7 | 19370 | 0.56 | 28 | 50 | 0.11 |
| 42 | 1.9 | 50000 | 0.61 | 2.4 | 4 | 0.58 |

TABLE 1-continued

|  | MT4 EC$_{50}$ (nM) | CC$_{50}$ (nM) | RLUC CCM (nM) | RLUC 50% HS (nM) | RLUC Shift | HLM stability L/h/Kg |
|---|---|---|---|---|---|---|
| 43 | 1.3 | 23608 | 0.71 | 97 | 137 | 0.29 |
| 44 | 4 | 44695 | 1.9 | 389 | 205 | 0.22 |
| 45 | 1.9 | 12404 | 0.46 | 0.86 | 2 | 0.17 |

TABLE 2

| Compound | GS No. | Structure | MS Cl | MS Cl improvement |
|---|---|---|---|---|
| A (186) | GS-1074961 | 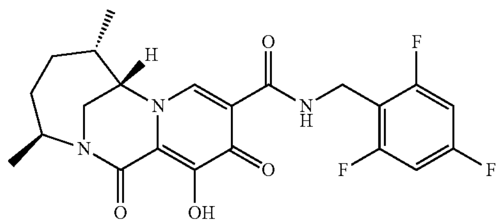 [SMILES: C[C@H]1CC[C@H](C)N2C[C@H]1n1cc(C(=O)NCc3c(F)cc(F)cc3F)c(=O)c(O)c1C2=O] | 0.68 | |
| Example 1 | GS-1152221 | 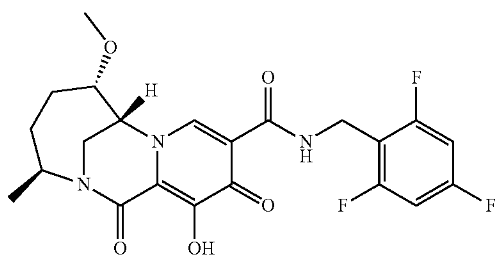 [SMILES: CO[C@H]1CC[C@H](C)N2C[C@H]1n1cc(C(=O)NCc3c(F)cc(F)cc3F)c(=O)c(O)c1C2=O] | 0.21 | 3.2 times relative to compound A |
| B (187) | GS-1075233 | 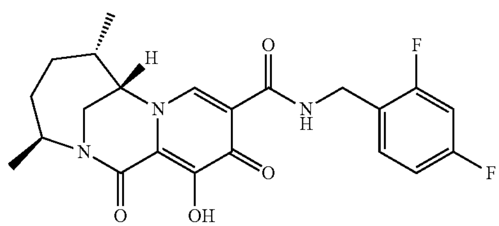 [SMILES: C[C@H]1CC[C@H](C)N2C[C@H]1n1cc(C(=O)NCc3ccc(F)cc3F)c(=O)c(O)c1C2=O] | 0.48 | |
| Example 3 | GS-1153195 | 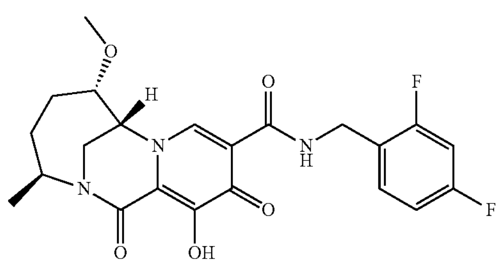 [SMILES: CO[C@H]1CC[C@H](C)N2C[C@H]1n1cc(C(=O)NCc3ccc(F)cc3F)c(=O)c(O)c1C2=O] | .15 | 3.2 times relative to compound B |
| C (176) | GS-1073795 | 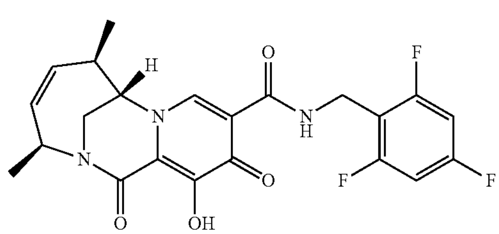 [SMILES: C[C@@H]1C=C[C@H](C)N2C[C@H]1n1cc(C(=O)NCc3c(F)cc(F)cc3F)c(=O)c(O)c1C2=O] | 0.51 | |

TABLE 2-continued

| Compound | GS No. | Structure | MS Cl | MS Cl improvement |
|---|---|---|---|---|
| Example 4 | GS-1153196 | 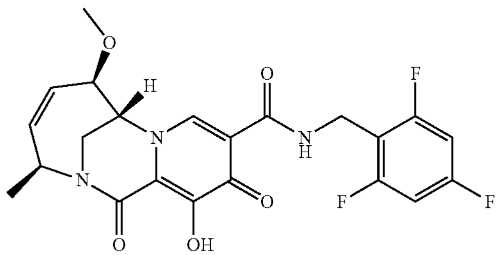 [SMILES: CO[C@@H]1C=C[C@H](C)N2C[C@H]1n1cc(C(=O)NCc3c(F)cc(F)cc3F)c(=O)c(O)c1C2=O] | 0.14 | 3.6 times relative to compound C |
| D (174) | GS-1073699 | 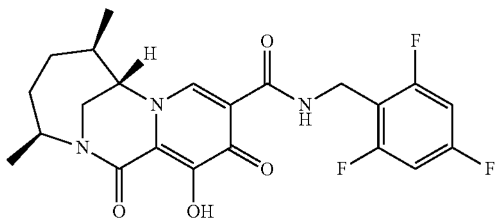 [SMILES: C[C@@H]1CC[C@H](C)N2C[C@H]1n1cc(C(=O)NCc3c(F)cc(F)cc3F)c(=O)c(O)c1C2=O] | 0.68 | |
| Example 6 | GS-1155372 | 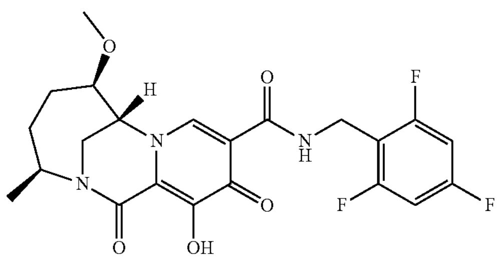 [SMILES: CO[C@@H]1CC[C@H](C)N2C[C@H]1n1cc(C(=O)NCc3c(F)cc(F)cc3F)c(=O)c(O)c1C2=O] | 0.29 | 2.3 times relative to compound D |
| Example 11 | GS-1152096 | 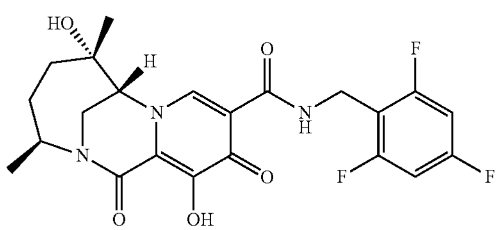 [SMILES: C[C@H]1CC[C@](C)(O)[C@H]2CN1C(=O)c1c(O)c(=O)c(C(=O)NCc3c(F)cc(F)cc3F)cn12] | 0.25 | 2.7 times relative to compound D |
| E (177) | GS-1073796 (lead) | 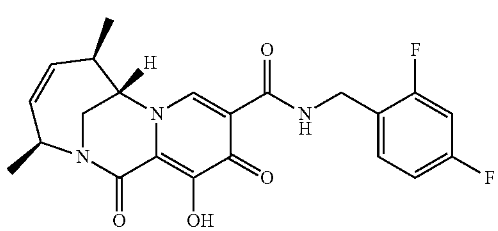 [SMILES: C[C@@H]1C=C[C@H](C)N2C[C@H]1n1cc(C(=O)NCc3ccc(F)cc3F)c(=O)c(O)c1C2=O] | 0.39 | |
| Example 7 | GS-1156005 | 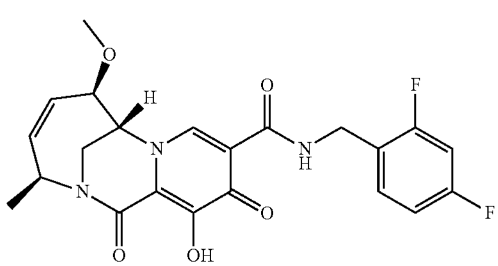 [SMILES: CO[C@@H]1C=C[C@H](C)N2C[C@H]1n1cc(C(=O)NCc3ccc(F)cc3F)c(=O)c(O)c1C2=O] | 0.2 | 2.0 times relative to compound E |

TABLE 2-continued

| Compound | GS No. | Structure | MS Cl | MS Cl improvement |
|---|---|---|---|---|
| Example 13 | GS-1151383 | 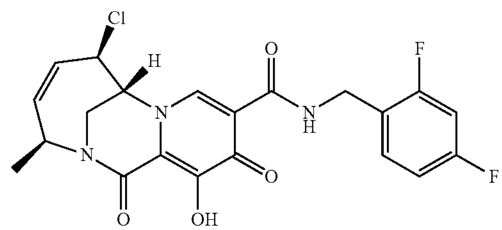 [SMILES: C[C@H]1C=C[C@@H](Cl)[C@H]2CN1C(=O)c1c(O)c(=O)c(C(=O)NCc3ccc(F)cc3F)cn12] | 0.26 | 1.5 times relative to compound E |
| F (175) | GS-1073701 | 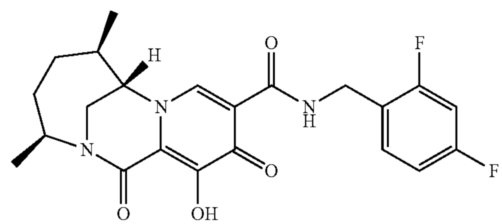 [SMILES: C[C@@H]1CC[C@H](C)N2C[C@H]1n1cc(C(=O)NCc3ccc(F)cc3F)c(=O)c(O)c1C2=O] | 0.49 | |
| Example 8 | GS-1156006 | 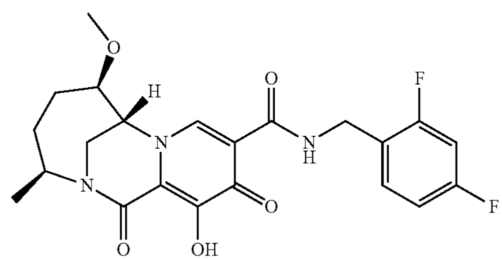 [SMILES: CO[C@@H]1CC[C@H](C)N2C[C@H]1n1cc(C(=O)NCc3ccc(F)cc3F)c(=O)c(O)c1C2=O] | .22 | 2.2 times relative to compound F |
| Example 12 | GS-1152107 | 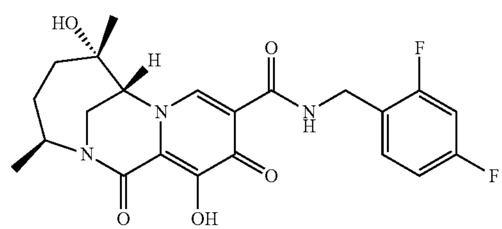 [SMILES: C[C@H]1CC[C@](C)(O)[C@H]2CN1C(=O)c1c(O)c(=O)c(C(=O)NCc3ccc(F)cc3F)cn12] | 0.15 | 3.3 times relative to compound F |
| Example 33 | GS-1159776 | 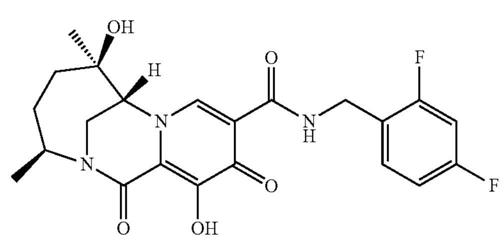 [SMILES: C[C@H]1CC[C@@](C)(O)[C@H]2CN1C(=O)c1c(O)c(=O)c(C(=O)NCc3ccc(F)cc3F)cn12] | 0.35 | |
| Example 35 | GS-1161234 | 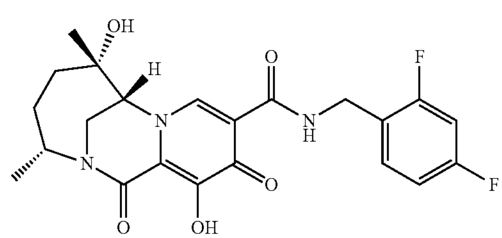 [SMILES: C[C@@H]1CC[C@](C)(O)[C@H]2CN1C(=O)c1c(O)c(=O)c(C(=O)NCc3ccc(F)cc3F)cn12] | 0.62 | |

All references, including publications, patents, and patent documents are incorporated are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter, and is not intended to limit the appended claims to the specific embodiments illustrated.

What is claimed:

1. A compound of Formula Ic:

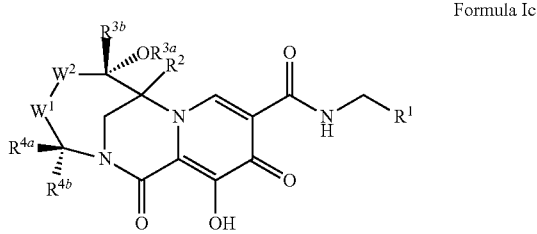

Formula Ic or a pharmaceutically acceptable salt thereof, wherein
$R^1$ is phenyl or pyridyl, wherein the phenyl or pyridyl is substituted with one, two, three, or four $R^{41}$, wherein each $R^{41}$ is independently a halogen;
$R^2$ is H or $C_{1-6}$alkyl;
$R^{3a}$ is H, —$C_{1-6}$alkyl, —$C_{1-4}$haloalkyl, or —$C_{3-6}$cycloalkyl;
$R^{3b}$ is H, —$C_{1-6}$alkyl, —$C_{1-4}$haloalkyl, or —$C_{1-4}$alkylene-O—$C_{1-4}$alkyl;
$R^{4a}$ is —$C_{1-3}$alkyl;
$R^{4b}$ is H;
$W^1$ is —$CR^{5a}R^{5b}$—;
$R^{5a}$ and $R^{5b}$ are independently H, $C_{1-6}$alkyl, $C_{1-4}$haloalkyl, or halo;
$W^2$ is —$CR^{6a}R^{6b}$—; and
$R^{6a}$ and $R^{6b}$ are independently H, $C_{1-6}$alkyl, $C_{1-4}$haloalkyl, hydroxyl, cyano, —O—$C_{1-4}$alkyl, or $C_{1-4}$alkylene-O—$C_{1-4}$alkyl;
wherein the compound of Formula Ic is not

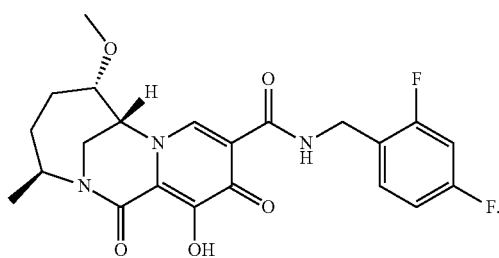 [SMILES: CO[C@H]1CC[C@H](C)N2C[C@H]1n1cc(C(=O)NCc3ccc(F)cc3F)c(=O)c(O)c1C2=O]

2. The compound of claim 1, or the pharmaceutically acceptable salt thereof, wherein $R^1$ is phenyl or pyridyl, wherein the phenyl or pyridyl is substituted with two or three $R^{41}$, wherein each $R^{41}$ is independently selected from chloro and fluoro.

3. The compound of claim 1, or the pharmaceutically acceptable salt thereof, wherein $R^1$ is phenyl substituted with one, two, three, or four $R^{41}$, wherein each $R^{41}$ is independently a halogen.

4. The compound of claim 1, or the pharmaceutically acceptable salt thereof, wherein $R^1$ is phenyl substituted with two or three $R^{41}$, wherein each $R^{41}$ is independently selected from chloro and fluoro.

5. The compound of claim 1, or the pharmaceutically acceptable salt thereof, wherein $R^1$ is selected from the group consisting of:

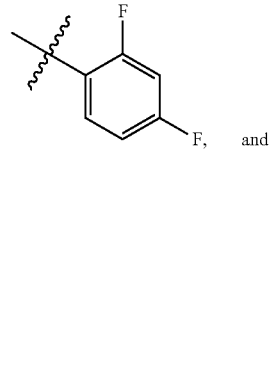

6. The compound of claim 1, or the pharmaceutically acceptable salt thereof, wherein each $R^{41}$ is independently chloro or fluoro.

7. The compound of claim 4, or the pharmaceutically acceptable salt thereof, wherein $R^2$ is H.

8. The compound of claim 7, or the pharmaceutically acceptable salt thereof, wherein $R^{3a}$ is —$C_{1-6}$alkyl or —$C_{1-4}$haloalkyl.

9. The compound of claim 8, or the pharmaceutically acceptable salt thereof, wherein $R^{3a}$ is —$C_{1-6}$alkyl.

10. The compound of claim 9, or the pharmaceutically acceptable salt thereof, wherein $R^{3a}$ is methyl or ethyl.

11. The compound of claim 9, or the pharmaceutically acceptable salt thereof, wherein $R^{3b}$ is H, —$C_{1-6}$alkyl, —$C_{1-4}$haloalkyl.

12. The compound of claim 11, or the pharmaceutically acceptable salt thereof, wherein $R^{3b}$ is H or —$C_{1-6}$alkyl.

13. The compound of claim 12, or the pharmaceutically acceptable salt thereof, wherein $R^{3b}$ is H or —$C_{1-3}$alkyl.

14. The compound of claim 13, or the pharmaceutically acceptable salt thereof, wherein $R^{3b}$ is H or methyl.

15. The compound of claim 14, or the pharmaceutically acceptable salt thereof, wherein $R^{3b}$ is H.

16. The compound of claim 14, or the pharmaceutically acceptable salt thereof, wherein $R^{5a}$ is H, $C_{1-6}$alkyl, $C_{1-4}$haloalkyl, or halo and $R^{5b}$ is H or halo.

17. The compound of claim 16, or the pharmaceutically acceptable salt thereof, wherein $R^{5a}$ is H or halo and $R^{5b}$ is H or halo.

18. The compound of claim 16, or the pharmaceutically acceptable salt thereof, wherein $R^{6a}$ is H and $R^{6b}$ is H, $C_{1-6}$alkyl, $C_{1-4}$haloalkyl, hydroxyl, cyano, —O—$C_{1-4}$alkyl, or $C_{1-4}$alkylene-O—$C_{1-4}$alkyl.

19. The compound of claim 18, or the pharmaceutically acceptable salt thereof, wherein $R^{6a}$ is H and $R^{6b}$ is H.

20. A pharmaceutical composition comprising a therapeutically effective amount of a compound of claim 1, or pharmaceutically acceptable salt thereof, and a pharmaceutically acceptable excipient.

21. A kit comprising a compound of claim 1, or a pharmaceutically acceptable salt thereof, and instructions for use.

22. A method of treating an HIV infection in a human having or at risk of having the infection, comprising administering to the human a therapeutically effective amount of a compound of claim 1, or pharmaceutically acceptable salt thereof.

\* \* \* \* \*